US011655452B2

(12) United States Patent
Ma et al.

(10) Patent No.: US 11,655,452 B2
(45) **Date of Patent: *May 23, 2023**

(54) CHIMERIC ANTIGEN RECEPTORS (CARS), COMPOSITIONS AND METHODS OF USE THEREOF

(71) Applicant: iCell Gene Therapeutics LLC, Stony Brook, NY (US)

(72) Inventors: Yupo Ma, Stony Brook, NY (US); Kevin Pinz, Stony Brook, NY (US); Xun Jiang, Stony Brook, NY (US); Masayuki Wada, Stony Brook, NY (US); Kevin Chen, Stony Brook, NY (US)

(73) Assignee: iCell Gene Therapeutics Inc., Stony Brook, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/739,596

(22) PCT Filed: Jun. 24, 2016

(86) PCT No.: PCT/US2016/039306

§ 371 (c)(1),
(2) Date: Dec. 22, 2017

(87) PCT Pub. No.: WO2016/210293

PCT Pub. Date: Dec. 29, 2016

(65) Prior Publication Data

US 2018/0187149 A1 Jul. 5, 2018

Related U.S. Application Data

(60) Provisional application No. 62/244,435, filed on Oct. 21, 2015, provisional application No. 62/235,840, filed on Oct. 1, 2015, provisional application No. 62/184,321, filed on Jun. 25, 2015.

(51) Int. Cl.
*C12N 5/0783* (2010.01)
*C07K 14/725* (2006.01)
*C07K 14/705* (2006.01)
*C07K 16/28* (2006.01)

(52) U.S. Cl.
CPC ........ *C12N 5/0636* (2013.01); *C07K 14/7051* (2013.01); *C07K 14/70517* (2013.01); *C07K 14/70521* (2013.01); *C07K 14/70578* (2013.01); *C07K 16/289* (2013.01); *C12N 5/0646* (2013.01); *C07K 2319/00* (2013.01); *C07K 2319/02* (2013.01); *C07K 2319/03* (2013.01); *C07K 2319/50* (2013.01); *C12N 2510/00* (2013.01)

(58) Field of Classification Search
CPC .............. C12N 5/0636; C07K 14/7051; C07K 2319/50
USPC ....................................................... 424/133.1
See application file for complete search history.

(56) References Cited

U.S. PATENT DOCUMENTS

| | | | |
|---|---|---|---|
| 8,399,645 B2 | 3/2013 | Campana et al. | |
| 9,328,156 B2 | 5/2016 | June et al. | |
| 10,117,896 B2 * | 11/2018 | Powell, Jr. | A61K 39/3955 |
| 10,253,086 B2 * | 4/2019 | Bitter | C07K 14/7051 |
| 10,273,280 B2 * | 4/2019 | Ma | A61K 35/15 |
| 10,472,613 B2 * | 11/2019 | Duchateau | A61P 37/04 |
| 11,173,179 B2 * | 11/2021 | Ma | A61K 38/177 |
| 2002/0009449 A1 | 1/2002 | Wallner et al. | |
| 2003/0147865 A1 | 8/2003 | Salomon et al. | |
| 2004/0265315 A1 | 12/2004 | Dingivan et al. | |
| 2005/0277587 A1 | 12/2005 | Chen et al. | |
| 2008/0254027 A1 | 10/2008 | Bernett et al. | |
| 2008/0254512 A1 | 10/2008 | Capon | |
| 2008/0299042 A1 | 12/2008 | Bechtel et al. | |
| 2009/0081157 A1 | 3/2009 | Kornbluth et al. | |
| 2009/0238791 A1 | 9/2009 | Jacques et al. | |
| 2009/0325188 A1 | 12/2009 | Glass | |
| 2012/0058082 A1 | 3/2012 | Kaplan et al. | |
| 2012/0070408 A1 | 3/2012 | Kaplan et al. | |
| 2012/0134970 A1 | 5/2012 | Yang et al. | |
| 2012/0258494 A1 | 10/2012 | Stitz | |
| 2013/0058936 A1 | 3/2013 | Bruenker et al. | |
| 2013/0259876 A1 | 10/2013 | Murphy et al. | |
| 2013/0287748 A1 | 10/2013 | June et al. | |
| 2013/0287752 A1 | 10/2013 | Davila et al. | |

(Continued)

FOREIGN PATENT DOCUMENTS

| | | |
|---|---|---|
| JP | 292749 | 6/2020 |
| WO | 2009091826 A2 | 7/2009 |

(Continued)

OTHER PUBLICATIONS

Chen et al. Cancer Immunol Immunother 66:475-489 (2017).*
Mihara et al. Journal of Hematology & Oncology 10:116-119 (2017).*
Zhang et al. Journal of Hematology & Oncology 11:102-116 (2018).*
Zhu et al. Cytotherapy 20: 394-406 (2018).*
Kang et al. Biomarker Research (2020) 8:14.*
Liu, Fang, et al., "First-in-Human CLL1-CD33 Compound Car T Cell Therapy Induces Complete Remission in Patients with Refractory Acute Myeloid Leukemia: Update on Phase 1 Clinical Trial", http://www.bloodjournal.org/content/132/Suppl_1/901?sso-checked=true.
John, Liza B., et al., "Anti-PD-1 Antibody Therapy Potently Enhances the Eradication of Established Tumors by Gene-Modified T Cells", Clin Cancer Res; 19(20) Oct. 15, 2013.

(Continued)

*Primary Examiner* — Lynn A Bristol
(74) *Attorney, Agent, or Firm* — Hoffmann & Baron, LLP

(57) ABSTRACT

The present invention relates to compositions and methods relating to chimeric antigen receptor (CAR) polypeptides and methods relating thereto. In one embodiment, the present invention relates to engineered cells having chimeric antigen receptor polypeptides directed to at least two targets. In another embodiment, the present invention relates to engineered cells having chimeric antigen receptor polypeptides and an enhancer moiety.

4 Claims, 69 Drawing Sheets

Specification includes a Sequence Listing.

(56) References Cited

U.S. PATENT DOCUMENTS

| | | | | |
|---|---|---|---|---|
| 2014/0099309 | A1* | 4/2014 | Powell, Jr. | A61P 35/00 424/135.1 |
| 2014/0106449 | A1 | 4/2014 | June et al. | |
| 2014/0286918 | A1 | 9/2014 | Dao | |
| 2014/0322183 | A1 | 10/2014 | Milone et al. | |
| 2015/0038684 | A1 | 2/2015 | Jensen | |
| 2015/0133640 | A1 | 5/2015 | Blein et al. | |
| 2015/0140019 | A1* | 5/2015 | June | A61P 43/00 424/178.1 |
| 2015/0307623 | A1 | 10/2015 | Abbot et al. | |
| 2015/0342993 | A1 | 12/2015 | Kloss et al. | |
| 2016/0068601 | A1* | 3/2016 | Brogdon | A61P 35/00 424/134.1 |
| 2016/0207989 | A1 | 7/2016 | Short | |
| 2016/0250258 | A1 | 9/2016 | Delaney et al. | |
| 2016/0340406 | A1 | 11/2016 | Zhao et al. | |
| 2017/0145108 | A1 | 5/2017 | Schreiber et al. | |
| 2017/0267742 | A1 | 9/2017 | Jensen et al. | |
| 2018/0066034 | A1* | 3/2018 | Ma | A61K 35/15 |
| 2018/0162939 | A1* | 6/2018 | Ma | A61P 35/00 |
| 2018/0187149 | A1* | 7/2018 | Ma | C07K 14/70517 |
| 2018/0371052 | A1* | 12/2018 | Ma | A61K 35/17 |
| 2019/0135894 | A1* | 5/2019 | Ma | C07K 14/70596 |
| 2019/0255108 | A1* | 8/2019 | Ma | A61K 38/177 |
| 2020/0024342 | A9* | 1/2020 | Ma | C07K 14/70517 |
| 2020/0078399 | A1* | 3/2020 | Fan | C07K 16/3061 |
| 2020/0223918 | A1* | 7/2020 | Ma | C07K 16/2812 |
| 2020/0283534 | A1* | 9/2020 | Ma | C07K 14/70578 |
| 2020/0308541 | A1* | 10/2020 | Ma | C12N 5/0646 |
| 2020/0371091 | A1* | 11/2020 | Pruteanu-Malinici | A61K 45/06 |
| 2022/0241327 | A1* | 8/2022 | Ma | A61K 35/17 |

FOREIGN PATENT DOCUMENTS

| | | | |
|---|---|---|---|
| WO | 2012079000 | A1 | 6/2012 |
| WO | WO2013126712 | A1 | 8/2013 |
| WO | WO2014055668 | A1 | 4/2014 |
| WO | WO2014100385 | A1 | 6/2014 |
| WO | WO2014127261 | A1 | 8/2014 |
| WO | WO2014184143 | A1 | 11/2014 |
| WO | WO2015018529 | A1 | 2/2015 |
| WO | WO2015075468 | A1 | 5/2015 |
| WO | WO2015075469 | A1 | 5/2015 |
| WO | WO2015075470 | A1 | 5/2015 |
| WO | WO2015120180 | A1 | 8/2015 |
| WO | WO2015121454 | A1 | 8/2015 |
| WO | WO2015157399 | A9 | 10/2015 |
| WO | WO2015168613 | A2 | 11/2015 |
| WO | WO2015172339 | A1 | 11/2015 |
| WO | WO2016014553 | A1 | 1/2016 |
| WO | WO2016102965 | A1 | 6/2016 |
| WO | WO2016210293 | A1 | 12/2016 |
| WO | WO2017/031863 | * | 3/2017 |
| WO | WO2017068361 | A1 | 4/2017 |

OTHER PUBLICATIONS

Rowley, Jesse, et al., "Expression of IL-15RA or an IL-15/IL-15RA fusion on CD8+ T cells modifies adoptively transferred T-cell function in cis", Eur. J. Immunol. 2009: 491-506.

Gill, Saar, MD, PhD, "Chimeric antigen receptor T-cell therapy in AML: How close are we?", Best Pract Res Clin Haematol. Dec. 2016; 29(4): 329-333. doi:10.1016/j.beha.2016.10.004.

Chen, KH, et al., "A compound chimeric antigen receptor strategy for targeting multiple myeloma", Leukemia (2018) 32, 402-412.

Petrov, Jessica C., et al. , "Compound CAR T-cells as a double-pronged approach for treating acute myeloid leukemia", Leukemia (2018) 32: 1317-1326.

Hamieh, Mohamad, et al., "CAR T cell trogocytosis and cooperative killing regulate tumour antigen escape", Mature 568, 112-116(2019).

Qin, Haiying, et al., "Novel CD19/CD22 Bicistronic Chimeric Antigen Receptors Outperform Single or Bivalent Cars in Eradicating CD19+CD22+, CD19-, and CD22- Pre-B Leukemia", Blood 2017, 130:810.

Grupp et al., "Chimeric Antigen Receptor-Modified T Cells for Acute Lymphoid Leukemia," New England Journal of Medicine, Apr. 18, 2013, vol. 368, No. 16, pp. 1509-1518.

Rowley et al., "Expression of IL-15RA or an IL-15/IL-15RA fusion on CD8+ T cells modifies adoptively transferred T-cell function in cis," Eur J Immunol, Jan. 29, 2009, vol. 39, No. 2, pp. 491-506.

John et al., "Anti-PD-1 Antibody Therapy Potently Enhances the Eradication of Established Tumors by Gene-Modified T Cells," Clin Cancer Res, Oct. 15, 2013, vol. 19, No. 20, pp. 5636-5646.

Penney et al., "Greater frequency of CD5-negative CD8(+) T cells against human immunodeficiency virus type 1 than other viruses is consistent with adaptation to antigenic variation," AIDS Res Ther, Sep. 15, 2014, vol. 11, No. 30, pp. 1-10.

Maus et al., "Antibody-modified T cells: CARs take the front seat for hematologic malignancies," Blood, Apr. 24, 2014, vol. 123, No. 17, pp. 2625-2635.

D'Amore et al., "Phase II trial of zanolimumab (HuMax-CD4) in relapsed or refractory non-cutaneous peripheral T cell lymphoma," Br J Haematol 2010, 150: 565-573.

Shenghui et al., "Elevated frequencies of CD4+CD25+CD127lo regulatory T cells is associated to poor prognosis in patients with acute myeloid leukemia," Int. J. Cancer 2011,129: 1373-1381.

Ehninger et al., "Distribution and levels of cell surface expression of CD33 and CD123 in acute myeloid leukemia," Blood Cancer Journal 2014, vol. 4, pp. 1-10.

Liu et al., "Tumor_Associated Macrophages Via Up-Regulation of PD1 Ligands Protect Neuroblastoma from Immunotherapy With NKT Cells Expressing GD2-Specific Chimeric Antigen Receptor," Molecular Therapy, vol. 23, Supp. 1, May 2015, Abstract 512. p. S205.

Rouce et al., "Equal opportunity CAR T cells," Blood 2017, 129:3275-3277.

Lai et al., "The Roles of CD4+ T Cells in Tumor Immunity," ISRN Immunology, vol. 2011, Article ID 497397, 6 pages, doi:10.5402/2011/497397.

Kebriaei et al., "Phase I trials using Sleeping Beauty to generate CD19-specific CAR T cells," The Journal of Clinical Investigation, vol. 126, No. 9, Sep. 2016, pp. 3363-3376 and Supplemental Tables.

Curran, Kevin, et al., "Chimeric Antigen Receptors for T Cell Immunotherapy: Current Understanding and Future Directions." The Journal of Gene Medicine, 14.(6), pp. 405-415, Jun. 2012.

Shirasu, N., et al., "Functional Design of Chimeric T-Cell Antigen Receptors for Adoptive Immunotherapy of Cancer: Architecture and Outcomes", Anticancer Research, 32(6), pp. 2377-2384, 2012.

Bridgeman, J.S., et al., "CD 3ζ-Based Chimeric Antigen Receptors Mediate T Cell Activation Via Cis-and Trans-Signalling Mechanisms: Implications for Optimization of Receptor Structure for Adoptive Cell Therapy", Clinical & Experimental Immunology, 175(2), pp. 258-267, 2014.

Kaiser, A.D., et al., "Towards a Commercial Process for the Manufacture of Genetically Modified T Cells for Therapy", Cancer Gene Therapy, 22(2), pp. 72-78, Jan. 2015.

Sentman, C.L., "Challenges of Creating Effective CARs for Cancer Therapy", Immunotherapy, 5(8), pp. 783-785, 2013.

Japanese Pending Claims Machine Translated.

Japanese Notice of Allowance.

Japanese Certificate of Patent.

Japanese Patent Granted Translation.

European Communication of Jun. 27, 2022.

Claims 1-4 from European Patent Appl. No. 16815399.7.

Brown et al., "Novel Treatments for Chronic Lymphocytic Leukemia and Moving Forward", American Society of Clinical Oncology Educational Book, vol. 34, 2014, pp. e317-e325, XP055201368.

Leavitt et al ., Concordant Modulation of Neutralization Resistance and High Infectivity of the Primary Human Immunodeficiency Virus Type 1 MN Strain and Definition of a Potential gp41 Binding Site in gp120 Journal of Virology, Jan. 2003, p. 560-570.

Schreiber et al., Cancer Immunoediting: Integrating Immunity's Roles in Cancer Suppression and Promotion; pp. 1565-1570.

(56) References Cited

OTHER PUBLICATIONS

Marzo et al., Fully Functional Memory CDS T Cells in the Absence of CD4 T Cells J Immunol 2004; 173:969-975.
Moeller et al., Sustained Antigen-Specific Antitumor Recall Response Mediated by Gene-Modified CD4+ T Helper-1 and CDS+ T Cells Cancer Res 2007; 67: (23). Dec. 1 pp. 11428-37.
Moeller et al Adoptive transfer of gene-engineered CD4 helper T cells induces potent primary and secondary tumor rejection Blood, Nov. 1, 2005 vol. 106, No. 9; pp. 2995-3003.
Gibson et al Risk of non-Hodgkin lymphoma subtypes in HIV-infected people during the HAART era: a population-based study AIDS. Sep. 24, 2014; 28(15): 2313-2318.
Beard et al., "Multiple chimeric antigen receptors successfully target chondroitin sulfate proteoglycan 4 in several different cancer histologies and cancer stem cells," Journal for ImmunoTherapy of Cancer 2014; 2(25), pp. 1-11.
Imboden et al., "Stimulation of CDS Enhances Signal Transduction by the T Cell Antigen Receptor," J. Clin. Invest. 1990; 85:130-134.
Rabinowich et al., "Signaling via CD7 molecules on human NK cells. Induction of tyrosine phosphorylation and beta 1 integrin-mediated adhesion to fibronectin," J. Immunol. 1994; 153:3504-3513.
Inoue et al., "Mechanisms of NK cell activation stimulated by CD2; granzyme B is released by CD2 crosslinking-stimulation on NK92 cell," J Osaka Dent Univ 2012 (October; 46(2): 229-235.
McNerney et al., "The CD2 family of natural killer cell receptors," Curr Top Microbiol Immuhnol 2006; 298:91-120.
Rabinowich et al., "Expression and function of CD7 molecule on human natural killer cells," J Immunol 1994; 152:517-526.
Liu et al., "Critical Role of CD2 Co-stimulation in Adaptive Natural Killer Cell Responses Revealed in NKG2CDeficient Humans," Cell Reports 2016; 15, 1088-1099.
Muyldermans et al., "Recognition of antigens by single domain antibody fragments: the superfluous luxury of paired domains", Trends in Biochemical Sciences, vol. 26,No. 4, Apr. 2001: pp. 230-235.
Wilkie et al., "Dual Targeting of ErbB2 and MUC1 in Breast Cancer using Chimeric Antigen Receptors Engineered to Provide Complementary Signaling", J Clin Immunol (2012) 32: 1059-1070.
Dotti et al., "Design and Development of Therapies using Chimeric Antigen Receptor-Expressing T Cells", Immunol Rev. Jan. 2014; 257(1); pp. 1-35.
Muyldermans et al., "Single domain camel antibodies: current status", Reviews in Molecular Biotechnology 74 (2001), 277-302.
Lai et al., International Scholarly Research Network 2011; pp. 1-6.
Liu et al., Molecular Therapy vol. 23, Supplement 1, May 2015 Abstract 512.

* cited by examiner

GFP NK cells + KG1a 24h
2 to 1
GFP NK cells + KG1a 24h
5 to 1
GFP NK cells + KG1a 24h
10 to 1
74.3%
1.9%
0.7%
23.2%
90.5%
1.4%
0.5%
7.6%
95%
1.6%
0.8%
2.6%
CD56-PE
CD33-APC
cCAR NK cells + KG1a 24h
2 to 1
cCAR NK cells + KG1a 24h
5 to 1
cCAR NK cells + KG1a 24h
10 to 1
84.8%
0.8%
0.3%
14%
95.6%
0.7%
0.3%
3.5%
98.2%
0.7%
0.2%
0.8%
CD56-PE
CD33-APC

M 1 2 3

75

50

Steps: T or NK cells armed with CARs targeting hematologic malignancies

1. Donor T cells or NK cells
2. Gene disruption or deletion of CD45
3. Insert of scFv CAR targeting CD45

24 well, duplicate, n=3
IL-2 was added at 48hr time point

HEK CD4IL15RA

CD4IL15RA T cells

CD4 and CD4IL15RA NK CAR cells lyse MOLT4 tumor cells, 1:1

SEQUENCE LISTING

```
<160> NUMBER OF SEQ ID NOS: 43

<210> SEQ ID NO 1
<211> LENGTH: 830
<212> TYPE: PRT
<213> ORGANISM: Artificial Sequence
<220> FEATURE:
<223> OTHER INFORMATION: synthetic sequence

<400> SEQUENCE: 1

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Asp Ser Leu
            20                  25                  30

Ala Val Ser Leu Gly Glu Arg Val Thr Met Asn Cys Lys Ser Ser Gln
        35                  40                  45

Ser Leu Leu Tyr Ser Thr Asn Gln Lys Asn Tyr Leu Ala Trp Tyr Gln
    50                  55                  60

Gln Lys Pro Gly Gln Ser Pro Lys Leu Leu Ile Tyr Trp Ala Ser Thr
65                  70                  75                  80

Arg Glu Ser Gly Val Pro Asp Arg Phe Ser Gly Ser Gly Ser Gly Thr
                85                  90                  95

Asp Phe Thr Leu Thr Ile Ser Ser Val Gln Ala Glu Asp Val Ala Val
            100                 105                 110

Tyr Tyr Cys Gln Gln Tyr Tyr Ser Tyr Arg Thr Phe Gly Gly Gly Thr
        115                 120                 125

Lys Leu Glu Ile Lys Gly Gly Gly Gly Ser Gly Gly Gly Gly Ser Gly
    130                 135                 140

Gly Gly Gly Ser Gln Val Gln Leu Gln Gln Ser Gly Pro Glu Val Val
145                 150                 155                 160

Lys Pro Gly Ala Ser Val Lys Met Ser Cys Lys Ala Ser Gly Tyr Thr
                165                 170                 175

Phe Thr Ser Tyr Val Ile His Trp Val Arg Gln Lys Pro Gly Gln Gly
            180                 185                 190

Leu Asp Trp Ile Gly Tyr Ile Asn Pro Tyr Asn Asp Gly Thr Asp Tyr
        195                 200                 205

Asp Glu Lys Phe Lys Gly Lys Ala Thr Leu Thr Ser Asp Thr Ser Thr
    210                 215                 220

Ser Thr Ala Tyr Met Glu Leu Ser Ser Leu Arg Ser Glu Asp Thr Ala
225                 230                 235                 240

Val Tyr Tyr Cys Ala Arg Glu Lys Asp Asn Tyr Ala Thr Gly Ala Trp
                245                 250                 255

Phe Ala Tyr Trp Gly Gln Gly Thr Leu Val Thr Val Ser Ser Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
```

```
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser Lys Arg Gly Arg
    370                 375                 380

Lys Lys Leu Leu Tyr Ile Phe Lys Gln Pro Phe Met Arg Pro Val Gln
385                 390                 395                 400

Thr Thr Gln Glu Glu Asp Gly Cys Ser Cys Arg Phe Pro Glu Glu Glu
                405                 410                 415

Glu Gly Gly Cys Glu Leu Arg Val Lys Phe Ser Arg Ser Ala Asp Ala
            420                 425                 430

Pro Ala Tyr Gln Gln Gly Gln Asn Gln Leu Tyr Asn Glu Leu Asn Leu
        435                 440                 445

Gly Arg Arg Glu Glu Tyr Asp Val Leu Asp Lys Arg Arg Gly Arg Asp
    450                 455                 460

Pro Glu Met Gly Gly Lys Pro Gln Arg Arg Lys Asn Pro Gln Glu Gly
465                 470                 475                 480

Leu Tyr Asn Glu Leu Gln Lys Asp Lys Met Ala Glu Ala Tyr Ser Glu
                485                 490                 495

Ile Gly Met Lys Gly Glu Arg Arg Arg Gly Lys Gly His Asp Gly Leu
            500                 505                 510

Tyr Gln Gly Leu Ser Thr Ala Thr Lys Asp Thr Tyr Asp Ala Leu His
        515                 520                 525

Met Gln Ala Leu Pro Pro Arg Gly Ser Gly Ala Thr Asn Phe Ser Leu
    530                 535                 540

Leu Lys Gln Ala Gly Asp Val Glu Glu Asn Pro Gly Pro Met Tyr Arg
545                 550                 555                 560

Met Gln Leu Leu Ser Cys Ile Ala Leu Ser Leu Ala Leu Val Thr Asn
                565                 570                 575

Ser Gly Ile His Val Phe Ile Leu Gly Cys Phe Ser Ala Gly Leu Pro
            580                 585                 590

Lys Thr Glu Ala Asn Trp Val Asn Val Ile Ser Asp Leu Lys Lys Ile
        595                 600                 605

Glu Asp Leu Ile Gln Ser Met His Ile Asp Ala Thr Leu Tyr Thr Glu
    610                 615                 620

Ser Asp Val His Pro Ser Cys Lys Val Thr Ala Met Lys Cys Phe Leu
625                 630                 635                 640

Leu Glu Leu Gln Val Ile Ser Leu Glu Ser Gly Asp Ala Ser Ile His
                645                 650                 655

Asp Thr Val Glu Asn Leu Ile Ile Leu Ala Asn Asn Ser Leu Ser Ser
            660                 665                 670

Asn Gly Asn Val Thr Glu Ser Gly Cys Lys Glu Cys Glu Glu Leu Glu
        675                 680                 685

Glu Lys Asn Ile Lys Glu Phe Leu Gln Ser Phe Val His Ile Val Gln
    690                 695                 700

Met Phe Ile Asn Thr Ser Ser Gly Gly Gly Ser Gly Gly Gly Gly Ser
705                 710                 715                 720
```

```
Gly Gly Gly Gly Ser Gly Gly Gly Gly Ser Gly Gly Gly Ser Leu Gln
                725                 730                 735

Ala Pro Arg Arg Ala Arg Gly Cys Arg Thr Leu Gly Leu Pro Ala Leu
            740                 745                 750

Leu Leu Leu Leu Leu Leu Arg Pro Pro Ala Thr Arg Gly Ile Thr Cys
        755                 760                 765

Pro Pro Pro Met Ser Val Glu His Ala Asp Ile Trp Val Lys Ser Tyr
    770                 775                 780

Ser Leu Tyr Ser Arg Glu Arg Tyr Ile Cys Asn Ser Gly Phe Lys Arg
785                 790                 795                 800

Lys Ala Gly Thr Ser Ser Leu Thr Glu Cys Val Leu Asn Lys Ala Thr
                805                 810                 815

Asn Val Ala His Trp Thr Thr Pro Ser Leu Lys Cys Ile Arg
            820                 825                 830


<210> SEQ ID NO 2
<211> LENGTH: 2509
<212> TYPE: DNA
<213> ORGANISM: Artificial Sequence
<220> FEATURE:
<223> OTHER INFORMATION: synthetic sequence

<400> SEQUENCE: 2

gcgatcgcat ggccttacca gtgaccgcct tgctcctgcc gctggccttg ctgctccacg     60

ccgccaggcc ggacatcgtg atgacccaaa gccccgacag cctggccgtg agcctgggcg    120

agagggtgac catgaactgc aaaagcagcc agtccctgct gtactccacc aaccagaaga    180

actacctggc ttggtatcaa cagaagcccg gacagagccc caagctgctg atctattggg    240

ccagcactag ggaaagcggc gtgcccgata ggttcagcgg cagcgggagc ggcacagact    300

tcactctgac cattagcagc gtgcaggctg aggatgtggc cgtctactac tgccagcagt    360

actacagcta caggaccttt gggggcggaa ctaagctgga gatcaaggga ggggggggat    420

ccgggggagg aggctccggc ggaggcggaa gccaagtgca actgcagcag agcggcccag    480

aggtggtcaa acctggggca agcgtgaaga tgagctgcaa ggctagcggc tataccttca    540

ccagctatgt gatccactgg gtgaggcaga aaccaggaca gggcctggac tggatcggct    600

acatcaaccc ctacaatgac ggcaccgatt atgacgaaaa attcaagggg aaggccaccc    660

tgaccagcga caccagcaca agcaccgcct acatggagct gtccagcctg aggtccgagg    720

acaccgccgt gtattactgt gccagggaga aggacaatta cgccaccggc gcttggttcg    780

cctactgggg ccagggcaca ctggtgacag tgagcagcac cacgacgcca gcgccgcgac    840

caccaacacc ggcgcccacc atcgcgtcgc agcccctgtc cctgcgccca gaggcgtgcc    900

ggccagcggc ggggggcgca gtgcacacga gggggctgga cttcgcctgt gatatctaca    960

tctgggcgcc cttggccggg acttgtgggg tccttctcct gtcactggtt atcacccttt   1020

actgcaggag taagaggagc aggctcctgc acagtgacta catgaacatg actccccgcc   1080

gccccgggcc cacccgcaag cattaccagc cctatgcccc accacgcgac ttcgcagcct   1140

atcgctccaa acggggcaga aagaaactcc tgtatatatt caaacaacca tttatgagac   1200

cagtacaaac tactcaagag gaagatggct gtagctgccg atttccagaa gaagaagaag   1260

gaggatgtga actgagagtg aagttcagca ggagcgcaga cgcccccgcg taccagcagg   1320

gccagaacca gctctataac gagctcaatc taggacgaag agaggagtac gatgttttgg   1380

acaagagacg tggccgggac cctgagatgg ggggaaagcc gcagagaagg aagaaccctc   1440
```

```
aggaaggcct gtacaatgaa ctgcagaaag ataagatggc ggaggcctac agtgagattg   1500

ggatgaaagg cgagcgccgg aggggcaagg ggcacgatgg cctttaccag ggtctcagta   1560

cagccaccaa ggacacctac gacgcccttc acatgcaggc cctgcccct cgcggaagcg   1620

gagccaccaa cttcagcctg ctgaagcagg ccggcgacgt ggaggagaac cccggcccca   1680

tgtacagaat gcagctgctg agctgcatcg ccctgagcct ggccctggtg accaacagcg   1740

gcatccacgt gttcatcctg ggctgcttca gcgccggcct gcccaagacc gaggccaact   1800

gggtgaacgt gatcagcgac ctgaagaaga tcgaggacct gatccagagc atgcacatcg   1860

acgccaccct gtacaccgag agcgacgtgc accccagctg caaggtgacc gccatgaagt   1920

gcttcctgct ggagctgcag gtgatcagcc tggagagcgg cgacgccagc atccacgaca   1980

ccgtggagaa cctgatcatc ctggccaaca acagcctgag cagcaacggc aacgtgaccg   2040

agagcggctg caaggagtgc gaggagctgg aggagaagaa catcaaggag ttcctgcaga   2100

gcttcgtgca catcgtgcag atgttcatca acaccagctc cggcggcggc tccggcggcg   2160

gcggctccgg cggcggcggc tccggcggcg gcggctccgg cggcggctcc ctgcaggccc   2220

ccagaagagc cagaggctgc agaaccctgg gcctgcccgc cctgctgctg ctgctgctgc   2280

tgagaccccc cgccaccaga ggcatcacct gccccccccc catgagcgtg gagcacgccg   2340

acatctgggt gaagagctac agcctgtaca gcagagagag atacatctgc aacagcggct   2400

tcaagagaaa ggccggcacc agcagcctga ccgagtgcgt gctgaacaag gccaccaacg   2460

tggcccactg gaccaccccc agcctgaagt gcatcagata agtttaaac               2509
```

```
<210> SEQ ID NO 3
<211> LENGTH: 995
<212> TYPE: PRT
<213> ORGANISM: Artificial Sequence
<220> FEATURE:
<223> OTHER INFORMATION: synthetic sequence

<400> SEQUENCE: 3

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175
```

-continued

```
Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Gln Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg Gly Ser Gly Ala Thr Asn Phe Ser Leu
                485                 490                 495

Leu Lys Gln Ala Gly Asp Val Glu Glu Asn Pro Gly Pro Met Ala Leu
            500                 505                 510

Pro Val Thr Ala Leu Leu Leu Pro Leu Ala Leu Leu Leu His Ala Ala
        515                 520                 525

Arg Pro Gln Ile Val Leu Ser Gln Ser Pro Ala Ile Leu Ser Ala Ser
    530                 535                 540

Pro Gly Glu Lys Val Thr Met Thr Cys Arg Ala Ser Ser Ser Val Ser
545                 550                 555                 560

Tyr Ile His Trp Phe Gln Gln Lys Pro Gly Ser Ser Pro Lys Pro Trp
                565                 570                 575

Ile Tyr Ala Thr Ser Asn Leu Ala Ser Gly Val Pro Val Arg Phe Ser
            580                 585                 590
```

```
Gly Ser Gly Ser Gly Thr Ser Tyr Ser Leu Thr Ile Ser Arg Val Glu
        595                 600                 605

Ala Glu Asp Ala Ala Thr Tyr Tyr Cys Gln Gln Trp Thr Ser Asn Pro
    610                 615                 620

Pro Thr Phe Gly Gly Gly Thr Lys Leu Glu Ile Lys Gly Gly Gly Gly
625                 630                 635                 640

Ser Gly Gly Gly Gly Ser Gly Gly Gly Gly Ser Gln Val Gln Leu Gln
                645                 650                 655

Gln Pro Gly Ala Glu Leu Val Lys Pro Gly Ala Ser Val Lys Met Ser
            660                 665                 670

Cys Lys Ala Ser Gly Tyr Thr Phe Thr Ser Tyr Asn Met His Trp Val
        675                 680                 685

Lys Gln Thr Pro Gly Arg Gly Leu Glu Trp Ile Gly Ala Ile Tyr Pro
    690                 695                 700

Gly Asn Gly Asp Thr Ser Tyr Asn Gln Lys Phe Lys Gly Lys Ala Thr
705                 710                 715                 720

Leu Thr Ala Asp Lys Ser Ser Ser Thr Ala Tyr Met Gln Leu Ser Ser
                725                 730                 735

Leu Thr Ser Glu Asp Ser Ala Val Tyr Tyr Cys Ala Arg Ser Thr Tyr
            740                 745                 750

Tyr Gly Gly Asp Trp Tyr Phe Asn Val Trp Gly Ala Gly Thr Thr Val
        755                 760                 765

Thr Val Ser Ala Thr Thr Thr Pro Ala Pro Arg Pro Pro Thr Pro Ala
    770                 775                 780

Pro Thr Ile Ala Ser Gln Pro Leu Ser Leu Arg Pro Glu Ala Cys Arg
785                 790                 795                 800

Pro Ala Ala Gly Gly Ala Val His Thr Arg Gly Leu Asp Phe Ala Cys
                805                 810                 815

Asp Ile Tyr Ile Trp Ala Pro Leu Ala Gly Thr Cys Gly Val Leu Leu
            820                 825                 830

Leu Ser Leu Val Ile Thr Leu Tyr Cys Arg Ser Lys Arg Ser Arg Leu
        835                 840                 845

Leu His Ser Asp Tyr Met Asn Met Thr Pro Arg Arg Pro Gly Pro Thr
    850                 855                 860

Arg Lys His Tyr Gln Pro Tyr Ala Pro Pro Arg Asp Phe Ala Ala Tyr
865                 870                 875                 880

Arg Ser Arg Val Lys Phe Ser Arg Ser Ala Asp Ala Pro Ala Tyr Gln
                885                 890                 895

Gln Gly Gln Asn Gln Leu Tyr Asn Glu Leu Asn Leu Gly Arg Arg Glu
            900                 905                 910

Glu Tyr Asp Val Leu Asp Lys Arg Arg Gly Arg Asp Pro Glu Met Gly
        915                 920                 925

Gly Lys Pro Gln Arg Arg Lys Asn Pro Gln Glu Gly Leu Tyr Asn Glu
    930                 935                 940

Leu Gln Lys Asp Lys Met Ala Glu Ala Tyr Ser Glu Ile Gly Met Lys
945                 950                 955                 960

Gly Glu Arg Arg Arg Gly Lys Gly His Asp Gly Leu Tyr Gln Gly Leu
                965                 970                 975

Ser Thr Ala Thr Lys Asp Thr Tyr Asp Ala Leu His Met Gln Ala Leu
            980                 985                 990

Pro Pro Arg
        995
```

```
<210> SEQ ID NO 4
<211> LENGTH: 3004
<212> TYPE: DNA
<213> ORGANISM: Artificial Sequence
<220> FEATURE:
<223> OTHER INFORMATION: synthetic sequence

<400> SEQUENCE: 4

gcgatcgcat ggccttacca gtgaccgcct tgctcctgcc gctggccttg ctgctccacg     60

ccgccaggcc ggacatccag atgacacaga ctacatcctc cctgtctgcc tctctgggag    120

acagagtcac catcagttgc agggcaagtc aggacattag taaatattta aattggtatc    180

agcagaaacc agatggaact gttaaactcc tgatctacca tacatcaaga ttacactcag    240

gagtcccatc aaggttcagt ggcagtgggt ctggaacaga ttattctctc accattagca    300

acctggagca agaagatatt gccacttact tttgccaaca gggtaatacg cttccgtaca    360

cgttcggagg ggggaccaag ctggagatca caggtggcgg tggctcgggc ggtggtgggt    420

cgggtggcgg cggatctgag gtgaaactgc aggagtcagg acctggcctg gtggcgccct    480

cacagagcct gtccgtcaca tgcactgtct caggggtctc attacccgac tatggtgtaa    540

gctggattcg ccagcctcca cgaaagggtc tggagtggct gggagtaata tggggtagtg    600

aaaccacata ctataattca gctctcaaat ccagactgac catcatcaag gacaactcca    660

agagccaagt tttcttaaaa atgaacagtc tgcaaactga tgacacagcc atttactact    720

gtgccaaaca ttattactac ggtggtagct atgctatgga ctactggggc caaggaacct    780

cagtcaccgt ctcctcaacc acgacgccag cgccgcgacc accaacaccg gcgcccacca    840

tcgcgtcgca gcccctgtcc ctgcgcccag aggcgtgccg gccagcggcg gggggcgcag    900

tgcacacgag ggggctggac ttcgcctgtg atatctacat ctgggcgccc ttggccggga    960

cttgtggggt ccttctcctg tcactggtta tcacccttta ctgcaaacgg ggcagaaaga   1020

aactcctgta tatattcaaa caaccattta tgagaccagt acaaactact caagaggaag   1080

atggctgtag ctgccgattt ccagaagaag aagaaggagg atgtgaactg agagtgaagt   1140

tcagcaggag cgcagacgcc cccgcgtacc agcagggcca gaaccagctc tataacgagc   1200

tcaatctagg acgaagagag gagtacgatg ttttggacaa gagacgtggc cgggaccctg   1260

agatgggggg aaagccgcag agaaggaaga accctcagga aggcctgtac aatgaactgc   1320

agaaagataa gatggcggag gcctacagtg agattgggat gaaaggcgag cgccggaggg   1380

gcaaggggca cgatggcctt taccagggtc tcagtacagc caccaaggac acctacgacg   1440

cccttcacat gcaggccctg ccccctcgcg gaagcggagc caccaacttc agcctgctga   1500

agcaggccgg cgacgtggag gagaaccccg gccccatggc cttaccagtg accgccttgc   1560

tcctgccgct ggccttgctg ctccacgccg ccaggccgca gatcgtgctg agccagagcc   1620

ctgccatcct gtccgcaagc ccaggcgaga aggtgaccat gacctgtagg gccagcagct   1680

ccgtgagcta catccactgg tttcagcaga agcctggaag cagccctaag ccctggatct   1740

acgccacaag caatctggct agcggcgtgc ccgtgaggtt cagcggcagc gggagcggga   1800

ccagctacag cctgactatc agcagggtgg aggccgagga cgccgccaca tactactgcc   1860

aacagtggac ctccaaccca cccacctttg gaggagggac aaaactggag atcaaagggg   1920

gcggagggtc cggaggcggc ggaagcgggg gagggggaag ccaggtccaa ctgcaacagc   1980

ccggagcaga actggtcaaa ccaggcgcca gcgtgaagat gagctgcaag gccagcgggt   2040

acaccttcac ttcctataac atgcactggg tgaagcagac cccaggaagg ggcctggagt   2100
```

```
ggatcggggc aatctatccc ggcaacggcg acacaagcta caaccagaag ttcaagggga   2160

aagccactct gaccgccgac aagtccagct ccaccgccta catgcagctg agctccctga   2220

ccagcgagga cagcgccgtg tactattgcg ccagaagcac ttattacgga ggggactggt   2280

acttcaacgt gtggggggca gggaccaccg tgaccgtgtc cgccaccacg acgccagcgc   2340

cgcgaccacc aacaccggcg cccaccatcg cgtcgcagcc cctgtccctg cgcccagagg   2400

cgtgccggcc agcggcgggg ggcgcagtgc acacgagggg gctggacttc gcctgtgata   2460

tctacatctg ggcgcccttg gccgggactt gtggggtcct tctcctgtca ctggttatca   2520

ccctttactg caggagtaag aggagcaggc tcctgcacag tgactacatg aacatgactc   2580

cccgccgccc cgggcccacc cgcaagcatt accagcccta tgccccacca cgcgacttcg   2640

cagcctatcg ctccagagtg aagttcagca ggagcgcaga cgcccccgcg taccagcagg   2700

gccagaacca gctctataac gagctcaatc taggacgaag agaggagtac gatgttttgg   2760

acaagagacg tggccgggac cctgagatgg ggggaaagcc gcagagaagg aagaaccctc   2820

aggaaggcct gtacaatgaa ctgcagaaag ataagatggc ggaggcctac agtgagattg   2880

ggatgaaagg cgagcgccgg aggggcaagg ggcacgatgg cctttaccag ggtctcagta   2940

cagccaccaa ggacacctac gacgcccttc acatgcaggc cctgccccct cgctaagttt   3000

aaac                                                                3004
```

<210> SEQ ID NO 5
<211> LENGTH: 1001
<212> TYPE: PRT
<213> ORGANISM: Artificial Sequence
<220> FEATURE:
<223> OTHER INFORMATION: synthetic sequence

<400> SEQUENCE: 5

```
Asp Arg Met Ala Leu Pro Val Thr Ala Leu Leu Leu Pro Leu Ala Leu
1               5                   10                  15

Leu Leu His Ala Ala Arg Pro Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Ile Thr Gly Gly Gly Gly Ser Gly Gly Gly Gly Ser Gly Gly Gly Gly
    130                 135                 140

Ser Glu Val Lys Leu Gln Glu Ser Gly Pro Gly Leu Val Ala Pro Ser
145                 150                 155                 160

Gln Ser Leu Ser Val Thr Cys Thr Val Ser Gly Val Ser Leu Pro Asp
                165                 170                 175

Tyr Gly Val Ser Trp Ile Arg Gln Pro Pro Arg Lys Gly Leu Glu Trp
            180                 185                 190

Leu Gly Val Ile Trp Gly Ser Glu Thr Thr Tyr Tyr Asn Ser Ala Leu
```

-continued

```
        195                 200                 205

Lys Ser Arg Leu Thr Ile Ile Lys Asp Asn Ser Lys Ser Gln Val Phe
    210                 215                 220

Leu Lys Met Asn Ser Leu Gln Thr Asp Asp Thr Ala Ile Tyr Tyr Cys
225                 230                 235                 240

Ala Lys His Tyr Tyr Tyr Gly Gly Ser Tyr Ala Met Asp Tyr Trp Gly
                245                 250                 255

Gln Gly Thr Ser Val Thr Val Ser Ser Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Gly Ser Gly Ala Thr Asn Phe Ser
                485                 490                 495

Leu Leu Lys Gln Ala Gly Asp Val Glu Glu Asn Pro Gly Pro Met Ala
            500                 505                 510

Leu Pro Val Thr Ala Leu Leu Leu Pro Leu Ala Leu Leu Leu His Ala
        515                 520                 525

Ala Arg Pro Asp Ile Gln Met Thr Gln Ser Pro Ser Ser Leu Ser Ala
    530                 535                 540

Ser Val Gly Asp Arg Val Thr Ile Thr Cys Arg Ser Ser Gln Ser Ile
545                 550                 555                 560

Val His Ser Val Gly Asn Thr Phe Leu Glu Trp Tyr Gln Gln Lys Pro
                565                 570                 575

Gly Lys Ala Pro Lys Leu Leu Ile Tyr Lys Val Ser Asn Arg Phe Ser
            580                 585                 590

Gly Val Pro Ser Arg Phe Ser Gly Ser Gly Ser Gly Thr Asp Phe Thr
        595                 600                 605

Leu Thr Ile Ser Ser Leu Gln Pro Glu Asp Phe Ala Thr Tyr Tyr Cys
    610                 615                 620
```

```
Phe Gln Gly Ser Gln Phe Pro Tyr Thr Phe Gly Gln Gly Thr Lys Val
625                 630                 635                 640

Glu Ile Lys Gly Gly Gly Gly Ser Gly Gly Gly Gly Ser Gly Gly Gly
                645                 650                 655

Gly Ser Glu Val Gln Leu Val Glu Ser Gly Gly Gly Leu Val Gln Pro
            660                 665                 670

Gly Gly Ser Leu Arg Leu Ser Cys Ala Ala Ser Gly Tyr Glu Phe Ser
        675                 680                 685

Arg Ser Trp Met Asn Trp Val Arg Gln Ala Pro Gly Lys Gly Leu Glu
    690                 695                 700

Trp Val Gly Arg Ile Tyr Pro Gly Asp Gly Asp Thr Asn Tyr Ser Gly
705                 710                 715                 720

Lys Phe Lys Gly Arg Phe Thr Ile Ser Ala Asp Thr Ser Lys Asn Thr
                725                 730                 735

Ala Tyr Leu Gln Met Asn Ser Leu Arg Ala Glu Asp Thr Ala Val Tyr
            740                 745                 750

Tyr Cys Ala Arg Asp Gly Ser Ser Trp Asp Trp Tyr Phe Asp Val Trp
        755                 760                 765

Gly Gln Gly Thr Leu Val Thr Val Ser Ser Thr Thr Thr Pro Ala Pro
    770                 775                 780

Arg Pro Pro Thr Pro Ala Pro Thr Ile Ala Ser Gln Pro Leu Ser Leu
785                 790                 795                 800

Arg Pro Glu Ala Cys Arg Pro Ala Ala Gly Gly Ala Val His Thr Arg
                805                 810                 815

Gly Leu Asp Phe Ala Cys Asp Ile Tyr Ile Trp Ala Pro Leu Ala Gly
            820                 825                 830

Thr Cys Gly Val Leu Leu Leu Ser Leu Val Ile Thr Leu Tyr Cys Lys
        835                 840                 845

Arg Gly Arg Lys Lys Leu Leu Tyr Ile Phe Lys Gln Pro Phe Met Arg
    850                 855                 860

Pro Val Gln Thr Thr Gln Glu Glu Asp Gly Cys Ser Cys Arg Phe Pro
865                 870                 875                 880

Glu Glu Glu Glu Gly Gly Cys Glu Leu Arg Val Lys Phe Ser Arg Ser
                885                 890                 895

Ala Asp Ala Pro Ala Tyr Gln Gln Gly Gln Asn Gln Leu Tyr Asn Glu
            900                 905                 910

Leu Asn Leu Gly Arg Arg Glu Glu Tyr Asp Val Leu Asp Lys Arg Arg
        915                 920                 925

Gly Arg Asp Pro Glu Met Gly Gly Lys Pro Arg Arg Lys Asn Pro Gln
    930                 935                 940

Glu Gly Leu Tyr Asn Glu Leu Gln Lys Asp Lys Met Ala Glu Ala Tyr
945                 950                 955                 960

Ser Glu Ile Gly Met Lys Gly Glu Arg Arg Arg Gly Lys Gly His Asp
                965                 970                 975

Gly Leu Tyr Gln Gly Leu Ser Thr Ala Thr Lys Asp Thr Tyr Asp Ala
            980                 985                 990

Leu His Met Gln Ala Leu Pro Pro  Arg
        995                 1000
```

<210> SEQ ID NO 6
<211> LENGTH: 3016
<212> TYPE: DNA
<213> ORGANISM: Artificial Sequence
<220> FEATURE:

<223> OTHER INFORMATION: synthetic sequence

<400> SEQUENCE: 6

```
gcgatcgcat ggccttacca gtgaccgcct tgctcctgcc gctggccttg ctgctccacg      60
ccgccaggcc ggacatccag atgacacaga ctacatcctc cctgtctgcc tctctgggag     120
acagagtcac catcagttgc agggcaagtc aggacattag taaatattta aattggtatc     180
agcagaaacc agatggaact gttaaactcc tgatctacca tacatcaaga ttacactcag     240
gagtcccatc aaggttcagt ggcagtgggt ctggaacaga ttattctctc accattagca     300
acctggagca agaagatatt gccacttact tttgccaaca gggtaatacg cttccgtaca     360
cgttcggagg ggggaccaag ctggagatca caggtggcgg tggctcgggc ggtggtgggt     420
cgggtggcgg cggatctgag gtgaaactgc aggagtcagg acctggcctg gtggcgccct     480
cacagagcct gtccgtcaca tgcactgtct caggggtctc attacccgac tatggtgtaa     540
gctggattcg ccagcctcca cgaaagggtc tggagtggct gggagtaata tggggtagtg     600
aaaccacata ctataattca gctctcaaat ccagactgac catcatcaag gacaactcca     660
agagccaagt tttcttaaaa atgaacagtc tgcaaactga tgacacagcc atttactact     720
gtgccaaaca ttattactac ggtggtagct atgctatgga ctactggggc caaggaacct     780
cagtcaccgt ctcctcaacc acgacgccag cgccgcgacc accaacaccg gcgcccacca     840
tcgcgtcgca gcccctgtcc ctgcgcccag aggcgtgccg gccagcggcg gggggcgcag     900
tgcacacgag ggggctggac ttcgcctgtg atatctacat ctgggcgccc ttggccggga     960
cttgtggggt ccttctcctg tcactggtta tcacccttta ctgcaaacgg ggcagaaaga    1020
aactcctgta tatattcaaa caaccattta tgagaccagt acaaactact caagaggaag    1080
atggctgtag ctgccgattt ccagaagaag aagaaggagg atgtgaactg agagtgaagt    1140
tcagcaggag cgcagacgcc cccgcgtacc agcagggcca gaaccagctc tataacgagc    1200
tcaatctagg acgaagagag gagtacgatg ttttggacaa gagacgtggc cgggaccctg    1260
agatgggggg aaagccgaga aggaagaacc ctcaggaagg cctgtacaat gaactgcaga    1320
aagataagat ggcggaggcc tacagtgaga ttgggatgaa aggcgagcgc cggaggggca    1380
aggggcacga tggcctttac cagggtctca gtacagccac caaggacacc tacgacgccc    1440
ttcacatgca ggccctgccc cctcgcggaa gcggagccac caacttcagc ctgctgaagc    1500
aggccggcga cgtggaggag aaccccggcc ccatggcctt accagtgacc gccttgctcc    1560
tgccgctggc cttgctgctc cacgccgcca ggccggatat ccagatgacc cagagcccca    1620
gctccctgtc cgcatccgtg ggcgacagag tgacaattac ctgtagaagc agccaaagca    1680
tcgtgcatag cgtcggcaac acttttctgg agtggtatca acagaagccc gggaaggccc    1740
ccaaactgct gatctacaag gtgagcaaca gattcagcgg ggtcccaagc agattctccg    1800
gcagcggctc cgggactgac ttcaccctga ccattagcag cctgcagcca gaggacttcg    1860
ccacatacta ctgcttccaa gggagccagt tcccctacac cttcggccaa ggcactaagg    1920
tggagatcaa agggggggga ggaagcggcg gaggagggag cggaggcggg ggatccgaag    1980
tgcaactggt cgaatccgga ggggggctgg tccagcctgg agggtccctg agactgagct    2040
gcgccgcaag cggctacgag ttctccaggt cctggatgaa ctgggtgagg caggccccag    2100
gaaaagggct ggaatgggtg ggcaggatct accctggcga cggcgatacc aactactccg    2160
gaaagttcaa gggcaggttc actatcagcg ccgacactag caagaatacc gcctacctgc    2220
agatgaatag cctgagggcc gaggacaccg ccgtgtatta ctgcgctaga gacggcagca    2280
```

```
gctgggattg gtacttcgac gtgtggggcc agggcactct ggtgactgtg agcagcacca   2340

cgacgccagc gccgcgacca ccaacaccgg cgcccaccat cgcgtcgcag cccctgtccc   2400

tgcgcccaga ggcgtgccgg ccagcggcgg ggggcgcagt gcacacgagg gggctggact   2460

tcgcctgtga tatctacatc tgggcgccct tggccgggac ttgtggggtc cttctcctgt   2520

cactggttat caccctttac tgcaaacggg gcagaaagaa actcctgtat atattcaaac   2580

aaccatttat gagaccagta caaactactc aagaggaaga tggctgtagc tgccgatttc   2640

cagaagaaga agaaggagga tgtgaactga gagtgaagtt cagcaggagc gcagacgccc   2700

ccgcgtacca gcagggccag aaccagctct ataacgagct caatctagga cgaagagagg   2760

agtacgatgt tttggacaag agacgtggcc gggaccctga gatgggggga aagccgagaa   2820

ggaagaaccc tcaggaaggc ctgtacaatg aactgcagaa agataagatg gcggaggcct   2880

acagtgagat tgggatgaaa ggcgagcgcc ggaggggcaa ggggcacgat ggcctttacc   2940

agggtctcag tacagccacc aaggacacct acgacgccct tcacatgcag gccctgcccc   3000

ctcgctaagt ttaaac                                                   3016
```

```
<210> SEQ ID NO 7
<211> LENGTH: 990
<212> TYPE: PRT
<213> ORGANISM: Artificial Sequence
<220> FEATURE:
<223> OTHER INFORMATION: synthetic sequence

<400> SEQUENCE: 7

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220
```

```
Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Gln Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg Gly Ser Gly Ala Thr Asn Phe Ser Leu
                485                 490                 495

Leu Lys Gln Ala Gly Asp Val Glu Glu Asn Pro Gly Pro Met Ala Leu
            500                 505                 510

Pro Val Thr Ala Leu Leu Leu Pro Leu Ala Leu Leu Leu His Ala Ala
        515                 520                 525

Arg Pro Asp Val Gln Ile Thr Gln Ser Pro Ser Tyr Leu Ala Ala Ser
    530                 535                 540

Pro Gly Glu Thr Ile Thr Ile Asn Cys Arg Ala Ser Lys Ser Ile Ser
545                 550                 555                 560

Lys Asp Leu Ala Trp Tyr Gln Glu Lys Pro Gly Lys Thr Asn Lys Leu
                565                 570                 575

Leu Ile Tyr Ser Gly Ser Thr Leu Gln Ser Gly Ile Pro Ser Arg Phe
            580                 585                 590

Ser Gly Ser Gly Ser Gly Thr Asp Phe Thr Leu Thr Ile Ser Ser Leu
        595                 600                 605

Glu Pro Glu Asp Phe Ala Met Tyr Tyr Cys Gln Gln His Asn Lys Tyr
    610                 615                 620

Pro Tyr Thr Phe Gly Gly Gly Thr Lys Leu Glu Ile Lys Gly Gly Gly
625                 630                 635                 640

Gly Ser Gly Gly Gly Gly Ser Gly Gly Gly Gly Ser Gln Val Gln Leu
```

```
                645                 650                 655

Gln Gln Pro Gly Ala Glu Leu Val Arg Pro Gly Ala Ser Val Lys Leu
            660                 665                 670

Ser Cys Lys Ala Ser Gly Tyr Thr Phe Thr Ser Tyr Trp Met Asn Trp
        675                 680                 685

Val Lys Gln Arg Pro Asp Gln Gly Leu Glu Trp Ile Gly Arg Ile Asp
    690                 695                 700

Pro Tyr Asp Ser Glu Thr His Tyr Asn Gln Lys Phe Lys Asp Lys Ala
705                 710                 715                 720

Ile Leu Thr Val Asp Lys Ser Ser Ser Thr Ala Tyr Met Gln Leu Ser
                725                 730                 735

Ser Leu Thr Ser Glu Asp Ser Ala Val Tyr Tyr Cys Ala Arg Gly Asn
            740                 745                 750

Trp Asp Asp Tyr Trp Gly Gln Gly Thr Thr Leu Thr Val Ser Ser Thr
        755                 760                 765

Thr Thr Pro Ala Pro Arg Pro Pro Thr Pro Ala Pro Thr Ile Ala Ser
    770                 775                 780

Gln Pro Leu Ser Leu Arg Pro Glu Ala Cys Arg Pro Ala Ala Gly Gly
785                 790                 795                 800

Ala Val His Thr Arg Gly Leu Asp Phe Ala Cys Asp Ile Tyr Ile Trp
                805                 810                 815

Ala Pro Leu Ala Gly Thr Cys Gly Val Leu Leu Leu Ser Leu Val Ile
            820                 825                 830

Thr Leu Tyr Cys Arg Ser Lys Arg Ser Arg Leu Leu His Ser Asp Tyr
        835                 840                 845

Met Asn Met Thr Pro Arg Arg Pro Gly Pro Thr Arg Lys His Tyr Gln
    850                 855                 860

Pro Tyr Ala Pro Pro Arg Asp Phe Ala Ala Tyr Arg Ser Arg Val Lys
865                 870                 875                 880

Phe Ser Arg Ser Ala Asp Ala Pro Ala Tyr Gln Gln Gly Gln Asn Gln
                885                 890                 895

Leu Tyr Asn Glu Leu Asn Leu Gly Arg Arg Glu Glu Tyr Asp Val Leu
            900                 905                 910

Asp Lys Arg Arg Gly Arg Asp Pro Glu Met Gly Gly Lys Pro Gln Arg
        915                 920                 925

Arg Lys Asn Pro Gln Glu Gly Leu Tyr Asn Glu Leu Gln Lys Asp Lys
    930                 935                 940

Met Ala Glu Ala Tyr Ser Glu Ile Gly Met Lys Gly Glu Arg Arg Arg
945                 950                 955                 960

Gly Lys Gly His Asp Gly Leu Tyr Gln Gly Leu Ser Thr Ala Thr Lys
                965                 970                 975

Asp Thr Tyr Asp Ala Leu His Met Gln Ala Leu Pro Pro Arg
            980                 985                 990
```

```
<210> SEQ ID NO 8
<211> LENGTH: 2989
<212> TYPE: DNA
<213> ORGANISM: Artificial Sequence
<220> FEATURE:
<223> OTHER INFORMATION: synthetic sequence

<400> SEQUENCE: 8

gcgatcgcat ggccttacca gtgaccgcct tgctcctgcc gctggccttg ctgctccacg      60

ccgccaggcc ggacatccag atgacacaga ctacatcctc cctgtctgcc tctctgggag     120
```

-continued

```
acagagtcac catcagttgc agggcaagtc aggacattag taaatattta aattggtatc    180
agcagaaacc agatggaact gttaaactcc tgatctacca tacatcaaga ttacactcag    240
gagtcccatc aaggttcagt ggcagtgggt ctggaacaga ttattctctc accattagca    300
acctggagca agaagatatt gccacttact tttgccaaca gggtaatacg cttccgtaca    360
cgttcggagg ggggaccaag ctggagatca caggtggcgg tggctcgggc ggtggtgggt    420
cgggtggcgg cggatctgag gtgaaactgc aggagtcagg acctggcctg gtggcgccct    480
cacagagcct gtccgtcaca tgcactgtct caggggtctc attacccgac tatggtgtaa    540
gctggattcg ccagcctcca cgaaagggtc tggagtggct gggagtaata tggggtagtg    600
aaaccacata ctataattca gctctcaaat ccagactgac catcatcaag gacaactcca    660
agagccaagt tttcttaaaa atgaacagtc tgcaaactga tgacacagcc atttactact    720
gtgccaaaca ttattactac ggtggtagct atgctatgga ctactggggc caaggaacct    780
cagtcaccgt ctcctcaacc acgacgccag cgccgcgacc accaacaccg gcgcccacca    840
tcgcgtcgca gcccctgtcc ctgcgcccag aggcgtgccg gccagcggcg gggggcgcag    900
tgcacacgag ggggctggac ttcgcctgtg atatctacat ctgggcgccc ttggccggga    960
cttgtggggt ccttctcctg tcactggtta tcacccttta ctgcaaacgg ggcagaaaga   1020
aactcctgta tatattcaaa caaccattta tgagaccagt acaaactact caagaggaag   1080
atggctgtag ctgccgattt ccagaagaag aagaaggagg atgtgaactg agagtgaagt   1140
tcagcaggag cgcagacgcc cccgcgtacc agcagggcca gaaccagctc tataacgagc   1200
tcaatctagg acgaagagag gagtacgatg ttttggacaa gagacgtggc cgggaccctg   1260
agatgggggg aaagccgcag agaaggaaga accctcagga aggcctgtac aatgaactgc   1320
agaaagataa gatggcggag gcctacagtg agattgggat gaaaggcgag cgccggaggg   1380
gcaaggggca cgatggcctt taccagggtc tcagtacagc caccaaggac acctacgacg   1440
cccttcacat gcaggccctg ccccctcgcg gaagcggagc caccaacttc agcctgctga   1500
agcaggccgg cgacgtggag gagaaccccg gccccatggc cttaccagtg accgccttgc   1560
tcctgccgct ggccttgctg ctccacgccg ccaggccgga cgtgcagatc acccagagcc   1620
ccagctacct ggccgccagc cccggcgaga ccatcaccat caactgcaga gccagcaaga   1680
gcatcagcaa ggacctggcc tggtaccagg agaagcccgg caagaccaac aagctgctga   1740
tctacagcgg cagcaccctg cagagcggca tccccagcag attcagcggc agcggcagcg   1800
gcaccgactt caccctgacc atcagcagcc tggagcccga ggacttcgcc atgtactact   1860
gccagcagca caacaagtac ccctacacct tcggcggcgg caccaagctg gagatcaagg   1920
gaggggggggg atccgggggga ggaggctccg gcggaggcgg aagccaggtg cagctgcagc   1980
agcccggcgc cgagctggtg agacccggcg ccagcgtgaa gctgagctgc aaggccagcg   2040
gctacacctt caccagctac tggatgaact gggtgaagca gagacccgac cagggcctgg   2100
agtggatcgg cagaatcgac ccctacgaca gcgagaccca ctacaaccag aagttcaagg   2160
acaaggccat cctgaccgtg gacaagagca gcagcaccgc ctacatgcag ctgagcagcc   2220
tgaccagcga ggacagcgcc gtgtactact gcgccagagg caactgggac gactactggg   2280
gccagggcac caccctgacc gtgagcagca ccacgacgcc agcgccgcga ccaccaacac   2340
cggcgcccac catcgcgtcg cagcccctgt ccctgcgccc agaggcgtgc cggccagcgg   2400
cggggggcgc agtgcacacg agggggctgg acttcgcctg tgatatctac atctgggcgc   2460
ccttggccgg gacttgtggg gtccttctcc tgtcactggt tatcaccctt tactgcagga   2520
```

```
gtaagaggag caggctcctg cacagtgact acatgaacat gactccccgc cgccccgggc   2580

ccacccgcaa gcattaccag ccctatgccc caccacgcga cttcgcagcc tatcgctcca   2640

gagtgaagtt cagcaggagc gcagacgccc ccgcgtacca gcagggccag aaccagctct   2700

ataacgagct caatctagga cgaagagagg agtacgatgt tttggacaag agacgtggcc   2760

gggaccctga gatgggggga aagccgcaga gaaggaagaa ccctcaggaa ggcctgtaca   2820

atgaactgca gaaagataag atggcggagg cctacagtga gattgggatg aaaggcgagc   2880

gccggagggg caaggggcac gatggccttt accagggtct cagtacagcc accaaggaca   2940

cctacgacgc ccttcacatg caggccctgc cccctcgcta agtttaaac               2989
```

```
<210> SEQ ID NO 9
<211> LENGTH: 1066
<212> TYPE: PRT
<213> ORGANISM: Artificial Sequence
<220> FEATURE:
<223> OTHER INFORMATION: synthetic sequence

<400> SEQUENCE: 9

Met Ala Leu Pro Val Thr Ala Leu Leu Leu Pro Leu Ala Leu Leu Leu
1               5                   10                  15

His Ala Ala Arg Pro Gln Ile Val Leu Thr Gln Ser Pro Ala Ile Met
            20                  25                  30

Ser Ala Ser Pro Gly Glu Lys Val Thr Ile Thr Cys Ser Ala Ser Ser
        35                  40                  45

Ser Ile Ser Tyr Met His Trp Phe Gln Gln Lys Pro Gly Thr Ser Pro
    50                  55                  60

Lys Leu Trp Ile Tyr Thr Thr Ser Asn Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95

Arg Met Glu Ala Glu Asp Ala Ala Thr Tyr Tyr Cys His Gln Arg Ser
            100                 105                 110

Thr Tyr Pro Leu Thr Phe Gly Ser Gly Thr Lys Leu Glu Leu Lys Gly
        115                 120                 125

Gly Gly Gly Ser Gly Gly Gly Gly Ser Gly Gly Gly Gly Ser Gln Val
    130                 135                 140

Gln Leu Gln Gln Ser Gly Ala Glu Leu Ala Lys Pro Gly Ala Ser Val
145                 150                 155                 160

Lys Met Ser Cys Lys Ala Ser Gly Tyr Thr Phe Thr Ser Tyr Arg Met
                165                 170                 175

His Trp Val Lys Gln Arg Pro Gly Gln Gly Leu Glu Trp Ile Gly Tyr
            180                 185                 190

Ile Asn Pro Ser Thr Gly Tyr Thr Glu Tyr Asn Gln Lys Phe Lys Asp
        195                 200                 205

Lys Ala Thr Leu Thr Ala Asp Lys Ser Ser Ser Thr Ala Tyr Met Gln
    210                 215                 220

Leu Ser Ser Leu Thr Phe Glu Asp Ser Ala Val Tyr Tyr Cys Ala Arg
225                 230                 235                 240

Gly Gly Gly Val Phe Asp Tyr Trp Gly Gln Gly Thr Thr Leu Thr Val
                245                 250                 255

Ser Ser Thr Thr Thr Pro Ala Pro Arg Pro Pro Thr Pro Ala Pro Thr
            260                 265                 270

Ile Ala Ser Gln Pro Leu Ser Leu Arg Pro Glu Ala Cys Arg Pro Ala
```

```
        275                 280                 285

Ala Gly Gly Ala Val His Thr Arg Gly Leu Asp Phe Ala Cys Asp Ile
    290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Arg Ser Lys Arg Ser Arg Leu Leu His
                325                 330                 335

Ser Asp Tyr Met Asn Met Thr Pro Arg Arg Pro Gly Pro Thr Arg Lys
            340                 345                 350

His Tyr Gln Pro Tyr Ala Pro Pro Arg Asp Phe Ala Ala Tyr Arg Ser
        355                 360                 365

Lys Arg Gly Arg Lys Lys Leu Leu Tyr Ile Phe Lys Gln Pro Phe Met
    370                 375                 380

Arg Pro Val Gln Thr Thr Gln Glu Glu Asp Gly Cys Ser Cys Arg Phe
385                 390                 395                 400

Pro Glu Glu Glu Glu Gly Gly Cys Glu Leu Arg Val Lys Phe Ser Arg
                405                 410                 415

Ser Ala Asp Ala Pro Ala Tyr Lys Gln Gly Gln Asn Gln Leu Tyr Asn
            420                 425                 430

Glu Leu Asn Leu Gly Arg Arg Glu Glu Tyr Asp Val Leu Asp Lys Arg
        435                 440                 445

Arg Gly Arg Asp Pro Glu Met Gly Gly Lys Pro Arg Arg Lys Asn Pro
    450                 455                 460

Gln Glu Gly Leu Tyr Asn Glu Leu Gln Lys Asp Lys Met Ala Glu Ala
465                 470                 475                 480

Tyr Ser Glu Ile Gly Met Lys Gly Glu Arg Arg Arg Gly Lys Gly His
                485                 490                 495

Asp Gly Leu Tyr Gln Gly Leu Ser Thr Ala Thr Lys Asp Thr Tyr Asp
            500                 505                 510

Ala Leu His Met Gln Ala Leu Pro Pro Arg Gly Ser Gly Ala Thr Asn
        515                 520                 525

Phe Ser Leu Leu Lys Gln Ala Gly Asp Val Glu Glu Asn Pro Gly Pro
    530                 535                 540

Met Ala Leu Pro Val Thr Ala Leu Leu Leu Pro Leu Ala Leu Leu Leu
545                 550                 555                 560

His Ala Ala Arg Pro Asp Val Gln Ile Thr Gln Ser Pro Ser Tyr Leu
                565                 570                 575

Ala Ala Ser Pro Gly Glu Thr Ile Thr Ile Asn Cys Arg Ala Ser Lys
            580                 585                 590

Ser Ile Ser Lys Asp Leu Ala Trp Tyr Gln Glu Lys Pro Gly Lys Thr
        595                 600                 605

Asn Lys Leu Leu Ile Tyr Ser Gly Ser Thr Leu Gln Ser Gly Ile Pro
    610                 615                 620

Ser Arg Phe Ser Gly Ser Gly Ser Gly Thr Asp Phe Thr Leu Thr Ile
625                 630                 635                 640

Ser Ser Leu Glu Pro Glu Asp Phe Ala Met Tyr Tyr Cys Gln Gln His
                645                 650                 655

Asn Lys Tyr Pro Tyr Thr Phe Gly Gly Gly Thr Lys Leu Glu Ile Lys
            660                 665                 670

Gly Gly Gly Gly Ser Gly Gly Gly Gly Ser Gly Gly Gly Gly Ser Gln
        675                 680                 685

Val Gln Leu Gln Gln Pro Gly Ala Glu Leu Val Arg Pro Gly Ala Ser
    690                 695                 700
```

```
Val Lys Leu Ser Cys Lys Ala Ser Gly Tyr Thr Phe Thr Ser Tyr Trp
705                 710                 715                 720

Met Asn Trp Val Lys Gln Arg Pro Asp Gln Gly Leu Glu Trp Ile Gly
                725                 730                 735

Arg Ile Asp Pro Tyr Asp Ser Glu Thr His Tyr Asn Gln Lys Phe Lys
            740                 745                 750

Asp Lys Ala Ile Leu Thr Val Asp Lys Ser Ser Ser Thr Ala Tyr Met
        755                 760                 765

Gln Leu Ser Ser Leu Thr Ser Glu Asp Ser Ala Val Tyr Tyr Cys Ala
    770                 775                 780

Arg Gly Asn Trp Asp Asp Tyr Trp Gly Gln Gly Thr Thr Leu Thr Val
785                 790                 795                 800

Ser Ser Thr Thr Thr Pro Ala Pro Arg Pro Pro Thr Pro Ala Pro Thr
                805                 810                 815

Ile Ala Ser Gln Pro Leu Ser Leu Arg Pro Glu Ala Cys Arg Pro Ala
            820                 825                 830

Ala Gly Gly Ala Val His Thr Arg Gly Leu Asp Phe Ala Cys Asp Ile
        835                 840                 845

Tyr Ile Trp Ala Pro Leu Ala Gly Thr Cys Gly Val Leu Leu Leu Ser
    850                 855                 860

Leu Val Ile Thr Leu Tyr Cys Arg Ser Lys Arg Ser Arg Leu Leu His
865                 870                 875                 880

Ser Asp Tyr Met Asn Met Thr Pro Arg Arg Pro Gly Pro Thr Arg Lys
                885                 890                 895

His Tyr Gln Pro Tyr Ala Pro Pro Arg Asp Phe Ala Ala Tyr Arg Ser
            900                 905                 910

Lys Arg Gly Arg Lys Lys Leu Leu Tyr Ile Phe Lys Gln Pro Phe Met
        915                 920                 925

Arg Pro Val Gln Thr Thr Gln Glu Glu Asp Gly Cys Ser Cys Arg Phe
    930                 935                 940

Pro Glu Glu Glu Glu Gly Gly Cys Glu Leu Arg Val Lys Phe Ser Arg
945                 950                 955                 960

Ser Ala Asp Ala Pro Ala Tyr Lys Gln Gly Gln Asn Gln Leu Tyr Asn
                965                 970                 975

Glu Leu Asn Leu Gly Arg Arg Glu Glu Tyr Asp Val Leu Asp Lys Arg
            980                 985                 990

Arg Gly Arg Asp Pro Glu Met Gly  Gly Lys Pro Arg Arg  Lys Asn Pro
        995                 1000                1005

Gln Glu  Gly Leu Tyr Asn Glu  Leu Gln Lys Asp Lys  Met Ala Glu
    1010                1015                1020

Ala Tyr  Ser Glu Ile Gly Met  Lys Gly Glu Arg Arg  Arg Gly Lys
    1025                1030                1035

Gly His  Asp Gly Leu Tyr Gln  Gly Leu Ser Thr Ala  Thr Lys Asp
    1040                1045                1050

Thr Tyr  Asp Ala Leu His Met  Gln Ala Leu Pro Pro  Arg
    1055                1060                1065
```

<210> SEQ ID NO 10
<211> LENGTH: 3217
<212> TYPE: DNA
<213> ORGANISM: Artificial Sequence
<220> FEATURE:
<223> OTHER INFORMATION: synthetic sequence

<400> SEQUENCE: 10

```
gcgatcgcat ggccttacca gtgaccgcct tgctcctgcc gctggccttg ctgctccacg     60
ccgccaggcc gcagatcgtg ctgacccaga gccccgccat catgagcgcc agccccggcg    120
agaaggtgac catcacctgc agcgccagca gcagcatcag ctacatgcac tggttccagc    180
agaagcccgg caccagcccc aagctgtgga tctacaccac cagcaacctg gccagcggcg    240
tgcccgccag attcagcggc agcggcagcg gcaccagcta cagcctgacc atcagcagaa    300
tggaggccga ggacgccgcc acctactact gccaccagag aagcacctac cccctgacct    360
tcggcagcgg caccaagctg gagctgaagg gagggggggg atccggggga ggaggctccg    420
gcggaggcgg aagccaggtg cagctgcagc agagcggcgc cgagctggcc aagcccggcg    480
ccagcgtgaa gatgagctgc aaggccagcg gctacacctt caccagctac agaatgcact    540
gggtgaagca gagacccggc cagggcctgg agtggatcgg ctacatcaac cccagcaccg    600
gctacaccga gtacaaccag aagttcaagg acaaggccac cctgaccgcc gacaagagca    660
gcagcaccgc ctacatgcag ctgagcagcc tgaccttcga ggacagcgcc gtgtactact    720
gcgccagagg cggcggcgtg ttcgactact ggggccaggg caccaccctg accgtgagca    780
gcaccacgac gccagcgccg cgaccaccaa caccggcgcc caccatcgcg tcgcagcccc    840
tgtccctgcg cccagaggcg tgccggccag cggcgggggg cgcagtgcac acgagggggc    900
tggacttcgc ctgtgatatc tacatctggg cgcccttggc cgggacttgt ggggtccttc    960
tcctgtcact ggttatcacc ctttactgca ggagtaagag gagcaggctc ctgcacagtg   1020
actacatgaa catgactccc cgccgccccg ggcccacccg caagcattac cagccctatg   1080
ccccaccacg cgacttcgca gcctatcgct ccaaacgggg cagaaagaaa ctcctgtata   1140
tattcaaaca accatttatg agaccagtac aaactactca agaggaagat ggctgtagct   1200
gccgatttcc agaagaagaa gaaggaggat gtgaactgag agtgaagttc agcaggagcg   1260
cagacgcccc cgcgtacaag cagggccaga accagctcta taacgagctc aatctaggac   1320
gaagagagga gtacgatgtt ttggacaaga gacgtggccg ggaccctgag atggggggaa   1380
agccgagaag gaagaaccct caggaaggcc tgtacaatga actgcagaaa gataagatgg   1440
cggaggccta cagtgagatt gggatgaaag gcgagcgccg gaggggcaag gggcacgatg   1500
gcctttacca gggtctcagt acagccacca aggacaccta cgacgccctt cacatgcagg   1560
ccctgccccc tcgcggaagc ggagctacta acttcagcct gctgaagcag gctggagacg   1620
tggaggagaa ccctggacct atggccttac cagtgaccgc cttgctcctg ccgctggcct   1680
tgctgctcca cgccgccagg ccggacgtgc agatcaccca gagccccagc tacctggccg   1740
ccagccccgg cgagaccatc accatcaact gcagagccag caagagcatc agcaaggacc   1800
tggcctggta ccaggagaag cccggcaaga ccaacaagct gctgatctac agcggcagca   1860
ccctgcagag cggcatcccc agcagattca gcggcagcgg cagcggcacc gacttcaccc   1920
tgaccatcag cagcctggag cccgaggact tcgccatgta ctactgccag cagcacaaca   1980
agtaccccta caccttcggc ggcggcacca agctggagat caagggaggg gggggatccg   2040
ggggaggagg ctccggcgga ggcggaagcc aggtgcagct gcagcagccc ggcgccgagc   2100
tggtgagacc cggcgccagc gtgaagctga gctgcaaggc cagcggctac accttcacca   2160
gctactggat gaactgggtg aagcagagac ccgaccaggg cctggagtgg atcggcagaa   2220
tcgaccccta cgacagcgag acccactaca accagaagtt caaggacaag gccatcctga   2280
ccgtggacaa gagcagcagc accgcctaca tgcagctgag cagcctgacc agcgaggaca   2340
```

```
gcgccgtgta ctactgcgcc agaggcaact gggacgacta ctggggccag ggcaccaccc   2400

tgaccgtgag cagcaccacg acgccagcgc cgcgaccacc aacaccggcg cccaccatcg   2460

cgtcgcagcc cctgtccctg cgcccagagg cgtgccggcc agcggcgggg ggcgcagtgc   2520

acacgagggg gctggacttc gcctgtgata tctacatctg ggcgcccttg gccgggactt   2580

gtggggtcct tctcctgtca ctggttatca ccctttactg caggagtaag aggagcaggc   2640

tcctgcacag tgactacatg aacatgactc cccgccgccc cgggcccacc cgcaagcatt   2700

accagcccta tgccccacca cgcgacttcg cagcctatcg ctccaaacgg ggcagaaaga   2760

aactcctgta tatattcaaa caaccattta tgagaccagt acaaactact caagaggaag   2820

atggctgtag ctgccgattt ccagaagaag aagaaggagg atgtgaactg agagtgaagt   2880

tcagcaggag cgcagacgcc cccgcgtaca agcagggcca gaaccagctc tataacgagc   2940

tcaatctagg acgaagagag gagtacgatg ttttggacaa gagacgtggc cgggaccctg   3000

agatgggggg aaagccgaga aggaagaacc ctcaggaagg cctgtacaat gaactgcaga   3060

aagataagat ggcggaggcc tacagtgaga ttgggatgaa aggcgagcgc cggaggggca   3120

aggggcacga tggcctttac cagggtctca gtacagccac caaggacacc tacgacgccc   3180

ttcacatgca ggccctgccc cctcgctaag tttaaac                            3217


<210> SEQ ID NO 11
<211> LENGTH: 985
<212> TYPE: PRT
<213> ORGANISM: Artificial Sequence
<220> FEATURE:
<223> OTHER INFORMATION: synthetic sequence

<400> SEQUENCE: 11

Met Ala Leu Pro Val Thr Ala Leu Leu Leu Pro Leu Ala Leu Leu Leu
1               5                   10                  15

His Ala Ala Arg Pro Gln Ile Val Leu Thr Gln Ser Pro Ala Ile Met
            20                  25                  30

Ser Ala Ser Pro Gly Glu Lys Val Thr Ile Thr Cys Ser Ala Ser Ser
        35                  40                  45

Ser Ile Ser Tyr Met His Trp Phe Gln Gln Lys Pro Gly Thr Ser Pro
    50                  55                  60

Lys Leu Trp Ile Tyr Thr Thr Ser Asn Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95

Arg Met Glu Ala Glu Asp Ala Ala Thr Tyr Tyr Cys His Gln Arg Ser
            100                 105                 110

Thr Tyr Pro Leu Thr Phe Gly Ser Gly Thr Lys Leu Glu Leu Lys Gly
        115                 120                 125

Gly Gly Gly Ser Gly Gly Gly Gly Ser Gly Gly Gly Gly Ser Gln Val
    130                 135                 140

Gln Leu Gln Gln Ser Gly Ala Glu Leu Ala Lys Pro Gly Ala Ser Val
145                 150                 155                 160

Lys Met Ser Cys Lys Ala Ser Gly Tyr Thr Phe Thr Ser Tyr Arg Met
                165                 170                 175

His Trp Val Lys Gln Arg Pro Gly Gln Gly Leu Glu Trp Ile Gly Tyr
            180                 185                 190

Ile Asn Pro Ser Thr Gly Tyr Thr Glu Tyr Asn Gln Lys Phe Lys Asp
        195                 200                 205
```

```
Lys Ala Thr Leu Thr Ala Asp Lys Ser Ser Ser Thr Ala Tyr Met Gln
    210                 215                 220

Leu Ser Ser Leu Thr Phe Glu Asp Ser Ala Val Tyr Tyr Cys Ala Arg
225                 230                 235                 240

Gly Gly Gly Val Phe Asp Tyr Trp Gly Gln Gly Thr Thr Leu Thr Val
                245                 250                 255

Ser Ser Thr Thr Thr Pro Ala Pro Arg Pro Pro Thr Pro Ala Pro Thr
            260                 265                 270

Ile Ala Ser Gln Pro Leu Ser Leu Arg Pro Glu Ala Cys Arg Pro Ala
        275                 280                 285

Ala Gly Gly Ala Val His Thr Arg Gly Leu Asp Phe Ala Cys Asp Ile
    290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Lys Arg Gly Arg Lys Lys Leu Leu Tyr
                325                 330                 335

Ile Phe Lys Gln Pro Phe Met Arg Pro Val Gln Thr Thr Gln Glu Glu
            340                 345                 350

Asp Gly Cys Ser Cys Arg Phe Pro Glu Glu Glu Glu Gly Gly Cys Glu
        355                 360                 365

Leu Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Gln Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg Gly Ser Gly Ala Thr Asn Phe Ser Leu Leu Lys Gln Ala Gly
                485                 490                 495

Asp Val Glu Glu Asn Pro Gly Pro Met Ala Leu Pro Val Thr Ala Leu
            500                 505                 510

Leu Leu Pro Leu Ala Leu Leu Leu His Ala Ala Arg Pro Asp Val Gln
        515                 520                 525

Ile Thr Gln Ser Pro Ser Tyr Leu Ala Ala Ser Pro Gly Glu Thr Ile
    530                 535                 540

Thr Ile Asn Cys Arg Ala Ser Lys Ser Ile Ser Lys Asp Leu Ala Trp
545                 550                 555                 560

Tyr Gln Glu Lys Pro Gly Lys Thr Asn Lys Leu Leu Ile Tyr Ser Gly
                565                 570                 575

Ser Thr Leu Gln Ser Gly Ile Pro Ser Arg Phe Ser Gly Ser Gly Ser
            580                 585                 590

Gly Thr Asp Phe Thr Leu Thr Ile Ser Ser Leu Glu Pro Glu Asp Phe
        595                 600                 605

Ala Met Tyr Tyr Cys Gln Gln His Asn Lys Tyr Pro Tyr Thr Phe Gly
    610                 615                 620

Gly Gly Thr Lys Leu Glu Ile Lys Gly Gly Gly Gly Ser Gly Gly Gly
```

```
625                 630                 635                 640

Gly Ser Gly Gly Gly Gly Ser Gln Val Gln Leu Gln Gln Pro Gly Ala
                645                 650                 655

Glu Leu Val Arg Pro Gly Ala Ser Val Lys Leu Ser Cys Lys Ala Ser
            660                 665                 670

Gly Tyr Thr Phe Thr Ser Tyr Trp Met Asn Trp Val Lys Gln Arg Pro
        675                 680                 685

Asp Gln Gly Leu Glu Trp Ile Gly Arg Ile Asp Pro Tyr Asp Ser Glu
    690                 695                 700

Thr His Tyr Asn Gln Lys Phe Lys Asp Lys Ala Ile Leu Thr Val Asp
705                 710                 715                 720

Lys Ser Ser Ser Thr Ala Tyr Met Gln Leu Ser Ser Leu Thr Ser Glu
                725                 730                 735

Asp Ser Ala Val Tyr Tyr Cys Ala Arg Gly Asn Trp Asp Asp Tyr Trp
            740                 745                 750

Gly Gln Gly Thr Thr Leu Thr Val Ser Ser Thr Thr Thr Pro Ala Pro
        755                 760                 765

Arg Pro Pro Thr Pro Ala Pro Thr Ile Ala Ser Gln Pro Leu Ser Leu
    770                 775                 780

Arg Pro Glu Ala Cys Arg Pro Ala Ala Gly Gly Ala Val His Thr Arg
785                 790                 795                 800

Gly Leu Asp Phe Ala Cys Asp Ile Tyr Ile Trp Ala Pro Leu Ala Gly
                805                 810                 815

Thr Cys Gly Val Leu Leu Leu Ser Leu Val Ile Thr Leu Tyr Cys Arg
            820                 825                 830

Ser Lys Arg Ser Arg Leu Leu His Ser Asp Tyr Met Asn Met Thr Pro
        835                 840                 845

Arg Arg Pro Gly Pro Thr Arg Lys His Tyr Gln Pro Tyr Ala Pro Pro
    850                 855                 860

Arg Asp Phe Ala Ala Tyr Arg Ser Arg Val Lys Phe Ser Arg Ser Ala
865                 870                 875                 880

Asp Ala Pro Ala Tyr Gln Gln Gly Gln Asn Gln Leu Tyr Asn Glu Leu
                885                 890                 895

Asn Leu Gly Arg Arg Glu Glu Tyr Asp Val Leu Asp Lys Arg Arg Gly
            900                 905                 910

Arg Asp Pro Glu Met Gly Gly Lys Pro Gln Arg Arg Lys Asn Pro Gln
        915                 920                 925

Glu Gly Leu Tyr Asn Glu Leu Gln Lys Asp Lys Met Ala Glu Ala Tyr
    930                 935                 940

Ser Glu Ile Gly Met Lys Gly Glu Arg Arg Arg Gly Lys Gly His Asp
945                 950                 955                 960

Gly Leu Tyr Gln Gly Leu Ser Thr Ala Thr Lys Asp Thr Tyr Asp Ala
                965                 970                 975

Leu His Met Gln Ala Leu Pro Pro Arg
            980                 985


<210> SEQ ID NO 12
<211> LENGTH: 2974
<212> TYPE: DNA
<213> ORGANISM: Artificial Sequence
<220> FEATURE:
<223> OTHER INFORMATION: synthetic sequence

<400> SEQUENCE: 12

gcgatcgcat ggccttacca gtgaccgcct tgctcctgcc gctggccttg ctgctccacg     60
```

```
ccgccaggcc gcagatcgtg ctgacccaga gccccgccat catgagcgcc agccccggcg    120
agaaggtgac catcacctgc agcgccagca gcagcatcag ctacatgcac tggttccagc    180
agaagcccgg caccagcccc aagctgtgga tctacaccac cagcaacctg gccagcggcg    240
tgcccgccag attcagcggc agcggcagcg gcaccagcta cagcctgacc atcagcagaa    300
tggaggccga ggacgccgcc acctactact gccaccagag aagcacctac cccctgacct    360
tcggcagcgg caccaagctg gagctgaagg gaggggggg atccgggga ggaggctccg      420
gcggaggcgg aagccaggtg cagctgcagc agagcggcgc cgagctggcc aagcccggcg    480
ccagcgtgaa gatgagctgc aaggccagcg gctacacctt caccagctac agaatgcact    540
gggtgaagca gagacccggc cagggcctgg agtggatcgg ctacatcaac cccagcaccg    600
gctacaccga gtacaaccag aagttcaagg acaaggccac cctgaccgcc gacaagagca    660
gcagcaccgc ctacatgcag ctgagcagcc tgaccttcga ggacagcgcc gtgtactact    720
gcgccagagg cggcggcgtg ttcgactact ggggccaggg caccaccctg accgtgagca    780
gcaccacgac gccagcgccg cgaccaccaa caccggcgcc caccatcgcg tcgcagcccc    840
tgtccctgcg cccagaggcg tgccggccag cggcgggggg cgcagtgcac acgagggggc    900
tggacttcgc ctgtgatatc tacatctggg cgcccttggc cgggacttgt ggggtccttc    960
tcctgtcact ggttatcacc ctttactgca aacggggcag aaagaaactc ctgtatatat   1020
tcaaacaacc atttatgaga ccagtacaaa ctactcaaga ggaagatggc tgtagctgcc   1080
gatttccaga agaagaagaa ggaggatgtg aactgagagt gaagttcagc aggagcgcag   1140
acgcccccgc gtaccagcag ggccagaacc agctctataa cgagctcaat ctaggacgaa   1200
gagaggagta cgatgttttg gacaagagac gtggccggga ccctgagatg gggggaaagc   1260
cgcagagaag gaagaaccct caggaaggcc tgtacaatga actgcagaaa gataagatgg   1320
cggaggccta cagtgagatt gggatgaaag gcgagcgccg gaggggcaag gggcacgatg   1380
gcctttacca gggtctcagt acagccacca aggacaccta cgacgccctt cacatgcagg   1440
ccctgccccc tcgcggaagc ggagctacta acttcagcct gctgaagcag gctggagacg   1500
tggaggagaa ccctggacct atggccttac cagtgaccgc cttgctcctg ccgctggcct   1560
tgctgctcca cgccgccagg ccggacgtgc agatcaccca gagccccagc tacctggccg   1620
ccagccccgg cgagaccatc accatcaact gcagagccag caagagcatc agcaaggacc   1680
tggcctggta ccaggagaag cccggcaaga ccaacaagct gctgatctac agcggcagca   1740
ccctgcagag cggcatcccc agcagattca gcggcagcgg cagcggcacc gacttcaccc   1800
tgaccatcag cagcctggag cccgaggact tcgccatgta ctactgccag cagcacaaca   1860
agtaccccta caccttcggc ggcggcacca agctggagat caagggaggg gggggatccg   1920
gggaggaggg ctccggcgga ggcggaagcc aggtgcagct gcagcagccc ggcgccgagc   1980
tggtgagacc cggcgccagc gtgaagctga gctgcaaggc cagcggctac accttcacca   2040
gctactggat gaactgggtg aagcagagac ccgaccaggg cctggagtgg atcggcagaa   2100
tcgaccccta cgacagcgag acccactaca accagaagtt caaggacaag gccatcctga   2160
ccgtggacaa gagcagcagc accgcctaca tgcagctgag cagcctgacc agcgaggaca   2220
gcgccgtgta ctactgcgcc agaggcaact gggacgacta ctggggccag ggcaccaccc   2280
tgaccgtgag cagcaccacg acgccagcgc cgcgaccacc aacaccggcg cccaccatcg   2340
cgtcgcagcc cctgtccctg cgcccagagg cgtgccggcc agcggcgggg ggcgcagtgc   2400
```

```
acacgagggg gctggacttc gcctgtgata tctacatctg ggcgcccttg gccgggactt   2460

gtggggtcct tctcctgtca ctggttatca ccctttactg caggagtaag aggagcaggc   2520

tcctgcacag tgactacatg aacatgactc cccgccgccc cgggcccacc cgcaagcatt   2580

accagcccta tgccccacca cgcgacttcg cagcctatcg ctccagagtg aagttcagca   2640

ggagcgcaga cgcccccgcg taccagcagg gccagaacca gctctataac gagctcaatc   2700

taggacgaag agaggagtac gatgttttgg acaagagacg tggccgggac cctgagatgg   2760

ggggaaagcc gcagagaagg aagaaccctc aggaaggcct gtacaatgaa ctgcagaaag   2820

ataagatggc ggaggcctac agtgagattg ggatgaaagg cgagcgccgg aggggcaagg   2880

ggcacgatgg cctttaccag ggtctcagta cagccaccaa ggacacctac gacgcccttc   2940

acatgcaggc cctgcccccct cgctaagttt aaac                              2974
```

```
<210> SEQ ID NO 13
<211> LENGTH: 546
<212> TYPE: PRT
<213> ORGANISM: Artificial Sequence
<220> FEATURE:
<223> OTHER INFORMATION: synthetic sequence

<400> SEQUENCE: 13

Met Ala Leu Pro Val Thr Ala Leu Leu Leu Pro Leu Ala Leu Leu Leu
1               5                   10                  15

His Ala Ala Arg Pro Ser Asp Ile Val Leu Thr Gln Ser Pro Ala Ser
            20                  25                  30

Leu Ala Val Ser Leu Gly Gln Arg Ala Thr Ile Ser Cys Arg Ala Ser
        35                  40                  45

Lys Ser Val Ser Thr Ser Gly Tyr Ser Tyr Leu His Trp Tyr Gln Gln
    50                  55                  60

Lys Pro Gly Gln Pro Pro Lys Leu Leu Ile Tyr Leu Ala Ser Asn Leu
65                  70                  75                  80

Glu Ser Gly Val Pro Ala Arg Phe Ser Gly Ser Gly Ser Gly Thr Asp
                85                  90                  95

Phe Thr Leu Asn Ile His Pro Val Glu Glu Glu Asp Ala Ala Thr Tyr
            100                 105                 110

Tyr Cys Gln His Ser Arg Glu Leu Pro Phe Thr Phe Gly Ser Gly Thr
        115                 120                 125

Lys Leu Glu Ile Lys Lys Ile Ser Gly Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Gln Val Gln Leu Val Glu Ser Gly Gly Gly Leu Val Gln Pro Gly
                165                 170                 175

Gly Ser Leu Lys Leu Ser Cys Ala Ala Ser Gly Phe Asp Phe Ser Arg
            180                 185                 190

Tyr Trp Met Ser Trp Val Arg Gln Ala Pro Gly Lys Gly Leu Glu Trp
        195                 200                 205

Ile Gly Glu Ile Asn Pro Thr Ser Ser Thr Ile Asn Phe Thr Pro Ser
    210                 215                 220

Leu Lys Asp Lys Val Phe Ile Ser Arg Asp Asn Ala Lys Asn Thr Leu
225                 230                 235                 240

Tyr Leu Gln Met Ser Lys Val Arg Ser Glu Asp Thr Ala Leu Tyr Tyr
                245                 250                 255

Cys Ala Arg Gly Asn Tyr Tyr Arg Tyr Gly Asp Ala Met Asp Tyr Trp
```

```
            260                 265                 270

Gly Gln Gly Thr Ser Val Thr Val Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Ser
            340                 345                 350

Lys Arg Ser Arg Leu Leu His Ser Asp Tyr Met Asn Met Thr Pro Arg
        355                 360                 365

Arg Pro Gly Pro Thr Arg Lys His Tyr Gln Pro Tyr Ala Pro Pro Arg
    370                 375                 380

Asp Phe Ala Ala Tyr Arg Ser Lys Arg Gly Arg Lys Lys Leu Leu Tyr
385                 390                 395                 400

Ile Phe Lys Gln Pro Phe Met Arg Pro Val Gln Thr Thr Gln Glu Glu
                405                 410                 415

Asp Gly Cys Ser Cys Arg Phe Pro Glu Glu Glu Glu Gly Gly Cys Glu
            420                 425                 430

Leu Arg Val Lys Phe Ser Arg Ser Ala Asp Ala Pro Ala Tyr Gln Gln
        435                 440                 445

Gly Gln Asn Gln Leu Tyr Asn Glu Leu Asn Leu Gly Arg Arg Glu Glu
    450                 455                 460

Tyr Asp Val Leu Asp Lys Arg Arg Gly Arg Asp Pro Glu Met Gly Gly
465                 470                 475                 480

Lys Pro Gln Arg Arg Lys Asn Pro Gln Glu Gly Leu Tyr Asn Glu Leu
                485                 490                 495

Gln Lys Asp Lys Met Ala Glu Ala Tyr Ser Glu Ile Gly Met Lys Gly
            500                 505                 510

Glu Arg Arg Arg Gly Lys Gly His Asp Gly Leu Tyr Gln Gly Leu Ser
        515                 520                 525

Thr Ala Thr Lys Asp Thr Tyr Asp Ala Leu His Met Gln Ala Leu Pro
    530                 535                 540

Pro Arg
545


<210> SEQ ID NO 14
<211> LENGTH: 1657
<212> TYPE: DNA
<213> ORGANISM: Artificial Sequence
<220> FEATURE:
<223> OTHER INFORMATION: synthetic sequence

<400> SEQUENCE: 14

gcgatcgcat ggccttacca gtgaccgcct tgctcctgcc gctggccttg ctgctccacg      60

ccgccaggcc gagcgacatc gtgctgaccc agagccccgc cagcctggcc gtgagcctgg     120

gccagagagc caccatcagc tgcagagcca gcaagagcgt gagcaccagc ggctacagct     180

acctgcactg gtaccagcag aagcccggcc agccccccaa gctgctgatc tacctggcca     240

gcaacctgga gagcggcgtg cccgccagat tcagcggcag cggcagcggc accgacttca     300

ccctgaacat ccaccccgtg gaggaggagg acgccgccac ctactactgc cagcacagca     360

gagagctgcc cttcaccttc ggcagcggca ccaagctgga gatcaagaag atcagcggcg     420
```

```
gcggcggcag cggcggcggc ggcagcggcg gcggcggcag cggcggcggc ggcagcggcg    480

gcggcggcag ccaggtgcag ctggtggaga gcggcggcgg cctggtgcag cccggcggca    540

gcctgaagct gagctgcgcc gccagcggct tcgacttcag cagatactgg atgagctggg    600

tgagacaggc ccccggcaag ggcctggagt ggatcggcga gatcaacccc accagcagca    660

ccatcaactt cacccccagc ctgaaggaca aggtgttcat cagcagagac aacgccaaga    720

acaccctgta cctgcagatg agcaaggtga gaagcgagga caccgccctg tactactgcg    780

ccagaggcaa ctactacaga tacggcgacg ccatggacta ctggggccag ggcaccagcg    840

tgaccgtgag caccacgacg ccagcgccgc gaccaccaac accggcgccc accatcgcgt    900

cgcagcccct gtccctgcgc ccagaggcgt gccggccagc ggcggggggc gcagtgcaca    960

cgagggggct ggacttcgcc tgtgatatct acatctgggc gcccttggcc gggacttgtg   1020

gggtccttct cctgtcactg gttatcaccc tttactgcag gagtaagagg agcaggctcc   1080

tgcacagtga ctacatgaac atgactcccc gccgccccgg gcccacccgc aagcattacc   1140

agccctatgc cccaccacgc gacttcgcag cctatcgctc caaacggggc agaaagaaac   1200

tcctgtatat attcaaacaa ccatttatga gaccagtaca aactactcaa gaggaagatg   1260

gctgtagctg ccgatttcca gaagaagaag aaggaggatg tgaactgaga gtgaagttca   1320

gcaggagcgc agacgccccc gcgtaccagc agggccagaa ccagctctat aacgagctca   1380

atctaggacg aagagaggag tacgatgttt tggacaagag acgtggccgg gaccctgaga   1440

tggggggaaa gccgcagaga aggaagaacc ctcaggaagg cctgtacaat gaactgcaga   1500

aagataagat ggcggaggcc tacagtgaga ttgggatgaa aggcgagcgc cggaggggca   1560

aggggcacga tggcctttac cagggtctca gtacagccac caaggacacc tacgacgccc   1620

ttcacatgca ggccctgccc cctcgctaag tttaaac                            1657
```

```
<210> SEQ ID NO 15
<211> LENGTH: 490
<212> TYPE: PRT
<213> ORGANISM: Artificial Sequence
<220> FEATURE:
<223> OTHER INFORMATION: synthetic sequence

<400> SEQUENCE: 15

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu
            20                  25                  30

Ala Val Ser Leu Gly Gln Arg Ala Thr Ile Ser Cys Arg Ala Ser Lys
        35                  40                  45

Ser Val Ser Thr Ser Gly Tyr Ser Tyr Leu His Trp Tyr Gln Gln Lys
    50                  55                  60

Pro Gly Gln Pro Pro Lys Leu Leu Ile Tyr Leu Ala Ser Asn Leu Glu
65                  70                  75                  80

Ser Gly Val Pro Ala Arg Phe Ser Gly Ser Gly Ser Gly Thr Asp Phe
                85                  90                  95

Thr Leu Asn Ile His Pro Val Glu Glu Glu Asp Ala Ala Thr Tyr Tyr
            100                 105                 110

Cys Gln His Ser Arg Glu Leu Pro Phe Thr Phe Gly Ser Gly Thr Lys
        115                 120                 125

Leu Glu Ile Lys Gly Gly Gly Gly Ser Gly Gly Gly Gly Ser Gly Gly
    130                 135                 140
```

```
Gly Gly Ser Gln Val Gln Leu Val Glu Ser Gly Gly Gly Leu Val Gln
145                 150                 155                 160

Pro Gly Gly Ser Leu Lys Leu Ser Cys Ala Ala Ser Gly Phe Asp Phe
                165                 170                 175

Ser Arg Tyr Trp Met Ser Trp Val Arg Gln Ala Pro Gly Lys Gly Leu
            180                 185                 190

Glu Trp Ile Gly Glu Ile Asn Pro Thr Ser Ser Thr Ile Asn Phe Thr
        195                 200                 205

Pro Ser Leu Lys Asp Lys Val Phe Ile Ser Arg Asp Asn Ala Lys Asn
    210                 215                 220

Thr Leu Tyr Leu Gln Met Ser Lys Val Arg Ser Glu Asp Thr Ala Leu
225                 230                 235                 240

Tyr Tyr Cys Ala Arg Gly Asn Tyr Tyr Arg Tyr Gly Asp Ala Met Asp
                245                 250                 255

Tyr Trp Gly Gln Gly Thr Ser Val Thr Val Ser Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
        355                 360                 365

Pro Arg Asp Phe Ala Ala Tyr Arg Ser Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Gln Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

<210> SEQ ID NO 16
<211> LENGTH: 1489
<212> TYPE: DNA
<213> ORGANISM: Artificial Sequence
<220> FEATURE:
<223> OTHER INFORMATION: synthetic sequence

<400> SEQUENCE: 16

```
gcgatcgcat ggccttacca gtgaccgcct tgctcctgcc gctggccttg ctgctccacg     60
```

```
ccgccaggcc ggacatcgtg ctgacccaga gccccgccag cctggccgtg agcctgggcc    120

agagggccac catcagctgc agggccagca agagcgtgag caccagcggc tacagctacc    180

tgcactggta ccagcagaag cccggccagc cccccaagct gctgatctac ctggccagca    240

acctggagag cggcgtgccc gccaggttca gcggcagcgg cagcggcacc gacttcaccc    300

tgaacatcca ccccgtggag gaggaggacg ccgccaccta ctactgccag cacagcaggg    360

agctgccctt caccttcggc agcggcacca agctggagat caagggaggg gggggatccg    420

ggggaggagg ctccggcgga ggcggaagcc aggtgcagct ggtggagagc ggcggcggcc    480

tggtgcagcc cggcggcagc ctgaagctga gctgcgccgc cagcggcttc gacttcagca    540

ggtactggat gagctgggtg aggcaggccc ccggcaaggg cctggagtgg atcggcgaga    600

tcaaccccac cagcagcacc atcaacttca cccccagcct gaaggacaag gtgttcatca    660

gcagggacaa cgccaagaac accctgtacc tgcagatgag caaggtgagg agcgaggaca    720

ccgccctgta ctactgcgcc aggggcaact actacaggta cggcgacgcc atggactact    780

ggggccaggg caccagcgtg accgtgagca ccacgacgcc agcgccgcga ccaccaacac    840

cggcgcccac catcgcgtcg cagcccctgt ccctgcgccc agaggcgtgc cggccagcgg    900

cggggggcgc agtgcacacg agggggctgg acttcgcctg tgatatctac atctgggcgc    960

ccttggccgg gacttgtggg gtccttctcc tgtcactggt tatcaccctt tactgcagga   1020

gtaagaggag caggctcctg cacagtgact acatgaacat gactccccgc cgccccgggc   1080

ccacccgcaa gcattaccag ccctatgccc caccacgcga cttcgcagcc tatcgctcca   1140

gagtgaagtt cagcaggagc gcagacgccc ccgcgtacca gcagggccag aaccagctct   1200

ataacgagct caatctagga cgaagagagg agtacgatgt tttggacaag agacgtggcc   1260

gggaccctga gatgggggga aagccgcaga gaaggaagaa ccctcaggaa ggcctgtaca   1320

atgaactgca gaaagataag atggcggagg cctacagtga gattgggatg aaaggcgagc   1380

gccggagggg caaggggcac gatggccttt accagggtct cagtacagcc accaaggaca   1440

cctacgacgc ccttcacatg caggccctgc cccctcgcta agtttaaac               1489
```

```
<210> SEQ ID NO 17
<211> LENGTH: 491
<212> TYPE: PRT
<213> ORGANISM: Artificial Sequence
<220> FEATURE:
<223> OTHER INFORMATION: synthetic sequence

<400> SEQUENCE: 17

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu
            20                  25                  30

Ala Val Ser Leu Gly Gln Arg Ala Thr Ile Ser Cys Arg Ala Ser Lys
        35                  40                  45

Ser Val Ser Thr Ser Gly Tyr Ser Tyr Leu His Trp Tyr Gln Gln Lys
    50                  55                  60

Pro Gly Gln Pro Pro Lys Leu Leu Ile Tyr Leu Ala Ser Asn Leu Glu
65                  70                  75                  80

Ser Gly Val Pro Ala Arg Phe Ser Gly Ser Gly Ser Gly Thr Asp Phe
                85                  90                  95

Thr Leu Asn Ile His Pro Val Glu Glu Glu Asp Ala Ala Thr Tyr Tyr
            100                 105                 110
```

```
Cys Gln His Ser Arg Glu Leu Pro Phe Thr Phe Gly Ser Gly Thr Lys
        115                 120                 125

Leu Glu Ile Lys Gly Gly Gly Gly Ser Gly Gly Gly Gly Ser Gly Gly
    130                 135                 140

Gly Gly Ser Gln Val Gln Leu Val Glu Ser Gly Gly Gly Leu Val Gln
145                 150                 155                 160

Pro Gly Gly Ser Leu Lys Leu Ser Cys Ala Ala Ser Gly Phe Asp Phe
                165                 170                 175

Ser Arg Tyr Trp Met Ser Trp Val Arg Gln Ala Pro Gly Lys Gly Leu
            180                 185                 190

Glu Trp Ile Gly Glu Ile Asn Pro Thr Ser Ser Thr Ile Asn Phe Thr
        195                 200                 205

Pro Ser Leu Lys Asp Lys Val Phe Ile Ser Arg Asp Asn Ala Lys Asn
    210                 215                 220

Thr Leu Tyr Leu Gln Met Ser Lys Val Arg Ser Glu Asp Thr Ala Leu
225                 230                 235                 240

Tyr Tyr Cys Ala Arg Gly Asn Tyr Tyr Arg Tyr Gly Asp Ala Met Asp
                245                 250                 255

Tyr Trp Gly Gln Gly Thr Ser Val Thr Val Ser Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Gln Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 18
<211> LENGTH: 1492
<212> TYPE: DNA
<213> ORGANISM: Artificial Sequence
<220> FEATURE:
<223> OTHER INFORMATION: synthetic sequence

<400> SEQUENCE: 18

```
gcgatcgcat ggccttacca gtgaccgcct tgctcctgcc gctggccttg ctgctccacg     60
ccgccaggcc ggacatcgtg ctgacccaga gccccgccag cctggccgtg agcctgggcc    120
agagggccac catcagctgc agggccagca agagcgtgag caccagcggc tacagctacc    180
tgcactggta ccagcagaag cccggccagc cccccaagct gctgatctac ctggccagca    240
acctggagag cggcgtgccc gccaggttca gcggcagcgg cagcggcacc gacttcaccc    300
tgaacatcca ccccgtggag gaggaggacg ccgccaccta ctactgccag cacagcaggg    360
agctgccctt caccttcggc agcggcacca agctggagat caagggaggg gggggatccg    420
gggggaggagg ctccggcgga ggcggaagcc aggtgcagct ggtggagagc ggcggcggcc    480
tggtgcagcc cggcggcagc ctgaagctga gctgcgccgc cagcggcttc gacttcagca    540
ggtactggat gagctgggtg aggcaggccc ccggcaaggg cctggagtgg atcggcgaga    600
tcaaccccac cagcagcacc atcaacttca cccccagcct gaaggacaag gtgttcatca    660
gcagggacaa cgccaagaac accctgtacc tgcagatgag caaggtgagg agcgaggaca    720
ccgccctgta ctactgcgcc aggggcaact actacaggta cggcgacgcc atggactact    780
ggggccaggg caccagcgtg accgtgagca ccacgacgcc agcgccgcga ccaccaacac    840
cggcgcccac catcgcgtcg cagcccctgt ccctgcgccc agaggcgtgc cggccagcgg    900
cggggggcgc agtgcacacg agggggctgg acttcgcctg tgatatctac atctgggcgc    960
ccttggccgg gacttgtggg gtccttctcc tgtcactggt tatcaccctt tactgcaaac   1020
ggggcagaaa gaaactcctg tatatattca aacaaccatt tatgagacca gtacaaacta   1080
ctcaagagga agatggctgt agctgccgat ttccagaaga agaagaagga ggatgtgaac   1140
tgagagtgaa gttcagcagg agcgcagacg cccccgcgta ccagcagggc cagaaccagc   1200
tctataacga gctcaatcta ggacgaagag aggagtacga tgttttggac aagagacgtg   1260
gccgggaccc tgagatgggg ggaaagccgc agagaaggaa gaaccctcag gaaggcctgt   1320
acaatgaact gcagaaagat aagatggcgg aggcctacag tgagattggg atgaaaggcg   1380
agcgccggag gggcaagggg cacgatggcc tttaccaggg tctcagtaca gccaccaagg   1440
acacctacga cgcccttcac atgcaggccc tgccccctcg ctaagtttaa ac           1492
```

<210> SEQ ID NO 19
<211> LENGTH: 997
<212> TYPE: PRT
<213> ORGANISM: Artificial Sequence
<220> FEATURE:
<223> OTHER INFORMATION: synthetic sequence

<400> SEQUENCE: 19

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser His Arg Phe Met
            20                  25                  30

Ser Thr Ser Val Gly Asp Arg Val Ser Ile Thr Cys Arg Ala Ser Gln
        35                  40                  45

Asp Val Asn Thr Ala Val Ser Trp Tyr Gln Gln Lys Pro Gly Gln Ser
    50                  55                  60

Pro Lys Leu Leu Ile Phe Ser Ala Ser Tyr Arg Tyr Thr Gly Val Pro
65                  70                  75                  80

Asp Arg Phe Thr Gly Ser Gly Ser Gly Ala Asp Phe Thr Leu Thr Ile
```

```
                85                  90                  95

Ser Ser Val Gln Ala Glu Asp Leu Ala Val Tyr Tyr Cys Gln Gln His
            100                 105                 110

Tyr Ser Thr Pro Trp Thr Phe Gly Gly Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Ile Gln Leu Val Gln Ser Gly Pro Asp Leu Lys Lys Pro Gly Glu Thr
145                 150                 155                 160

Val Lys Leu Ser Cys Lys Ala Ser Gly Tyr Thr Phe Thr Asn Phe Gly
                165                 170                 175

Met Asn Trp Val Lys Gln Ala Pro Gly Lys Gly Phe Lys Trp Met Ala
            180                 185                 190

Trp Ile Asn Thr Thr Arg Tyr Thr Gly Glu Ser Tyr Phe Ala Asp Asp
        195                 200                 205

Phe Lys Gly Arg Phe Ala Phe Ser Val Glu Thr Ser Ala Thr Thr Ala
    210                 215                 220

Tyr Leu Gln Ile Asn Asn Leu Lys Thr Glu Asp Thr Ala Thr Tyr Phe
225                 230                 235                 240

Cys Ala Arg Gly Glu Ile Tyr Tyr Gly Tyr Asp Gly Gly Phe Ala Tyr
                245                 250                 255

Trp Gly Gln Gly Thr Leu Val Thr Val Ser Ala Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Gln Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg Gly Ser Gly Ala Thr
                485                 490                 495

Asn Phe Ser Leu Leu Lys Gln Ala Gly Asp Val Glu Glu Asn Pro Gly
            500                 505                 510
```

```
Pro Ala Leu Pro Val Thr Ala Leu Leu Leu Pro Leu Ala Leu Leu Leu
        515                 520                 525

His Ala Ala Arg Pro Asp Ile Gln Met Thr Gln Ser Pro Ser Ser Leu
    530                 535                 540

Ser Ala Ser Val Gly Asp Arg Val Thr Ile Thr Cys Lys Ala Ser Gln
545                 550                 555                 560

Asp Val Gly Ile Ala Val Ala Trp Tyr Gln Gln Lys Pro Gly Lys Val
                565                 570                 575

Pro Lys Leu Leu Ile Tyr Trp Ala Ser Thr Arg His Thr Gly Val Pro
            580                 585                 590

Asp Arg Phe Ser Gly Ser Gly Ser Gly Thr Asp Phe Thr Leu Thr Ile
        595                 600                 605

Ser Ser Leu Gln Pro Glu Asp Val Ala Thr Tyr Tyr Cys Gln Gln Tyr
    610                 615                 620

Ser Ser Tyr Pro Tyr Thr Phe Gly Gln Gly Thr Lys Val Glu Ile Lys
625                 630                 635                 640

Gly Gly Gly Gly Ser Gly Gly Gly Gly Ser Gly Gly Gly Gly Ser Glu
                645                 650                 655

Val Gln Leu Val Glu Ser Gly Gly Gly Leu Val Gln Pro Gly Gly Ser
            660                 665                 670

Leu Arg Leu Ser Cys Ala Ala Ser Gly Phe Asp Phe Ser Arg Tyr Trp
        675                 680                 685

Met Ser Trp Val Arg Gln Ala Pro Gly Lys Gly Leu Glu Trp Ile Gly
    690                 695                 700

Glu Ile Asn Pro Asp Ser Ser Thr Ile Asn Tyr Ala Pro Ser Leu Lys
705                 710                 715                 720

Asp Lys Phe Ile Ile Ser Arg Asp Asn Ala Lys Asn Ser Leu Tyr Leu
                725                 730                 735

Gln Met Asn Ser Leu Arg Ala Glu Asp Thr Ala Val Tyr Tyr Cys Ala
            740                 745                 750

Arg Pro Asp Gly Asn Tyr Trp Tyr Phe Asp Val Trp Gly Gln Gly Thr
        755                 760                 765

Leu Val Thr Val Ser Ser Thr Thr Thr Pro Ala Pro Arg Pro Pro Thr
    770                 775                 780

Pro Ala Pro Thr Ile Ala Ser Gln Pro Leu Ser Leu Arg Pro Glu Ala
785                 790                 795                 800

Cys Arg Pro Ala Ala Gly Gly Ala Val His Thr Arg Gly Leu Asp Phe
                805                 810                 815

Ala Cys Asp Ile Tyr Ile Trp Ala Pro Leu Ala Gly Thr Cys Gly Val
            820                 825                 830

Leu Leu Leu Ser Leu Val Ile Thr Leu Tyr Cys Arg Ser Lys Arg Ser
        835                 840                 845

Arg Leu Leu His Ser Asp Tyr Met Asn Met Thr Pro Arg Arg Pro Gly
    850                 855                 860

Pro Thr Arg Lys His Tyr Gln Pro Tyr Ala Pro Pro Arg Asp Phe Ala
865                 870                 875                 880

Ala Tyr Arg Ser Arg Val Lys Phe Ser Arg Ser Ala Asp Ala Pro Ala
                885                 890                 895

Tyr Gln Gln Gly Gln Asn Gln Leu Tyr Asn Glu Leu Asn Leu Gly Arg
            900                 905                 910

Arg Glu Glu Tyr Asp Val Leu Asp Lys Arg Arg Gly Arg Asp Pro Glu
        915                 920                 925
```

```
Met Gly Gly Lys Pro Gln Arg Arg Lys Asn Pro Gln Glu Gly Leu Tyr
    930                 935                 940

Asn Glu Leu Gln Lys Asp Lys Met Ala Glu Ala Tyr Ser Glu Ile Gly
945                 950                 955                 960

Met Lys Gly Glu Arg Arg Arg Gly Lys Gly His Asp Gly Leu Tyr Gln
                965                 970                 975

Gly Leu Ser Thr Ala Thr Lys Asp Thr Tyr Asp Ala Leu His Met Gln
            980                 985                 990

Ala Leu Pro Pro Arg
        995


<210> SEQ ID NO 20
<211> LENGTH: 2994
<212> TYPE: DNA
<213> ORGANISM: Artificial Sequence
<220> FEATURE:
<223> OTHER INFORMATION: synthetic sequence

<400> SEQUENCE: 20

atggccttac cagtgaccgc cttgctcctg ccgctggcct tgctgctcca cgccgccagg     60

ccggatgtgg tgatgaccca gagccatcgc tttatgagca ccagcgtggg cgatcgcgtg    120

agcattacct gccgcgcgag ccaggatgtg aacaccgcgg tgagctggta tcagcagaaa    180

ccgggccaga gcccgaaact gctgattttt agcgcgagct atcgctatac cggcgtgccg    240

gatcgcttta ccggcagcgg cagcggcgcg gattttaccc tgaccattag cagcgtgcag    300

gcggaagatc tggcggtgta ttattgccag cagcattata gcaccccgtg gacctttggc    360

ggcggcacca aactggaaat taaaggaggg gggggatccg gggaggagg ctccggcgga     420

ggcggaagcc agattcagct ggtgcagagc ggcccggatc tgaaaaaacc gggcgaaacc    480

gtgaaactga gctgcaaagc gagcggctat acctttacca actttggcat gaactgggtg    540

aaacaggcgc cgggcaaagg ctttaaatgg atggcgtgga ttaacaccac ccgctatacc    600

ggcgaaagct attttgcgga tgattttaaa ggccgctttg cgtttagcgt ggaaaccagc    660

gcgaccaccg cgtatctgca gattaacaac ctgaaaaccg aagataccgc gacctatttt    720

tgcgcgcgcg gcgaaattta ttatggctat gatggcggct ttgcgtattg ggccagggc     780

accctggtga ccgtgagcgc gaccacgacg ccagcgccgc gaccaccaac accggcgccc    840

accatcgcgt cgcagcccct gtccctgcgc ccagaggcgt gccggccagc ggcggggggc    900

gcagtgcaca cgagggggct ggacttcgcc tgtgatatct acatctgggc gcccttggcc    960

gggacttgtg gggtccttct cctgtcactg gttatcaccc tttactgcaa acggggcaga   1020

aagaaactcc tgtatatatt caaacaacca tttatgagac cagtacaaac tactcaagag   1080

gaagatggct gtagctgccg atttccagaa gaagaagaag gaggatgtga actgagagtg   1140

aagttcagca ggagcgcaga cgcccccgcg taccagcagg gccagaacca gctctataac   1200

gagctcaatc taggacgaag agaggagtac gatgttttgg acaagagacg tggccgggac   1260

cctgagatgg ggggaaagcc gcagagaagg aagaaccctc aggaaggcct gtacaatgaa   1320

ctgcagaaag ataagatggc ggaggcctac agtgagattg ggatgaaagg cgagcgccgg   1380

aggggcaagg ggcacgatgg cctttaccag ggtctcagta cagccaccaa ggacacctac   1440

gacgcccttc acatgcaggc cctgccccct cgcggaagcg gagccaccaa cttcagcctg   1500

ctgaagcagg ccggcgacgt ggaggagaac cccggccccg ccttaccagt gaccgccttg   1560

ctcctgccgc tggccttgct gctccacgcc gccaggccgg atattcagat gacccagagc   1620
```

```
ccgagcagcc tgagcgcgag cgtgggcgat cgcgtgacca ttacctgcaa agcgagccag   1680

gatgtgggca ttgcggtggc gtggtatcag cagaaaccgg gcaaagtgcc gaaactgctg   1740

atttattggg cgagcacccg ccataccggc gtgccggatc gctttagcgg cagcggcagc   1800

ggcaccgatt ttaccctgac cattagcagc ctgcagccgg aagatgtggc gacctattat   1860

tgccagcagt atagcagcta tccgtatacc tttggccagg gcaccaaagt ggaaattaaa   1920

ggaggggggg gatccggggg aggaggctcc ggcggaggcg gaagcgaagt gcagctggtg   1980

gaaagcggcg gcggcctggt gcagccgggc ggcagcctgc gcctgagctg cgcggcgagc   2040

ggctttgatt ttagccgcta ttggatgagc tgggtgcgcc aggcgccggg caaaggcctg   2100

gaatggattg gcgaaattaa cccggatagc agcaccatta actatgcgcc gagcctgaaa   2160

gataaattta ttattagccg cgataacgcg aaaaacagcc tgtatctgca gatgaacagc   2220

ctgcgcgcgg aagataccgc ggtgtattat tgcgcgcgcc cggatggcaa ctattggtat   2280

tttgatgtgt ggggccaggg caccctggtg accgtgagca gcaccacgac gccagcgccg   2340

cgaccaccaa caccggcgcc caccatcgcg tcgcagcccc tgtccctgcg cccagaggcg   2400

tgccggccag cggcgggggg cgcagtgcac acgagggggc tggacttcgc ctgtgatatc   2460

tacatctggg cgcccttggc cgggacttgt ggggtccttc tcctgtcact ggttatcacc   2520

ctttactgca ggagtaagag gagcaggctc ctgcacagtg actacatgaa catgactccc   2580

cgccgccccg ggcccacccg caagcattac cagccctatg ccccaccacg cgacttcgca   2640

gcctatcgct ccagagtgaa gttcagcagg agcgcagacg cccccgcgta ccagcagggc   2700

cagaaccagc tctataacga gctcaatcta ggacgaagag aggagtacga tgttttggac   2760

aagagacgtg gccgggaccc tgagatgggg ggaaagccgc agagaaggaa gaaccctcag   2820

gaaggcctgt acaatgaact gcagaaagat aagatggcgg aggcctacag tgagattggg   2880

atgaaaggcg agcgccggag gggcaagggg cacgatggcc tttaccaggg tctcagtaca   2940

gccaccaagg acacctacga cgcccttcac atgcaggccc tgccccctcg ctaa         2994
```

<210> SEQ ID NO 21
<211> LENGTH: 997
<212> TYPE: PRT
<213> ORGANISM: Artificial Sequence
<220> FEATURE:
<223> OTHER INFORMATION: synthetic sequence

<400> SEQUENCE: 21

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser His Arg Phe Met
            20                  25                  30

Ser Thr Ser Val Gly Asp Arg Val Ser Ile Thr Cys Arg Ala Ser Gln
        35                  40                  45

Asp Val Asn Thr Ala Val Ser Trp Tyr Gln Gln Lys Pro Gly Gln Ser
    50                  55                  60

Pro Lys Leu Leu Ile Phe Ser Ala Ser Tyr Arg Tyr Thr Gly Val Pro
65                  70                  75                  80

Asp Arg Phe Thr Gly Ser Gly Ser Gly Ala Asp Phe Thr Leu Thr Ile
                85                  90                  95

Ser Ser Val Gln Ala Glu Asp Leu Ala Val Tyr Tyr Cys Gln Gln His
            100                 105                 110

Tyr Ser Thr Pro Trp Thr Phe Gly Gly Gly Thr Lys Leu Asp Ile Lys
        115                 120                 125
```

```
Gly Gly Gly Gly Ser Gly Gly Gly Gly Ser Gly Gly Gly Gly Ser Gln
    130                 135                 140

Ile Gln Leu Val Gln Ser Gly Pro Asp Leu Lys Lys Pro Gly Glu Thr
145                 150                 155                 160

Val Lys Leu Ser Cys Lys Ala Ser Gly Tyr Thr Phe Thr Asn Phe Gly
                165                 170                 175

Met Asn Trp Val Lys Gln Ala Pro Gly Lys Gly Phe Lys Trp Met Ala
            180                 185                 190

Trp Ile Asn Thr Tyr Thr Gly Glu Ser Tyr Phe Ala Asp Asp Phe Lys
        195                 200                 205

Gly Arg Phe Ala Phe Ser Val Glu Thr Ser Ala Thr Thr Ala Tyr Leu
    210                 215                 220

Gln Ile Asn Asn Leu Lys Thr Glu Asp Thr Ala Thr Tyr Phe Cys Ala
225                 230                 235                 240

Arg Gly Glu Ile Tyr Tyr Gly Tyr Asp Gly Gly Phe Ala Tyr Trp Gly
                245                 250                 255

Gln Gly Thr Leu Val Thr Val Ser Ala Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Gln Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg Gly Ser Gly Ala Thr Asn Phe
                485                 490                 495

Ser Leu Leu Lys Gln Ala Gly Asp Val Glu Glu Asn Pro Gly Pro Met
            500                 505                 510

Ala Leu Pro Val Thr Ala Leu Leu Leu Pro Leu Ala Leu Leu Leu His
        515                 520                 525

Ala Ala Arg Pro Asp Ile Gln Met Thr Gln Ser Pro Ser Ser Leu Ser
    530                 535                 540
```

```
Ala Ser Val Gly Asp Arg Val Thr Ile Thr Cys Lys Ala Ser Gln Asp
545                 550                 555                 560

Val Gly Ile Ala Val Ala Trp Tyr Gln Gln Lys Pro Gly Lys Val Pro
                565                 570                 575

Lys Leu Leu Ile Tyr Trp Ala Ser Thr Arg His Thr Gly Val Pro Asp
            580                 585                 590

Arg Phe Ser Gly Ser Gly Ser Gly Thr Asp Phe Thr Leu Thr Ile Ser
        595                 600                 605

Ser Leu Gln Pro Glu Asp Val Ala Thr Tyr Tyr Cys Gln Gln Tyr Ser
    610                 615                 620

Ser Tyr Pro Tyr Thr Phe Gly Gln Gly Thr Lys Val Glu Ile Lys Gly
625                 630                 635                 640

Gly Gly Gly Ser Gly Gly Gly Gly Ser Gly Gly Gly Gly Ser Glu Val
                645                 650                 655

Gln Leu Val Glu Ser Gly Gly Gly Leu Val Gln Pro Gly Gly Ser Leu
            660                 665                 670

Arg Leu Ser Cys Ala Ala Ser Gly Phe Asp Phe Ser Arg Tyr Trp Met
        675                 680                 685

Ser Trp Val Arg Gln Ala Pro Gly Lys Gly Leu Glu Trp Ile Gly Glu
    690                 695                 700

Ile Asn Pro Asp Ser Ser Thr Ile Asn Tyr Ala Pro Ser Leu Lys Asp
705                 710                 715                 720

Lys Phe Ile Ile Ser Arg Asp Asn Ala Lys Asn Ser Leu Tyr Leu Gln
                725                 730                 735

Met Asn Ser Leu Arg Ala Glu Asp Thr Ala Val Tyr Tyr Cys Ala Arg
            740                 745                 750

Pro Asp Gly Asn Tyr Trp Tyr Phe Asp Val Trp Gly Gln Gly Thr Leu
        755                 760                 765

Val Thr Val Ser Ser Thr Thr Thr Pro Ala Pro Arg Pro Pro Thr Pro
    770                 775                 780

Ala Pro Thr Ile Ala Ser Gln Pro Leu Ser Leu Arg Pro Glu Ala Cys
785                 790                 795                 800

Arg Pro Ala Ala Gly Gly Ala Val His Thr Arg Gly Leu Asp Phe Ala
                805                 810                 815

Cys Asp Ile Tyr Ile Trp Ala Pro Leu Ala Gly Thr Cys Gly Val Leu
            820                 825                 830

Leu Leu Ser Leu Val Ile Thr Leu Tyr Cys Lys Arg Gly Arg Lys Lys
        835                 840                 845

Leu Leu Tyr Ile Phe Lys Gln Pro Phe Met Arg Pro Val Gln Thr Thr
    850                 855                 860

Gln Glu Glu Asp Gly Cys Ser Cys Arg Phe Pro Glu Glu Glu Glu Gly
865                 870                 875                 880

Gly Cys Glu Leu Arg Val Lys Phe Ser Arg Ser Ala Asp Ala Pro Ala
                885                 890                 895

Tyr Gln Gln Gly Gln Asn Gln Leu Tyr Asn Glu Leu Asn Leu Gly Arg
            900                 905                 910

Arg Glu Glu Tyr Asp Val Leu Asp Lys Arg Arg Gly Arg Asp Pro Glu
        915                 920                 925

Met Gly Gly Lys Pro Gln Arg Arg Lys Asn Pro Gln Glu Gly Leu Tyr
    930                 935                 940

Asn Glu Leu Gln Lys Asp Lys Met Ala Glu Ala Tyr Ser Glu Ile Gly
945                 950                 955                 960

Met Lys Gly Glu Arg Arg Arg Gly Lys Gly His Asp Gly Leu Tyr Gln
```

965 970 975

Gly Leu Ser Thr Ala Thr Lys Asp Thr Tyr Asp Ala Leu His Met Gln
980 985 990

Ala Leu Pro Pro Arg
995

<210> SEQ ID NO 22
<211> LENGTH: 3009
<212> TYPE: DNA
<213> ORGANISM: Artificial Sequence
<220> FEATURE:
<223> OTHER INFORMATION: synthetic sequence

<400> SEQUENCE: 22
cgatcgcatg gccttaccag tgaccgcctt gctcctgccg ctggccttgc tgctccacgc 60
cgccaggccg gatgtggtga tgacccagag ccatcgcttt atgagcacca gcgtgggaga 120
tcgagtgagc attacctgcc gcgcgagcca ggatgtgaac accgcggtga gctggtatca 180
gcagaaaccg ggccagagcc cgaaactgct gatttttagc gcgagctatc gctataccgg 240
cgtgccggat cgctttaccg gcagcggcag cggcgcggat tttaccctga ccattagcag 300
cgtgcaggcg gaagatctgg cggtgtatta ttgccagcag cattatagca ccccgtggac 360
ctttggcggc ggcaccaaac tggatattaa aggagggggg ggatccgggg gaggaggctc 420
cggcggaggc ggaagccaga ttcagctggt gcagagcggc ccggatctga aaaaaccggg 480
cgaaaccgtg aaactgagct gcaaagcgag cggctatacc tttaccaact ttggcatgaa 540
ctgggtgaaa caggcgccgg gcaaaggctt taaatggatg gcgtggatta acacctatac 600
cggcgaaagc tattttgcgg atgattttaa aggccgcttt gcgtttagcg tggaaaccag 660
cgcgaccacc gcgtatctgc agattaacaa cctgaaaacc gaagataccg cgacctattt 720
ttgcgcgcgc ggcgaaattt attatggcta tgatggcggc tttgcgtatt ggggccaggg 780
caccctggtg accgtgagcg cgaccacgac gccagcgccg cgaccaccaa caccggcgcc 840
caccatcgcg tcgcagcccc tgtccctgcg cccagaggcg tgccggccag cggcgggggg 900
cgcagtgcac acgagggggc tggacttcgc ctgtgatatc tacatctggg cgcccttggc 960
cgggacttgt ggggtccttc tcctgtcact ggttatcacc ctttactgca aacggggcag 1020
aaagaaactc ctgtatatat tcaagcaacc atttatgaga ccagtacaaa ctactcaaga 1080
ggaagatggc tgtagctgcc gatttccaga agaagaagaa ggaggatgtg aactgagagt 1140
gaagttcagc aggagcgcag acgcccccgc gtaccagcag ggccagaacc agctctataa 1200
cgagctcaat ctaggacgaa gagaggagta cgatgttttg gacaagagac gtggccggga 1260
ccctgagatg gggggaaagc cgcagagaag gaagaaccct caggaaggcc tgtacaatga 1320
actgcagaaa gataagatgg cggaggccta cagtgagatt gggatgaaag gcgagcgccg 1380
gaggggcaag gggcacgatg gcctttacca gggtctcagt acagccacca aggacaccta 1440
cgacgccctt cacatgcagg ccctgccccc tcgcggaagc ggagccacca acttcagcct 1500
gctgaagcag gccggcgacg tggaggagaa ccccggcccc atggccttac cagtgaccgc 1560
cttgctcctg ccgctggcct tgctgctcca cgccgccagg ccggatattc agatgaccca 1620
gagcccgagc agcctgagcg cgagcgtggg cgaccgcgtg accattacct gcaaagcgag 1680
ccaggatgtg ggcattgcgg tggcgtggta tcagcagaaa ccgggcaaag tgccgaaact 1740
gctgatttat tgggcgagca cccgccatac cggcgtgccg gatcgcttta gcggcagcgg 1800
cagcggcacc gatttaccc tgaccattag cagcctgcag ccggaagatg tggcgaccta 1860
ttattgccag cagtatagca gctatccgta tacctttggc cagggcacca aagtggaaat 1920
taaaggaggg gggggatccg ggggaggagg ctccggcgga ggcggaagcg aagtgcagct 1980
ggtggaaagc ggcggcggcc tggtgcagcc gggcggcagc ctgcgcctga gctgcgcggc 2040
gagcggcttt gattttagcc gctattggat gagctgggtg cgccaggcgc cgggcaaagg 2100
cctggaatgg attggcgaaa ttaacccgga tagcagcacc attaactatg cgccgagcct 2160
gaaagataaa tttattatta gccgcgataa cgcgaaaaac agcctgtatc tgcagatgaa 2220
cagcctgcgc gcggaagata ccgcggtgta ttattgcgcg cgcccggatg gcaactattg 2280
gtattttgat gtgtggggcc agggcaccct ggtgaccgtg agcagcacca cgacgccagc 2340
gccgcgacca ccaacaccgg cgcccaccat cgcgtcgcag cccctgtccc tgcgcccaga 2400
ggcgtgccgg ccagcggcgg ggggcgcagt gcacacgagg gggctggact tcgcctgtga 2460
tatctacatc tgggcgccct tggccgggac ttgtggggtc cttctcctgt cactggttat 2520
caccctttac tgcaaacggg gcagaaagaa actcctgtat atattcaagc aaccatttat 2580
gagaccagta caaactactc aagaggaaga tggctgtagc tgccgatttc cagaagaaga 2640
agaaggagga tgtgaactga gagtgaagtt cagcaggagc gcagacgccc ccgcgtacca 2700
gcagggccag aaccagctct ataacgagct caatctagga cgaagagagg agtacgatgt 2760
tttggacaag agacgtggcc gggaccctga gatgggggga aagccgcaga gaaggaagaa 2820
ccctcaggaa ggcctgtaca atgaactgca gaaagataag atggcggagg cctacagtga 2880
gattgggatg aaaggcgagc gccggagggg caaggggcac gatggccttt accagggtct 2940
cagtacagcc accaaggaca cctacgacgc ccttcacatg caggccctgc cccctcgcta 3000
agtttaaac 3009

<210> SEQ ID NO 23
<211> LENGTH: 423
<212> TYPE: DNA
<213> ORGANISM: Artificial Sequence
<220> FEATURE:
<223> OTHER INFORMATION: synthetic sequence

<400> SEQUENCE: 23
agctagctgc agtaacgcca ttttgcaagg catggaaaaa taccaaacca agaatagaga 60
agttcagatc aagggcgggt acatgaaaat agctaacgtt gggccaaaca ggatatctgc 120
ggtgagcagt ttcggccccg gcccggggcc aagaacagat ggtcaccgca gtttcggccc 180
cggcccgagg ccaagaacag atggtcccca gatatggccc aaccctcagc agtttcttaa 240
gacccatcag atgtttccag gctcccccaa ggacctgaaa tgaccctgcg ccttatttga 300
attaaccaat cagcctgctt ctcgcttctg ttcgcgcgct tctgcttccc gagctctata 360
aaagagctca caacccctca ctcggcgcgc cagtcctccg acagactgag tcgcccgggt 420
acc 423

<210> SEQ ID NO 24
<211> LENGTH: 165
<212> TYPE: PRT
<213> ORGANISM: Artificial Sequence
<220> FEATURE:
<223> OTHER INFORMATION: synthetic sequence

<400> SEQUENCE: 24

Met Ser Gly Leu Gly Arg Ser Arg Arg Gly Gly Arg Ser Arg Val Asp
1 5 10 15

```
Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser
                165


<210> SEQ ID NO 25
<211> LENGTH: 54
<212> TYPE: PRT
<213> ORGANISM: Artificial Sequence
<220> FEATURE:
<223> OTHER INFORMATION: synthetic sequence

<400> SEQUENCE: 25

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala
    50


<210> SEQ ID NO 26
<211> LENGTH: 204
<212> TYPE: PRT
<213> ORGANISM: Artificial Sequence
<220> FEATURE:
<223> OTHER INFORMATION: synthetic sequence

<400> SEQUENCE: 26

Ser Gly Pro Val Lys Glu Leu Val Gly Ser Val Gly Gly Ala Val Thr
1               5                   10                  15

Phe Pro Leu Lys Ser Lys Val Lys Gln Val Asp Ser Ile Val Trp Thr
            20                  25                  30

Phe Asn Thr Thr Pro Leu Val Thr Ile Gln Pro Glu Gly Gly Thr Ile
        35                  40                  45

Ile Val Thr Gln Asn Arg Asn Arg Glu Arg Val Asp Phe Pro Asp Gly
    50                  55                  60

Gly Tyr Ser Leu Lys Leu Ser Lys Leu Lys Lys Asn Asp Ser Gly Ile
65                  70                  75                  80

Tyr Tyr Val Gly Ile Tyr Ser Ser Ser Leu Gln Gln Pro Ser Thr Gln
```

```
                85                  90                  95

Glu Tyr Val Leu His Val Tyr Glu His Leu Ser Lys Pro Lys Val Thr
            100                 105                 110

Met Gly Leu Gln Ser Asn Lys Asn Gly Thr Cys Val Thr Asn Leu Thr
        115                 120                 125

Cys Cys Met Glu His Gly Glu Glu Asp Val Ile Tyr Thr Trp Lys Ala
    130                 135                 140

Leu Gly Gln Ala Ala Asn Glu Ser His Asn Gly Ser Ile Leu Pro Ile
145                 150                 155                 160

Ser Trp Arg Trp Gly Glu Ser Asp Met Thr Phe Ile Cys Val Ala Arg
                165                 170                 175

Asn Pro Val Ser Arg Asn Phe Ser Ser Pro Ile Leu Ala Arg Lys Leu
            180                 185                 190

Cys Glu Gly Ala Ala Asp Asp Pro Asp Ser Ser Met
        195                 200


<210> SEQ ID NO 27
<211> LENGTH: 46
<212> TYPE: PRT
<213> ORGANISM: Artificial Sequence
<220> FEATURE:
<223> OTHER INFORMATION: synthetic sequence

<400> SEQUENCE: 27

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys
        35                  40                  45


<210> SEQ ID NO 28
<211> LENGTH: 242
<212> TYPE: PRT
<213> ORGANISM: Artificial Sequence
<220> FEATURE:
<223> OTHER INFORMATION: synthetic sequence

<400> SEQUENCE: 28

Asp Pro Asn Phe Trp Leu Gln Val Gln Glu Ser Val Thr Val Gln Glu
1               5                   10                  15

Gly Leu Cys Val Leu Val Pro Cys Thr Phe Phe His Pro Ile Pro Tyr
            20                  25                  30

Tyr Asp Lys Asn Ser Pro Val His Gly Tyr Trp Phe Arg Glu Gly Ala
        35                  40                  45

Ile Ile Ser Arg Asp Ser Pro Val Ala Thr Asn Lys Leu Asp Gln Glu
    50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Arg Asp Asn
                85                  90                  95

Gly Ser Tyr Phe Phe Arg Met Glu Arg Gly Ser Thr Lys Tyr Ser Tyr
            100                 105                 110

Lys Ser Pro Gln Leu Ser Val His Val Thr Asp Leu Thr His Arg Pro
        115                 120                 125

Lys Ile Leu Ile Pro Gly Thr Leu Glu Pro Gly His Ser Lys Asn Leu
    130                 135                 140
```

```
Thr Cys Ser Val Ser Trp Ala Cys Glu Gln Gly Thr Pro Pro Ile Phe
145                 150                 155                 160

Ser Trp Leu Ser Ala Ala Pro Thr Ser Leu Gly Pro Arg Thr Thr His
                165                 170                 175

Ser Ser Val Leu Ile Ile Thr Pro Arg Pro Gln Asp His Gly Thr Asn
            180                 185                 190

Leu Thr Cys Gln Val Lys Phe Ala Gly Ala Gly Val Thr Thr Glu Arg
        195                 200                 205

Thr Ile Gln Leu Asn Val Thr Tyr Val Pro Gln Asn Pro Thr Thr Gly
    210                 215                 220

Ile Phe Pro Gly Asp Gly Ser Gly Lys Gln Glu Thr Arg Ala Gly Val
225                 230                 235                 240

Val His


<210> SEQ ID NO 29
<211> LENGTH: 287
<212> TYPE: PRT
<213> ORGANISM: Artificial Sequence
<220> FEATURE:
<223> OTHER INFORMATION: synthetic sequence

<400> SEQUENCE: 29

Thr Lys Glu Asp Pro Asn Pro Pro Ile Thr Asn Leu Arg Met Lys Ala
1               5                   10                  15

Lys Ala Gln Gln Leu Thr Trp Asp Leu Asn Arg Asn Val Thr Asp Ile
            20                  25                  30

Glu Cys Val Lys Asp Ala Asp Tyr Ser Met Pro Ala Val Asn Asn Ser
        35                  40                  45

Tyr Cys Gln Phe Gly Ala Ile Ser Leu Cys Glu Val Thr Asn Tyr Thr
    50                  55                  60

Val Arg Val Ala Asn Pro Pro Phe Ser Thr Trp Ile Leu Phe Pro Glu
65                  70                  75                  80

Asn Ser Gly Lys Pro Trp Ala Gly Ala Glu Asn Leu Thr Cys Trp Ile
                85                  90                  95

His Asp Val Asp Phe Leu Ser Cys Ser Trp Ala Val Gly Pro Gly Ala
            100                 105                 110

Pro Ala Asp Val Gln Tyr Asp Leu Tyr Leu Asn Val Ala Asn Arg Arg
        115                 120                 125

Gln Gln Tyr Glu Cys Leu His Tyr Lys Thr Asp Ala Gln Gly Thr Arg
    130                 135                 140

Ile Gly Cys Arg Phe Asp Asp Ile Ser Arg Leu Ser Ser Gly Ser Gln
145                 150                 155                 160

Ser Ser His Ile Leu Val Arg Gly Arg Ser Ala Ala Phe Gly Ile Pro
                165                 170                 175

Cys Thr Asp Lys Phe Val Val Phe Ser Gln Ile Glu Ile Leu Thr Pro
            180                 185                 190

Pro Asn Met Thr Ala Lys Cys Asn Lys Thr His Ser Phe Met His Trp
        195                 200                 205

Lys Met Arg Ser His Phe Asn Arg Lys Phe Arg Tyr Glu Leu Gln Ile
    210                 215                 220

Gln Lys Arg Met Gln Pro Val Ile Thr Glu Gln Val Arg Asp Arg Thr
225                 230                 235                 240

Ser Phe Gln Leu Leu Asn Pro Gly Thr Tyr Thr Val Gln Ile Arg Ala
                245                 250                 255

Arg Glu Arg Val Tyr Glu Phe Leu Ser Ala Trp Ser Thr Pro Gln Arg
```

```
            260                 265                 270

Phe Glu Cys Asp Gln Glu Glu Gly Ala Asn Thr Arg Ala Trp Arg
        275                 280                 285


<210> SEQ ID NO 30
<211> LENGTH: 272
<212> TYPE: PRT
<213> ORGANISM: Artificial Sequence
<220> FEATURE:
<223> OTHER INFORMATION: synthetic sequence

<400> SEQUENCE: 30

Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190

Leu Ser Trp Thr His Val His Pro Lys Gly Pro Lys Ser Leu Leu Ser
        195                 200                 205

Leu Glu Leu Lys Asp Asp Arg Pro Ala Arg Asp Met Trp Val Met Glu
    210                 215                 220

Thr Gly Leu Leu Leu Pro Arg Ala Thr Ala Gln Asp Ala Gly Lys Tyr
225                 230                 235                 240

Tyr Cys His Arg Gly Asn Leu Thr Met Ser Phe His Leu Glu Ile Thr
                245                 250                 255

Ala Arg Pro Val Leu Trp His Trp Leu Leu Arg Thr Gly Gly Trp Lys
            260                 265                 270


<210> SEQ ID NO 31
<211> LENGTH: 6
<212> TYPE: PRT
<213> ORGANISM: Artificial Sequence
<220> FEATURE:
<223> OTHER INFORMATION: synthetic sequence

<400> SEQUENCE: 31

Pro Ile Cys Val Thr Val
1               5
```

<210> SEQ ID NO 32
<211> LENGTH: 47
<212> TYPE: PRT
<213> ORGANISM: Artificial Sequence
<220> FEATURE:
<223> OTHER INFORMATION: synthetic sequence

<400> SEQUENCE: 32

```
Lys Ile Ser His Phe Leu Lys Met Glu Ser Leu Asn Phe Ile Arg Ala
1               5                   10                  15

His Thr Pro Tyr Ile Asn Ile Tyr Asn Cys Glu Pro Ala Asn Pro Ser
            20                  25                  30

Glu Lys Asn Ser Pro Ser Thr Gln Tyr Cys Tyr Ser Ile Gln Ser
        35                  40                  45
```

<210> SEQ ID NO 33
<211> LENGTH: 480
<212> TYPE: PRT
<213> ORGANISM: Artificial Sequence
<220> FEATURE:
<223> OTHER INFORMATION: synthetic sequence

<400> SEQUENCE: 33

```
Asp Ser Ser Lys Trp Val Phe Glu His Pro Glu Thr Leu Tyr Ala Trp
1               5                   10                  15

Glu Gly Ala Cys Val Trp Ile Pro Cys Thr Tyr Arg Ala Leu Asp Gly
            20                  25                  30

Asp Leu Glu Ser Phe Ile Leu Phe His Asn Pro Glu Tyr Asn Lys Asn
        35                  40                  45

Thr Ser Lys Phe Asp Gly Thr Arg Leu Tyr Glu Ser Thr Lys Asp Gly
    50                  55                  60

Lys Val Pro Ser Glu Gln Lys Arg Val Gln Phe Leu Gly Asp Lys Asn
65                  70                  75                  80

Lys Asn Cys Thr Leu Ser Ile His Pro Val His Leu Asn Asp Ser Gly
                85                  90                  95

Gln Leu Gly Leu Arg Met Glu Ser Lys Thr Glu Lys Trp Met Glu Arg
            100                 105                 110

Ile His Leu Asn Val Ser Glu Arg Pro Phe Pro Pro His Ile Gln Leu
        115                 120                 125

Pro Pro Glu Ile Gln Glu Ser Gln Glu Val Thr Leu Thr Cys Leu Leu
    130                 135                 140

Asn Phe Ser Cys Tyr Gly Tyr Pro Ile Gln Leu Gln Trp Leu Leu Glu
145                 150                 155                 160

Gly Val Pro Met Arg Gln Ala Ala Val Thr Ser Thr Ser Leu Thr Ile
                165                 170                 175

Lys Ser Val Phe Thr Arg Ser Glu Leu Lys Phe Ser Pro Gln Trp Ser
            180                 185                 190

His His Gly Lys Ile Val Thr Cys Gln Leu Gln Asp Ala Asp Gly Lys
        195                 200                 205

Phe Leu Ser Asn Asp Thr Val Gln Leu Asn Val Lys His Thr Pro Lys
    210                 215                 220

Leu Glu Ile Lys Val Thr Pro Ser Asp Ala Ile Val Arg Glu Gly Asp
225                 230                 235                 240

Ser Val Thr Met Thr Cys Glu Val Ser Ser Ser Asn Pro Glu Tyr Thr
                245                 250                 255

Thr Val Ser Trp Leu Lys Asp Gly Thr Ser Leu Lys Lys Gln Asn Thr
            260                 265                 270
```

```
Phe Thr Leu Asn Leu Arg Glu Val Thr Lys Asp Gln Ser Gly Lys Tyr
        275                 280                 285

Cys Cys Gln Val Ser Asn Asp Val Gly Pro Gly Arg Ser Glu Glu Val
    290                 295                 300

Phe Leu Gln Val Gln Tyr Ala Pro Glu Pro Ser Thr Val Gln Ile Leu
305                 310                 315                 320

His Ser Pro Ala Val Glu Gly Ser Gln Val Glu Phe Leu Cys Met Ser
                325                 330                 335

Leu Ala Asn Pro Leu Pro Thr Asn Tyr Thr Trp Tyr His Asn Gly Lys
            340                 345                 350

Glu Met Gln Gly Arg Thr Glu Glu Lys Val His Ile Pro Lys Ile Leu
        355                 360                 365

Pro Trp His Ala Gly Thr Tyr Ser Cys Val Ala Glu Asn Ile Leu Gly
    370                 375                 380

Thr Gly Gln Arg Gly Pro Gly Ala Glu Leu Asp Val Gln Tyr Pro Pro
385                 390                 395                 400

Lys Lys Val Thr Thr Val Ile Gln Asn Pro Met Pro Ile Arg Glu Gly
                405                 410                 415

Asp Thr Val Thr Leu Ser Cys Asn Tyr Asn Ser Ser Asn Pro Ser Val
            420                 425                 430

Thr Arg Tyr Glu Trp Lys Pro His Gly Ala Trp Glu Glu Pro Ser Leu
        435                 440                 445

Gly Val Leu Lys Ile Gln Asn Val Gly Trp Asp Asn Thr Thr Ile Ala
    450                 455                 460

Cys Ala Ala Cys Asn Ser Trp Cys Ser Trp Ala Ser Pro Val Ala Leu
465                 470                 475                 480


<210> SEQ ID NO 34
<211> LENGTH: 480
<212> TYPE: PRT
<213> ORGANISM: Artificial Sequence
<220> FEATURE:
<223> OTHER INFORMATION: synthetic sequence

<400> SEQUENCE: 34

Gln Ser Pro Thr Pro Ser Pro Thr Gly Leu Thr Thr Ala Lys Met Pro
1               5                   10                  15

Ser Val Pro Leu Ser Ser Asp Pro Leu Pro Thr His Thr Thr Ala Phe
            20                  25                  30

Ser Pro Ala Ser Thr Phe Glu Arg Glu Asn Asp Phe Ser Glu Thr Thr
        35                  40                  45

Thr Ser Leu Ser Pro Asp Asn Thr Ser Thr Gln Val Ser Pro Asp Ser
    50                  55                  60

Leu Asp Asn Ala Ser Ala Phe Asn Thr Thr Gly Val Ser Ser Val Gln
65                  70                  75                  80

Thr Pro His Leu Pro Thr His Ala Asp Ser Gln Thr Pro Ser Ala Gly
                85                  90                  95

Thr Asp Thr Gln Thr Phe Ser Gly Ser Ala Ala Asn Ala Lys Leu Asn
            100                 105                 110

Pro Thr Pro Gly Ser Asn Ala Ile Ser Asp Val Pro Gly Glu Arg Ser
        115                 120                 125

Thr Ala Ser Thr Phe Pro Thr Asp Pro Val Ser Pro Leu Thr Thr Thr
    130                 135                 140

Leu Ser Leu Ala His His Ser Ser Ala Ala Leu Pro Ala Arg Thr Ser
145                 150                 155                 160
```

Asn Thr Thr Ile Thr Ala Asn Thr Ser Asp Ala Tyr Leu Asn Ala Ser
165 170 175

Glu Thr Thr Thr Leu Ser Pro Ser Gly Ser Ala Val Ile Ser Thr Thr
180 185 190

Thr Ile Ala Thr Thr Pro Ser Lys Pro Thr Cys Asp Glu Lys Tyr Ala
195 200 205

Asn Ile Thr Val Asp Tyr Leu Tyr Asn Lys Glu Thr Lys Leu Phe Thr
210 215 220

Ala Lys Leu Asn Val Asn Glu Asn Val Glu Cys Gly Asn Asn Thr Cys
225 230 235 240

Thr Asn Asn Glu Val His Asn Leu Thr Glu Cys Lys Asn Ala Ser Val
245 250 255

Ser Ile Ser His Asn Ser Cys Thr Ala Pro Asp Lys Thr Leu Ile Leu
260 265 270

Asp Val Pro Pro Gly Val Glu Lys Phe Gln Leu His Asp Cys Thr Gln
275 280 285

Val Glu Lys Ala Asp Thr Thr Ile Cys Leu Lys Trp Lys Asn Ile Glu
290 295 300

Thr Phe Thr Cys Asp Thr Gln Asn Ile Thr Tyr Arg Phe Gln Cys Gly
305 310 315 320

Asn Met Ile Phe Asp Asn Lys Glu Ile Lys Leu Glu Asn Leu Glu Pro
325 330 335

Glu His Glu Tyr Lys Cys Asp Ser Glu Ile Leu Tyr Asn Asn His Lys
340 345 350

Phe Thr Asn Ala Ser Lys Ile Ile Lys Thr Asp Phe Gly Ser Pro Gly
355 360 365

Glu Pro Gln Ile Ile Phe Cys Arg Ser Glu Ala Ala His Gln Gly Val
370 375 380

Ile Thr Trp Asn Pro Pro Gln Arg Ser Phe His Asn Phe Thr Leu Cys
385 390 395 400

Tyr Ile Lys Glu Thr Glu Lys Asp Cys Leu Asn Leu Asp Lys Asn Leu
405 410 415

Ile Lys Tyr Asp Leu Gln Asn Leu Lys Pro Tyr Thr Lys Tyr Val Leu
420 425 430

Ser Leu His Ala Tyr Ile Ile Ala Lys Val Gln Arg Asn Gly Ser Ala
435 440 445

Ala Met Cys His Phe Thr Thr Lys Ser Ala Pro Pro Ser Gln Val Trp
450 455 460

Asn Met Thr Val Ser Met Thr Ser Asp Asn Ser Met His Val Lys Cys
465 470 475 480

<210> SEQ ID NO 35
<211> LENGTH: 65
<212> TYPE: PRT
<213> ORGANISM: Artificial Sequence
<220> FEATURE:
<223> OTHER INFORMATION: synthetic sequence

<400> SEQUENCE: 35

Ile Thr Cys Pro Pro Pro Met Ser Val Glu His Ala Asp Ile Trp Val
1 5 10 15

Lys Ser Tyr Ser Leu Tyr Ser Arg Glu Arg Tyr Ile Cys Asn Ser Gly
20 25 30

Phe Lys Arg Lys Ala Gly Thr Ser Ser Leu Thr Glu Cys Val Leu Asn
35 40 45

```
Lys Ala Thr Asn Val Ala His Trp Thr Thr Pro Ser Leu Lys Cys Ile
    50                  55                  60

Arg
65


<210> SEQ ID NO 36
<211> LENGTH: 153
<212> TYPE: PRT
<213> ORGANISM: Artificial Sequence
<220> FEATURE:
<223> OTHER INFORMATION: synthetic sequence

<400> SEQUENCE: 36

Met Tyr Arg Met Gln Leu Leu Ser Cys Ile Ala Leu Ser Leu Ala Leu
1               5                   10                  15

Val Thr Asn Ser Gly Ile His Val Phe Ile Leu Gly Cys Phe Ser Ala
            20                  25                  30

Gly Leu Pro Lys Thr Glu Ala Asn Trp Val Asn Val Ile Ser Asp Leu
        35                  40                  45

Lys Lys Ile Glu Asp Leu Ile Gln Ser Met His Ile Asp Ala Thr Leu
    50                  55                  60

Tyr Thr Glu Ser Asp Val His Pro Ser Cys Lys Val Thr Ala Met Lys
65                  70                  75                  80

Cys Phe Leu Leu Glu Leu Gln Val Ile Ser Leu Glu Ser Gly Asp Ala
                85                  90                  95

Ser Ile His Asp Thr Val Glu Asn Leu Ile Ile Leu Ala Asn Asn Ser
            100                 105                 110

Leu Ser Ser Asn Gly Asn Val Thr Glu Ser Gly Cys Lys Glu Cys Glu
        115                 120                 125

Glu Leu Glu Glu Lys Asn Ile Lys Glu Phe Leu Gln Ser Phe Val His
    130                 135                 140

Ile Val Gln Met Phe Ile Asn Thr Ser
145                 150


<210> SEQ ID NO 37
<211> LENGTH: 24
<212> TYPE: PRT
<213> ORGANISM: Artificial Sequence
<220> FEATURE:
<223> OTHER INFORMATION: synthetic sequence

<400> SEQUENCE: 37

Asn Ser Glu Leu Leu Ser Leu Ile Asn Asp Met Pro Ile Thr Asn Asp
1               5                   10                  15

Gln Lys Lys Leu Met Ser Asn Asn
            20


<210> SEQ ID NO 38
<211> LENGTH: 17
<212> TYPE: PRT
<213> ORGANISM: Artificial Sequence
<220> FEATURE:
<223> OTHER INFORMATION: synthetic sequence

<400> SEQUENCE: 38

Gly Thr Gly Gly Thr Gly Thr Gly Ala Gly Thr Ala Gly Gly Thr Ala
1               5                   10                  15

Ala
```

```
<210> SEQ ID NO 39
<211> LENGTH: 17
<212> TYPE: PRT
<213> ORGANISM: Artificial Sequence
<220> FEATURE:
<223> OTHER INFORMATION: synthetic sequence

<400> SEQUENCE: 39

Gly Ala Gly Thr Thr Thr Thr Gly Cys Ala Thr Thr Gly Gly Cys Gly
1               5                   10                  15

Gly


<210> SEQ ID NO 40
<211> LENGTH: 17
<212> TYPE: PRT
<213> ORGANISM: Artificial Sequence
<220> FEATURE:
<223> OTHER INFORMATION: synthetic sequence

<400> SEQUENCE: 40

Gly Ala Gly Gly Gly Thr Gly Gly Thr Thr Gly Thr Cys Ala Ala Thr
1               5                   10                  15

Gly


<210> SEQ ID NO 41
<211> LENGTH: 17
<212> TYPE: DNA
<213> ORGANISM: Artificial Sequence
<220> FEATURE:
<223> OTHER INFORMATION: synthetic sequence

<400> SEQUENCE: 41

gtggtgtgag taggtaa                                                    17


<210> SEQ ID NO 42
<211> LENGTH: 17
<212> TYPE: DNA
<213> ORGANISM: Artificial Sequence
<220> FEATURE:
<223> OTHER INFORMATION: synthetic sequence

<400> SEQUENCE: 42

gagttttgca ttggcgg                                                    17


<210> SEQ ID NO 43
<211> LENGTH: 17
<212> TYPE: DNA
<213> ORGANISM: Artificial Sequence
<220> FEATURE:
<223> OTHER INFORMATION: synthetic sequence

<400> SEQUENCE: 43

gagggtggtt gtcaatg                                                    17
```

CHIMERIC ANTIGEN RECEPTORS (CARS), COMPOSITIONS AND METHODS OF USE THEREOF

CROSS-REFERENCE TO RELATED APPLICATIONS

This application is a national stage filing under 35 USC § 371 of International PCT Application number PCT/US2016/039306, and claims the benefit of under 35 USC § 119(e) of US Provisional Application Nos. 62/184,321, filed Jun. 25, 2015; 62/235,840, filed on Oct. 1, 2015; and 62/244,435, filed Oct. 21, 2015 all of which are incorporated herein by reference in its entirety.

BACKGROUND

T cells, a type of lymphocyte, play a central role in cell-mediated immunity. They are distinguished from other lymphocytes, such as B cells and natural killer cells (NK cells), by the presence of a T-cell receptor (TCR) on the cell surface. T helper cells, also called CD4+ T or CD4 T cells, express CD4 glycoprotein on their surface. Helper T cells are activated when exposed to peptide antigens presented by MHC (major histocompatibility complex) class II molecules. Once activated, these cells proliferate rapidly and secrete cytokines that regulate immune response. Cytotoxic T cells, also known as CD8+ T cells or CD8 T cells, express CD8 glycoprotein on the cell surface. The CD8+ T cells are activated when exposed to peptide antigens presented by MHC class I molecules. Memory T cells, a subset of T cells, persist long term and respond to their cognate antigen, thus providing the immune system with "memory" against past infections and/or tumor cells.

T cells can be genetically engineered to produce special receptors on their surface called chimeric antigen receptors (CARs). CARs are proteins that allow the T cells to recognize a specific protein (antigen) on tumor cells. These engineered CAR T cells are then grown in the laboratory until they number in the billions. The expanded population of CAR T cells is then infused into the patient.

Clinical trials to date have shown chimeric antigen receptor (CAR) T cells to have great promise in hematologic malignancies resistant to standard chemotherapies. Most notably, CD19-specific CAR (CD19CAR) T-cell therapies have had remarkable results including long-term remissions in B-cell malignancies (Kochenderfer, Wilson et al. 2010, Kalos, Levine et al. 2011, Porter, Levine et al. 2011, Davila, Riviere et al. 2013, Grupp, Frey et al. 2013, Grupp, Kalos et al. 2013, Kalos, Nazimuddin et al. 2013, Kochenderfer, Dudley et al. 2013, Kochenderfer, Dudley et al. 2013, Lee, Shah et al. 2013, Park, Riviere et al. 2013, Maude, Frey et al. 2014).

Despite the success of CAR therapy in B-cell leukemia and lymphoma, the application of CAR therapy to T-cell malignancies has not yet been well established. Given that T-cell malignancies are associated with dramatically poorer outcomes compared to those of B-cell malignancies (Abramson, Feldman et al. 2014), CAR therapy in this respect has the potential to further address a great clinical need.

To date, current efforts have focused on CAR T-cells demonstrating efficacy in various B-cell malignancies. While initial remission rates of approximately 90% are common in B-ALL using CD19CAR, most of these relapse within a year. The relapse is at least in part due to the antigen escape. Thus, more effective CAR T cell treatments in order to prevent the relapse is urgently needed. Target discovery and selection are the initial step as there are no general rules to ensure or guide CAR design that are efficacious.

There are some roadblocks that hinder the broader adoption of CAR therapeutic approach. Among the most general challenges are: (1) selection of antigen target and chimeric antigen receptor(s); (2) CAR design; (3) tumor heterogeneity, particularly the variance in the surface expression of tumor antigens. Targeting single antigen carries the risk of immune escape and this could be overcome by targeting multiple desired antigens.

Most CAR chimeric antigen receptors are scFvs derived from monoclonal antibodies and some of these monoclonal antibodies have been used in the clinical trials or treatment for diseases. However, they have limited efficacy, which suggests that alternative and more potent targeting approaches, such as CARs are required. scFvs are the most commonly used chimeric antigen receptor for CARs. However, CAR affinity binding and locations of the recognized epitope on the antigen could affect the function. Additionally the level of the surface CAR expression on the T cells or NK cells is affected by an appropriate leader sequence and promoter. Furthermore, overexpressed CAR proteins can be toxic to cells.

Therefore, there remains a need for improved chimeric antigen receptor-based therapies that allow for more effective, safe, and efficient targeting of T-cell associated malignancies.

SUMMARY OF THE INVENTION

In one embodiment, the present disclosure provides an engineered cell having a first chimeric antigen receptor polypeptide including a first antigen recognition domain, a first signal peptide, a first hinge region, a first transmembrane domain, a first co-stimulatory domain, and a first signaling domain; and a second chimeric antigen receptor polypeptide including a second antigen recognition domain, a second signal peptide, a second hinge region, a second transmembrane domain, a second co-stimulatory domain, and a second signaling domain; wherein the first antigen recognition domain is different than the second antigen recognition domain.

In another embodiment, the present disclosure provides an engineered polypeptide including a chimeric antigen receptor and an enhancer.

In another embodiment, the present disclosure provides an engineered polypeptide including a chimeric antigen receptor polypeptide and an enhancer.

In another embodiment, the present disclosure provides an engineered chimeric antigen receptor polypeptide, the polypeptide including: a signal peptide, a CD45 antigen recognition domain, a hinge region, a transmembrane domain, at least one co-stimulatory domain, and a signaling domain. In another embodiment, the present disclosure provides a polynucleotide encoding for the aforementioned polypeptide.

In another embodiment, the present disclosure provides an engineered cell having the engineered polypeptide or polynucleotide described above.

In another embodiment, the present disclosure provides a method of reducing the number of target cells including the steps of (i.) contacting said target cells with an effective amount of an engineered cell having at least one chimeric antigen receptor polypeptide, for engineered cells having multiple chimeric antigen receptor polypeptides, each chimeric antigen receptor polypeptides are independent; and (ii.) optionally, assaying for the reduction in the number of said cells. The target cells include at least one cell surface antigen selected from the group consisting of interleukin 6 receptor, NY-ESO-1, alpha fetoprotein (AFP), glypican-3 (GPC3), BAFF-R, BCMA, TACI, LeY, CD5, CD13, CD14, CD15 CD19, CD20, CD22, CD33, CD41, CD45, CD61, CD64, CD68, CD117, CD123, CD138, CD267, CD269, CD38, Flt3 receptor, and CS1.

In another embodiment, the present disclosure provides methods for treating B-cell lymphoma, T-cell lymphoma, multiple myeloma, chronic myeloid leukemia, B-cell acute lymphoblastic leukemia (B-ALL), and cell proliferative diseases by administering any of the engineered cells described above to a patient in need thereof.

BRIEF DESCRIPTION OF DRAWINGS

FIG. 15A: Flow cytometry depictions of co-cultures. FIG. 15B: right: graphical summary of lysis vs. E:T ratio.

FIG. 16A: flow cytometry depictions of co-cultures. FIG. 16B: graphical summary of lysis vs. E:T ratio.

FIG. 18A: flow cytometry depictions of co-cultures. FIG. 18B: graphical summary of lysis vs. E:T ratio.

FIG. 19A: flow cytometry depictions of co-cultures. FIG. 19B: graphical summary of lysis vs. E:T ratio.

FIG. 20A: flow cytometry depictions of co-cultures. FIG. 20B: graphical summary of lysis vs. E:T ratio.

DETAILED DESCRIPTION

Figure 1:
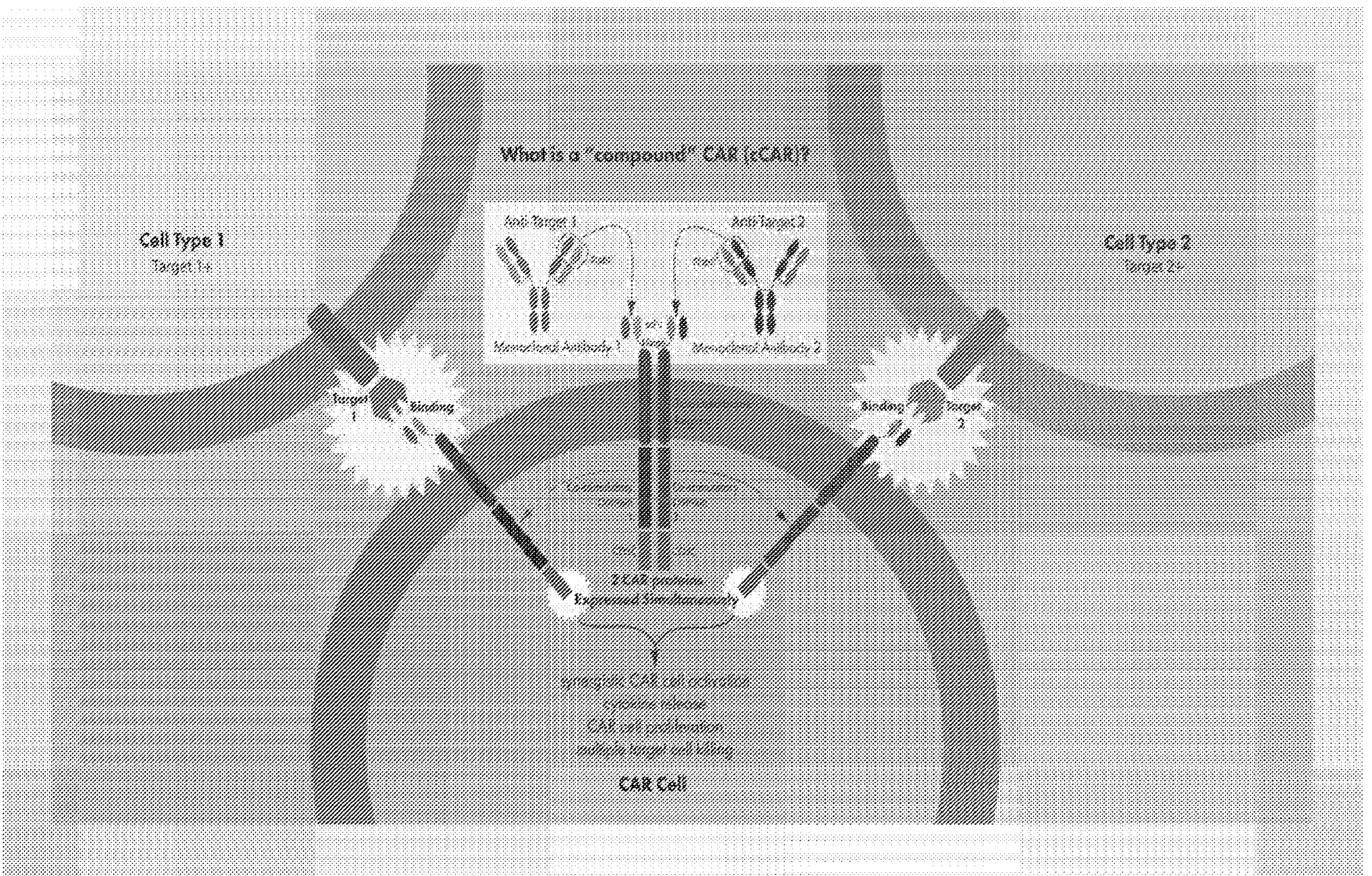
FIG. 1. A schematic representation of cCAR construct (hereinafter, "multiple CAR or compound CAR"). Multiple or compound CAR targets multiple antigens (e.g. cell type 1 or cell type 2 or the same cell type). Multiple or cCAR T cell immunotherapies comprises individual component CAR comprising a different or same antigen recognition domain, a hinge region, a transmembrane domain, various co-stimulatory domain(s) and an intracellular signaling domain.

The disclosure provides chimeric antigen receptor (CAR) compositions, methods of making and using thereof.

A chimeric antigen receptor (CAR) polypeptide includes a signal peptide, an antigen recognition domain, a hinge region, a transmembrane domain, at least one co-stimulatory domain, and a signaling domain.

First-generation CARs include CD3z as an intracellular signaling domain, whereas second-generation CARs include at least one single co-stimulatory domain derived from various proteins. Examples of co-stimulatory domains include, but are not limited to, CD28, CD2, 4-1BB (CD137, also referred to as "4-BB"), and OX-40 (CD124). Third generation CARs include two co-stimulatory domains, such as, without limiting, CD28, 4-1BB, CD134 (OX-40), CD2 and/or CD137 (4-1BB).

As used herein, the terms "peptide," "polypeptide," and "protein" are used interchangeably, and refer to a compound having amino acid residues covalently linked by peptide bonds. A protein or peptide must contain at least two amino acids, and no limitation is placed on the maximum number of amino acids that can include a protein's or peptide's sequence. Polypeptides include any peptide or protein having two or more amino acids joined to each other by peptide bonds. As used herein, the term refers to both short chains, which also commonly are referred to in the art as peptides, oligopeptides, and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "signal peptide" includes a peptide sequence that directs the transport and localization of the peptide and any attached polypeptide within a cell, e.g. to a certain cell organelle (such as the endoplasmic reticulum) and/or the cell surface.

The signal peptide is a peptide of any secreted or transmembrane protein that directs the transport of the polypeptide of the disclosure to the cell membrane and cell surface, and provides correct localization of the polypeptide of the present disclosure. In particular, the signal peptide of the present disclosure directs the polypeptide of the present disclosure to the cellular membrane, wherein the extracellular portion of the polypeptide is displayed on the cell surface, the transmembrane portion spans the plasma membrane, and the active domain is in the cytoplasmic portion, or interior of the cell.

In one embodiment, the signal peptide is cleaved after passage through the endoplasmic reticulum (ER), i.e. is a cleavable signal peptide. In an embodiment, the signal peptide is human protein of type I, II, III, or IV. In an embodiment, the signal peptide includes an immunoglobulin heavy chain signal peptide.

The "antigen recognition domain" includes a polypeptide that is selective for or targets an antigen, receptor, peptide ligand, or protein ligand of the target; or a polypeptide of the target.

The antigen recognition domain may be obtained from any of the wide variety of extracellular domains or secreted proteins associated with ligand binding and/or signal transduction. The antigen recognition domain may include a portion of Ig heavy chain linked with a portion of Ig light chain, constituting a single chain fragment variable (scFv) that binds specifically to a target antigen. The antibody nay be monoclonal or polyclonal antibody or may be of any type that binds specifically to the target antigen. In another embodiment, the antigen recognition domain can be a receptor or ligand. In particular embodiments, the target antigen is specific for a specific disease condition and the disease condition may be of any kind as long as it has a cell surface antigen, which may be recognized by at least one of the chimeric receptor construct present in the compound CAR architecture. In a specific embodiment, the chimeric receptor may be for any cancer for which a specific monoclonal or polyclonal antibody exists or is capable of being generated. In particular, cancers such as neuroblastoma, small cell lung cancer, melanoma, ovarian cancer, renal cell carcinoma, colon cancer, Hodgkin's lymphoma, and childhood acute lymphoblastic leukemia have antigens specific for the chimeric receptors.

The target specific antigen recognition domain preferably includes an antigen binding domain derived from an antibody against an antigen of the target, or a peptide binding an antigen of the target, or a peptide or protein binding an antibody that binds an antigen of the target, or a peptide or protein ligand (including but not limited to a growth factor, a cytokine, or a hormone) binding a receptor on the target, or a domain derived from a receptor (including but not limited to a growth factor receptor, a cytokine receptor or a hormone receptor) binding a peptide or protein ligand on the target.

In one embodiment, the antigen recognition domain includes the binding portion or variable region of a monoclonal or polyclonal antibody directed against (selective for) the target.

In another embodiment, the antigen recognition domain includes Camelid single domain antibody, or portions thereof. In one embodiment, Camelid single-domain antibodies include heavy-chain antibodies found in camelids, or VHH antibody. A VHH antibody of camelid (for example camel, dromedary, llama, and alpaca) refers to a variable fragment of a camelid single-chain antibody (See Nguyen et al, 2001; Muyldermans, 2001), and also includes an isolated VHH antibody of camelid, a recombinant VHH antibody of camelid, or a synthetic VHH antibody of camelid.

In another embodiment, the antigen recognition domain includes ligands that engage their cognate receptor. By way of example, APRIL is a ligand that binds the TAC1 receptor or the BCMA receptor. In accordance with an invention disclosed herein, the antigen recognition domain includes APRIL, or a fragment thereof. By way of further example, BAFF is a ligand that binds the BAFF-R receptor or the BCMA receptor. In accordance with an invention disclosed herein, the antigen recognition domain includes BAFF, or a fragment thereof. In another embodiment, the antigen recognition domain is humanized.

It is understood that the antigen recognition domain may include some variability within its sequence and still be selective for the targets disclosed herein. Therefore, it is contemplated that the polypeptide of the antigen recognition domain may be at least 95%, at least 90%, at least 80%, or at least 70% identical to the antigen recognition domain polypeptide disclosed herein and still be selective for the targets described herein and be within the scope of the disclosure.

The target includes interleukin 6 receptor, NY-ESO-1, alpha fetoprotein (AFP), glypican-3 (GPC3), BCMA, BAFF-R, TACI, LeY, CD5, CD13, CD14, CD15 CD19, CD20, CD22, CD33, CD41, CD61, CD64, CD68, CD117, CD123, CD138, CD267, CD269, CD38, Flt3 receptor, CS1, CD45, ROR1, PSMA, MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, CD30, EGFRvIII, immunoglobin kappa and lambda, CD38, CD52, CD3, CD4, CD8, CD5, CD7, CD2, and CD138

In another embodiment, the target includes any portion interleukin 6 receptor, NY-ESO-1, alpha fetoprotein (AFP), glypican-3 (GPC3), BCMA, BAFF-R, TACI, LeY, CD5, CD13, CD14, CD15 CD19, CD20, CD22, CD33, CD41, CD61, CD64, CD68, CD117, CD123, CD138, CD267, CD269, CD38, Flt3 receptor, CS1, CD45, TACI, ROR1, PSMA, MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, CD30, EGFRvIII, immunoglobin kappa and lambda, CD38, CD52, CD3, CD4, CD8, CD5, CD7, CD2, and CD138.

In one embodiment, the target includes surface exposed portions of interleukin 6 receptor, NY-ESO-1, alpha fetoprotein (AFP), glypican-3 (GPC3), BCMA, BAFF-R, TACI, LeY, CD5, CD13, CD14, CD15 CD19, CD20, CD22, CD33, CD41, CD61, CD64, CD68, CD117, CD123, CD138, CD267, CD269, CD38, Flt3 receptor, CS1, CD45, TACI, ROR1, PSMA, MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, CD30, EGFRvIII, immunoglobin kappa and lambda, CD38, CD52, CD3, CD4, CD8, CD5, CD7, CD2, and CD138 polypeptides.

In another embodiment, the target antigens include viral or fungal antigens, such as E6 and E7 from the human papillomavirus (HPV) or EBV (Epstein Barr virus) antigens; portions thereof; or surface exposed regions thereof.

In one embodiment, the TACI antigen recognition domain includes SEQ ID NO. 24.

In one embodiment, the BCMA antigen recognition domain includes SEQ ID NO. 25.

In one embodiment, the CS1 antigen recognition domain includes SEQ ID NO. 26.

In one embodiment, the BAFF-R antigen recognition domain includes SEQ ID NO. 27.

In one embodiment, the CD33 antigen recognition domain includes SEQ ID NO. 28.

In one embodiment, the CD123 antigen recognition domain includes SEQ ID NO. 29.

In one embodiment, the CD19 antigen recognition domain includes SEQ ID NO. 30.

In one embodiment, the CD20 antigen recognition domain includes SEQ ID NO. 31. In another embodiment, the CD20 antigen recognition domain includes SEQ ID NO. 32.

In one embodiment, the CD22 antigen recognition domain includes SEQ ID NO. 33.

In on embodiment, the CD45 antigen recognition domain includes SEQ ID NO. 34

The hinge region is a sequence positioned between for example, including, but not limited to, the chimeric antigen receptor, and at least one co-stimulatory domain and a signaling domain. The hinge sequence may be obtained including, for example, from any suitable sequence from any genus, including human or a part thereof. Such hinge regions are known in the art. In one embodiment, the hinge region includes the hinge region of a human protein including CD-8 alpha, CD28, 4-1BB, OX40, CD3-zeta, T cell receptor α or β chain, a CD3 zeta chain, CD28, CD3ε, CD45, CD4, CD5, CD8, CD8a, CD9, CD16, CD22, CD33, CD37, CD64, CD80, CD86, CD134, CD137, ICOS, CD154, functional derivatives thereof, and combinations thereof.

In one embodiment the hinge region includes the CD8 a hinge region.

In some embodiments, the hinge region includes one selected from, but is not limited to, immunoglobulin (e.g. IgG1, IgG2, IgG3, IgG4, and IgD).

The transmembrane domain includes a hydrophobic polypeptide that spans the cellular membrane. In particular, the transmembrane domain spans from one side of a cell membrane (extracellular) through to the other side of the cell membrane (intracellular or cytoplasmic).

The transmembrane domain may be in the form of an alpha helix or a beta barrel, or combinations thereof. The transmemebrane domain may include a polytopic protein, which has many transmembrane segments, each alpha-helical, beta sheets, or combinations thereof.

In one embodiment, the transmembrane domain that is naturally associated with one of the domains in the CAR is used. In another embodiment, the transmembrane domain is selected or modified by amino acid substitution to avoid binding of such domains to the transmembrane domains of the same or different surface membrane proteins to minimize interactions with other members of the receptor complex.

For example, a transmembrane domain includes a transmembrane domain of a T-cell receptor α or β chain, a CD3 zeta chain, CD28, CD3ε, CD45, CD4, CD5, CD7, CD8, CD9, CD16, CD22, CD33, CD37, CD64, CD80, CD86, CD68, CD134, CD137, ICOS, CD41, CD154, functional derivatives thereof, and combinations thereof.

In one embodiment, the transmembrane domain is artificially designed so that more than 25%, more than 50% or more than 75% of the amino acid residues of the domain are hydrophobic residues such as leucine and valine. In one embodiment, a triplet of phenylalanine, tryptophan and valine is found at each end of the synthetic transmembrane domain.

In one embodiment, the transmembrane domain is the CD8 transmembrane domain. In another embodiment, the transmembrane domain is the CD28 transmembrane domain. Such transmembrane domains are known in the art.

The signaling domain and co-stimulatory domain include polypeptides that provide activation of an immune cell to stimulate or activate at least some aspect of the immune cell signaling pathway.

In an embodiment, the signaling domain includes the polypeptide of a functional signaling domain of CD3 zeta, common FcR gamma (FCER1G), Fc gamma RIIa, FcR beta (Fc Epsilon Rib), CD3 gamma, CD3 delta, CD3 epsilon, CD79a, CD79b, DNAX-activating protein 10 (DAP10), DNAX-activating protein 12 (DAP12), active fragments thereof, functional derivatives thereof, and combinations thereof. Such signaling domains are known in the art.

In an embodiment, the CAR polypeptide further includes one or more co-stimulatory domains. In an embodiment, the co-stimulatory domain is a functional signaling domain from a protein including OX40; CD27; CD28; CD30; CD40; PD-1; CD2; CD7; CD258; Natural killer Group 2 member C (NKG2C); Natural killer Group 2 member D (NKG2D), B7-H3; a ligand that binds to at least one of CD83, ICAM-1, LFA-1 (CD11a/CD18), ICOS, and 4-1BB (CD137); CDS; ICAM-1; LFA-1 (CD1a/CD18); CD40; CD27; CD7; B7-H3; NKG2C; PD-1; ICOS; active fragments thereof; functional derivatives thereof; and combinations thereof.

As used herein, the at least one co-stimulatory domain and signaling domain may be collectively referred to as the intracellular domain. As used herein, the hinge region and the antigen recognition may be collectively referred to as the extracellular domain.

The present disclosure further provides a polynucleotide encoding the chimeric antigen receptor polypeptide described above.

The term "polynucleotide" as used herein is defined as a chain of nucleotides. Polynucleotide includes DNA and RNA. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and polymerase chain reaction (PCR), and the like, and by synthetic means.

The polynucleotide encoding the CAR is easily prepared from an amino acid sequence of the specified CAR by any conventional method. A base sequence encoding an amino acid sequence can be obtained from the aforementioned NCBI RefSeq IDs or accession numbers of GenBenk for an amino acid sequence of each domain, and the nucleic acid of the present disclosure can be prepared using a standard molecular biological and/or chemical procedure. For example, based on the base sequence, a polynucleotide can be synthesized, and the polynucleotide of the present disclosure can be prepared by combining DNA fragments which are obtained from a cDNA library using a polymerase chain reaction (PCR).

In one embodiment, the polynucleotide disclosed herein is part of a gene, or an expression or cloning cassette.

The polynucleotide described above can be cloned into a vector. A "vector" is a composition of matter which includes an isolated polynucleotide and which can be used to deliver the isolated polynucleotide to the interior of a cell. Numerous vectors are known in the art including, but not limited to, linear polynucleotides, polynucleotides associated with ionic or amphiphilic compounds, plasmids, phagemid, cosmid, and viruses. Viruses include phages, phage derivatives. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like. In one embodiment, vectors include cloning vectors, expression vectors, replication vectors, probe generation vectors, integration vectors, and sequencing vectors.

In an embodiment, the vector is a viral vector. In an embodiment, the viral vector is a retroviral vector or a lentiviral vector. In an embodiment, the engineered cell is virally transduced to express the polynucleotide sequence.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the patient either in vivo or ex vivo. A number of retroviral systems are known in the art. In some embodiments, adenovirus vectors are used. A number of adenovirus vectors are known in the art. In one embodiment, lentivirus vectors are used.

Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endomiclease sites, and one or more selectable markers, (e.g., WO 01/96584; WO 01/29058; and U.S. Pat. No. 6,326,193).

Lentiviral vectors have been well known for their capability of transferring genes into human T cells with high efficiency but expression of the vector-encoded genes is dependent on the internal promoter that drives their expression. A strong promoter is particularly important for the third or fourth generation of CARs that bear additional co-stimulatory domains or genes encoding proliferative cytokines as increased CAR body size does not guarantee equal levels of expression. There are a wide range of promoters with different strength and cell-type specificity. Gene therapies using CAR T cells rely on the ability of T cells to express adequate CAR body and maintain expression over a long period of time. The EF-1α promoter has been commonly selected for the CAR expression.

The present invention relates to an expression vector containing a strong promoter for high level gene expression in T cells or NK cells. In further embodiment, the inventor discloses a strong promoter useful for high level expression of CARs in T cells or NK cells. In particular embodiments, a strong promoter relates to the SFFV promoter, which is selectively introduced in an expression vector to obtain high levels of expression and maintain expression over a long period of time in T cells or NK cells. Expressed genes prefer CARs, T cell co-stimulatory factors and cytokines used for immunotherapy.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1a (EF-1a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the disclosure should not be limited to the use of constitutive promoters, inducible promoters are also contemplated as part of the disclosure. The use of an inducible promoter provides a molecular switch capable of turning on expression of the polynucleotide sequence, which is operatively linked when such expression is desired, or turning off the expression when expression is not desired. Examples of inducible promoters include, but are not limited to a metalothionine promoter, a glucocorticoid promoter, a progesterone promoter, and a tetracycline promoter.

Expression of chimeric antigen receptor polynucleotide may be achieved using, for example, expression vectors including, but not limited to, at least one of a SFFV (spleen-focus forming virus) (for example, SEQ ID NO. 23) or human elongation factor 11α (EF) promoter, CAG (chicken beta-actin promoter with CMV enhancer) promoter human elongation factor 1α (EF) promoter. Examples of less-strong/lower-expressing promoters utilized may include, but is not limited to, the simian virus 40 (SV40) early promoter, cytomegalovirus (CMV) immediate-early promoter, Ubiquitin C (UBC) promoter, and the phosphoglycerate kinase 1 (PGK) promoter, or a part thereof. Inducible expression of chimeric antigen receptor may be achieved using, for example, a tetracycline responsive promoter, including, but not limited to, TRE3GV (Tet-response element, including all generations and preferably, the 3rd generation), inducible promoter (Clontech Laboratories, Mountain View, Calif.) or a part or a combination thereof.

In a preferred embodiment, the promoter is an SFFV promoter or a derivative thereof. It has been unexpectedly discovered that SFFV promoter provides stronger expression and greater persistence in the transduced cells in accordance with the present disclosure.

"Expression vector" refers to a vector including a recombinant polynucleotide comprising expression control sequences operatively linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide. The expression vector may be a bicistronic or multicistronic expression vectors. Bicistronic or multicistronic expression vectors may include (1) multiple promoters fused to each of the open reading frames; (2) insertion of splicing signals between genes; fusion of genes whose expressions are driven by a single promoter; (3) insertion of proteolytic cleavage sites between genes (self-cleavage peptide); and (iv) insertion of internal ribosomal entry sites (IRESs) between genes.

In one embodiment, the disclosure provides an engineered cell having at least one chimeric antigen receptor polypeptide or polynucleotide.

An "engineered cell" means any cell of any organism that is modified, transformed, or manipulated by addition or modification of a gene, a DNA or RNA sequence, or protein or polypeptide. Isolated cells, host cells, and genetically engineered cells of the present disclosure include isolated immune cells, such as NK cells and T cells that contain the DNA or RNA sequences encoding a chimeric antigen receptor or chimeric antigen receptor complex and express the chimeric receptor on the cell surface. Isolated host cells and engineered cells may be used, for example, for enhancing an NK cell activity or a T lymphocyte activity, treatment of cancer, and treatment of infectious diseases.

In an embodiment, the engineered cell includes immunoregulatory cells. Immunoregulatory cells include T-cells, such as CD4 T-cells (Helper T-cells), CD8 T-cells (Cytotoxic T-cells, CTLs), and memory T cells or memory stem cell T cells. In another embodiment, T-cells include Natural Killer T-cells (NK T-cells).

In an embodiment, the engineered cell includes Natural Killer cells. Natural killer cells are well known in the art. In one embodiment, natural killer cells include cell lines, such as NK-92 cells. Further examples of NK cell lines include NKG, YT, NK-YS, HANK-1, YTS cells, and NKL cells.

NK cells mediate anti-tumor effects without the risk of GvHD and are short-lived relative to T-cells. Accordingly, NK cells would be exhausted shortly after destroying cancer cells, decreasing the need for an inducible suicide gene on CAR constructs that would ablate the modified cells.

In accordance with the present disclosure, it was surprisingly found that NK cells provide a readily available cell to be engineered to contain and express the chimeric antigen receptor polypeptides disclosed herein.

Allogeneic or autologous NK cells induce a rapid immune response but disappear relatively rapidly from the circulation due to their limited lifespan. Thus, applicants surprisingly discovered that there is reduced concern of persisting side effects using CAR cell based therapy.

The disclosure includes a method of generating a cCAR. In some embodiments, the cCAR is generated using T-cells. In other embodiments, cCAR is using primary NK cells isolated from the peripheral blood or cord blood and NK-92 cells, such that they are administered "off-the-shelf" to any mammal with a disease or cancer.

According to one aspect of the present invention, NK cells can be expanded and transfected with CAR polynucleotides in accordance to the present invention. NK cells can be derived from cord blood, peripheral blood, iPS cells and embryonic stem cells. According to one aspect of the present invention, NK-92 cells may be expanded and transfected with CAR. NK-92 is a continuously growing cell line that has features and characteristics of natural killer (NK) cells (Arai, Meagher et al. 2008). NK-92 cell line is IL-2 dependent and has been proven to be safe (Arai, Meagher et al. 2008) and feasible. CAR expressing NK-92 cells can be expanded in the serum free-medium with or without co-culturing with feeder cells. A pure population of NK-92 carrying the CAR of interest may be obtained by sorting.

In one embodiment, engineered cells include allogeneic T cells obtained from donors that are modified to inactivate components of TCR (T cell receptor) involved in MHC recognition. As a result, TCR deficient T cells would not cause graft versus host disease (GVHD).

In some embodiments, the engineered cell may be modified to prevent expression of cell surface antigens. For example, an engineered cell may be genetically modified to delete the native CD45 gene to prevent expression and cell surface display thereof.

In some embodiments, the engineered cell includes an inducible suicide gene ("safety switch") or a combination of safety switches, which may be assembled on a vector, such as, without limiting, a retroviral vector, lentiviral vector, adenoviral vector or plasmid. Introduction of a "safety switch" greatly increases safety profile and limits on-target or off-tumor toxicities of the compound CARs. The "safety switch" may be an inducible suicide gene, such as, without limiting, caspase 9 gene, thymidine kinase, cytosine deaminase (CD) or cytochrome P450. Other safety switches for elimination of unwanted modified T cells involve expression of CD20 or CD19 or truncated epidermal growth factor receptor in T cells. All possible safety switches are have been contemplated and are embodied in the present invention.

In some embodiments, the suicide gene is integrated into the engineered cell genome.

In one embodiment, the present disclosure provides an engineered cell having a CD45 chimeric antigen receptor polynucleotide. In one embodiment, the CD45 CAR polypeptide includes SEQ ID NO. 13 and corresponding polynucleotide sequence SEQ ID NO. 14. In another embodiment, the CD45 CAR polypeptide includes SEQ ID NO. 15, and corresponding polynucleotide sequence SEQ ID NO. 16. In another embodiment, the CD45 CAR polypeptide includes SEQ ID NO. 17, and corresponding polynucleotide sequence SEQ ID NO. 18.

Multiple CAR Units

The present disclosure provides an engineered cell having at least two distinct CAR polypeptides.

As used herein, compound CAR (cCAR) or multiple CAR refers to an engineered cell having at least two distinct chimeric antigen receptor polypeptides. As used herein, a "distinct chimeric antigen receptor polypeptide" has a unique antigen recognition domain, a signal peptide, a hinge region, a transmembrane domain, at least one costimulatory domain, and a signaling domain. Therefore, two unique chimeric antigen receptor polypeptides will have different antigen recognition domains. The signal peptide, hinge region,transmembranedomain, at least one costimulatory domain, and signaling domain may be the same or different between the two distinct chimeric antigen receptor polypeptides. As used herein, a chimeric antigen receptor (CAR) unit refers to a distinct chimeric antigen receptor polypeptide, or a polynucleotide encoding for the same.

As used herein, a unique antigen recognition domain is one that is specific for or targets a single target, or a single epitope of a target.

In some embodiments, the compound CAR targets the same antigen. For example, cCAR targets different epitopes or parts of a single antigen. In some embodiments, each of the CAR units present in the compound CAR targets different antigen specific to the same or different disease condition or side effects caused by a disease condition.

In some embodiments, the compound CAR targets two different antigens.

Creation of compound CARs bearing different CAR units can be quiet challenging: (1) CAR-CAR interactions might have a deleterious effect and an appropriate CAR design is a key to offset this effect; (2) a compound CAR in a single construct could increase the length of the expression cassette, which may cause the reduction of the viral titer and level of protein expression; (3) an appropriate design to include various CAR body elements particularly to select a strategy to express multiple CARs in a single vector is required; (4) A strong promoter is particularly important for a compound CAR that bears additional units of CAR; (5) The hinge region in the CAR needs to is designed so that interaction of the hinge region between each CAR unit is avoided preferably; (6) two or more units of CARs expressing in a cell may cause toxic effects (CAR-CAR interaction). Applicants herein provide a novel and surprising CAR compositions and methods to overcome these hurdles.

In one embodiment, the present disclosure provides an engineered cell having multiple CAR units. This allows a single engineered cell to target multiple antigens. Targeting multiple surface markers or antigens simultaneously with a multiple CAR units prevents selection of resistant clones and reduces tumor recurrence. Multiple CAR T cell immunotherapies, with each individual component CAR comprising various domains and activation sites has not yet been developed for any malignancies.

In one aspect of the present invention, cCAR includes multiple CAR units. In some embodiments, cCAR includes at least two CAR units. In another embodiment, the cCAR includes at least three CAR units. In another embodiment, the cCAR includes at least four units.

In one embodiment, the present disclosure provides an engineered cell having at least two distinct chimeric antigen receptor polypeptides, each having a different antigen recognition domain.

In a preferred embodiment, the engineered cell having at least two distinct chimeric antigen receptor polypeptides is a primary NK cells isolated from the peripheral blood or cord blood and NK-92 cells, such that they are administered "off-the-shelf" to any mammal with a disease or cancer.

In one embodiment, the engineered cell includes (i.) a first chimeric antigen receptor polypeptide comprising a first antigen recognition domain, a first signal peptide, a first hinge region, a first transmembrane domain, a first co-stimulatory domain, and a first signaling domain; and (ii.) a second chimeric antigen receptor polypeptide comprising a second antigen recognition domain, a second signal peptide, a second hinge region, a second transmembrane domain, a second co-stimulatory domain, and a second signaling domain. The first antigen recognition domain is different from the second antigen recognition domain.

In a preferred embodiment, each engineered CAR unit polynucleotide have different nucleotide sequences in order to avoid homologous recombination.

In one embodiment, the target of the first antigen recognition domain is selected from the group consisting of interleukin 6 receptor, NY-ESO-1, alpha fetoprotein (AFP), glypican-3 (GPC3), BAFF-R, BCMA, TACI, LeY, CD5, CD13, CD14, CD15 CD19, CD20, CD22, CD33, CD41, CD61, CD64, CD68, CD117, CD123, CD138, CD267, CD269, CD38, Flt3 receptor, and CS1; and the target of the second recognition domain is selected from the group consisting of interleukin 6 receptor, NY-ESO-1, alpha fetoprotein (AFP), glypican-3 (GPC3), BAFF-R, BCMA, TACI, LeY, CD5, CD13, CD14, CD15 CD19, CD20, CD22, CD33, CD41, CD61, CD64, CD68, CD117, CD123, CD138, CD267, CD269, CD38, Flt3 receptor, and CS1.

In one embodiment, the engineered cell includes a first chimeric antigen receptor polypeptide having a CD19 antigen recognition domain and second chimeric antigen receptor polypeptide having a CD20 recognition domain. In one embodiment, this engineered cell includes a polypeptide of SEQ ID NO. 3 and corresponding polynucleotide of SEQ ID NO. 4.

In one embodiment, the engineered cell includes a first chimeric antigen receptor polypeptide having a CD19 antigen recognition domain and second chimeric antigen receptor polypeptide having a CD22 antigen recognition domain. In one embodiment, this engineered cell includes a polypeptide of SEQ ID NO. 5 and corresponding polynucleotide of SEQ ID NO. 6.

In one embodiment, the engineered cell includes a first chimeric antigen receptor polypeptide having a CD19 antigen recognition domain and second chimeric antigen receptor polypeptide having a CD123 antigen recognition domain. In one embodiment, this engineered cell includes a polypeptide of SEQ ID NO. 7 and corresponding polynucleotide of SEQ ID NO. 8.

In one embodiment, the engineered cell includes a first chimeric antigen receptor polypeptide having a CD33 antigen recognition domain and second chimeric antigen receptor polypeptide having a CD123antigen recognition domain. In one embodiment, this engineered cell includes a polypeptide of SEQ ID NO. 9 and corresponding polynucleotide of SEQ ID NO. 10. In another embodiment, this engineered cell includes a polypeptide of SEQ ID NO. 11 and corresponding polynucleotide of SEQ ID NO. 12.

In one embodiment, the engineered cell includes a first chimeric antigen receptor polypeptide having a BAFF-R antigen recognition domain and second chimeric antigen receptor polypeptide having a CS lantigen recognition domain.

In one embodiment, the engineered cell includes a first chimeric antigen receptor polypeptide having a CD269 antigen recognition domain and second chimeric antigen receptor polypeptide having a CS1 antigen recognition domain. In one embodiment, the engineered cell includes a polypeptide including SEQ ID NO. 19 and corresponding polynucleotide SEQ ID NO. 20. In one embodiment, the engineered cell includes a polpeptide including SEQ ID NO. 21 and corresponding polynucleotide SEQ ID NO. 22.

In one embodiment, the engineered cell includes a first chimeric antigen receptor polypeptide having a CD33 antigen recognition domain and second chimeric antigen receptor polypeptide having a CD123 antigen recognition domain.

In one embodiment, each CAR unit includes the same or different hinge region. In another embodiment, each CAR unit includes the same or different transmembrane region. In another embodiment, each CAR unit includes the same or different intracellular domain.

In one embodiment, each CAR unit includes the CD3 zeta chain signaling domain.

In one embodiment, each distinct CAR unit includes different co-stimulatory domains to avoid interaction. For example, the first chimeric antigen receptor polypeptide includes a 4-BB co-stimulatory domain; and the second chimeric antigen receptor polypeptide includes a CD28 co-stimulatory domain.

In another embodiment, the hinge region is designed to exclude amino acids that may cause undesired intra- or intermolecular interactions. For example, the hinge region may be designed to exclude or minimize cysteine residues to prevent formation of disulfide bonds. In another embodiment, the hinge region may be designed to exclude or minimize hydrophobic residues to prevent unwanted hydrophobic interactions.

Compound CAR can perform killing independently or in combination. Multiple or compound CAR comprises same or different hinge region, same or different transmembrane, same or different co-stimulatory and same or different intracellular domains. Preferably, the hinge region is selected to avoid the interaction site.

The compound CAR of the present invention may target same or different tumor populations in T or NK cells. The first CAR, for example, may target the bulky tumor population and the next or the second CAR, for example, may eradicate cancer or leukemic stem cells, to avoid cancer relapses.

In accordance with the present invention it was surprisingly found that the compound CAR in a T or NK cells targeting different or same tumor populations combat tumor factors causing cancer cells resistant to the CAR killing activity, thereby producing down regulation of the target antigen from the cancer cell surface. It was also surprisingly found that this enables the cancer cell to “hide” from the CAR therapy referred to as “antigen escape” and tumor heterogeneity, by which different tumor cells can exhibit distinct surface antigen expression profiles.

Engineered Cell Having CAR Polypeptide and Enhancer

In another embodiment, the present disclosure provides an engineered cell having at least one chimeric antigen receptor polypeptide and an enhancer.

In one embodiment, the present disclosure provides an engineered cell having at least two distinct chimeric antigen receptor polypeptides and an enhancer.

As used herein, an enhancer includes a biological molecule that promotes or enhances the activity of the engineered cell having the chimeric antigen receptor polypeptide. Enhancers include cytokines. In another embodiment, enhancers include IL-2, IL-7, IL-12, IL-15, IL-21, PD-1, PD-L1, CSF1R, CTAL-4, TIM-3, and TGFR beta, receptors for the same, and functional fragments thereof.

Enhancers may be expressed by the engineered cell described herein and displayed on the surface of the engineered cell or the enhancer may be secreted into the surrounding extracellular space by the engineered cell. Methods of surface display and secretion are well known in the art. For example, the enhancer may be a fusion protein with a peptide that provides surface display or secretion into the extracellular space.

The effect of the enhancer may be complemented by additional factors such as enhancer receptors and functional fragments thereof. The additional factors may be co-expressed with the enhancer as a fusion protein or expressed as a separate peptide and secreted into the extracellular space.

In one embodiment, the enhancer is IL-15. In this instance, the additional factor is the IL-15 receptor, and functional fragments thereof. Functional fragments include the IL-15 receptor, IL-15RA, and the sushi domain of IL-15RA. An example of a suitable sushi domain includes SEQ ID NO. 35. In accordance with the present disclosure, any chimeric antigen receptor polypeptide disclosed herein includes the Human Interleukin 15 with human interleukin 2 signal peptide SEQ ID NO. 36.

Interleukin (IL)-15 and its specific receptor chain, IL-15Rα (IL-15-RA) play a key functional role in various effector cells, including NK and CD8 T cells. CD8+ T cells can be modified to express autocrine growth factors including, but not limited to, IL-2, Il-7, IL21 or IL-15, to sustain survival following transfer in vivo. Without wishing to be bound by theory, it is believed that IL-15 could overcome the CD4 deficiency to induce primary and recall memory CD8T cells. Overexpression of IL-15-RA or an IL-15 IL-RA fusion on CD8 T cells significantly enhances its survival and proliferation in-vitro and in-vivo. In some embodiments, CD4CAR or any CAR can include expressing any one or more of moieties, IL-15, IL15RA and IL-15/IL-15R or IL15-RA/IL-15, or a part or a combination thereof, to enhance survival or proliferation of CAR T or NK, and to improve expansion of memory CAR CD8+ T cells.

The present disclosure relates to an engineered cell having a CAR as described herein and any one or more of moieties of IL-15, IL15RA and IL-15/IL-15R or IL15-RA/IL-15, or a part or a combination thereof, to enhance survival or persistent or proliferation of CAR T or NK for treating cancer in a patient.

In one embodiment, the engineered cell includes a CD4 chimeric antigen receptor polypeptide and IL-15RA (SEQ ID NO. 1), and corresponding polynucleotide (SEQ ID NO. 2).

Methods of Generating Engineered Cells

Any of the polynucleotides disclosed herein may be introduced into an engineered cell by any method known in the art.

In one embodiment, CAR polynucleotides are delivered to the engineered cell by any viral vector as disclosed herein.

In one embodiment, to achieve enhanced safety profile or therapeutic index, the any of the engineered cells disclosed herein be constructed as a transient RNA-modified "biodegradable" version or derivatives, or a combination thereof. The RNA-modified CARs of the present invention may be electroporated into T cells or NK cells. The expression of the compound CAR may be gradually diminished over few days.

In some embodiments of the present invention, any of the engineered cells disclosed herein may be constructed in a transponson system (also called a "Sleeping Beauty"), which integrates the CAR DNA into the host genome without a viral vector.

Methods of Generating an Engineered Cell Having Multiple CAR Units

In another embodiment, the present disclosure provides a method making an engineered cell having at least two CAR units.

In some embodiments, multiple units of CAR are expressed in a T or NK cell using bicistronic or multicistronic expression vectors. There are several strategies can be employed to construct bicistronic or multicistronic vectors including, but not limited to, (1) multiple promoters fused to the CARs' open reading frames; (2) insertion of splicing signals between units of CAR; fusion of CARs whose expressions are driven by a single promoter; (3) insertion of proteolytic cleavage sites between units of CAR (self-cleavage peptide); and (iv) insertion of internal ribosomal entry sites (IRESs).

In a preferred embodiment, multiple CAR units are expressed in a single open reading frame (ORF), thereby creating a single polypeptide having multiple CAR units. In this embodiment, an amino acid sequence or linker containing a high efficiency cleavage site is disposed between each CAR unit.

As used herein, high cleavage efficiency is defined as more than 50%, more than 70%, more than 80%, or more than 90% of the translated protein is cleaved. Cleavage efficiency may be measured by Western Blot analysis, as described by Kim 2011.

Furthermore, in a preferred embodiment, there are equal amounts of cleavage product, as shown on a Western Blot analysis.

Examples of high efficiency cleavage sites include porcine teschovirus-1 2A (P2A), FMDV 2A (abbreviated herein as F2A); equine rhinitis A virus (ERAV) 2A (E2A); and Thoseaasigna virus 2A (T2A), cytoplasmic polyhedrosis virus 2A (BmCPV2A) and flacherie Virus 2A (BmIFV2A), or a combination thereof. In a preferred embodiment, the high efficiency cleavage site is P2A. High efficiency cleavage sites are described in Kim J H, Lee S-R, Li L-H, Park H-J, Park J-H, Lee K Y, et al. (2011) High Cleavage Efficiency of a 2A Peptide Derived from Porcine Teschovirus-1 in Human Cell Lines, Zebrafish and Mice. PLoS ONE 6(4): e18556, the contents of which are incorporated herein by reference.

In embodiments wherein multiple CAR units are expressed in a single open reading frame (ORF), expression is under the control of a strong promoter. Examples of strong promoters include the SFFV promoter, and derivatives thereof.

Engineered Cell Having CAR Polypeptide and Enhancer

In another embodiment, the present disclosure provides a method making an engineered cell that expresses at least one CAR unit and an enhancer.

In some embodiments, at least one CAR unit and enhancer is expressed in a T or NK cell using bicistronic or multicistronic expression vectors. There are several strategies can be employed to construct bicistronic or multicistronic vectors including, but not limited to, (1) multiple promoters fused to the CARs' open reading frames; (2) insertion of splicing signals between units of CAR; fusion of CARs whose expressions are driven by a single promoter; (3) insertion of proteolytic cleavage sites between units of CAR (self-cleavage peptide); and (iv) insertion of internal ribosomal entry sites (IRESs).

In a preferred embodiment, at least one CAR unit and an enhancer are expressed in a single open reading frame (ORF), thereby creating a single polypeptide having at least one CAR unit and an enhancer. In this embodiment, an amino acid sequence or linker containing a high efficiency cleavage site is disposed between each CAR unit and between a CAR unit and enhancer. In this embodiment, the ORF is under the control of a strong promoter. Examples of strong promoters include the SFFV promoter, and derivatives thereof.

Furthermore, in a preferred embodiment, there are equal amounts of cleavage product, as shown on a Western Blot analysis.

Methods of Treatment Using the Compositions Disclosed Herein

In another embodiment, the present invention provides a method of targeting CD45 for conditioning prior to allogenic transplantation in cancer treatment. CD45 is also known as leukocyte common antigen (LCA) and is a tyrosine phosphatase expressed on virtually all cells of hematopoietic origin except erythrocytes and platelets. Most hematologic malignancies express CD45. For instance, 85% to 90% acute lymphoid and myeloid leukemias express CD45. CD45 is not found in non-hematopoietic origin. In addition, CD45 is expressed at a high density of an average copy number of approximately 200,000 molecules per cells oil malignant cells and leukocytes. CD45 presents an ideal target for a variety of hematologic malignancies. However, CAR T and NK cells also express CD45. Without inactivation of endogenous CD45, CAR T or NK cells armed with CARs targeting CD45 may result in self-killing.

The association of CD45 with TCR complexes is essential in regulation of 7-cell activation in response to antigen. The inability of CD45-deficient T cells to present antigen is due to reduced signaling through the T cell receptors (TCRs). TCRs are cell surface receptors that play an essential role in the activation of T cells in response to the presentation of antigen. The TCR is generally made from two chains, alpha and beta, which are associated with the transducing subunits, the CD3, to form the T-cell receptor complex present on the cell surface.

It was surprisingly found that multiple CARs (Compound CARs, cCAR) of the present invention combat a key mechanism by which cancer cells resist CAR activity, i.e., the downregulation or heterogeneous expression of the target antigen from the cancer cell surface. This mechanism allows the cancer cell to "hide" from the CAR therapy, a phenomenon referred to as 'antigen escape'. The present disclosure pre-empts cancer antigen escape by recognizing a combination of two or more antigens to rapidly eliminate the tumor.

The invention provides a method of simultaneous targeting of multi-antigens using a cCAR resulting in improved tumor control by minimizing the possibility of tumor selection on the basis of target antigen loss or down-regulation.

The disclosed invention includes compound (multiple or compound) cCAR in a T or NK cell targeting different or same surface antigens present in tumor cells. The compound chimeric antigen receptors of present invention comprise at least multiple chimeric receptor constructs linked by a linker and target same or different antigens. For example, each of the CAR construct present in the compound CAR (cCAR) construct includes an antigen recognition domain, an extracellular domain, a transmembrane domain and/or a cytoplasmic domain. The extracellular domain and transmembrane domain can be derived from any desired source for such domains. The multiple CAR constructs are linked by a linker. The expression of the compound CAR construct is driven by a promoter. The linker may be a peptide or a part of a protein,which is self-cleaved after a protein or peptide is generated (also called as a self-cleaving peptide).

In one embodiments, the compound CARs of the present invention target Myelodysplastic Syndrome and acute myeloid leukemia (AML) opulation. Myelodysplastic Syndrome (MDS) remains an incurable hematopoietic stem cell malignancy that occurs most frequently among the elderly, with about 14,000 new cases each year in the USA. About 30-40% of MDS cases progress to AML. The incidence of MDS continues to increase as our population ages. Although MDS and AML have been studied intensely, no satisfactory treatments have been developed.

The compositions and methods of this invention can be used to generate a population of T lymphocyte or NK cells that deliver both primary and co-stimulatory signals for use in immunotherapy in the treatment of cancer, in particular, the treatment of lung cancer, melanoma, breast cancer, prostate cancer, colon cancer, renal cell carcinoma, ovarian cancer, brain cancer, sarcoma, leukemia and lymphoma.

Immunotherapeutics generally rely on the use of immune effector cells and molecules to target and destroy cancer cells. The effector may be a lymphocyte carrying a surface molecule that interacts, either directly or indirectly, with a tumor cell target. Various effector cells include cytotoxic T cells, NK cells and NK-92 cells. The compositions and methods described in the present invention may be utilized in conjunction with other types of therapy for cancer, such as chemotherapy, surgery, radiation, gene therapy,and so forth. The compositions and methods described in the present invention may be utilized in other disease conditions that rely on immune responses such as inflammation, immune diseases, and infectious diseases.

In some embodiments, the compound CAR of the present invention may act as a bridge to bone marrow transplant, by achieving complete remission for patients who have minimal residual disease and are no longer responding to chemotherapy. In other embodiments, the compound CAR eliminates leukemic cells followed by bone marrow stem cell rescue to support leukopenia.

In some embodiments, the compound CAR of the present disclosure can combat a key mechanism by which cancer cells resist CAR activity by the down-regulation of the target antigen. In another embodiment, the invented compound CAR can also combat the heterogeneity of cancer cells, which creates significant challenges in a regular CAR T/NK cell therapy. In a further embodiment, the disclosed compound CAR is designed that the first CAR targets the bulky tumor population and another eradicates cancer or leukemic stem cells to avoid cancer relapses.

In one embodiment, the present disclosure provides a method of destroying cells having a CD33 antigen or a CD123 antigen, or both by contacting said cells with an engineered cell having at least one of chimeric antigen receptor polypeptide having a CD33 antigen recognition domain and chimeric antigen receptor polypeptide having a CD23 antigen recognition domain. The engineered cell may be a T or NK cell.

Cells having at least one of the CD33 antigen and the CD123 antigen include acute myeloid leukemia, precursor acute lymphoblastic leukemia, chronic myeloproliferative neoplasms, chronic myeloid leukemia, myelodysplasia syndromes, blastic plasmocytoid dendritic neoplasms (BPDCN), Hodgkin's lymphoma, mastocytosis, and hairy cell leukemia cells.

In another embodiment, the present disclosure provides a method of providing myeloblative conditioning regimens for hematopoietic stem cell transplantation. In this embodiment, a T or NK engineered cell having a CD33 unit and a CD123 unit is administered to a patient in need thereof.

In further embodiments, the present disclosure provides a method of eradicating or killing leukemic stem cells (LSCs) or bulk leukemic cells expressing CD123 or CD33, or both. In this embodiment, a T or NK engineered cell having a CD33 unit and a CD123 unit is administered to a patient in need thereof.

In further embodiments, the compound CAR in a T or NK cell may be used to eradicate or kill CD34+ CD38− leukemic stem cells or bulk leukemic cells expressing CD123 or CD33 or both.

In some embodiments, a compound CAR targets cells expressing CD19 or CD20 antigens or both. In another embodiment, a compound CAR targets cells expressing CD19 or CD22 antigens or both. The targeted cells may be cancer cells, such as, without limiting, B-cell lymphomas or leukemias. In further embodiments, the target antigens can include at least one of this group, but not limited to, ROR1, PSMA, MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, CD30, EGFRvIII, immunoglobin kappa and lambda, CD38, CD52, CD3, CD4, CD8, CD5, CD7, CD2, and CD138. The target antigens can also include viral or fungal antigens, such as E6 and E7 from the human papillomavirus (HPV) or EBV (Epstein Barr virus) antigens.

In some embodiments, the compound CAR targets cells expressing CD19 or CD123 antigen or both. The targeted cells are cancer cells, such as, without limiting, B-cell lymphomas or leukemias.

In further embodiments, the compound CAR targets cells expressing CS1 and/or B-cell maturation antigens (BCMA) or both. In another embodiment, the targeting cells are malignant plasma cells, such as, without limiting, multiple myeloma.

In some embodiments, the compound CAR targets cells expressing multiple antigens including, but not limited to, CS1, BCMA, CD267, BAFF-R, CD38, CD138, CD52, CD19, CD20, interleukin 6 receptor and NY-ESO-1 antigens. In another embodiment, the targeting cells are malignant plasma cells such as, without limiting, multiple myeloma.

In some embodiments, the compound CAR targets cells expressing multiple antigens including but not limited to, alpha fetoprotein (AFP) and Glypican-3 (GPC3). In another embodiment, the targeting cells are hepatocellular carcinoma, fibrolamellar carcinoma, hepatoblastoma, undifferentiated embryonal sarcoma and mesenchymal hamartoma of liver, lung-squamous cell carcinoma, testicular nonseminomatous germ cell tumors, liposarcoma, ovarian and extragonadal yolk sac tumors, ovarian choriocarcinoma, teratomas, ovarian clear cell carcinoma, and placental site trophoblastic tumor.

In accordance with the present invention, the T or NK cell comprising compound CARs targeting different or same antigens offset tumor escape and enables simultaneous targeting of tumor cells.

The T or NK host cells comprising compound CAR disclosed herein is embodied in the present disclosure. The nucleotide and polypeptide constructs, sequences, host cells, vectors of the compound CAR is considered to be part of the present disclosure and is embodied herein.

In some embodiments, the compound CAR is administrated in combination with any chemotherapy agents currently being developed or available in the market. In some embodiments, the compound CAR is administrated as a first line treatment for diseases including, but not limited to, hematologic malignancies, cancers, non-hematologic malignances, inflammatory diseases, infectious diseases such as HIV and HTLV and others. In one embodiment, T cells expressing the compound CAR are co-administrated with NK cells expressing the same or different compound CAR as an adaptive immunotherapy. Compound CAR NK cells provide rapid, innate activity targeting cells while compound T cells provide relative long-lasting adaptive immune activity.

In one embodiment, the cells expressing a compound CAR are administrated as a bridge to bone marrow stem transplantation for mammals, e.g. patients who are resistant to chemotherapies and are not qualified for bone marrow stem cell transplantation.

In some embodiments, the compound CAR co-expresses a transgene and releases a transgenic product, such as IL-12 in the targeted tumor lesion and further modulates the tumor microenvironment.

In one embodiment, cells expressing a compound CAR are administrated to a mammal for bone marrow myeloid ablation as a part of the treatment to a disease.

In a specific embodiment, the cells expressing a compound CAR can be T cells or NK cells, administrated to a mammal, e.g. human. The presented disclosure includes a method of treating a mammal having a disorder or disease by administration of a compound CAR. The targeted cells may be cancer cells such as, or cells affected by any other disease condition, such as infectious diseases, inflammation, and autoimmune disorders.

The present invention is intended to include the use of fragments mutants, or variants (e.g., modified forms) of the compound CAR or antigens that retain the ability to induce stimulation and proliferation of T/NK cells. A "fore of the protein" is intended to mean a protein that shares a significant homology with at least one CAR or antigen and is capable of effecting stimulation and proliferation of T/NK cells. The terms "biologically active" or "biologically active form of the protein," as used herein, are meant to include forms of the proteins or variants that are capable of effecting anti-tumor activity of the cells.

The compositions and methods of this invention can be used to generate a population of T/NK cells that deliver both primary and co-stimulatory signals for use in immunotherapy in the treatment of cancer, in particular the treatment of lung cancer, melanoma, breast cancer, prostate cancer, colon cancer, renal cell carcinoma, ovarian cancer, neuroblastoma, rhabdomyosarcoma, leukemia and lymphoma. The compositions and methods described in the present invention may be utilized in conjunction with other types of therapy for cancer, such as chemotherapy, surgery, radiation, gene therapy, and so forth.

In some embodiments, the invention discloses a method of depletion B cells, immature B cells, memory B cells, plasmablasts, long lived plasma cells, or plasma cells in patients with an autoimmune disease by administering to patients with CAR or compound CAR T cells or NK cells. CAR targeted cells are B or plasma cells expressing one or two or all of antigens, BCMA, TACI and BAFF-R. The autoimmune diseases include systemic scleroderma, multiple sclerosis, psoriasis, dermatitis, inflammatory bowel diseases (such as Crohn's disease and ulcerative colitis), systemic lupus erythematosus, vasculitis, rheumatoid arthritis, Sjorgen's syndrome, polymyositis, granulomatosis and vasculitis, Addison's disease, antigen-antibody complex mediated diseases and anti-glomerular basement men brane disease.

Multiple extracellular cell markers are now being studied for value as tumor-associated antigens and thus potential targets for CAR T/NK cell therapy. However, expression of these antigens on healthy tissue leading to on-target, off-tumor adverse events remains a major safety concern in addition to off-target toxicities. Furthermore, a major limitation of CAR T/NK cell therapy is in the possibility of selecting for antigen escape variants when targeting molecules non-essential to tumorigenesis. Thus, malignant cells that persist with little or no expression of the target antigens may evade CAR T/NK cells, despite their high-affinity action.

In accordance with the present invention, natural killer (NK) cells represent alternative cytotoxic effectors for CAR driven killing. Unlike T-cells, NK cells do not need pre-activation and constitutively exhibit cytolytic functions. Further expression of cCARs in NK cells allow NK cells to effectively kill cancers, particularly cancer cells that are resistant to NK cell treatment.

Further, NK cells are known to mediate anti-cancer effects without the risk of inducing graft-versus-host disease (GvHD).

Studies have shown an aberrant overexpression of CD123 on CD34+ CD38− AML cells, while the normal bone marrow counterpart CD34+ CD38− does not express CD123 (Jordan, Upchurch et al. 2000). This population of CD123+, CD34+CD38− has been considered as LSCs as these cells are able to initiate and maintain the leukemic process into immunodeficient mice.

The number of CD34+/CD38−/CD123+ LSCs can be used to predict the clinical outcome for AML patients. The CD34+/CD38−/CD123+ cells, greater than 15% in AML patients, are associated with a lack of complete remission and unfavorable cytogenetic profiles. In addition, the presence of more than 1% of CD34+/CD38−/CD123+ cells could also have a negative impact on disease-free survival and overall survival.

At the present, therapies for MDS and AML have focused on the leukemic blast cells because they are very abundant and clearly represent the most immediate problem for patients. Importantly, leukemic stem cells (LSCs) are quite different from most of the other leukemia cells ("blast" cells), and they constitute a rare subpopulation. While killing blast cells can provide short-term relief, LSCs, if not destroyed, will always re-grow, causing the patient to relapse. It is imperative that LSCs be destroyed in order to achieve durable cures for MDS disease. Unfortunately, standard drug regimens are not effective against MDS or AML LSCs. Therefore, it is critical to develop of new therapies that can specifically target both the leukemic stem cell population and the bulky leukemic population. The compound CAR disclosed in the present invention target both of these populations and is embodied herein.

In accordance to the present invention, it was surprisingly found that NK cells provide an off-the-shelf product that may be used as an allogeneic product for treatment. Thus, according to the present invention, cCAR cell therapy needs to be performed on a patient-specific basis as required by the current state of art. The applicants of the present invention have discovered a novel immunotherapy, where the patient's lymphocytes or tumor infiltrated lymphocytes need not be isolated for an effective CAR cell based therapy.

Allogeneic or autologous NK cells are expected to induce a rapid immune response but disappear relatively rapidly from the circulation due to their limited lifespan. Thus, applicants surprisingly discovered that there is reduced concern of persisting side effects using cCAR cell based therapy.

According to one aspect of the present invention, NK cells can be expanded and transfected with cCAR in accordance to the present invention. NK cells can be derived from cord blood, peripheral blood, iPS cells and embryonic stem cells. According to one aspect of the present invention, NK-92 cells may be expanded and transfected with cCAR. NK-92 is a continuously growing cell line that has features and characteristics of natural killer (NK) cells. NK-92 cell line is IL-2 dependent and has been proven to be safe and feasible. cCAR expressing NK-92 cells can be expanded in the serum free-medium with or without co-culturing with feeder cells. A pure population of NK-92 carrying the cCAR of interest may be obtained by sorting.

Identification of appropriate surface target antigens is a prerequisite for developing CAR T/NK cells in adaptive immune therapy.

In one aspect of the present invention, CD123 antigen is one of the targets for cCAR therapy. CD123, the alpha chain of the interleukin 3 receptor, is overexpressed on a variety of hematologic malignancies, including acute myeloid leukemia (AML), B-cell acute lymphoblastic leukemia (B-ALL), hairy cell leukemia, and blastic plasmocytoid dendritic neoplasms. CD123 is absent or minimally expressed on normal hematopoietic stem cells. More importantly, CD123 is expressed on a subset of leukemic cells related to leukemic stem cells (LSCs), the ablation of which is essential in preventing disease refractoriness and relapse.

In one aspect of the present invention, CD 33 antigen is one of the targets for cCAR therapy. CD33 is a transmembrane receptor expressed on 90% of malignant cells in acute myeloid leukemia. Thus, according to the present invention, CD123 and CD33 target antigens are particularly attractive from a safety standpoint.

In accordance with the present invention, the compound CD33CD123 CARs may be highly effective for therapeutic treatment of chronic myeloid leukemia (CML) population. In chronic myeloid leukemia (CML), there is a rare subset of cells that are CD34+CD38−. This population is considered as comprised of LSCs. Increased number of LSCs is associated with the progression of the disease. A small-molecule Bcr-Abl tyrosine kinase inhibitor (TKI) is shown to significantly improve the overall survival in CP-CML patients. However, LSCs are thought to be resistant to TKI therapy. A novel therapy targeting CML resistant LSCs is urgently needed for treatment of CML and the novel therapy is embodied in the compound CD33CD123 CAR disclosed in the present invention. CD123 expression is high in the CD34+CD38− population. In accordance with the present invention, the compound CD33CD123 CARs is highly effective for therapeutic treatment of this population.

In one embodiment of the present invention, leukemic cells expressing both CD123 and CD33 in the cCAR is used as a therapeutic treatment. CD33 is expressed on cells of myeloid lineage, myeloid leukemic blasts, and mature monocytes but not normal pluripotent hematopoietic stem cells (Griffin, Linch et al. 1984). CD33 is widely expressed in leukemic cells in CML, myeloproliferative neoplasms, and MDS.

As a significant number of patient with acute myeloid leukemia (AML) are refractory to standard chemotherapy regimens or experience disease relapse following treatment (Burnett 2012), the development of CAR T cell immunotherapy for AML has the potential to address a great clinical need. In the majority of these patients, leukemic cells express both CD123 and CD33, giving broad clinical applicability to the compound CD33CD123 CAR disclosed herein. Thus, the present invention discloses a novel multiple cCAR T/NK cell construct comprising multiple CAR targeting multiple leukemia-associated antigens, thereby offsetting antigen escape mechanism, targeting leukemia cells, including leukemic stem cells, by synergistic effects of co-stimulatory domain activation and thereby providing a more potent, safe and effective therapy.

The present invention further discloses compound CAR construct, with enhanced potency of anti-tumor activity against cells co-expressing target antigens, and yet retains sensitivity to tumor cells only expressing one antigen. In addition, each CAR of the compound CAR includes one or two co-stimulatory domains and potent killing capability in presence of the specific target.

In pre-clinical studies on dual specificity, trans-signaling CARs targeting solid tumors including breast cancer and epithelial ovarian cancer, a CD3ζ intracellular signaling domain is separated from co-stimulatory domains from second generation of CARs. In other words, one CAR contains the first generation of CAR without any co-stimulatory domain, and another lacks a CD3 zeta intracellular domain. Therefore, the presence of both target antigens is required for T cell activation and potent killing. Thus, they were proposed as a way to decrease off-tumor toxicity caused by healthy tissue expression of one of the two target antigens, increasing target specificity, but at the expense of sensitivity. In one embodiment, the compound CAR is a compound CD123CD19 CAR. It has been shown that more than 90% of B-ALLs express CD123 in a subset of population Like AML and MDS, it has been considered that a rare LSC population exists in B-ALL. Therefore, targeting both leukemic stem cell and bulky leukemic populations in accordance to the present invention, can be applied to B-ALLs. CD123 and CD19 surface antigens expressed in the B-ALLs may be targets as CD19 is widely expressed in different stages of B-cell lymphoid populations, in accordance with the present invention.

Multiple myeloma (MM) is the second most common hematologic malignancy in the US and is derived from clonal plasma cells accumulated in the bone marrow or extramedullary sites. MM is an incurable disease with a median survival of approximately 4.5 years (Kumar, Rajkumar et al. 2008). Anti-Myeloma CARs in Pre-clinical Development have been developed and CAR targets include CD38, CS1, B cell maturation Antigen (BCMA) and CD38. However, heterogeneity of surface antigen expression commonly occurs in malignant plasma cells (Ruiz-Arguelles and San Miguel 1994), which makes it a difficult target for CARs. Malignant plasma cells also express low levels of CD19. Previously it has been shown that myeloma stem cells also express some B-cell markers including CD19. Targeting this population could be effective in the treatment of myeloma in conjunction with standard and other myeloma CAR therapies.

Multiple myeloma (MM) is a haematological malignancy with a clonal expansion of plasma cells. Despite important advances in the treatment, myeloma remains an incurable disease; thus novel therapeutic approaches are urgently needed.

CS1 (also called as CD319 or SLAMF7) is a protein encoded by the SLAMF7 gene. The surface antigen CS1 is a robust marker for normal plasma cells and myeloma cells (malignant plasma cells).

Tumour necrosis factor receptor superfamily, member 17 (TNFRSF17), also referred to as B-cell maturation antigen (BCMA) or CD269 is almost exclusively expressed at the terminal stages of plasma cells and malignant plasma cells. Its expression is absent other tissues, indicating the potential as a target for CAR T or NK cells.

Malignant plasma cells display variable degrees of antigenic heterogeneity for CD269 and CS1. A single CAR unit product targeting either CD269 or CS1 could target the majority of the cells in a bulk tumor resulting in an initial robust anti-tumor response. Subsequently residual rare non-targeted cells are expanded and cause a disease relapse. While multiple myeloma is particularly heterogeneous, this phenomena could certainty apply to other leukemias or tumors. A recent clinical trial at NIH using BCMA CAR T cells showed a promising result with a complete response in some patients with multiple myeloma. However, these patients relapsed after 17 weeks, which may be due to the antigen escape. The antigen escape is also seen in CD19 CAR and NY-ESO1 CAR T cell treatments. Thus, there is an urgent need for more effective CAR T cell treatment in order to prevent the relapse.

In one aspect of the present invention, BCMA and CS1 are the targets for BCMACS1 CAR therapy.

In some embodiments, a compound CAR targets cells expressing BCMA or CS1 antigens or both. The targeted cells may be cancer cells, such as, without limiting, lymphomas, or leukemias or plasma cell neoplasms. In further embodiments, plasma cell neoplasms is selected from plasma cell leukemia, multiple myeloma, plasmacytoma, heavy chain diseases, amyloidosis, waldestrom's macroglobulinema, heavy chain diseases, solitary bone plamacytoma, monoclonal gammopathy of undetermined significance (MGUS) and smoldering multiple myeloma.

BAFF (B-cell-activation factor) and APRIL (a proliferation-induced ligand) are two TNF homologs that bind specifically TACI (also called as TNFRSF1 3B or CD267) and BCMA with high affinity. BAFF (also known as BLyS) binds BAFF-R and functionally involves in the enhancement of survival and proliferation of later stage of B cells. BAFF has been shown to involve some autoimmune disorders. APRIL plays an important role in the enhancement of antibody class switching. Both BAFF and APRIL have been implicated as growth and survival factors for malignant plasma cells.

Figure 45:
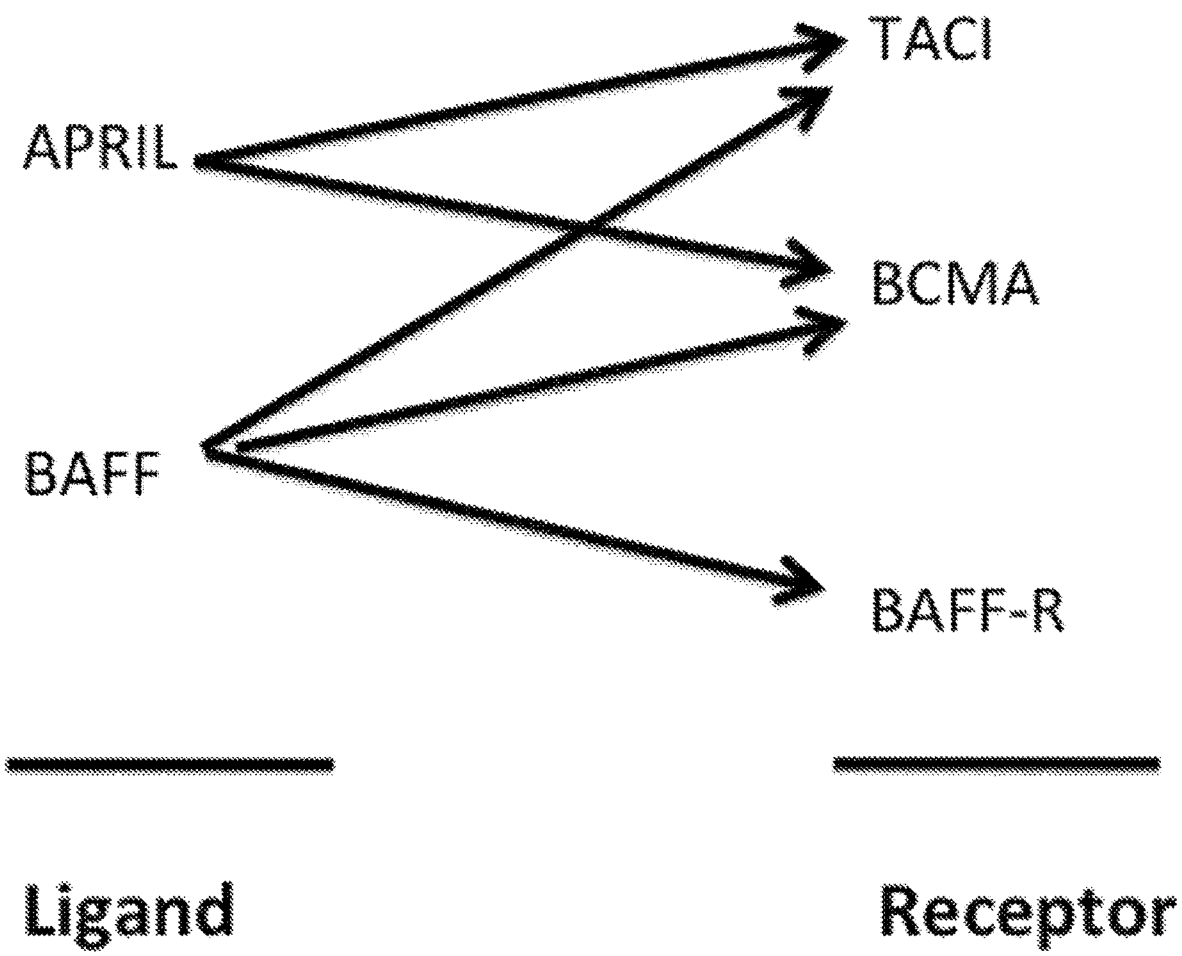
FIG. 45. Ligand receptor interactions in malignant plasma cells. The APRIL ligand binds TAC1 or BCMA. The BAFF ligand binds TAC1, BCMA, or BAFF-R.

Ligand-receptor interactions in the malignant plasma cells are described in FIG. 45.

In some embodiments, a compound CAR targets cells expressing TACI or CS1 antigens or both. In another embodiment, a compound CAR targets cells expressing TACI or CS1 antigens or both. The targeted cells may be cancer cells, such as, without limiting, lymphomas, or leukemias or plasma cell neoplasms. In further embodiments, plasma cell neoplasms is selected from plasma cell leukemia, multiple myeloma, plasmacytoma, heavy chain diseases, amyloidosis, waldestrom's macroglobulinema, heavy chain diseases, solitary bone plamacytoma, monoclonal gammopathy of undetermined significance (MGUS) and smoldering multiple myeloma. The target cells may also be one or two or multiple different cell types of B cells, immature B cells, naïve B cells, centroblasts, centrocytes, memory B cells, plasmablasts, long lived plasma cells, plasma cells. These cells involve autoimmune diseases include systemic scleroderma, multiple sclerosis, psoriasis, dermatitis, inflammatory bowel diseases (such as Crohn's disease and ulcerative colitis), systemic lupus erythematosus, vasculitis, rheumatoid arthritis, Sjorgen's syndrome, polymyositis, granulomatosis and vasculitis, Addison's disease, antigen-antibody complex mediated diseases, and anti-glomerular basement membrane disease.

In some embodiments, a compound CAR targets cells expressing BAFF-R or CS1 antigens or both. In another embodiment, a compound CAR targets cells expressing BAFF-R or CS1 antigens or both. The targeted cells may be cancer cells, such as, without limiting, lymphomas,or leukemias or plasma cell neoplasms. In further embodiments, plasma cell neoplasms is selected from plasma cell leukemia, multiple myeloma, plasmacytoma, heavy chain diseases, amyloidosis, waldestrom's macroglobulinema, heavy chain diseases, solitary bone plamacytoma, monoclonal gammopathy of undetermined significance (MGUS) and smoldering multiple myeloma.

In some embodiments, a compound CAR (cCAR) targets cells expressing one or two or all of BAFF-R, BCMA, TACI and CS1 antigens.

In some embodiments, a unit of CAR in a cCAR can comprise: 1) a scFv against either BAFF-R, BCMA, TACI and CS1; 2) a hinge region; 3) co-stimulatory domain(s) and intracellular signaling domain.

In some embodiments, a unit of CAR in a cCAR can comprise: 1) BCMA or TACI or BAFF-R binding domain, or APRIL binding domain; 2) a hinge region; 3) co-stimulatory domain(s) and intracellular signaling domain.

In a further embodiment, BCMA or TAC1 or BAFF-R binding domain can be a part of or entire APRIL and BAFF molecules.

In some embodiments, a unit of CAR in a cCAR can comprise: 1) a scFv against BCMA or CS1; 2) a hinge region; 3) co-stimulatory domain(s) and intracellular signaling domain.

In further embodiments, cCAR can comprise one or two or multiple units of CAR. Each unit CAR could bear same or different hinge region and co-stimulatory domain.

In further embodiments, the target antigens can include at least one of this group, but not limited to, ROR1, PSMA, MAGE A3, Glycolipid, glypican 3, F77, GD-2, WT1, CEA, HER-2/neu, MAGE-3, MAGE-4, MAGE-5, MAGE-6, alpha-fetoprotein, CA 19-9, CA 72-4, NY-ESO, FAP, ErbB, c-Met, MART-1, CD30, EGFRvIII, immunoglobin kappa and lambda, CD38, CD52, CD3, CD4, CD8, CD5, CD7, CD2, and CD138. The target antigens can also include viral or fungal antigens, such as E6 and E7 from the human papillomavirus (HPV) or EBV (Epstein Barr virus) antigens.

In some embodiments, a cCAR targets a cell expressing either CD19 or CD20 antigens or both of them. In another embedment, a cCAR targets a cell expressing either CD19 or CD22 antigens or both of them. The targeting cells are cancer cells such as B-cell lymphomas or leukemias.

Acute graft-versus-host disease (GVHD) remains the most important cause of morbidity and mortality after allogeneic hematopoietic stem cell transplantation. In the effector phase of GVHD, T cell receptor (TCR), a heterodimer of alpha and beta chains, is expressed on the surface of T cells, TCR recognizes some antigens on the HLA molecule on host cells, enhances T cell proliferation, and releases cytotoxic agents that cause the damage on host cells. TCR gene inactivation is efficient at preventing potential graft-versus-host reaction. The inactivation of TCRs can result in the prevention of the TCR recognition of alloantigen and thus GVHD. The role of CD45 on NK cells is quite different from that of T cells. NK cells from CD45-difficient mice have normal cytotoxic activity against the prototypic tumor cell line, Yac-1. In addition, CD45-deficient NK cells proliferate normally and respond to IL15 and IL-21. Therefore, CD45 disruption or deletion would not affect the NK cell killing and proliferation. The present disclosure includes methods of permanent deletion of CD45 in a T or NK cell with subsequent stable introduction of CD45-specific CARs. As a result, the engineered T cells display the desired properties of redirected specificity for CD45 without causing self-killing and response to presentation of antigen. In a further embodiment, the engineered T cells may have efficacy as an off-the-shelf therapy for treating malignancies or other diseases. The present disclosure relates to a method where T-cells are engineered to allow proliferation when TCR signaling is reduced or lost through the inactivation or deletion of endogenous CD45. The reduction or loss of TCR signaling could result in the prevention of GVHD. In a further embodiment, T cells reducing or losing the TCR signaling by the inactivation of CD45 could be used as an "off the shelf" therapeutic product.

The present disclosure includes methods of modified T or NK cells, which comprises: (a) modifying T or NK cells by inactivating CD45; (b) expanding these modified cells; (c) sorting modified T or NK cells, which do not express CD45; (d) introducing CD45CAR. In embodiments, the CD45CAR gene encodes a chimeric antigen receptor (CAR), wherein the CAR comprises at least one of an antigen recognition domain, a hinge region, a transmembrane domain, and T cell activation domains, and the antigen recognition domain is redirected against CD45 surface antigen present on a cell. The antigen recognition domain includes a monoclonal antibody or a polyclonal antibody directed against CD45 antigen. The antigen recognition domain includes the binding portion or a variable region of a monoclonal or a polyclonal antibody.

In some embodiments, the modified T cells are obtained from allogeneic donors and used as an 'off-the-shelf product".

Targeting CD45 using CAR T or NK cells may cause self-killing as T and NK cells express this surface antigen. To overcome this drawback, the inventor proposes to inactivate CD45 gene using engineered CRISPR/Cas9 system, zinc finger nuclease (ZFNs) and TALE nucleases (TALENs) and meganucleases. The loss of CD45 in T or NK cells is further transduced with CARs targeting neoplasms expressing CD45.

The disclosure includes methods for eliminating or reducing abnormal or malignant cells in bone marrow, blood and organs. In some embodiments, malignant cells expressing CD45 are present in patients with acute leukemia, chronic leukemia, B and T cell lymphomas, myeloid leukemia, Acute lymphoblastic lymphoma or leukemia, primary effusion lymphoma, Reticulohistiocytoma, transient myeloproliferative disorder of Down's syndrome, lymphocyte predominant Hodgkin's lymphoma, myeloid leukemia or sarcoma, dendrocytoma, histiocytic sarcoma, Giant cell tumor of tendon sheath, interdigitating dendritic cell sarcoma, post-transplant lymphoproliferative disorders, etc.

In some embodiments, CD45CAR cells can be used to make space in the bone marrow for bone marrow stem cell transplant by removing hematopoietic cells, at the same time removing leukemic/lymphoma cells or immunologic cells capable of graft rejection. In a further embodiment, CD45CAR cells may be used for pre-treatment of patients before their undergoing a bone marrow transplant to receive stem cells. In a further embodiment, CD45CAR can be used as myeloblative conditioning regimens for hematopoietic stem cell transplantation.

In some embodiment, CD45CAR cells are utilized for treating or preventing a residual disease after stem cell transplant and/or chemotherapy.

In some embodiments, the CD45CAR is part of an expressing gene or a cassette. In a preferred embodiment, the expressing gene or the cassette may include an accessory gene or a tag or a part thereof, in addition to the CD45CAR. The accessory gene may be an inducible suicide gene or a part thereof, including, but not limited to, caspase 9 gene, thymidine kinase, cytosine deaminase (CD) or cytochrome P450. The "suicide gene" ablation approach improves safety of the gene therapy and kills cells only when activated by a specific compound or a molecule. In some embodiments, the suicide gene is inducible and is activated using a specific chemical inducer of dimerization (CID).

In some embodiments, safety switch can include the accessory tags are a c-myc tag, CD20, CD52 (Campath), truncated EGFR gene (EGFRt) or a part or a combination thereof. The accessory tag may be used as a nonimmunogenic selection tool or for tracking markers. In some embodiments, safety switch can include a 24-residue peptide that corresponds to residues 254-277 of the RSV F glycoprotein A2 strain (NSELLSLINDMPITNDQKKLMSNN) (SEQ ID NO: 37). In some embodiments, safety switch can include the amino acid sequence of TNF $\alpha$ bound by monoclonal anti-TNF $\alpha$ drugs.

Administration of any of the engineered cells described herein may be supplemented with the co-administration of a CAR enhancing agent. Examples of CAR enhancing agents include immunomodulatory drugs that enhance CAR activities, such as, but not limited to agents that target immune-checkpoint pathways, inhibitors of colony stimulating factor-1 receptor (CSF1R) for better therapeutic outcomes. Agents that target immune-checkpoint pathways include small molecules, proteins, or antibodies that bind inhibitory immune receptors CTLA-4, PD-1, and PD-L1, and result in CTLA-4 and PD-1/PD-L1 blockades. As used herein, enhancing agent includes enhancer as described above.

As used herein, "patient" includes mammals. The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human. A patient includes subject.

In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old.

The terms "effective amount" and "therapeutically effective amount" of an engineered cell as used herein mean a sufficient amount of the engineered cell to provide the desired therapeutic or physiological or effect or outcome. Such, an effect or outcome includes reduction or amelioration of the symptoms of cellular disease. Undesirable effects, e.g. side effects, are sometimes manifested along with the desired therapeutic effect; hence, a practitioner balances the potential benefits against the potential risks in determining what an appropriate "effective amount" is. The exact amount required swill vary from patient to patient, depending on the species, age and general condition of the patient, mode of administration and the like. Thus, it may not be possible to specify an exact "effective amount". However, an appropriate "effective amount" in any individual case may be determined by one of ordinary skill in the art using only routine experimentation. Generally, the engineered cell or engineered cells is/are given in an amount and under conditions sufficient to reduce proliferation of target cells.

Following administration of the delivery system for treating, inhibiting, or preventing a cancer, the efficacy of the therapeutic engineered cell can be assessed in various ways well known to the skilled practitioner. For instance, one of ordinary skill in the art will understand that a therapeutic engineered cell delivered in conjunction with the chemo-adjuvant is efficacious in treating or inhibiting a cancer in a patient by observing that the therapeutic engineered cell reduces the cancer cell load or prevents a further increase in cancer cell load. Cancer cell loads can be measured by methods that are known in the art, for example, using polymerase chain reaction assays to detect the presence of certain cancer cell nucleic acids or identification of certain cancer cell markers in the blood using, for example, an antibody assay to detect the presence of the markers in a sample (e.g., but not limited to, blood) from a subject or patient, or by measuring the level of circulating cancer cell antibody levels in the patient.

Throughout this specification, quantities are defined by ranges, and by lower and upper boundaries of ranges. Each lower boundary can be combined with each upper boundary to define a range. The lower and upper boundaries should each be taken as a separate element.

Reference throughout this specification to "one embodiment," "an embodiment," "one example," or "an example" means that a particular feature, structure or characteristic described in connection with the embodiment or example is included in at least one embodiment of the present embodiments. Thus, appearances of the phrases "in one embodiment," "in an embodiment," "one example," or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus.

Further, unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any one, two, three, or four of the members, e.g., a and c; a, d, and e; b, c, d, and e; etc.

As used herein, a XXXX antigen recognition domain is a polypeptide that is selective for XXXX. Therefore, XXXX is the target. For example, a CD38 antigen recognition domain is a polypeptide that is specific for CD38.

As used herein, CDXCAR refers to a chimeric antigen receptor having a CDX antigen recognition domain.

The present disclosure may be better understood with reference to the examples, set forth below. The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure.

EXAMPLES

Generation of Compound CAR (cCAR)

The construction of the CD33CD123 cCAR follows the schematic in FIG. 1A. It includes SFFV (spleen focus-forming virus) promoter that drives the expression of the functional compound CAR (cCAR) bearing two different units of CARs. The antigen receptor head, a scFv (single-chain variable fragment) nucleotide sequence of the anti-CD33 and anti-CD123. A P2A peptide derived from picornavirus is utilized due to the highly efficient mechanism of its self-cleaving dynamics for bicistronic genetic constructs. The self-cleaving P2A peptide serves to link the two independent units of CARs, CD33CAR, and CD123CAR together during expression. The advantages of this approach over an internal ribosomal entry site (IRES), which is commonly used in the literature, include its small size and high cleavage efficiency between two unit proteins upstream and downstream of the 2A peptide. In addition, the use of self-cleaving P2A peptide can avoid a problem of differences in expression levels between gene before and after IRES when IRES is applied.

The modular unit, CD33CAR includes the CD33 scFv domain, a CD8a hinge region, a CD8a transmembrane domain, 4-BB co-stimulatory domain and an intracellular domain of CD3 zeta chain. The second modular CAR, CD123CAR bears the same hinge, transmembrane and intracellular signaling domains as CD33CAR but different scFv, and co-stimulatory domains. The CD33 CAR recognizes its corresponding antigen and the CD123 CAR binds to its corresponding antigen. The hinge region was designed such that sequences where disulfide interactions are avoided. Different co-stimulatory domains, 4-BB and CD28 were used. The CD33CD123 compound CAR was subcloned into a lentiviral plasmid.

Generation of a High-Efficiency Compound CAR (cCAR)

Figure 2A:
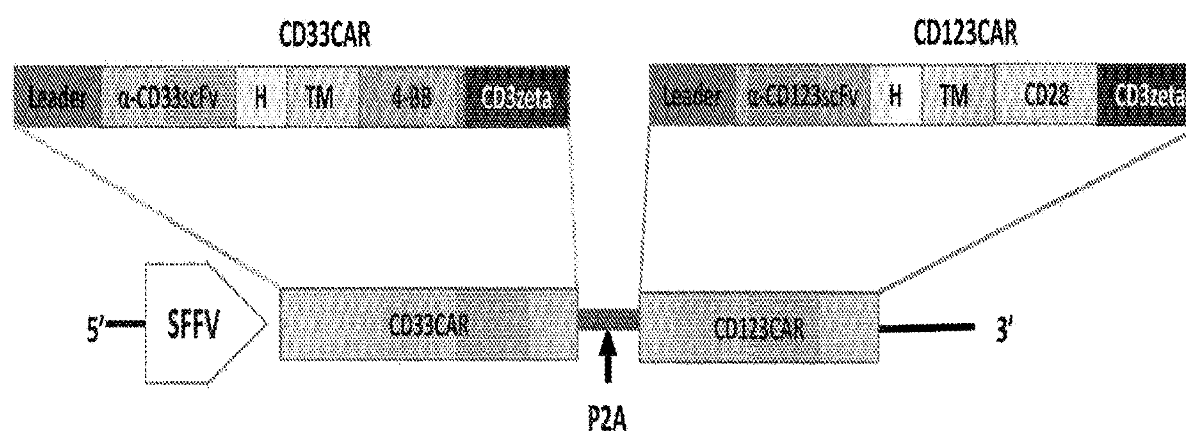
FIG. 2A. A schematic representation of cCAR-T construct. The construct comprises a SFFV promoter driving the expression of-multiple modular units of CARs linked by a P2A peptide. Upon cleavage of the linker, the cCARs split and engage upon targets expressing CD33 and/or CD123. As a novel cCAR construct, the activation domains of the construct may include, but is not limited to, 4-1BB on the CD33 CAR segment and a CD28 region on the CD123 CAR.
Figure 2B:
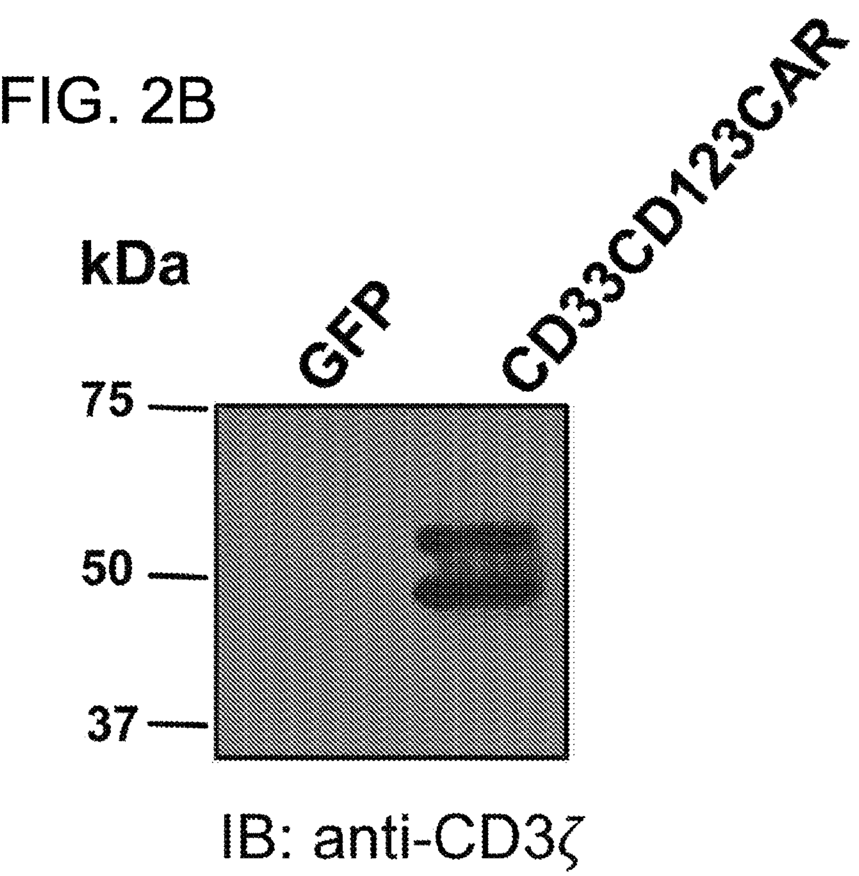
FIG. 2B. A Western blot depicting the expression of transduced CD33CD123 cCAR-T cells. The figure depicts expression of two different CAR proteins, i.e., CD33 CAR and CD123 CARs. The cCAR-T cells expressing both CD33 and CD123 CARs upon cleavage of the linker generate two distinct and consistently intense protein bands. Green Fluroscent Protein (GFP) is included as negative control.
Figure 2C:
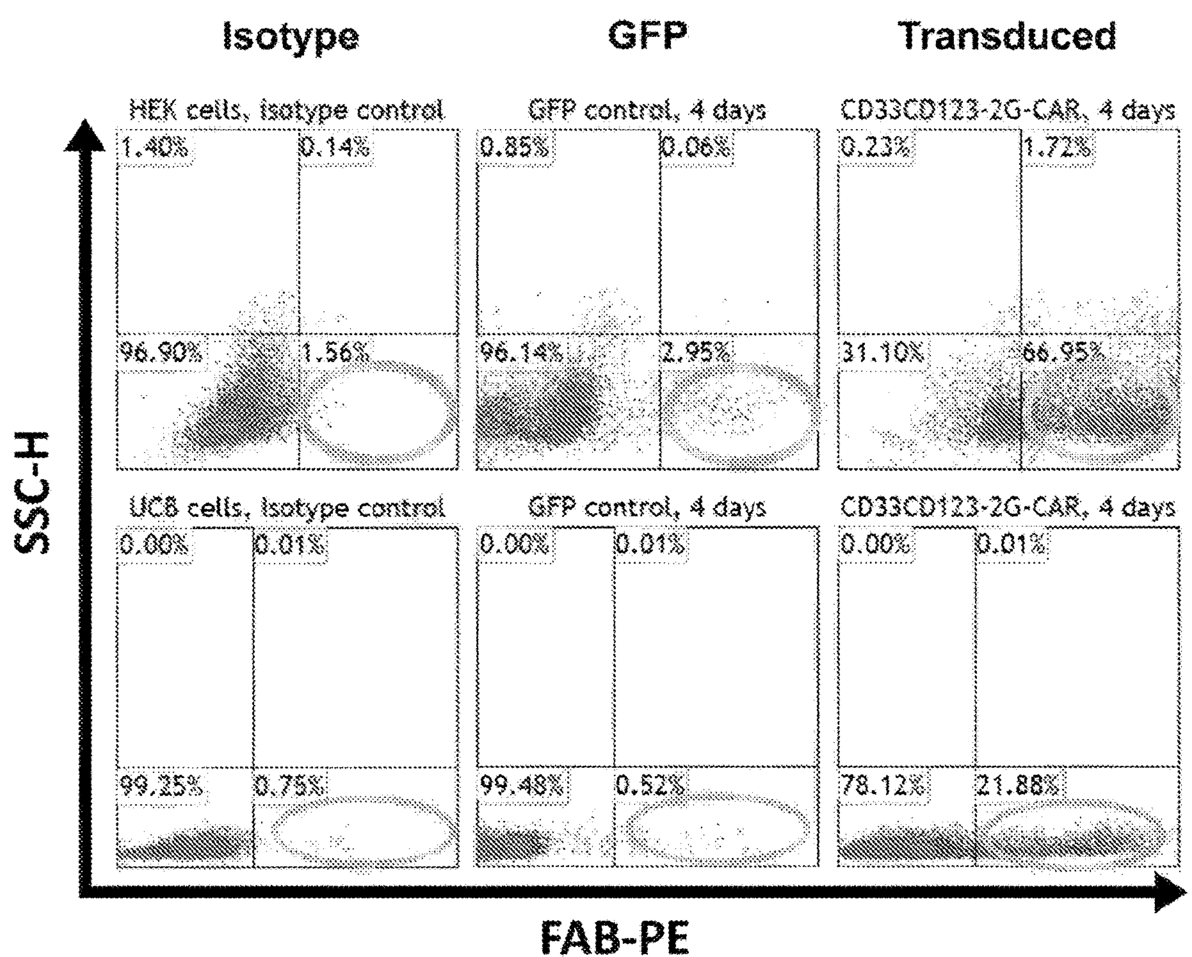
FIG. 2C. Flow cytometry representing the efficiency of transduction. Upper panel shows the lentiviral titer for CD33CD123 cCARs (also referred to as CD33CD123-2G-CAR) tested on 293FT HEK (human embryonic kidney) cells to gauge maximum transduction efficiency before usage on UCB (umbilical cord blood) and PB (peripheral blood) T-cells. Lower panel shows CD33CD123 cCAR (also referred to as CD33CD123-2G-CAR) T-cells transduced with lentiviral vectors comprising CD33CD123 cCAR construct and GFP-transduced cells as control Percentages indicated by yellow circles are proxies for transduction efficiency.

Compound CAR lentivirus was generated by transfection of HEK-293 FT cells with Lipofectamine 2000 according to manufacturer's directions, except with 2× the vector DNA due to a large size of insert, in order to increase titer as shown in FIG. 2. After about 12-16 hours incubation, media containing Lipofectamine was removed and replaced with DMEM containing 10% FBS, 20 mM HEPES, 1 mM sodium pyruvate and 1 mM sodium butyrate. After about 24 hours, these supernatant was harvested and refrigerated, and replaced with fresh media. After about another 24 hours, this was collected and combined with the previous supernatant, and filtered through a 0.45 μM filter disc. Supernatant was split into aliquots, flash frozen with liquid nitrogen and stored at −80° C. HEK-293 FT cells were harvested, stored frozen, and lysed for subsequent electrophoresis and Western blotting.

PB (peripheral blood) or CB (human umbilical cord blood) buffy coat cells were activated 2 days with anti-CD3 antibody and IL-2. cCAR lentiviral supernatant was spinoculated onto retronectin-coated multiwell plates. Activated T cells were transduced in multiple wells with lentiviral supernatant at a low concentration of about $0.3\times10^6$ cells/mL to increase transduction efficiency (FIG. 2).

Following the first overnight transduction, cells were added directly to a second virus-coated plate for a second transduction without washing, unless the cells did not look healthy. Following the second overnight transduction, cells were washed, combined and incubated in tissue culture treated plates. CAR T cells were allowed to expand for up to about 5 days prior to co-culture killing assays. After about 3 days of incubation, cells were incubated with goat anti-mouse F(Ab')2 or goat IgG (isotype) antibodies conjugated with biotin, washed and followed by incubation with streptavidin-PE and conjugated anti-human CD3. After washing and suspension in 2% formalin, cells were then analyzed by flow cytometry to determine percent transduction efficiency.

Characterization of the CD33CD123 cCAR

Transfected CD33CD123 cCAR HEK293T cells were subjected to Western blot analysis in order to confirm the compound construct. Immunoblot with an anti-CD3ζ monoclonal antibody showed bands of predicted size for the compoundCAR CD3ζ fusion protein (FIG. 1B). Importantly, two distinct bands of similar intensity were observed on the blot signaling the successful high cleavage action of the P2A peptide as expected. No CD3ζ expression was seen for the GFP control vector as expected. The surface expression of scFv was also tested on HEK 293 cells (FIG. 1C) and primary T cells (FIG. 1C).

The compound CD33CD23CAR lentivirus was tested for transduction efficiency in the HEK293 cell line and analyzed by flow cytometry (Beckman Coulter) (FIG. 1C). Flow cytometry showed that about 67% of HEK cells expressed CD33CD123 CARs. Human peripheral blood (PB) is often used for autologous T cell therapy. Human PB buffy coat cells were activated with anti-CD3 antibody and IL-2, and transduced with either CD4CAR or control (GFP) lentiviruses. After transduction, flow cytometry analysis showed that about 22% of T-cells expressed the CD33CD123CAR (FIG. 1C).

Results

CD33CD123 cCAR T-Cells Derived From Umbilical Cord Blood (UCB) and Peripheral Blood (PB) Specifically Kill CD33-Expressing Tumor Cells CD33CD123 cCAR T cells or GFP T cells (control) were incubated with target cells at ratios ranging from 0.5:1 from 50:1, preferably, at about 2:1, 5:1, 10:1, 20:1, 50:1, at about 100,000, 200,000, 500,000, about 1 million, or 2 million effector cells to about 50,000, 100,000, 200,000 target cells, respectively) in about 1-2 mL T cell culture media, without IL-2 for about 24 h. Target cells were leukemic cell lines and leukemia cells from a patient with leukemia. After about 24 hours of co-culture, cells were stained with mouse anti-human CD33, CD123, CD34 and CD3 antibodies.

Figure 3:
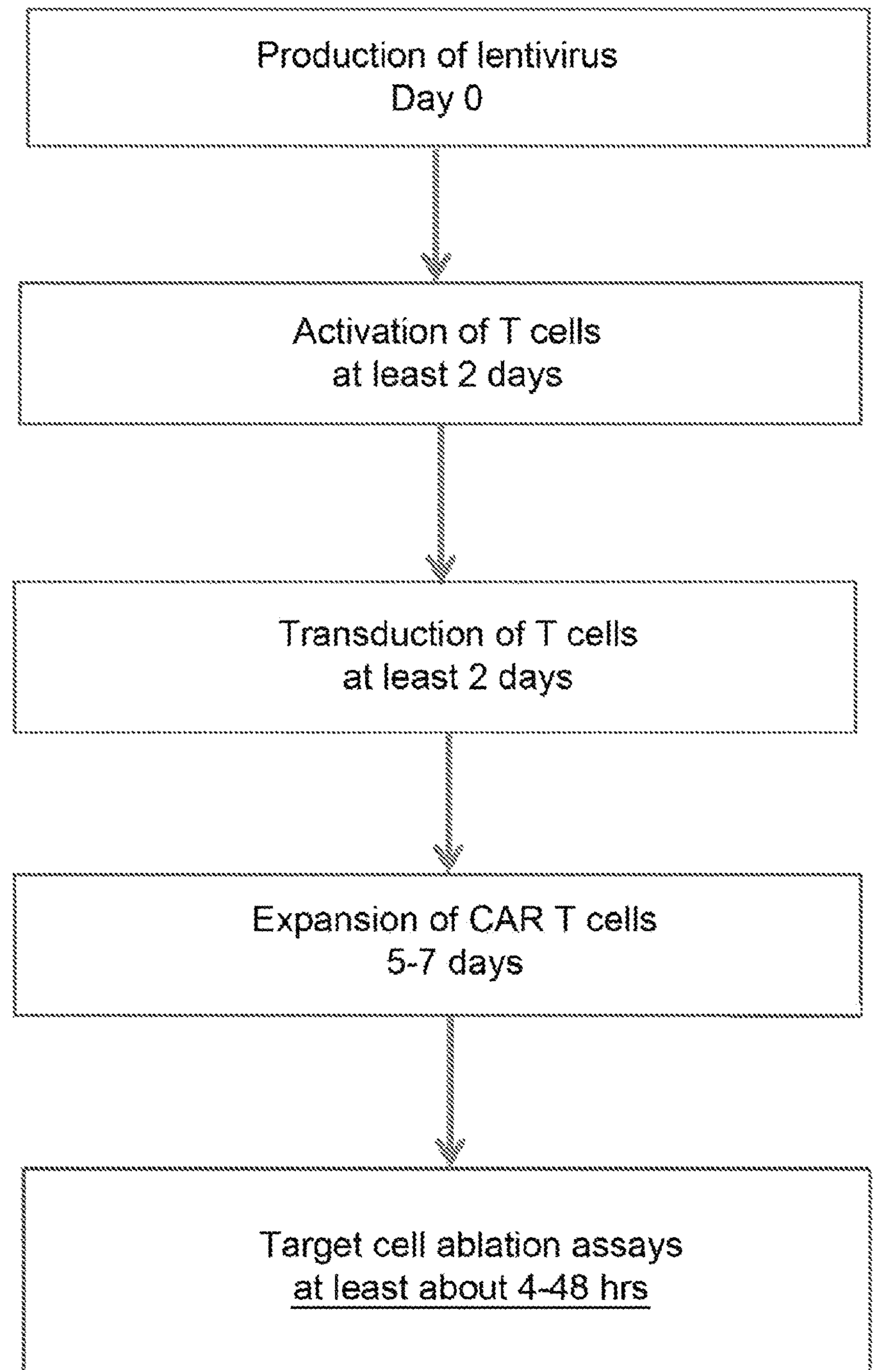
FIG. 3. Schematic showing a method of generating a high-efficiency compound CAR (cCAR).

CD33CD123 cCAR T cells expressing the CD33CAR and CD123 CAR were generated and tested for anti-leukemic functions using the HL60 and KG-1a cell lines. The HL60 cell line is a promyelocytic leukemia cell line highly enriched for CD33. About100% of its cell population is CD33+ with a small subset (<10%) of it being dim CD123+. In culture, this cell line was tested to determine the effectiveness of the CD33CD123 CAR with an emphasis on targeting CD33-expressing leukemic cells. Additionally, due to the strong expression of CD33 in HL60, it is CD33CD123 cCAR action may be profound. Indeed, during 24 h co-culture conditions with various ratios of effector to target cells, the CD33CD123 cCAR exhibited significant leukemic cell killing properties (FIG. 3). CB-derived CD33CD123 CAR T-cells were first tested for their ability to kill HL60 cells. At about 24 h incubation and low effector:target (E:T) ratios ranging from about 0.5:1 to 50:1, preferably, 1:1 to about 5:1, more preferably about 2:1 to 4:1, CD33CD123 CAR cells eliminated about 55% of the CD33 expressing HL60 cells when compared to GFP control. At a ratio of about 5:1, the killing action rose to about 82%.

Figure 4:
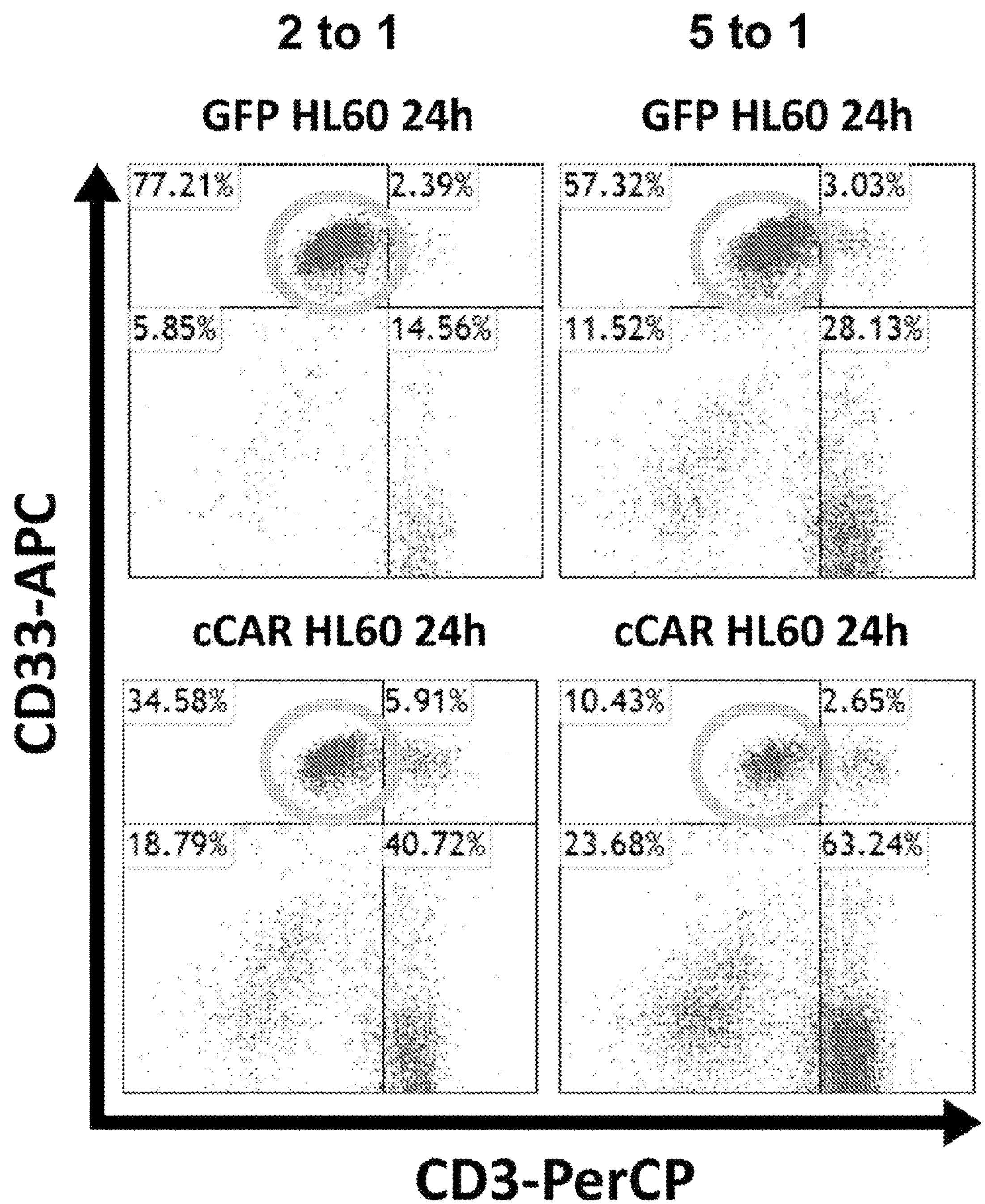
FIG. 4. A co-culture assay representing the incubation of CD33CD123-2G CAR-T cells (cCAR) with the promyelocytic leukemia cell line HL60. cCAR-T cell (lower panel) is compared to control GFP transduced T-cell (upper panel). The efficacy of the killing is measured by the population of CD33+ cells that is left over after incubation for about 24 hours (enclosed in yellow circles).

CD33CD123 CAR derived from peripheral blood mononuclear cells (PBMCs) were co-cultured with the myelogenous leukemia cell line KG1a, which also expresses about 100% CD33 at moderate levels compared to HL60 and 50-80% CD123. KG1a is, therefore, a relatively dual target cell population that is double positive for the antigens targeted by the CD33CD123 CAR. At about 24 hours of incubation and low effector:target (E:T) ratios ranging from about 0.5:1 to 50:1 were used. While at a low E:T ratio of about 2:1, the CD33CD123 CAR exhibited modest anti-leukemic activity about 26%, an increase in E:T ratio to 10:1 resulted in a killing of KG1a of about 62% compared to GFP control (FIG. 4), signaling that the intensity of the CD33 marker may be an indicator for the efficacy of killing with HL60 presenting strongly and harnessing more CAR action than KG1a. These experiments provide evidence for the function of the whole CD33CD123 CAR against its relevant antigen presenting cell populations.

Figure 5:
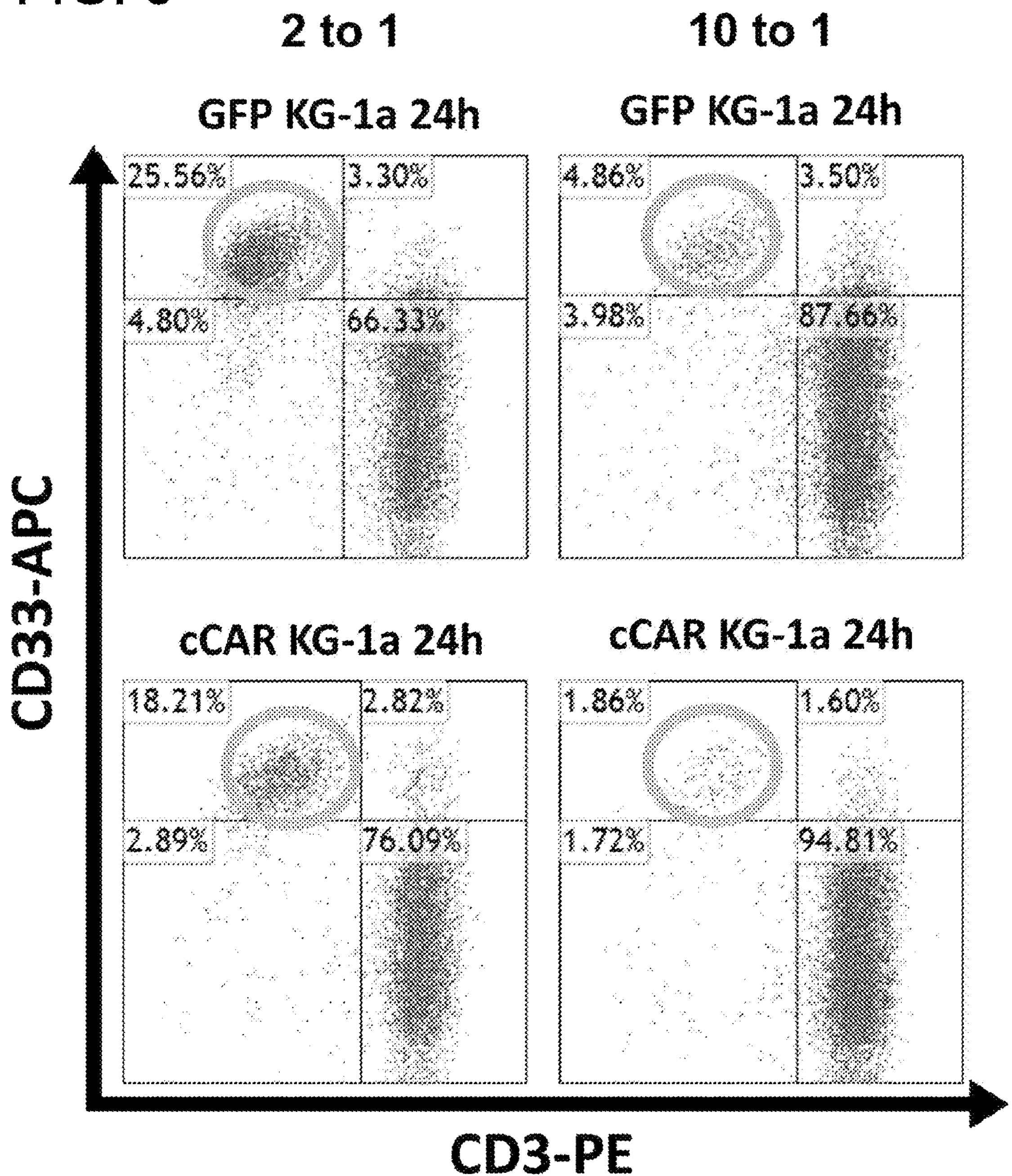
FIG. 5. A co-culture assay representing incubation of cCAR-T cells with the myelogenous leukemia cell line KG-1a, which expresses about 100% CD33 and about 50-80% CD123. cCAR-T cell (lower panel) is compared to control GFP transduced T-cell (upper panel). The efficacy of the killing is measured by the population of CD33+ cells that is left over after incubation for about 24 hours.

Additional compound CAR, CD33CD123-BB cCAR has been generated. This compound CAR comprises two independent units of CARs, CD33 and CD123. The first CAR comprises scFv binding to CD33 and the second CAR bears a different scFv recognizing CD123. Both CARs contain the same hinge region, transmembrane, co-stimulatory and intracellular domains. CD33CD123-BB cCAR lentiviruses were produced and their killing ability was tested in KG-1a cells. As shown in FIG. 5, there was substantial killing at a ratio of about 10:1 but it is less potent than that of CD33CD123 cCAR.

CD33CD123 cCAR Possesses Activity Against Patient Samples Expressing CD33 and/or CD123

Figure 6:
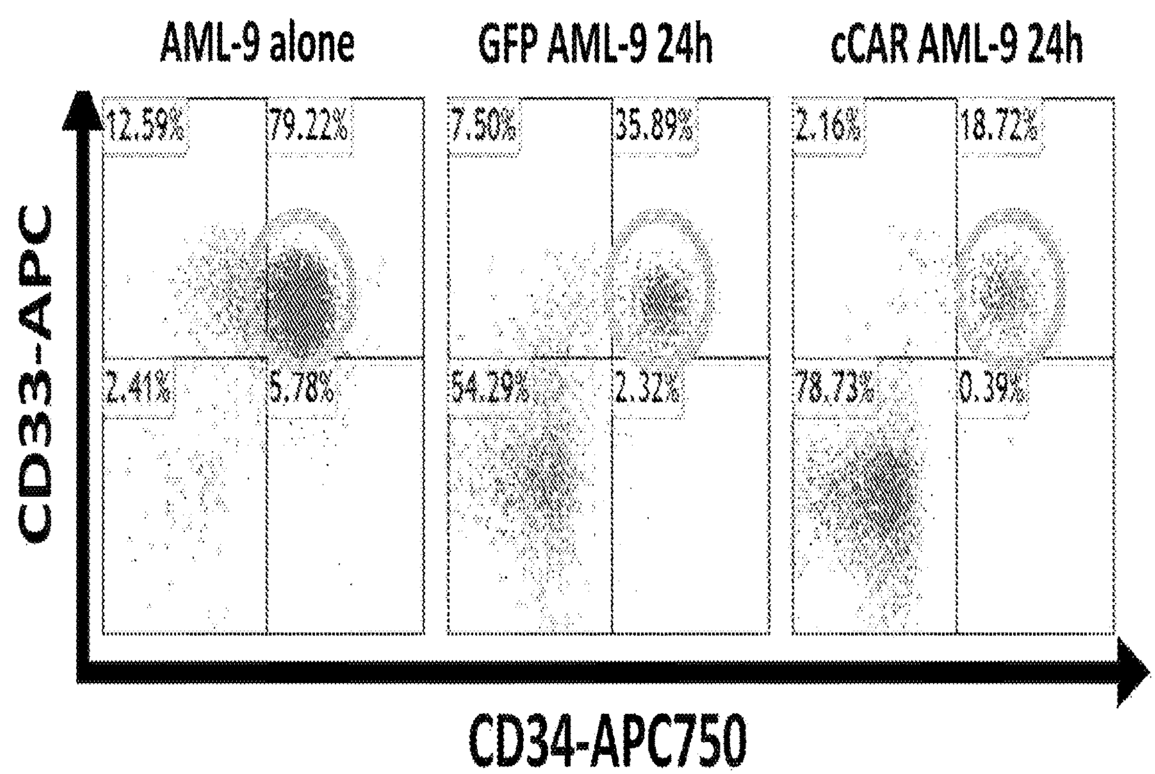
FIG. 6. A co-culture assay representing incubation of cCAR-T cells with AML patient samples (here referred to as AML-9). The patient cells include mixed populations of cells, such as for example, leukemia cells, monocytes, and other types of blasts. CD33 acts as a marker for CAR-T action as well as CD34, a specific marker for leukemia cells. The CAR-T panel (right) is compared to control GFP transduced T-cells (middle). The efficacy of the killing is measured by the population of CD33+/CD34+ cells that is left over after incubation for at least 24 hours.

In addition to cell line experiments, studies were also conducted on patient samples in order to test the function of each individual CAR unit. An aggressive acute myeloid leukemia (AML), AML-9 was used for testing efficacy of the CD33CD123 cCAR. Due to the heterogeneity of the patient cell population, which includes multiple cell types in the AML-9 sample, leukemic blasts were gated with CD34 and CD33, as they were positive for these two markers. The depletion of this CD33+CD34+ population of leukemic cells was observed to be 48% over the GFP control at a ratio of CAR T cell:target cell (FIG. 6).

Figure 7:
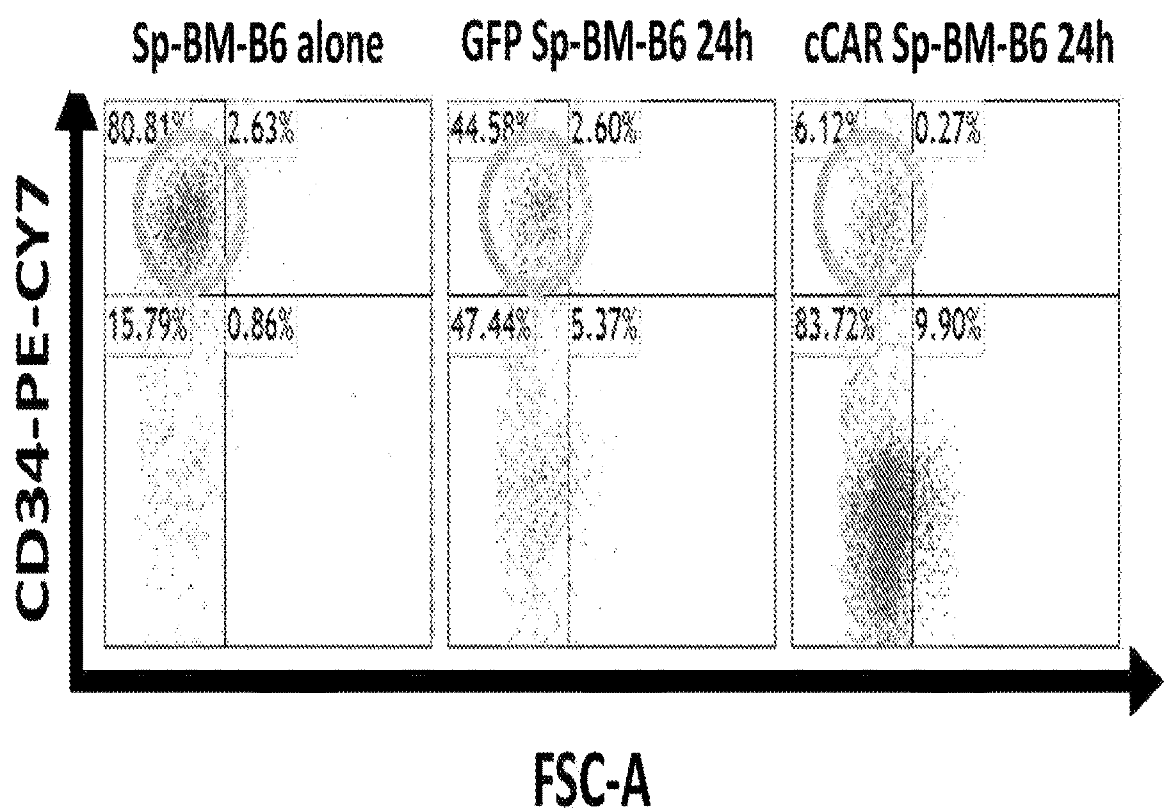
FIG. 7. A co-culture assay representing incubation of cCAR-T cells with B-ALL patient samples (here referred to as Sp-BM-B6). The patient cells include mixed populations of cells, such as, for example, leukemia cells, monocytes, and other types of blasts. CD34 acts as a specific marker for leukemia cells. The CAR-T panel (right) is compared to control GFP transduced T-cells (middle). The efficacy of the killing is measured by the population of CD34+ cells left over after incubation for at least 24 hours.

Leukemic cells that were CD123 positive and CD33 negative were also tested. For this purpose, human B cell acute lympoblastic leukemia (B-ALL) sample, Sp-BM-B6 was chosen. All leukemic blasts in this sample were CD34+ CD33−, and more than about 50% positive for CD123. Depletion of the CD34+ leukemic cell population by CD33CD123 cCAR T cells was about 86% as compared to that of the GFP control (FIG. 7). Based on the cell line and human sample studies, our data strongly suggest that the compound CD33CD123 CAR is able to target leukemic cells expressing CD33 or CD123 or both.

CD33CD123 cCAR NK Cells Targeting Leukemia Cells Expressing CD33 or CD23 or Both Natural killer (NK) cells are CD56+ CD3− and can efficiently kill infected and tumor cells like CD8+ T cells. Unlike CD8+ T cells, NK cells launch cytotoxicity against tumors without the requirement of activation to kill cells. NK cells are safer effector cells, as they may avoid the potentially lethal complications of cytokine storms. However, the use of either CD33 or CD123 or both CAR NK cells in killing leukemias is entirely unexplored.

Production of CD33CD123 cCAR NK Cells

Figure 8:
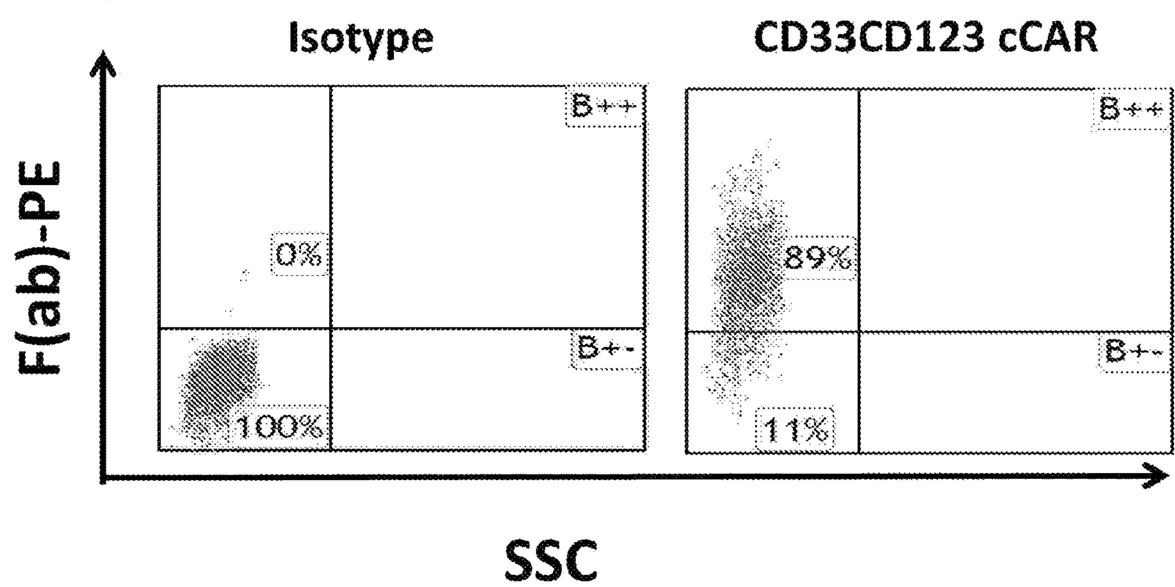
FIG. 8. CD33CD123 cCAR expression in NK-92 cells. The CD33CD123 cCAR expression are detected using goat-anti-mouse antibody, F(ab)2.

NK-92 cells were transduced with CD33CD123 CAR lentiviral supernatant in two consecutive overnight transductions with a change of retronectin- and virus-coated plates in between. The transduced cells were expanded for 3 or 4 days and then analyzed by flow cytometry for CAR expression. Cells were harvested and incubated with goat anti-mouse F(Ab+)2 at about 1:250 for about 30 minutes. Cells were washed, suspended and stained with streptavidin-PE for about 30 minutes. Cells were washed and suspended in 2% formalin, and analyzed by flow cytometry. NK-92 cells expressing CD33CD123 cCAR were then labeled as above and sorted on FACSAria, with the top 0.2% of F(Ab+)2-expressing cells collected and cultured. Subsequent labeling of sorted, expanded cells showed about 89% of NK-92 cell positive for anti-mouse F(Ab+)2 (FIG. 8).

CD33CD123 cCAR NK Cells Efficiently Lyse or Eliminate Leukemic Cells

First, we tested the function of CD33CD123 cCAR NK-92 cells by assessing their ability to kill a HL-60 cancerous cell line in co-culture. Virtually all HL-60 cells highly express CD33 but CD123 expression in this cell line is only less than 10% (weak). Therefore, it is likely that the killing ability of CD33CD123cCAR is dependent on the ability for cCAR to properly targeting CD33.

Figure 9:
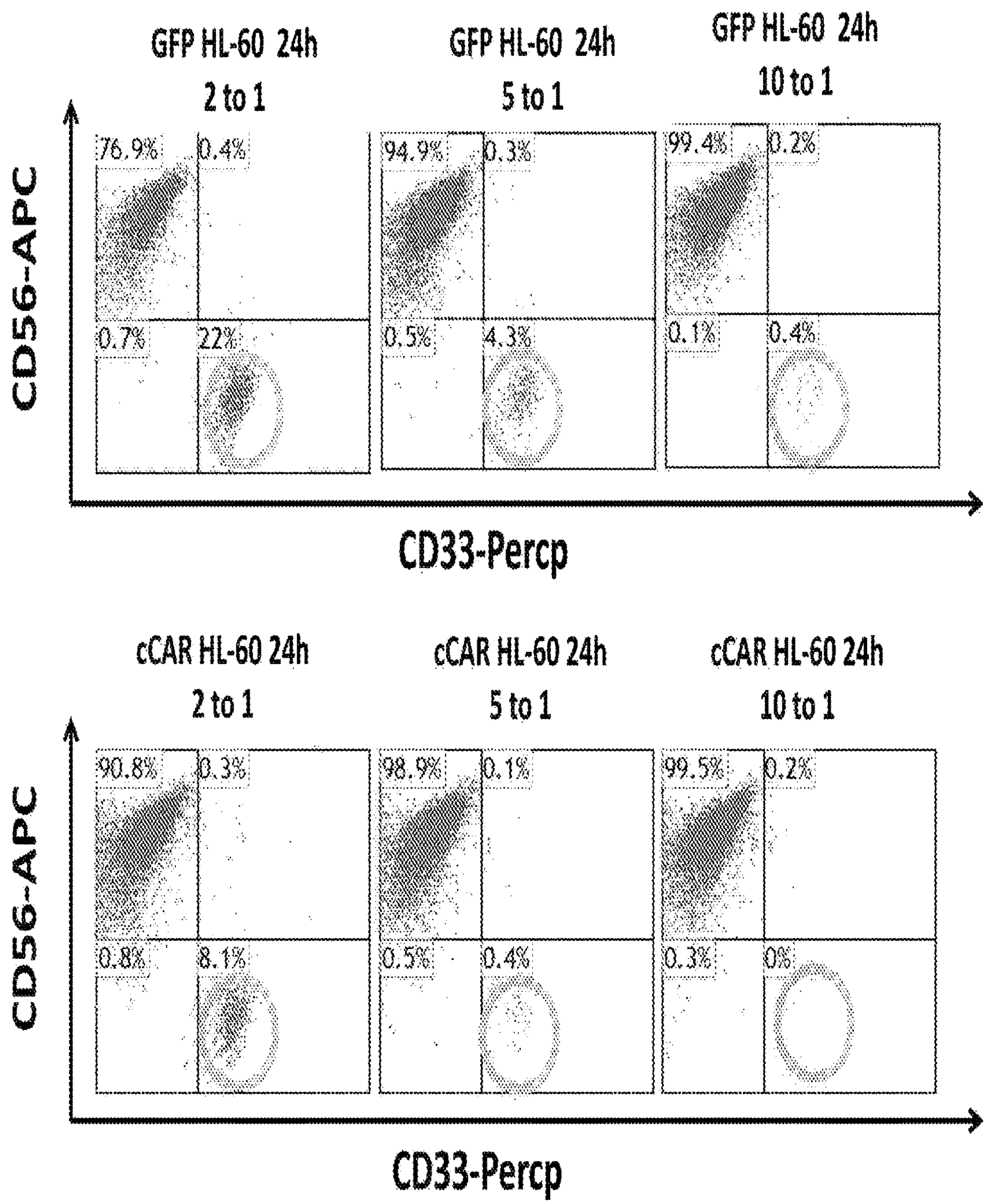
FIG. 9. A co-culture assay representing incubation of cCAR NK-92 cells with HL-60. The cCAR NK-92 cells are compared with GFP transduced NK-92 cells. The efficacy of the killing is measured by the population of CD33+ cells left over after incubation for about 24 hours.
Figure 11:
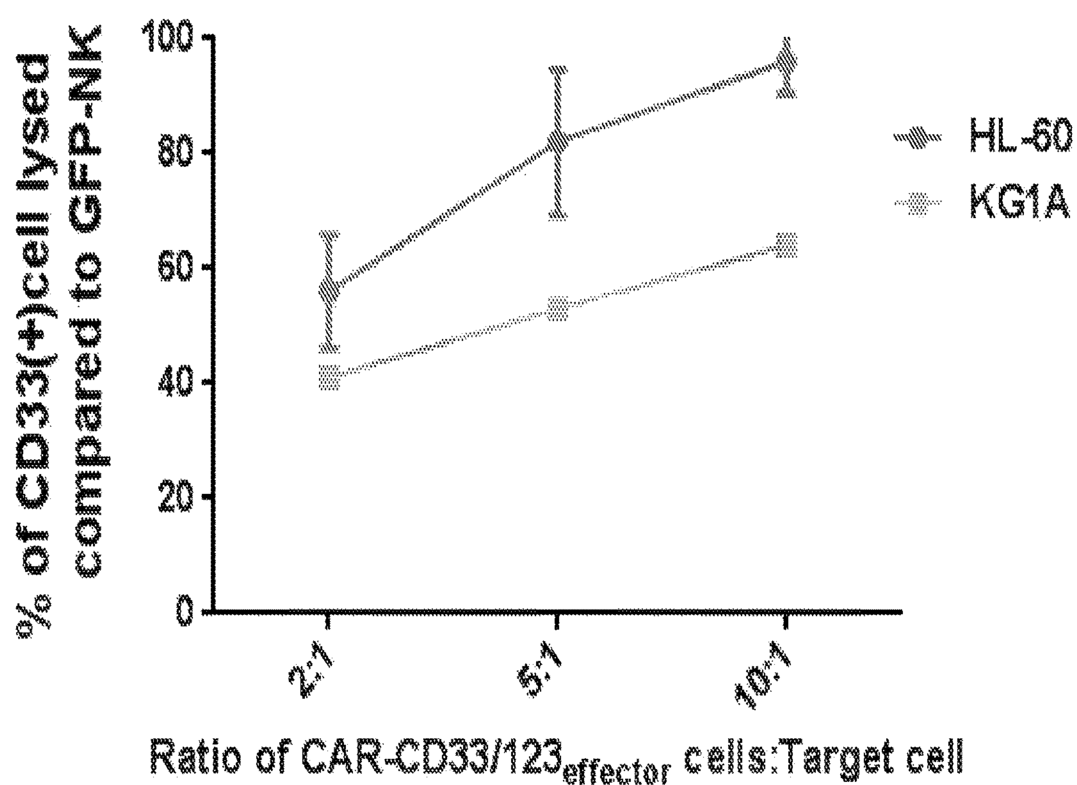
FIG. 11. Dose response of CD33CD123 cCAR (CAR-CD33/123) NK-92 cells with HL-60 or KG1a. The efficacy of the killing is measured by the population of CD33+ cells left over after incubation for about 24 hours.

CD33CD123 cCAR NK-92 cells were co-cultured with the HL-60 cells for about 24 hours in NK cell media without IL-2. After the incubation, the CD33CD123 cCAR NK-92 cells were labeled and compared to a control of non-CAR, GFP NK-92 cells. Dramatic killing of HL-60 cells by CD33CD123 cCAR NK-92 cells was observed as compared to the control, GFP NK-92 cells. Moreover, the killing ability of CD33CD123 cCAR NK-92 cells was dose-dependent, with a about 10 to 1 ratio of about 100% compared to the control (FIGS. 9 and 11).

Figure 10:
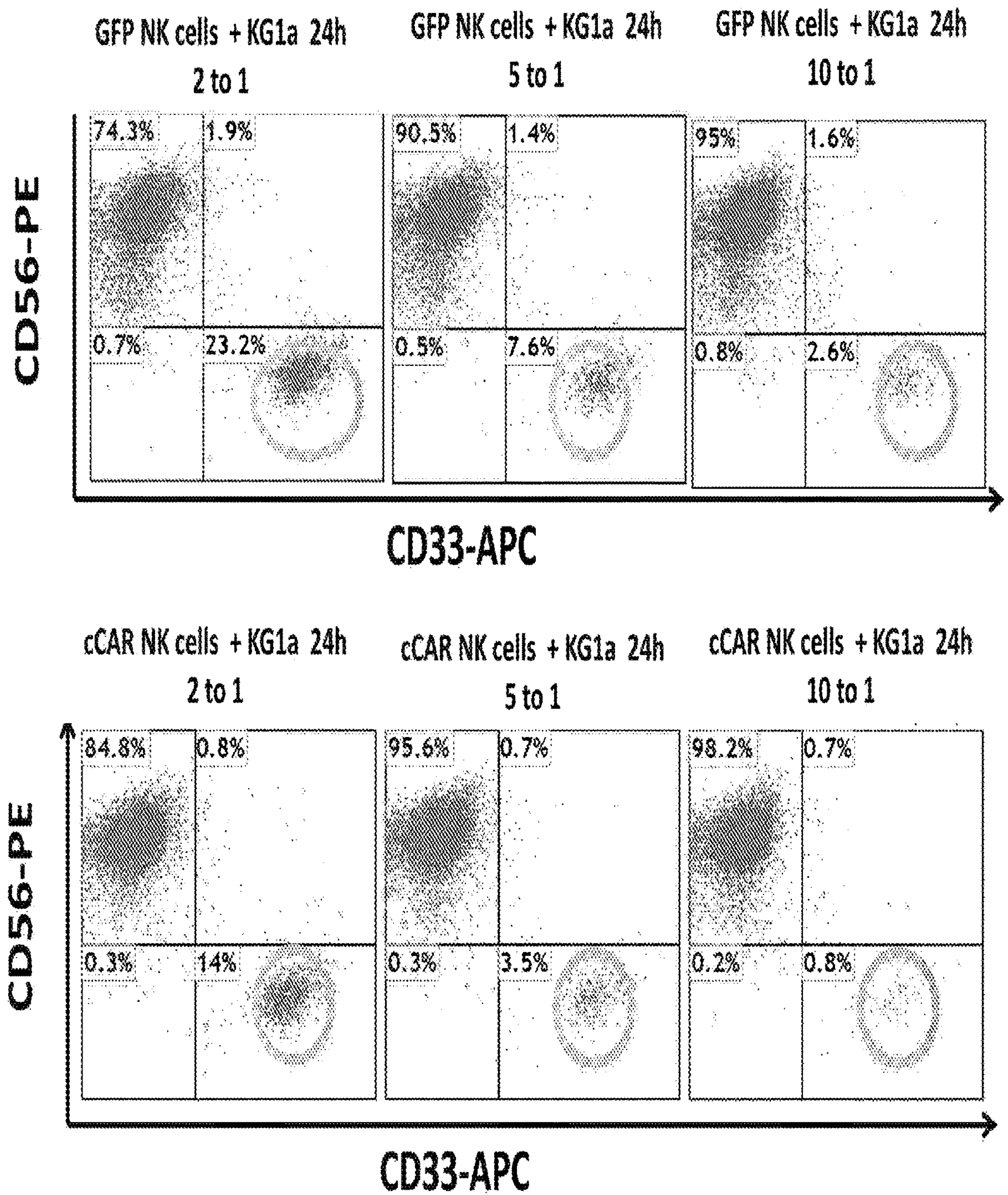
FIG. 10. A co-culture assay representing incubation of cCAR NK-92 cells with KG1a. The cCAR NK cell panel is compared with GFP transduced NK-92 cells. The efficacy of the killing is measured by the population of CD33+ cells left over after incubation for about 24 hours.

A second co-culture experiment using the myeloid leukemia cell line was performed using KG1a, which expresses CD33 in all cells but at a moderate level compared to that of HL-60. The CD123 antigen is expressed in about 50-80% of KG1a cells. The experimental design was similar to the first experiment of the HL-60 killing assay described above, with the same incubation time, effector:cancer cell ratios and GFP NK-92 cell controls. Results show a remarkable killing of KG1a cells by CD33CD123 cCAR NK-92 cells in a dose-dependent manner as compared to the GFP NK-92 cell control. At a ratio of effector:target of 10:1, killing of KG1a cells by CD33CD123 cCAR NK-92 cells was about 85% as compared to that of GFP control (FIGS. 10 and 11).

Figure 12:
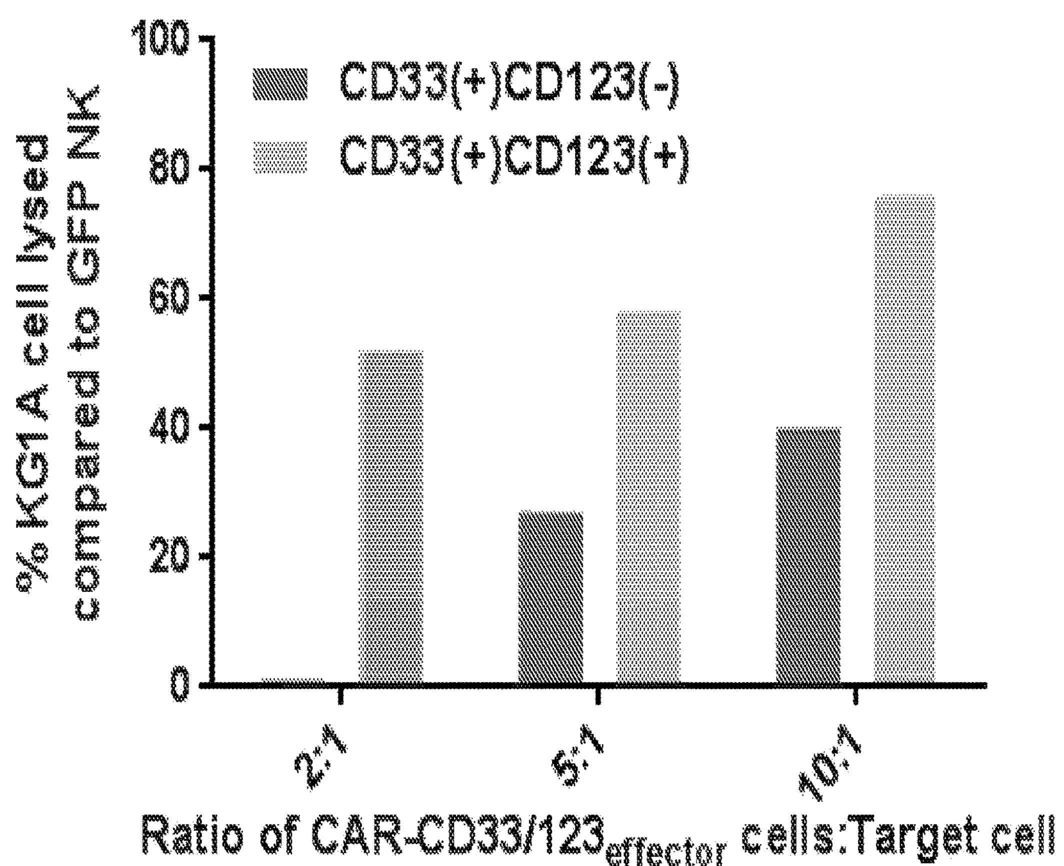
FIG. 12. A comparison of CD33CD123 cCAR NK-92 cell killing ability with control in two populations of KG11 cells. Assays were performed at different ratios of CAR-CD33/123 (CD33CD123 cCAR NK-92 cells) and target cells, kG1a. The efficacy of the killing is measured by the population of CD33+CD123+ or CD33+CD123− cells left over after incubation for about 24 hours.

Analysis of KG1a cells showed two different populations, CD33+CD123− and CD33+CD123−. FIG. 11 showed a dose dependent increase in cell killing seen in both populations. Surprisingly, the double positive population showed a higher efficient killing for each increased ratio, suggesting a possible synergistic effect of two modular CARs of CD33 and CD123 (FIG. 12).

Generation of CD19CD20, CD19CD22, CD19CD138 cCARs

Figure 13:
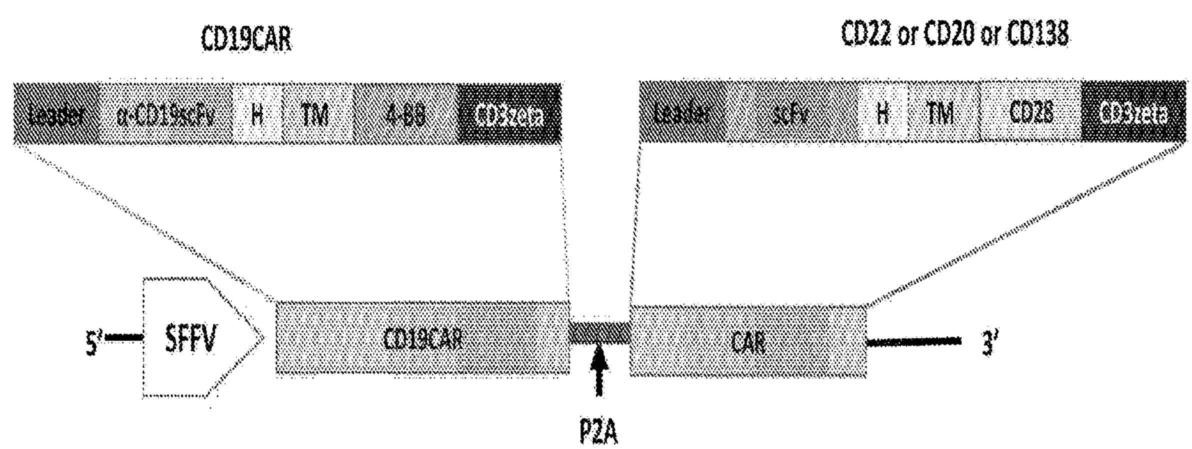
FIG. 13. A schematic representation of cCAR. The construct comprises a SFFV promoter driving the expression of multiple modular units of CARs linked by a linker. Upon cleavage of the linker, the cCARs split and engage upon targets expressing combinations of various target antigens: CD19 and/or CD20, and/or CD22 and/or 138. Multiple cCARs utilize the same or different co-stimulatory domains, such as, without limiting 4-1BB (also labeled as 4-BB) and/or CD28.

The three cCARs have been generated (FIG. 13) using the similar strategy to that of the CD33CD123 cCAR described above.

Generation of cCAR Including BCMA CS1 cCAR and BCMA CD19 cCAR for Treatment of Multiple Myeloma Pre-clinical studies have been developed for cCARs to target surface antigens including CD38, CS1, CD138, B cell maturation antigen (BCMA) and CD38. CD19 CAR has also demonstrated some efficacy for the treatment of multiple myeloma in a phase I clinical trial. However, given that the heterogeneity of surface antigen expression commonly occurs in malignant plasma cells(Ruiz-Arguelles and San Miguel 1994), it is unlikely that a single target is sufficient to eliminate this disease. BCMA CS1 cCAR, BCMA CD19 cCAR, BCMA CD38 cCAR and BCMA CD138 cCAR were generated and the experimental design was similar to that of CD33CD123 cCAR as described above.

Figure 14A:
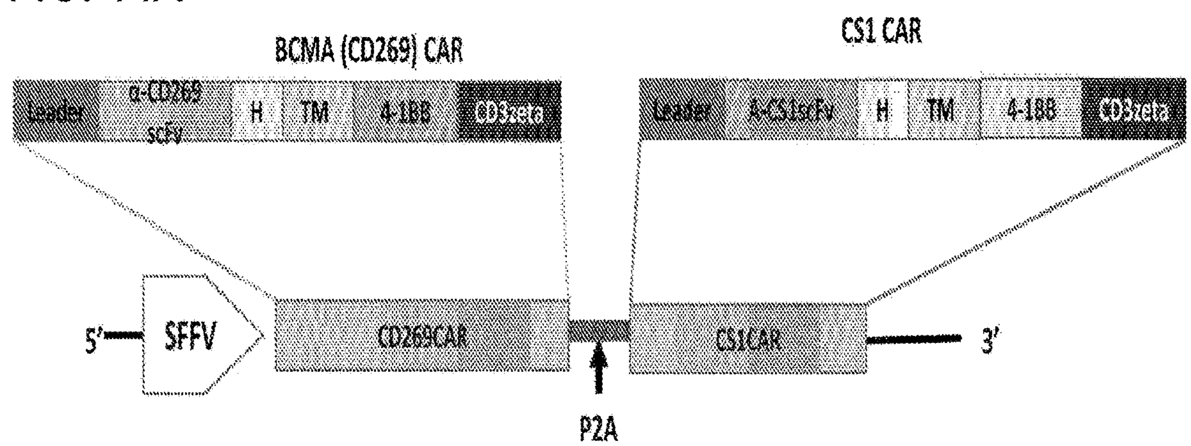
FIGS. 14A-C. BCMA-CS1 cCAR construct scheme (BC1cCAR). (A) The construct consists a SFFV promoter driving the expression of two modular units of CAR linked by a P2A peptide. Upon cleavage of this P2A peptide, the cCARs split and engage upon targets expressing BCMA and/or CS1. Two unit CARs use same co-stimulatory domain, 4-1BB. (B) Flow cytometry analysis of BC1cCAR expression on T cell surface for vector (left) and BC1cCAR (right, highlighted by a square) showing 15.3% positive for F(Ab)2. Gating done against isotype controls. (C) Preliminary functional validation of BC1cCAR-T cells by co-culturing K562 cells transduced with BCMA cDNA (BCMA-K562) (obtained from Kochenderfer, NIH). Bar graph shows lysis of the BCMA-K562 cell line vs. control T-cells as well as lysis of wild-type K562 (wt-K562) vs. control.
Figure 14B:
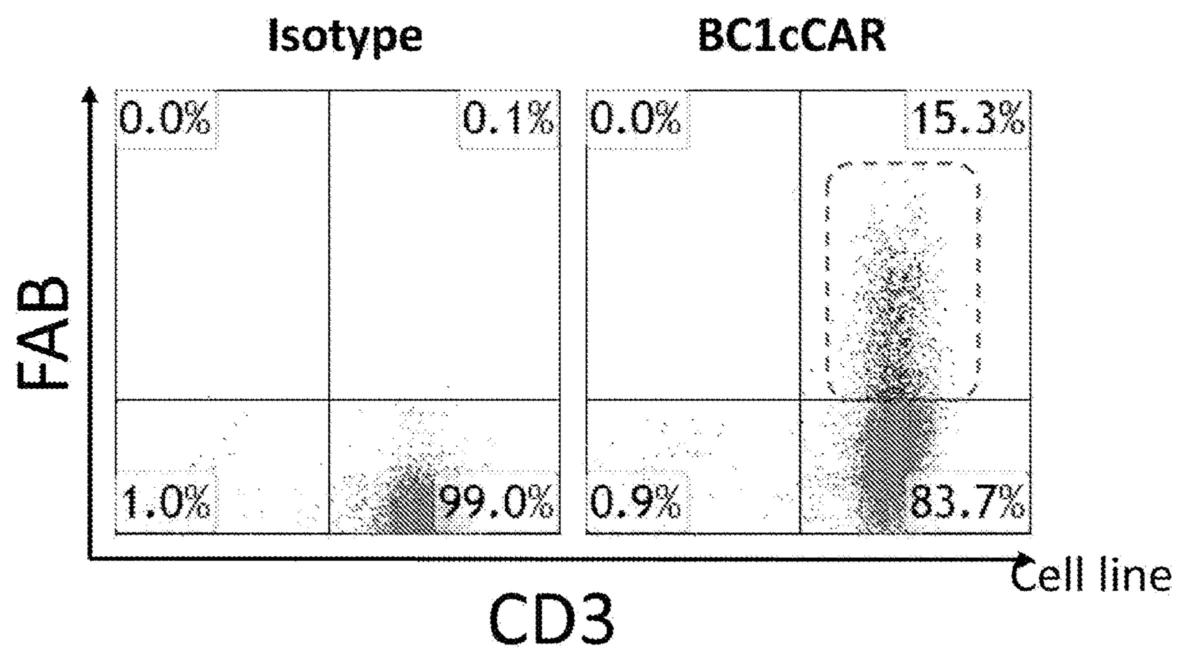
Figure 14C:
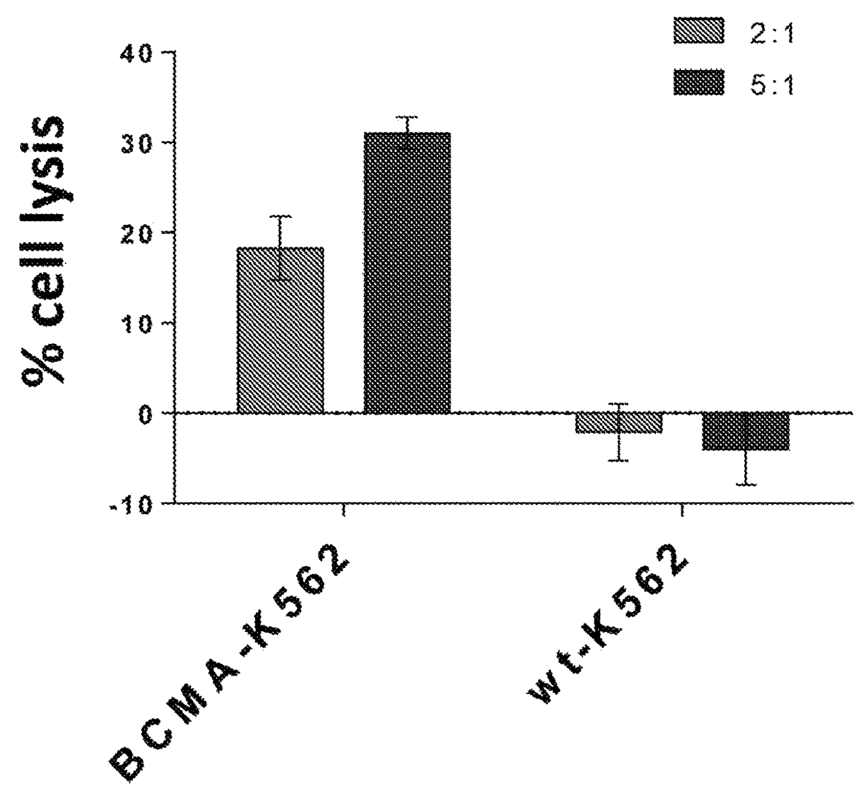

Generation of cCAR Including BCMA CS1 cCAR (BC1cCAR) for Treatment of Multiple Myeloma Generation and Characterization of BCMA-CS1 cCAR (BC1cCAR) Construct BC1cCAR's modular design consists of an anti-CD269 (BCMA, B-cell maturation antigen) single-chain variable fragment (scFv) region fused to an anti-CD319 (CS1) scFv by a self-cleaving P2A peptide, CD8-derived hinge (H) and transmembrane (TM) regions, and tandem 4-1BB co-activation domains linked to the CD3ζ signaling domain (FIG. 14A). A strong spleen focus forming virus promoter (SFFV) and a CD8 leader sequence were used for efficient expression of the BC1cCAR) CAR molecule on the T-cell surface. Two unit CARs use same co-stimulatory domain, 4-1BB. Transfected BC1cCAR HEK293T cells were subjected to Western blot analysis in order to confirm the compound construct. Immunoblot with an anti-CD3ζ monoclonal antibody showed bands of predicted size for the compound CAR CD3ζ fusion protein (FIG. 14E). Importantly, two distinct bands of similar intensity were observed on the blot signaling the successful high cleavage action of the P2A peptide as expected. No CD3ζ expression was seen for the GFP control vector as expected.

Generation of BC1cCAR (cCAR) T-Cells

T-cells isolated from umbilical cord blood (UCB) buffy coats were transduced with BC1cCAR lentivirus after 2 days of activation. Two unit CARs used the same co-stimulatory domain, 4-1BB. BC1cCAR's transduction efficiency was determined to be about 15% as determined by flow cytometry (FIG. 14B). BC1cCAR T-cells were first tested on a CML (chronic myeloid leukemia) cell line negative for the myeloma markers, BCMA and CS1. As expected, there was no lysis from either control T-cells or BC1cCAR T-cells against wild-type K562 (FIG. 14C). BCMA-K562 (Kochenderfer, NIH) were K562 cells transduced with BCMA expressing cDNA to express BCMA at >80% of the cell population. BC1cCAR T-cells were co-cultured with this cell line at E:T ratios of 2:1 and 5:1 and show over 30% lysis as compared to control (undetectable) (FIG. 14C). These results are compatible with other cultures performed on antigen-transduced cell lines for other CARs, such as CS1CAR T-cells.

Figure 14D:
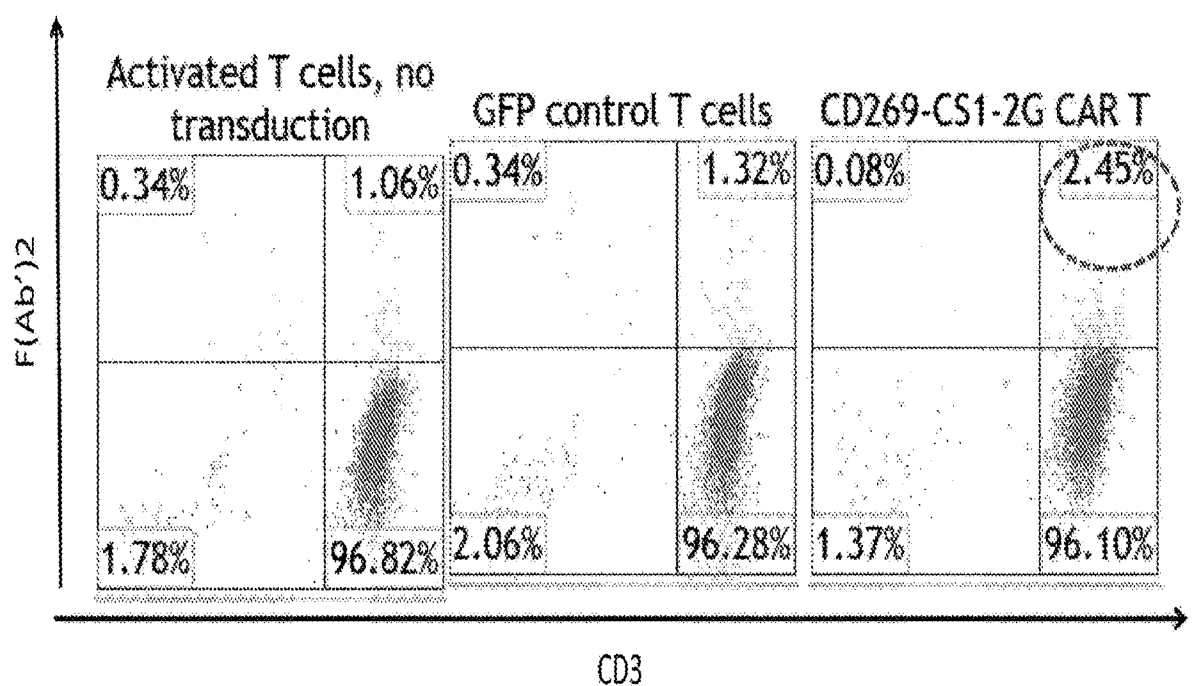
FIG. 14D. BCMA-CS1-2G construct using two different co-stimulatory domains either 4-1BB or CD28 for each unit. The construct includes a SFFV promoter driving the expression of two modular units of CAR linked by a P2A peptide. Upon cleavage of this P2A peptide, the cCARs split and engage targets expressing BCMA and/or CS1. Two unit CARs use a different co-stimulatory domain, either 4-1BB or CD28. Flow cytometry analysis of BC1cCAR expression on T cell surface for vector (left) and BC1cCAR (right, highlighted by a square) showing rare positive cells for F(Ab)2. Gating done against isotype controls.
Figure 14E:
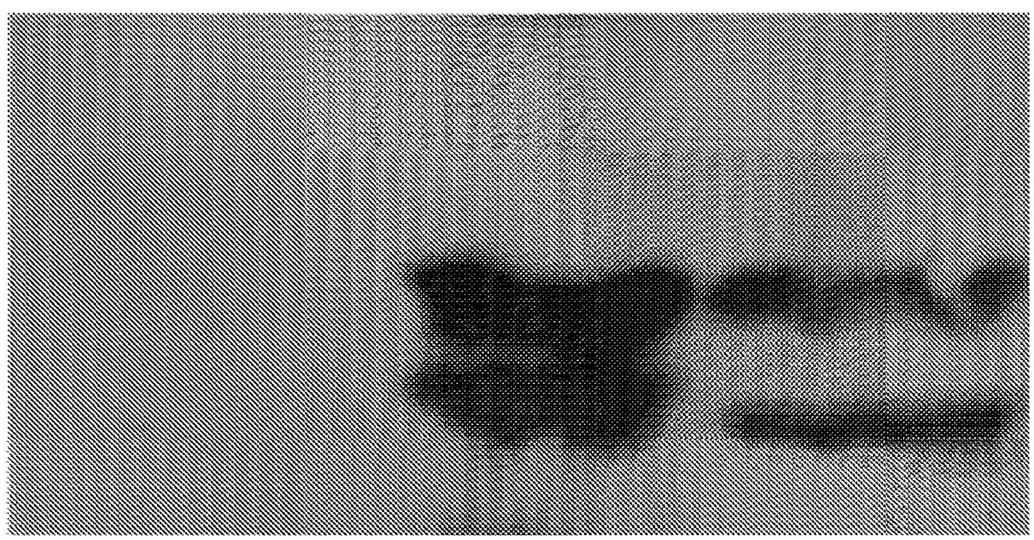
FIG. 14E. Protein expression of BC1cCAR and BCMA-CS1-2G in HEK-293FT cells. HEK-293FT cells were transfected with lentiviral plasmids for GFP (lane 1), BC1cCAR (lane 2), CD269-CS1-2G (lane 3) 48 hours after transfection, supernatant was removed, and cells were also removed. Cells were lysed for Western blot and probe with mouse anti-human CD3z antibody.

However, when BCMA-CS1-2G (a cCAR) used a different co-stimulatory domain, either 4-BB or CD28 for each unit, rare surface CAR expression was detected, which indicate that an appropriate selection of a co-stimulatory domain may be important for ensuring the surface CAR expression on T cells (FIG. 14D). Although protein was detected in HEK cells by Western blotting (FIG. 14E), we were unable to detect surface expression in activated T cells transduced with CD269-CS1-2G lentiviral supernatant. This may be due to an inability to export the expressed protein to the cell membrane. In future, we may need to optimize the sequence of this construct to allow for greater cell surface expression.

BC1cCAR T-Cells Specifically Lyse $BCMA^+$ and $CS1^+$ Cell Lines

Figure 15A:
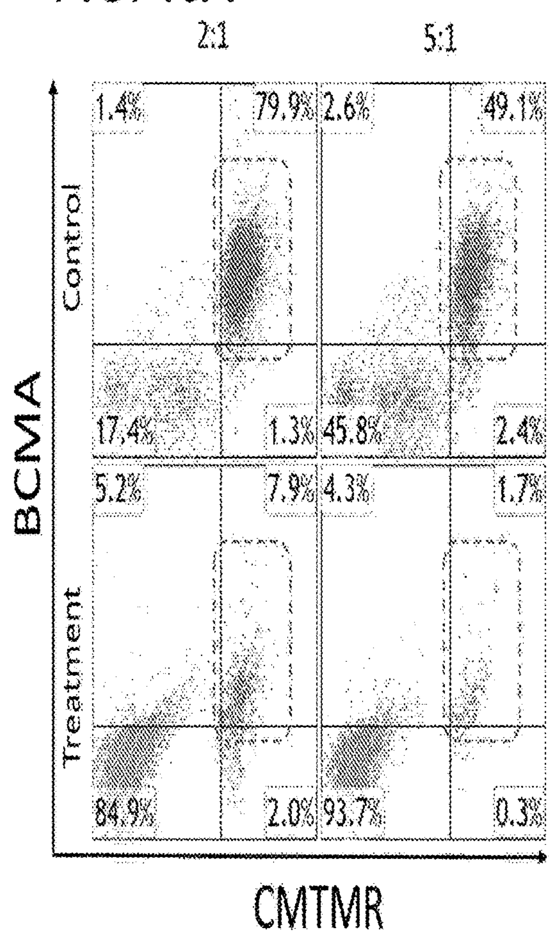
FIGS. 15A-B. MM1S cell line co-culture. Co-cultures were carried out under 24 hours and collected and analyzed via flow cytometry. Target MM1S cells (myeloma cells) were labeled with Cytotracker (CMTMR) dye to distinguish it from effector T-cells. Populations were gated by anti-BCMA (CD269) and anti-CS1 (CD319) antibodies.
Figure 15B:
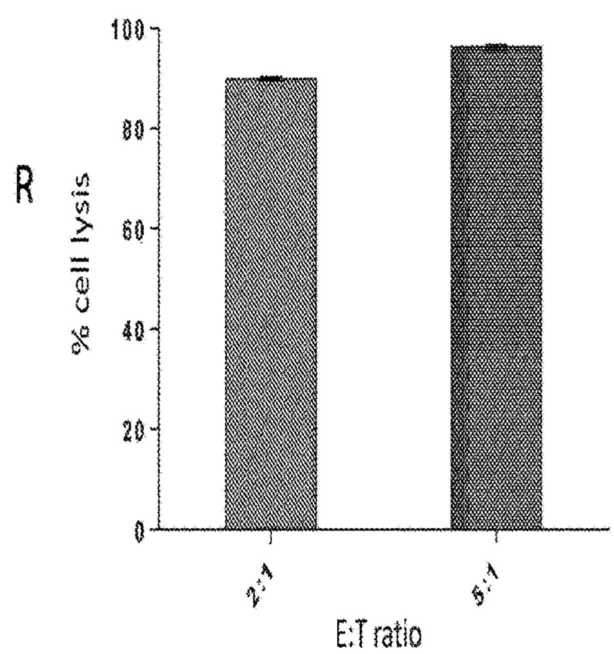
Figure 16A:
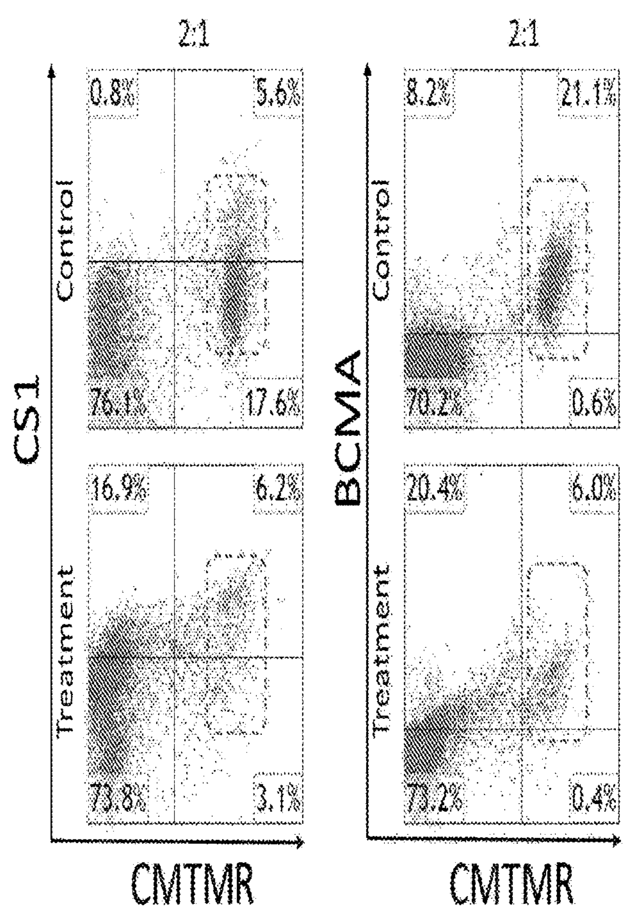
FIGS. 16A-B. RPMI-8226 cell line co-culture. Co-cultures were carried out under 24 hours and collected and analyzed via flow cytometry. Target RPMI-8226 cells were labeled with Cytotracker (CMTMR) dye to distinguish it from effector T-cells. Populations were gated by anti-BCMA (CD269) and anti-CS1 (CD319) antibodies.
Figure 16B:
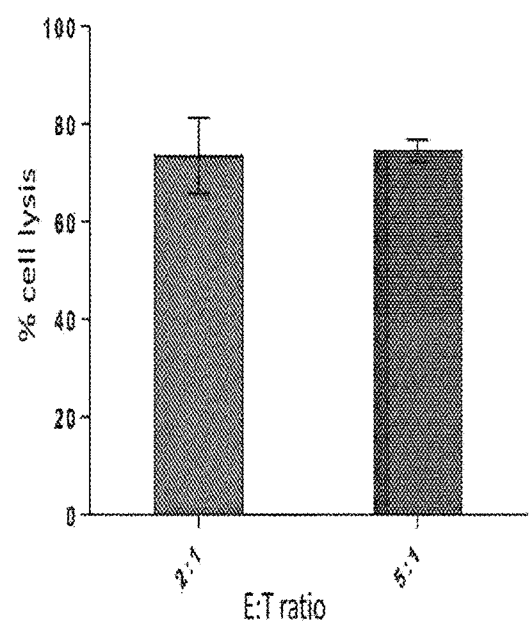
Figure 17A:
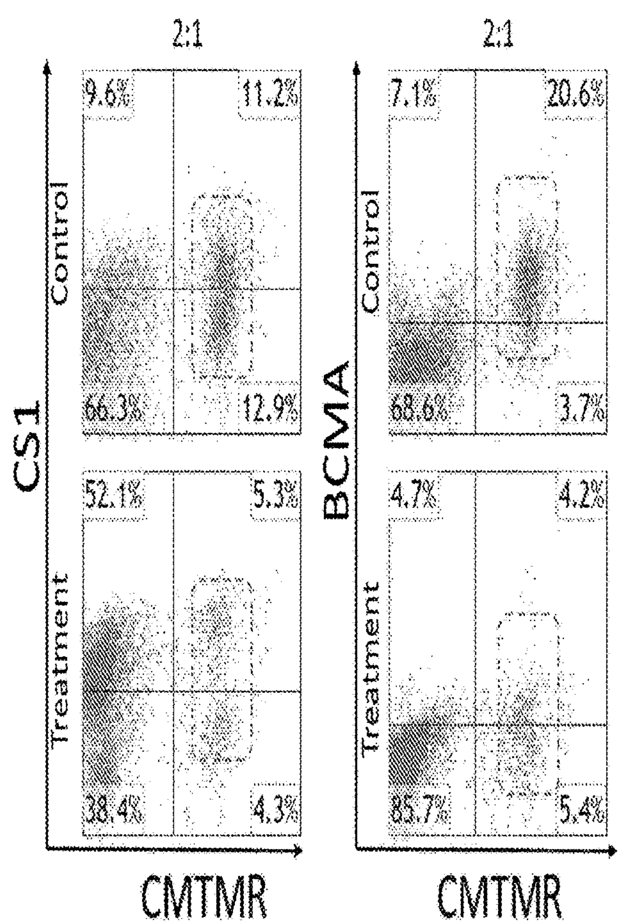
FIGS. 17A-B. U266 cell line co-culture. Co-cultures were carried out under 24 hours and collected, and analyzed via flow cytometry. Target U266 cells were labeled with Cytotracker (CMTMR) dye to distinguish it from effector T-cells. Populations were gated by anti-BCMA (CD269) and anti-CS1 (CD319) antibodies. (A) flow cytometry depictions of co-cultures. (B) graphical summary of lysis vs. E:T ratio.
Figure 17B:
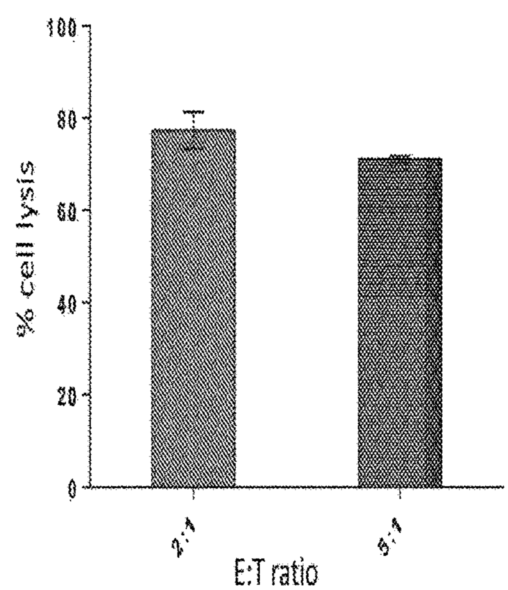

To assess the cytotoxicity ability of BC1cCAR T-cells, we conducted co-culture assays with myeloma cell lines: MM1S ($BMCA^+$ $CS1^{+)}$, RPMI-8226 ($BCMA^+$ $CS1^-$), and U266 ($BCMA^+$ $CS1^{dim}$). The ability of the BC1cCAR T-cells to lyse the target cells was quantified by flow cytometry analysis, and target cells were stained with Cytotracker dye (CMTMR). In 24 hour co-cultures, the BC1cCAR exhibited virtually complete lysis of MM1S cells, with over 90% depletion of target cells at an E:T ratio of 2:1 and over 95% depletion at an E:T of 5:1 (FIG. 15). In RPMI-8226 cells, BC1cCAR lysed over 70% of $BCMA^+$ target cells at an E:T ratio of 2:1, and over 75% at an E:T of 5:1(FIG. 16). In 24 hour co-culture with U266 target cells, BC1cCAR lysed 80% of $BCMA^+$ U266 cells at an E:T ratio of 2:1, reaching saturation (FIG. 17).

Figure 18A:
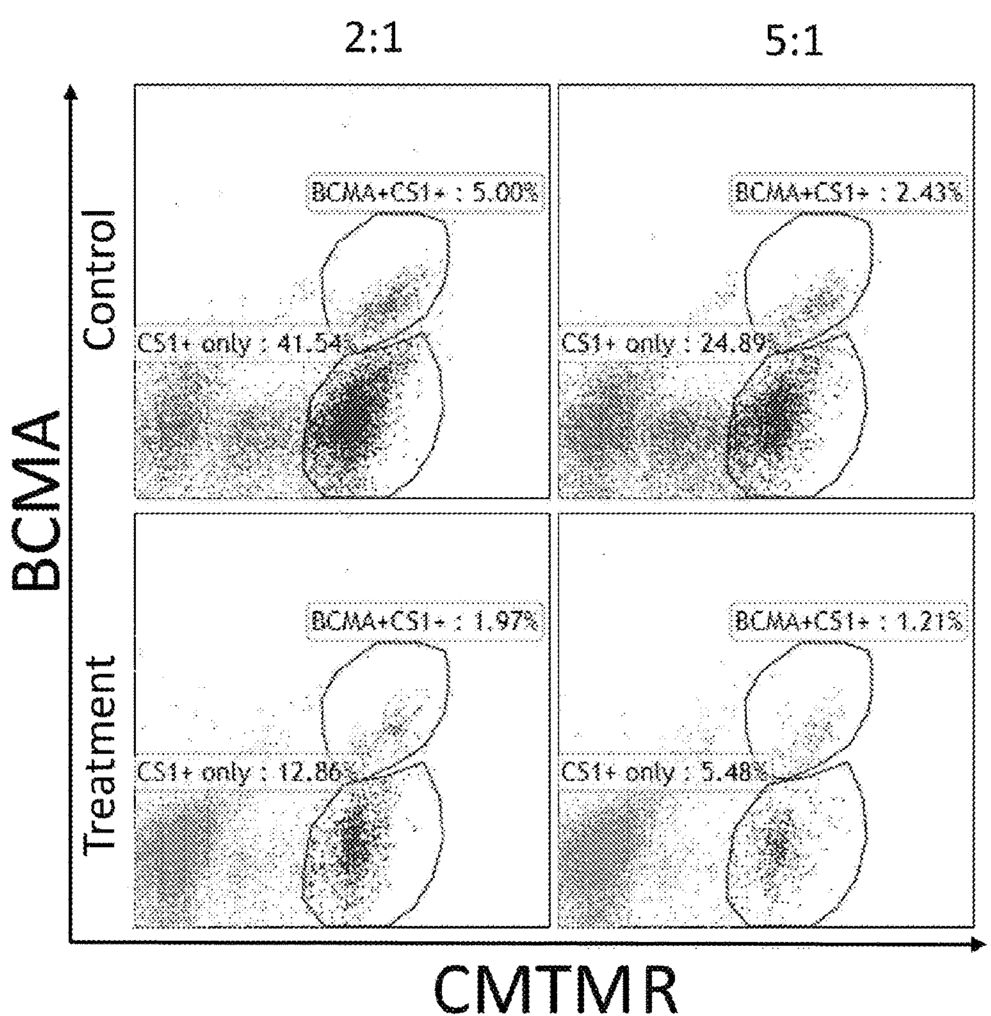
FIGS. 18A-B. MM10-G primary patient sample co-culture and specific lysis. Co-cultures were carried out under 24 hours and collected and analyzed via flow cytometry. Target MM10-G cells were labeled with Cytotracker (CMTMR) dye to distinguish it from effector T-cells. Populations were gated by anti-BCMA (CD269) and anti-CS1 (CD319) antibodies. Notably, gating shows MM10-G presenting with distinct $BCMA^+$ and $CS1^+$ populations.
Figure 18B:
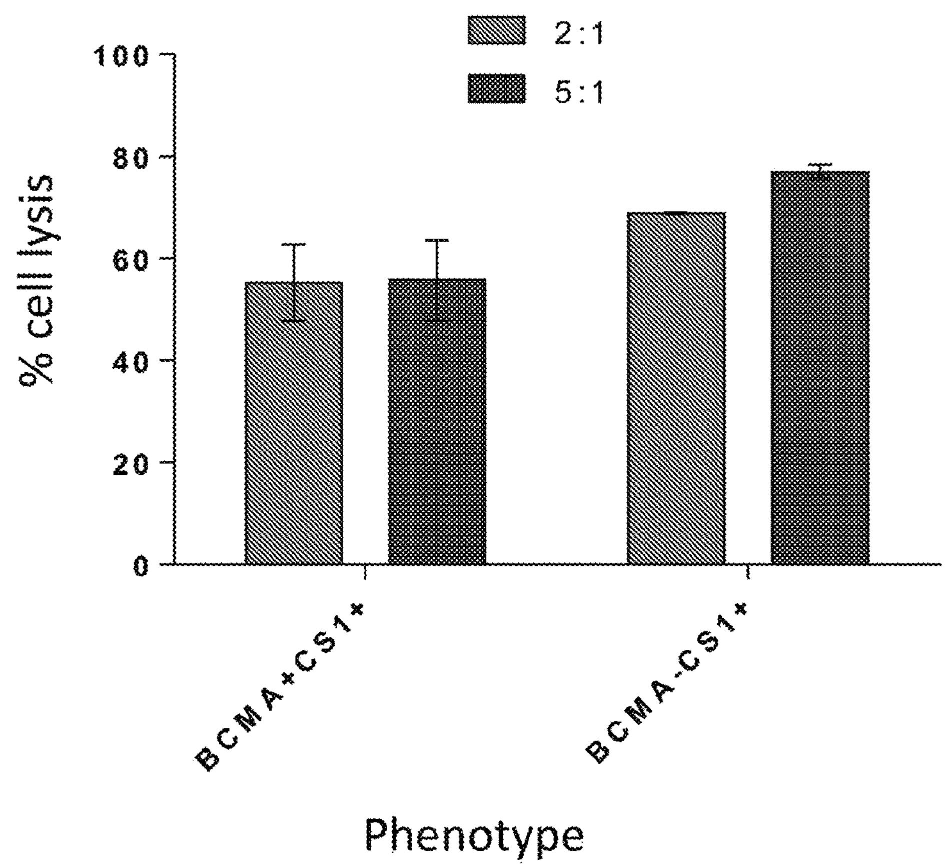
Figure 19A:
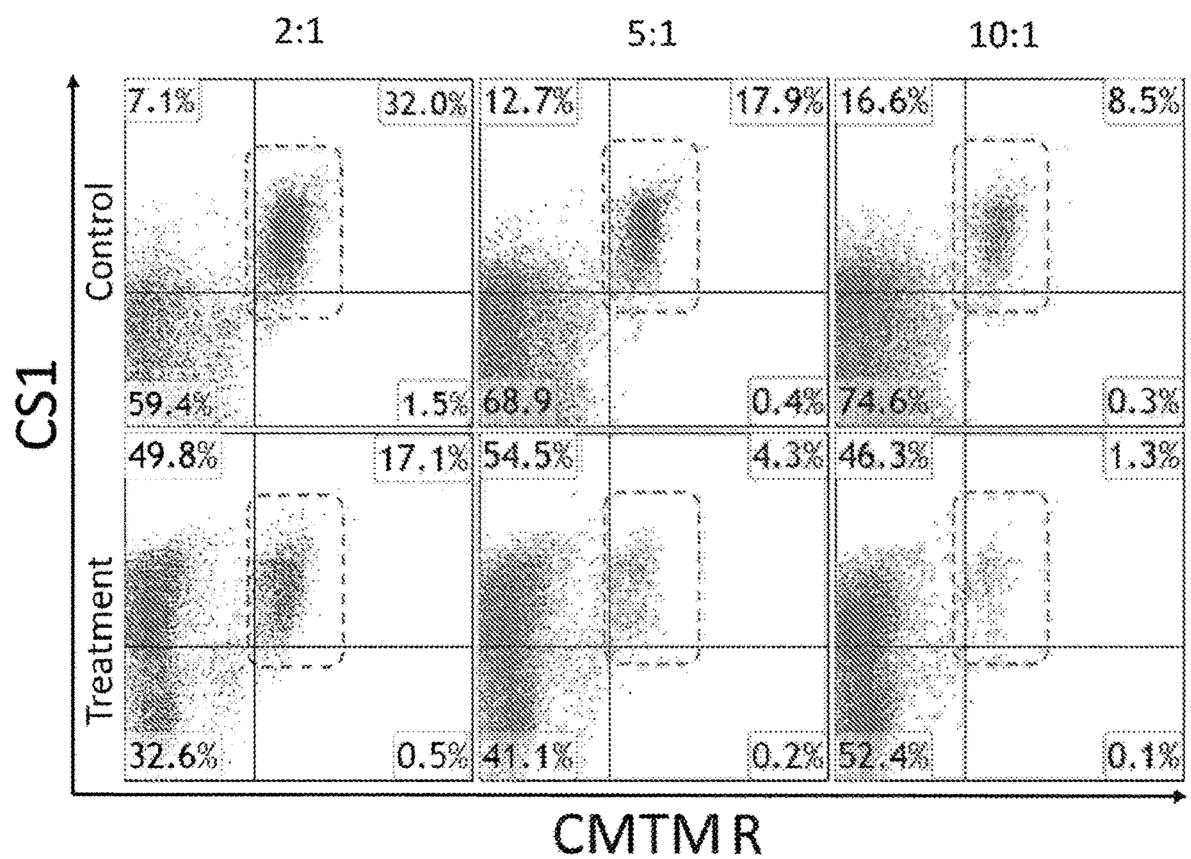
FIGS. 19A-B. MM7-G primary patient sample co-culture and specific lysis. Co-cultures were carried out under 24 hours and collected and analyzed via flow cytometry. Target MM7-G cells were labeled with Cytotracker (CMTMR) dye to distinguish it from effector T-cells. Populations were gated by anti-BCMA (CD269) and anti-CS1 (CD319) antibodies.
Figure 19B:
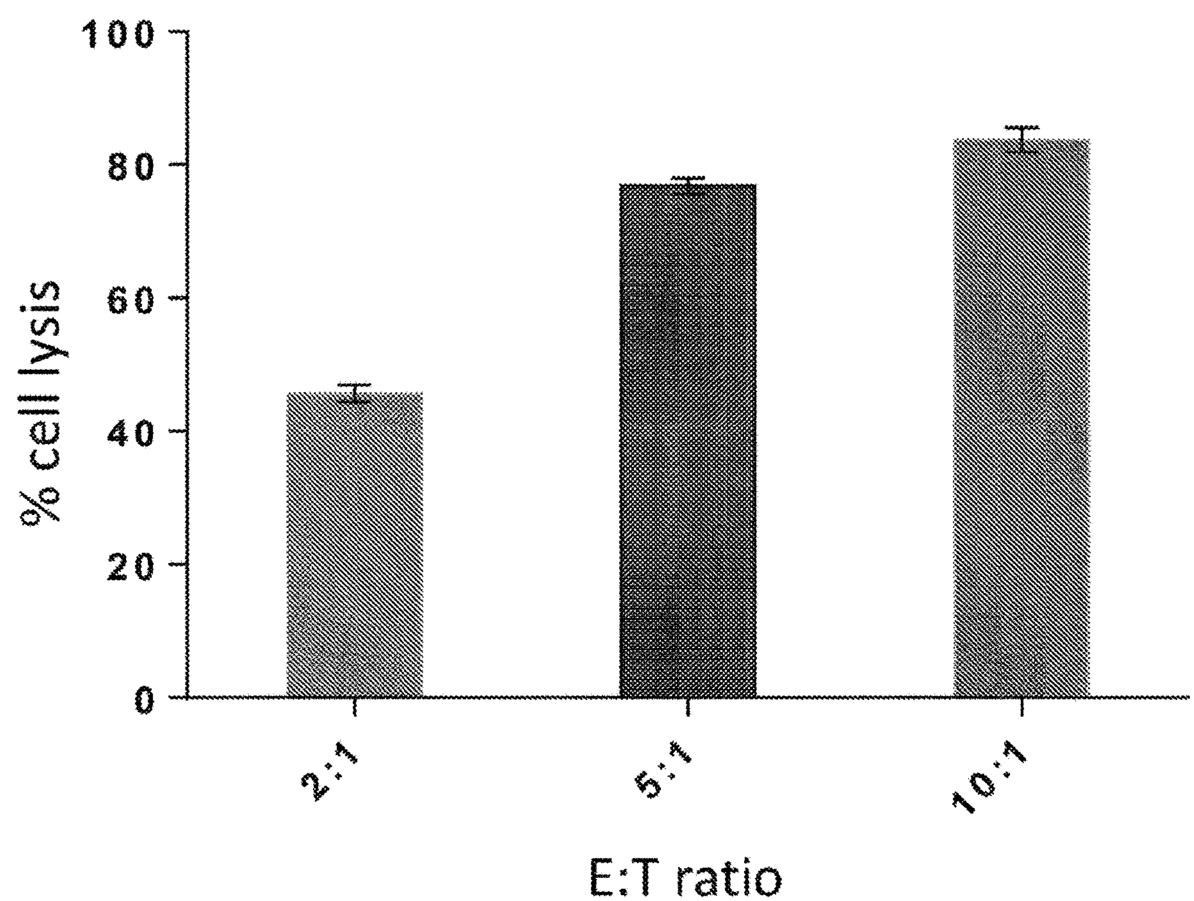
Figure 20A:
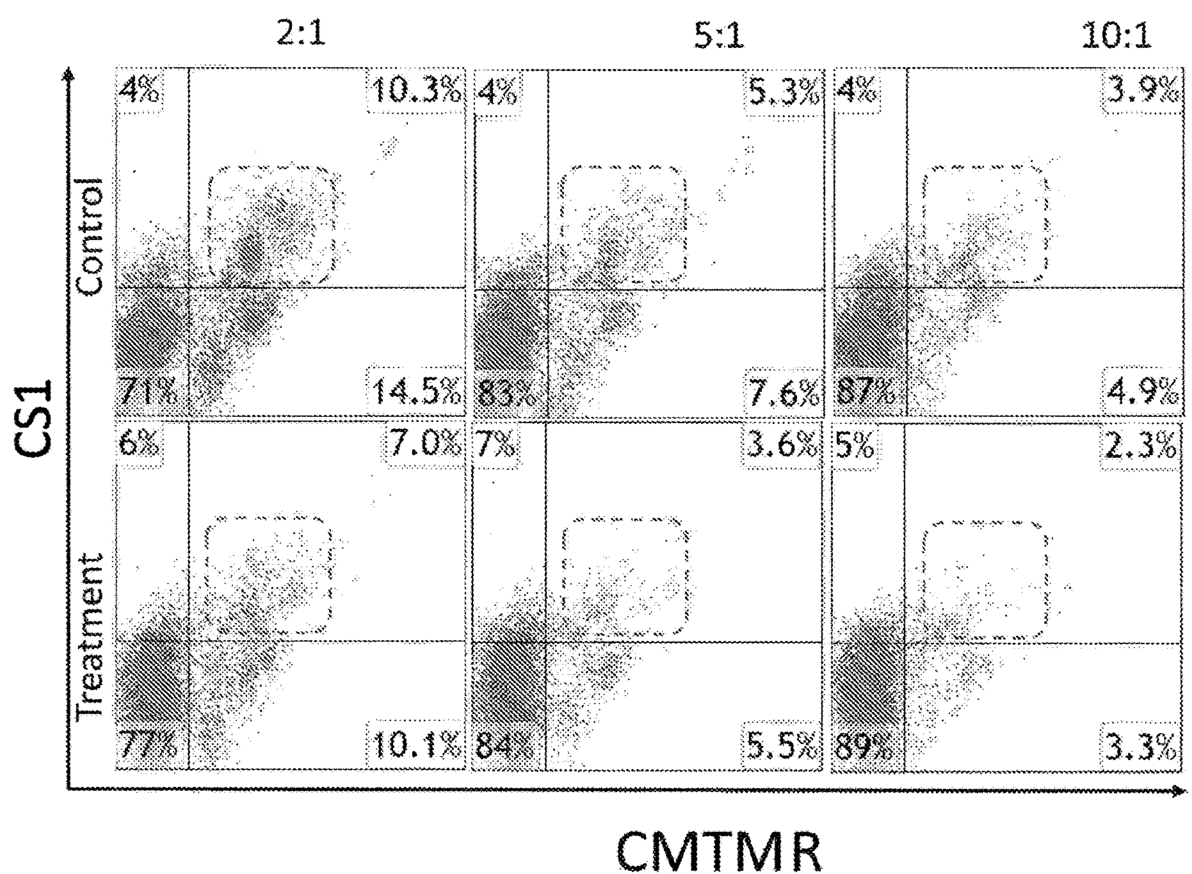
FIGS. 20A-B. MM11-G primary patient sample co-culture and specific lysis. Co-cultures were carried out under 24 hours and collected and analyzed via flow cytometry. Target MM11-G cells were labeled with Cytotracker (CMTMR) dye to distinguish it from effector T-cells. Populations were gated by anti-BCMA (CD269) and anti-CS1 (CD319) antibodies.
Figure 20B:
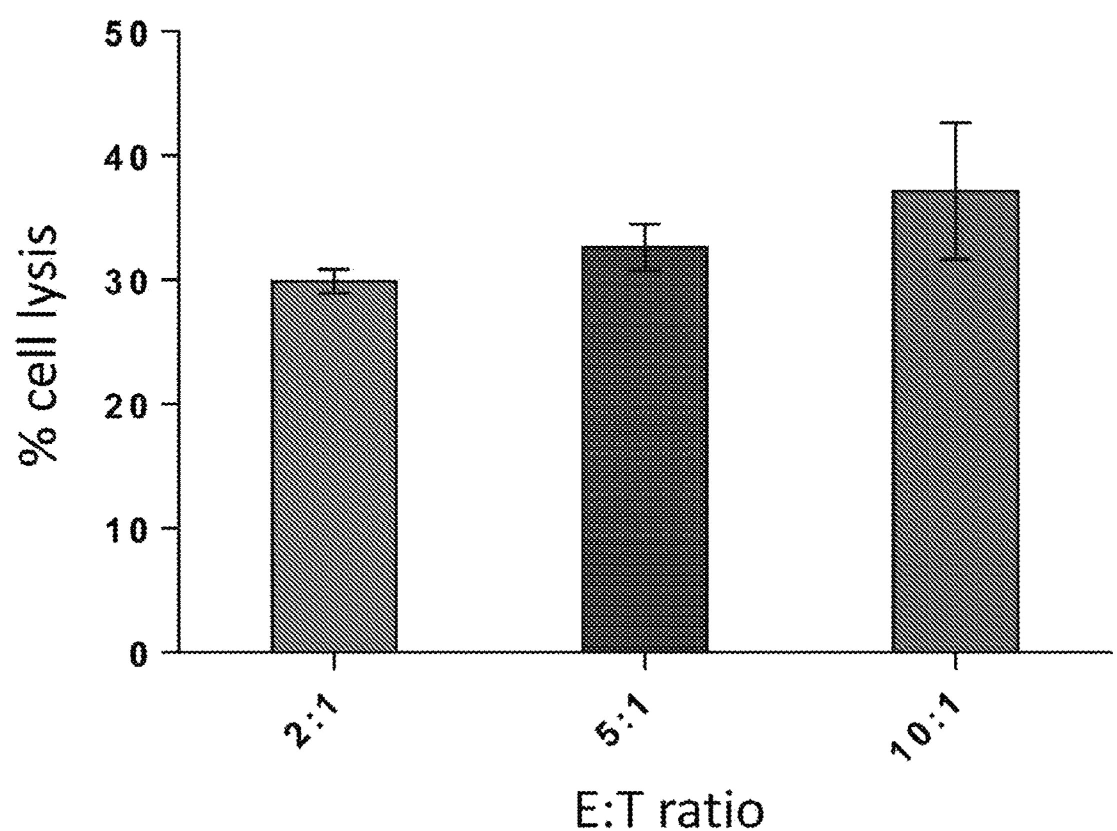

BC1cCAR T-Cells Specifically Target $BCMA^+$ and $CS1^+$ Populations in Primary Patient Myeloma Samples Flow cytometry analysis of the MM10-G patient sample reveals distinct and consistent $BCMA^+$ and $CS1^+$ population subsets (FIG. 18). MM7-G sample shows a complete $BCMA^+$ $CS1^+$ phenotype while MM11-G exhibits a noisy $BCMA^{dim}CS1^{dim}$ phenotype likely attributable to its property of being a bone-marrow aspirate. After 24 hours, BC1cCAR T-cells show robust ablation of the MM7-G primary patient sample, with over 75% lysis at an E:T ratio of 5:1, increasing to over 85% at 10:1 (FIG. 19). Against the MM11-G (FIG. 20), BC1cCAR T-cells were able to lyse over 45% of $BCMA^+$ $CS1^+$ population at an E:T of 10:1.

BC1cCAR show targeted and specific lysis ability, by significantly ablating both the $BCMA^+$ $CS1^+$ and the $BCMA^-$ $CS1^+$ population subsets in MM10-G co-cultures over 24 hours. At an E:T ratio of 2:1, BC1cCAR T-cells ablate over 60% of the $BCMA^+$ $CS1^+$ population, and 70% of the $CS1^+$ only population. At an E:T ratio of 5:1, the ablation of $CS1^+$ only population increases to 80% (FIG. 18).

BC1cCAR T-Cells Exhibit Significant Control and Reduction of Tumor In Vivo

Figure 21:
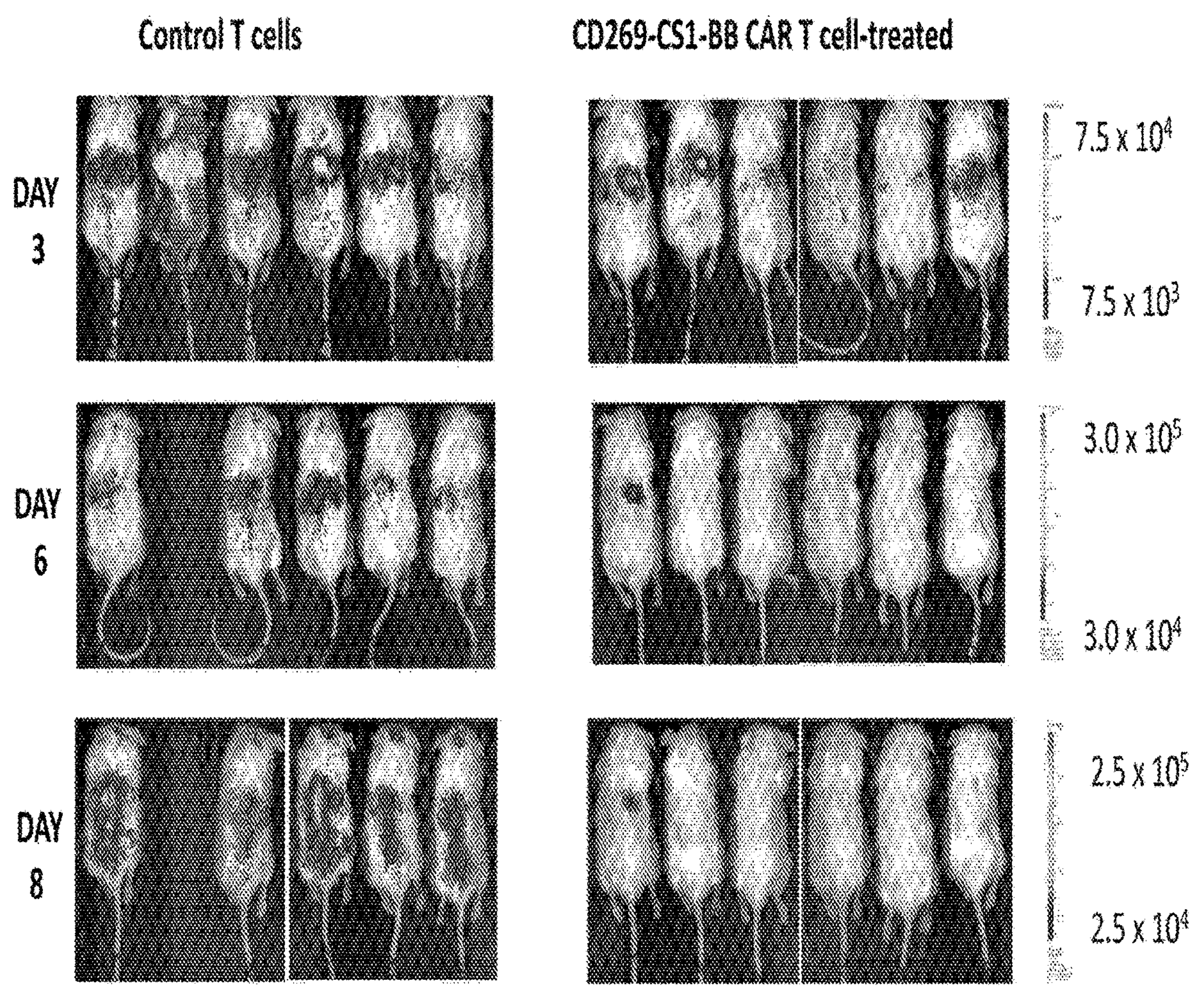
FIG. 21. CD269-CS1-BBCAR NK cells demonstrate anti-leukemic effects in vivo. NSG mice were sublethally irradiated and intravenously injected the following day with luciferase-expressing MM.1S multiple myeloma cells to induce measurable tumor formation. After 3 days, the mice were intravenously injected with $8\times10^6$ CD269-CS1-BB-CAR NK cells or vector control NK control cells. On days 3, 6, and 8, mice were injected subcutaneously with RediJect D-Luciferin and subjected to IVIS imaging. Average light intensity measured for the CD269-CS1-BBCAR NK injected mice was compared to that of vector control NK injected mice.
Figure 22:
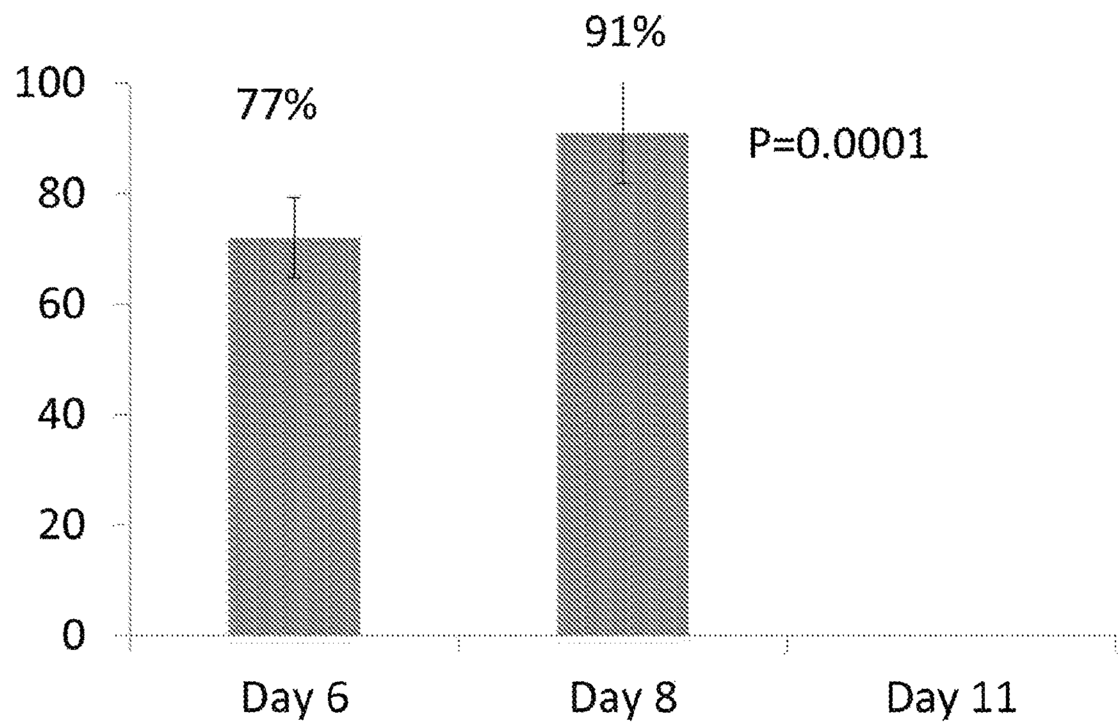
FIG. 22. Percent survival of mice was measured and compared between the two groups based on the studies from FIG. 21.

In order to evaluate the in vivo anti-tumor activity of BC1cCAR T cells, we developed a xenogeneic mouse model using NSG mice sublethally irradiated and intravenously injected with luciferase-expressing MM.1S cells, a multiple myeloma cell line, to induce measurable leukemic formation. Three days following tumor cell injection, mice were intravenously injected with $8\times10^6$ BC1cCAR T cells or vector control cells in a single dose. On days 3, 6, and 8, mice were injected subcutaneously with RediJect D-Luciferin (Perkin Elmer) and subjected to IVIS imaging to measure tumor burden (FIG. 21). Average light intensity measured for the BC1cCAR T cells injected mice was compared to that of vector control injected mice in order to determine the percentage of tumor cells in treated versus control mice (FIGS. 21 and 22). Unpaired T test analysis revealed an extremely significant difference (P=0.0001) between the two groups by day 8 with less light intensity and thus less tumor burden in the BC1cCAR T cells injected group compared to control ($p<0.0001$). On day 1, and every other day afterwards, tumor size area was measured and the average tumor size between the two groups was compared (FIG. 21). In summary, these in vivo data indicate that CD269-CS1-BBCAR T cells significantly reduce tumor burden in MM.1S-injected NSG mice when compared to vector control NK control cells.

CD45 CAR Therapy

Figure 23:
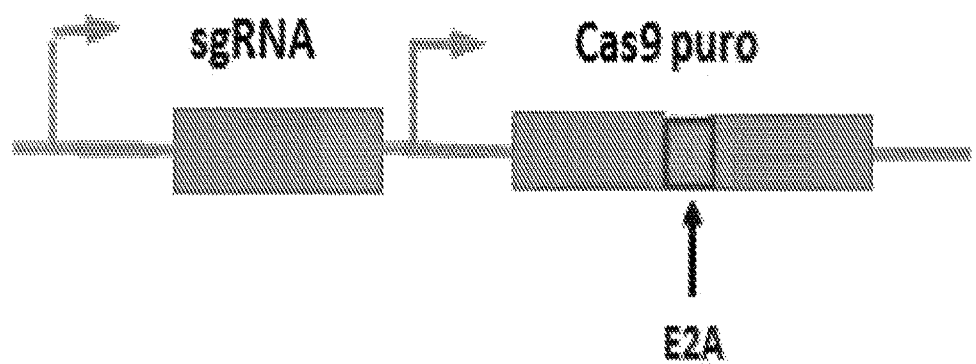
FIG. 23. CRISPR/Cas9 interference system. The expression of sgRNA and Cas9 puromycin is driven by the U6 and SFFV promoters, respectively. The Cas9 is linked with puromycin resistant gene by E2A self-cleaving sequences.

Three pairs of sgRNA are designed with CHOPCHOP to target the gene of interest. Gene-specific sgRNAs are then cloned into the lentiviral vector (Lenti U6-sgRNA-SFFV-Cas9-puro-wpre) expressing a human Cas9 and puromycin resistance genes linked with an E2A self-cleaving linker. The U6-sgRNA cassette is in front of the Cas9 element. The expression of sgRNA and Cas9puro is driven by the U6 promoter and SFFV promoter, respectively (FIG. 23).

sgRNA and Cas9puro is driven by the U6 promoter and SFFV promoter, respectively (FIG. 23).

The following gene-specific sgRNA sequences were used and constructed, In a non-limiting embodiment of the invention, exemplary gene-specific sgRNAs have been designed and constructed as set forth below: CD45 sgRNA construct::

```
Lenti-U6-sgCD45a-SFFV-Cas9-puro
                                   (SEQ ID NO: 41)
GTGGTGTGAGTAGGTAA

Lenti-U6-sgCD45b-SFFV-Cas9-puro
                                   (SEQ ID NO: 42)
GAGTTTTGCATTGGCGG

Lenti-U6-sgCD45c-SFFV-Cas9-puro
                                   (SEQ ID NO: 43)
GAGGGTGGTTGTCAATG
```

Figure 24:
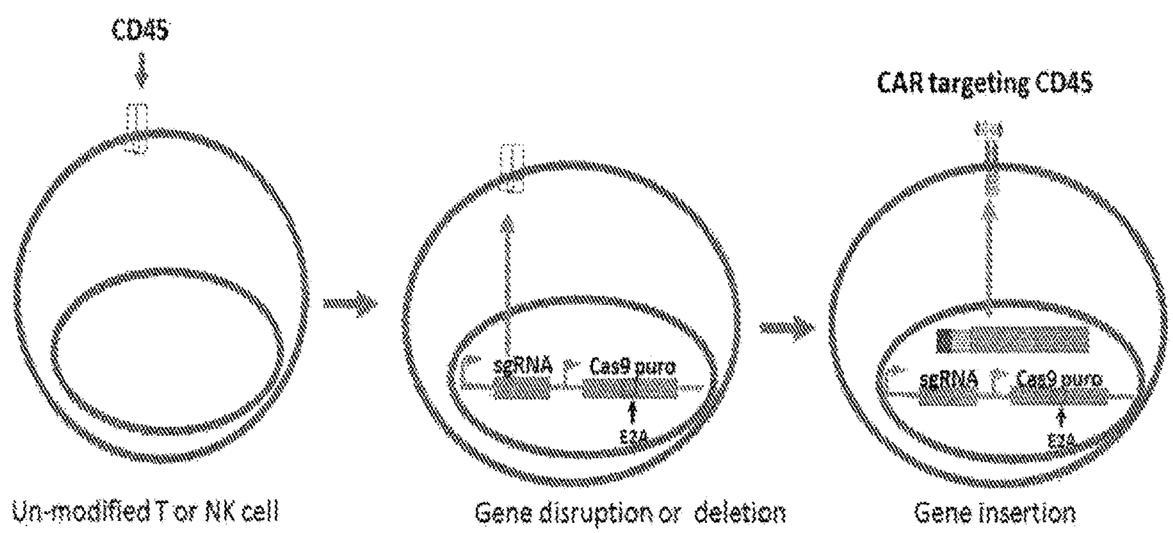
FIG. 24. A schematic providing an example of the steps for generation of CAR T or NK cell targeting hematologic malignancies.

FIG. 24 shows steps of generation of CD45 CAR T or NK cell targeting hematologic malignancies.

CRISPR/Cas Nucleases Target to CD45 on NK Cells

Figure 25:
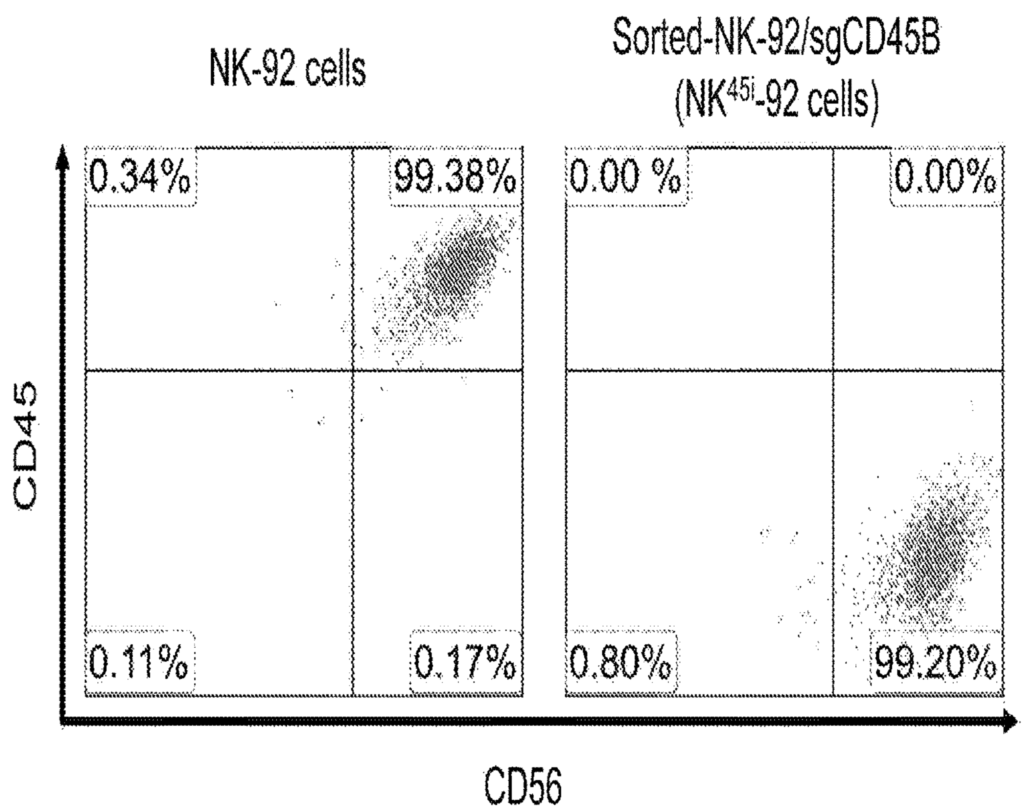
FIG. 25. Generation and cell sorting of stable CD45 knockdown NK-92 cells using CRISPR/Cas9 lentivirus system. Flow cytometry analysis indicated the CD45 expression levels on NK-92 cell surface (left panels). After transduction of sgCD45B CRISPR into NK-92 cells, transduced cells were cultured in medium containing puromycin for a few weeks. CD45 negative NK-92 cells were determined using CD45 antibody and were sorted. The purity of stable $NK^{45i}$-92 (CD45 knockdown) NK-92 cells were determined by Flow cytometry analysis (right panel). This data showed that $NK^{45i}$-92 cells were successfully generated and obtained.

Lentiviruses carried gene-specific sgRNAs were used to transduce NK-92 cells. The loss of CD45 expression on NK-92 cells was determined by flow cytometry analysis. The CD45 negative population of NK-92 cells was sorted and expanded (FIG. 25). The sorted and expanded CD45 negative NK-92 cells were used to generate CD45CAR NK cells. The resulting CD45CAR NK cells were used to test their ability of killing CD45+ cells.

Figure 26:
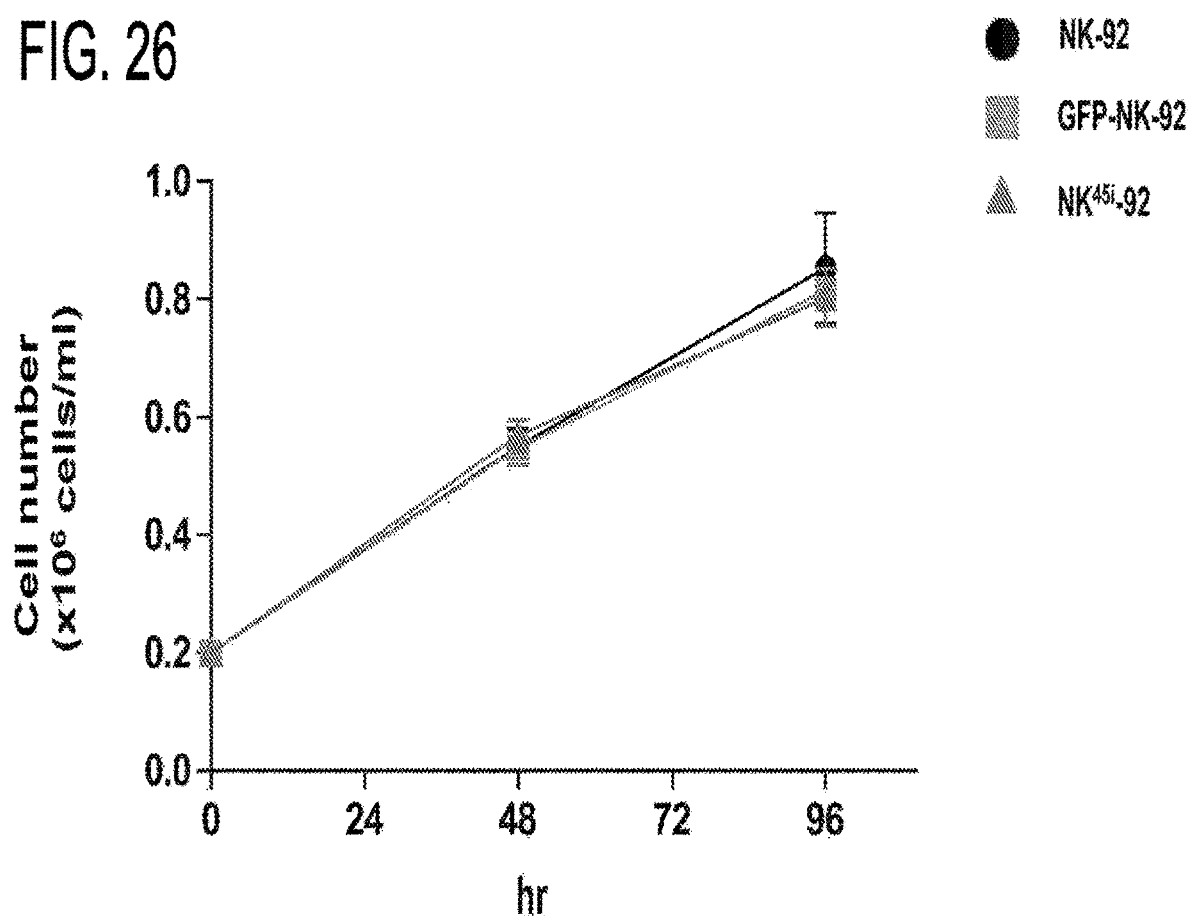
FIG. 26. Cell growth curve of wild type, GFP transduced NK-92 or $NK^{45i}$-92NK cells. To evaluate the effect for cell proliferation caused by CD45-knockdown (KD) in NK-92 cells, the number of cells of NK-92(●), GFP-transduced NK-92(■) and $NK^{45i}$-92(▲) were counted at 48 h and 96 h after seeding into 24 well plates. IL-2 was added at 48 h time point. (n=3 independent experiments performed in duplicate). Data are mean±S.D. These data indicated that knockdown of CD45 receptor on NK-92 show similar cell growth curve compared to non-transduced NK-92 or GFP-transduced NK-92 cells.
Figure 27A:
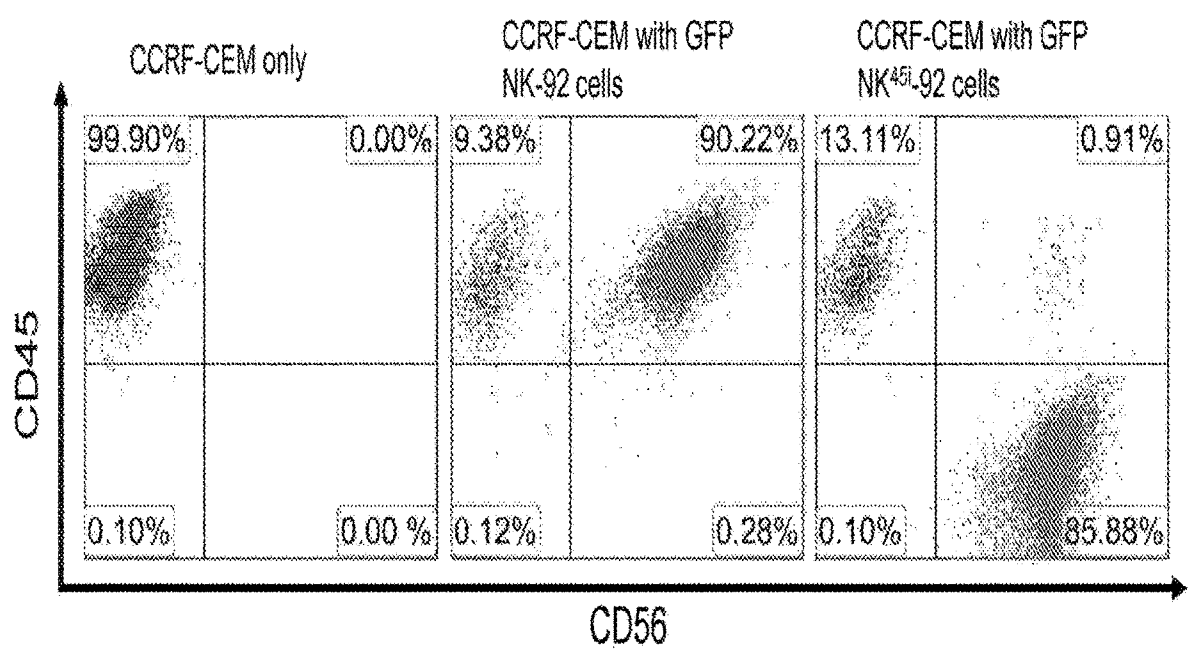
FIGS. 27A-B. Co-culture assay with CCRF-CEM (target: T) and GFP NK-92 or GFP $NK^{45i}$-92 cells (effector: E), 5:1 (E:T) ratio. 16 hours incubation. (A) Flow cytometry analysis of CCRF-CEM only (blue dot in left panel), in co-culture with CCRF-CEM and control GFP transduced NK-92 cells (middle panel) or GFP $NK^{45i}$-92 cells (right panel). Blue dots in all of panels indicates the leftover target CCRF-CEM cells and red dots shows effector cells by co-culture assay. All of incubation time were 16 h and the ratio of effector T-cells: target cell was 5:1. All experiments were performed in duplicate. (B) Bar graph indicates the percent of cell lysis by the GFP transduced $NK^{45i}$-92 cells compared to the control GFP transduced NK92 cells in co-culture assay with CCRF-CEM. These data suggest that knockdown of CD45 in NK-92 cells does not show a significant difference for killing activity against CCRF-CEM cells compared to GFP-control NK-92 cells in vitro co-culture assay. Blue dotes are in the upper left quadrant.
Figure 27B:
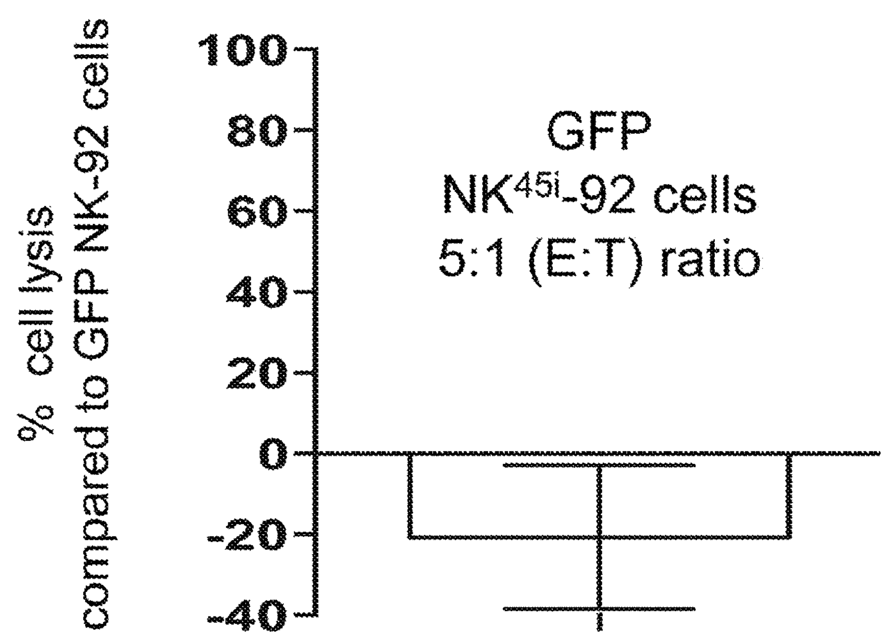

Functional Characterization of CD45 Inactivated NK-92 Cells ($NK^{45i}$-92) After CRISPR/Cas Nucleases Target We demonstrated that, following CRISPR/Cas nuclease inactivation of CD45, the growth of $NK^{45i}$-92 cells was similar to that of the wild NK-92 cells (FIG. 26). Inactivation of CD45 did not significantly affect the cell proliferation of NK-92. In addition, we showed that the lysis ability of $NK^{45i}$-92 cells was compatible to that of wild type, NK-92 when cells were co-cultured with leukemic cells, CCRF (FIG. 27).

Figure 28A:
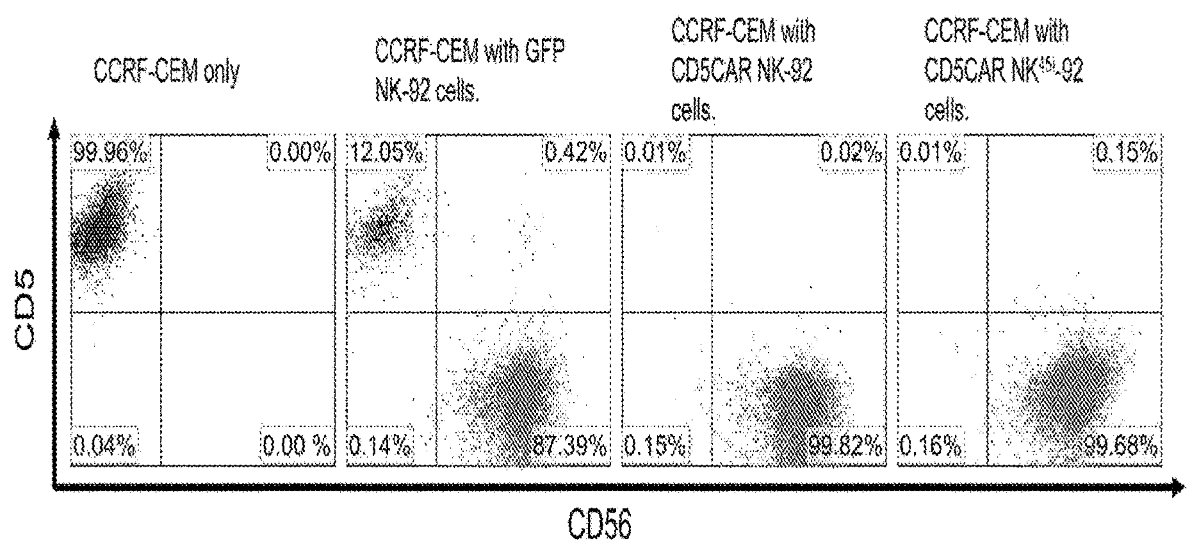
FIGS. 28A-B. Co-culture assay with CCRF-CEM (target: T) and GFP NK-92, CD5CAR NK-92 or CD5CAR $NK^{45i}$-92 cells (effector: E). 5:1 (E:T) ratio. 16 hours incubation (A) Flow cytometry analysis of CCRF-CEM only (left panel), in co-culture with CCRF-CEM and control GFP NK-92 cells (middle left panel), CD5CAR NK-92 cells (middle right panel), CD5CAR $NK^{45i}$-92 cells (right panel) from right to left. Blue dots in all of panels indicates the leftover target CCRF-CEM cells and red dots shows effector cells by co-culture assay. All of incubation times were 16 h and the ratio of effector T-cells: target cell is 5:1. All experiments were performed in duplicate. (B) Bar graph indicates the percent of cell lysis by the CD5CAR NK-92 cells or CD5CAR $NK^{45i}$-92 cells compared to the control GFP NK92 cells in co-culture assay with CCRF-CEM. Data are mean±S.D. Both of CD5CAR NK-cells and CD5CAR $NK^{45i}$-92 cells shows near to 100% cell killing activity against CD5-potitive CCRF-CEM compared to control GFP NK-92 cells. These data suggest that CD5CAR NK-cells and CD5CAR $NK^{45i}$-92 cells can effectively lyse CCRF-CEM cells that express CD5 compared to GFP-control NK-92 cells in vitro co-culture assay, and provide proof that knock-down of CD45 does not affect cell function for killing activity in NK-92 cells. Blue dots are in the upper left quadrant of the first two panels starting from the left.
Figure 28B:
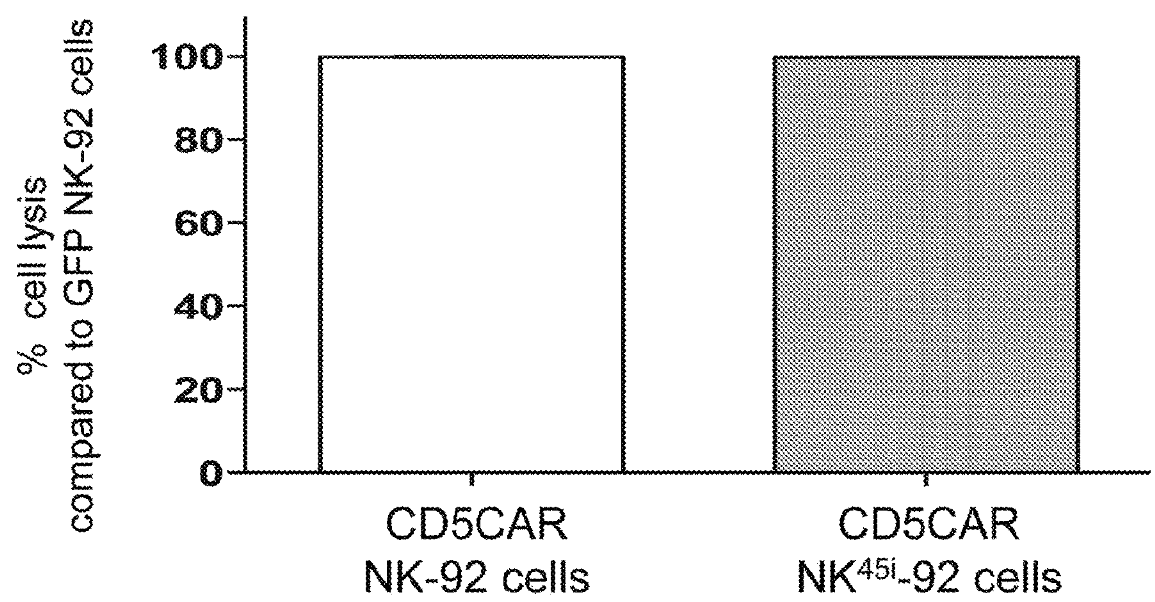

To demonstrate that CD45-inactivated NK-92 was compatible with CAR lysis, $NK^{45i}$-92 cells and their wild type, NK-92 were transduced with lentiviruses expressing CD5CAR or GFP. The resulting CD5CAR $NK^{45i}$-92 cells and GFP $NK^{45i}$-92 were sorted by FACS, and used to compare their ability of killing targeted cells. CD5CAR $NK^{45i}$-92 cells displayed the ability of robustly killing CD5 target leukemic cells at ratios (E:T), 2:1 and 5:1 when they were co-cultured with CCRF-CEM cells. We showed that there was a similar efficacy of elimination of CCRF-CEM cells in vitro between CD5CAR $NK^{45i}$-92 and CD5 CAR NK-92 cells (FIG. 28). This suggests that the loss of CD45 expression does not diminish the anti-tumor activity of CAR NK-cells.

Generation of CD45CAR Construct

Figure 29A:
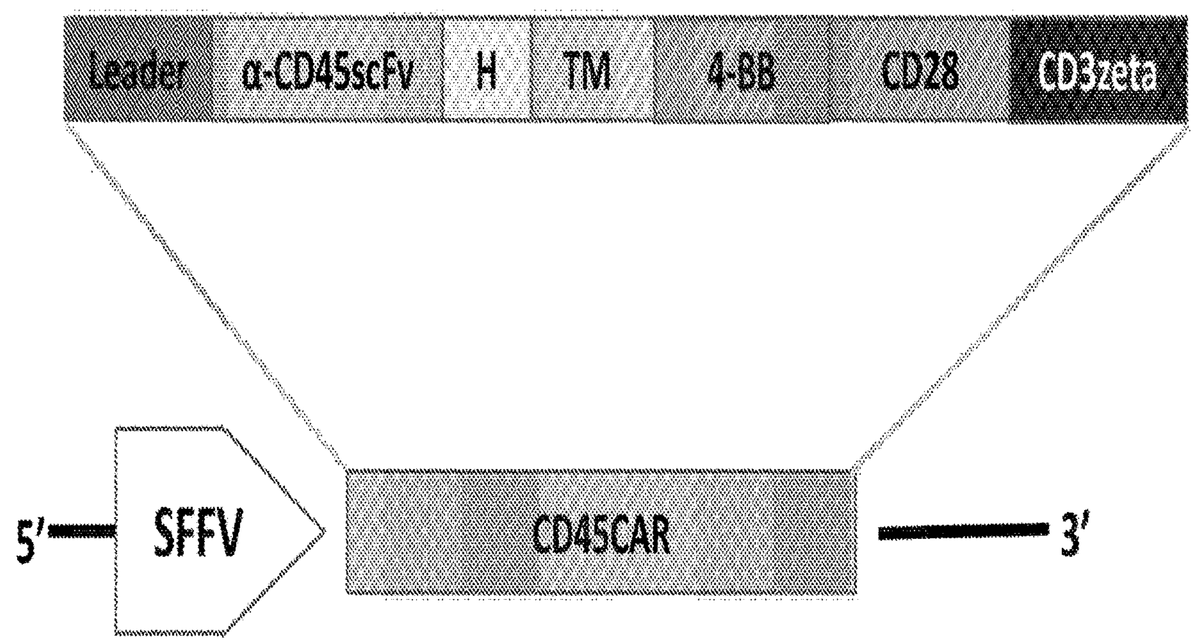
FIGS. 29A-B. Organization of the CD45CAR construct and its expression. (A) Schematic representation of the CD45CAR lentiviral vector. The CD45CAR construct is a modularized signaling domain containing: a leader sequence, an anti-CD45scFv, a hinge domain (H), a trans-membrane domain (TM), two co-stimulatory domains (CD28 and 4-1BB) that define the construct as a $3^{rd}$ generation CAR, and the intracellular signaling domain CD3 zeta. (B), HEK-293FT cells were transfected with lentiviral plasmids for GFP (lane 1) and CD45CAR (lane 2). 48 hours after transfection, supernatant was removed, and cells were also removed. Cells were lysed for Western blot and probe with mouse anti-human CD3z antibody.
Figure 29B:
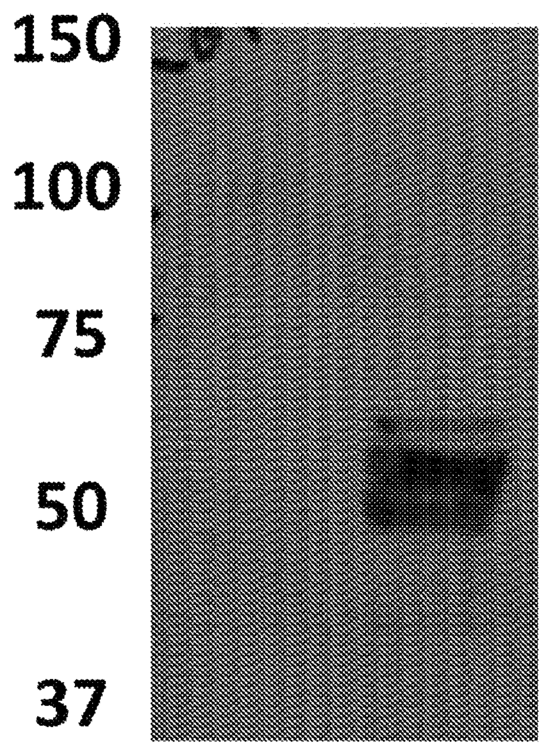

We next investigate that CD45CAR in $NK^{45i}$-92 cells response to the CD45 antigen in leukemic cells. We generated CD45CAR. CD45CAR consists of an anti-CD45 single-chain variable fragment (scFv) region, CD8-derived hinge (H) and transmembrane (TM) regions, and tandem CD28 and 4-1BB co-activation domains linked to the CD3ζ signaling domain (FIG. 29A). A strong spleen focus forming virus promoter (SFFV) and a CD8 leader sequence were used. CD45CAR protein was characterized by Western blot of HEK293-FT cells transfected with CD45CAR lentiviral plasmid with appropriate vector control. Additionally, anti-CD3zeta monoclonal antibody immunoblots revealed bands of predicted size for the CD45CAR protein with no bands observed in vector control (FIG. 29B).

CD45CAR $NK^{45i}$-92 NK Cells

Figure 30A:
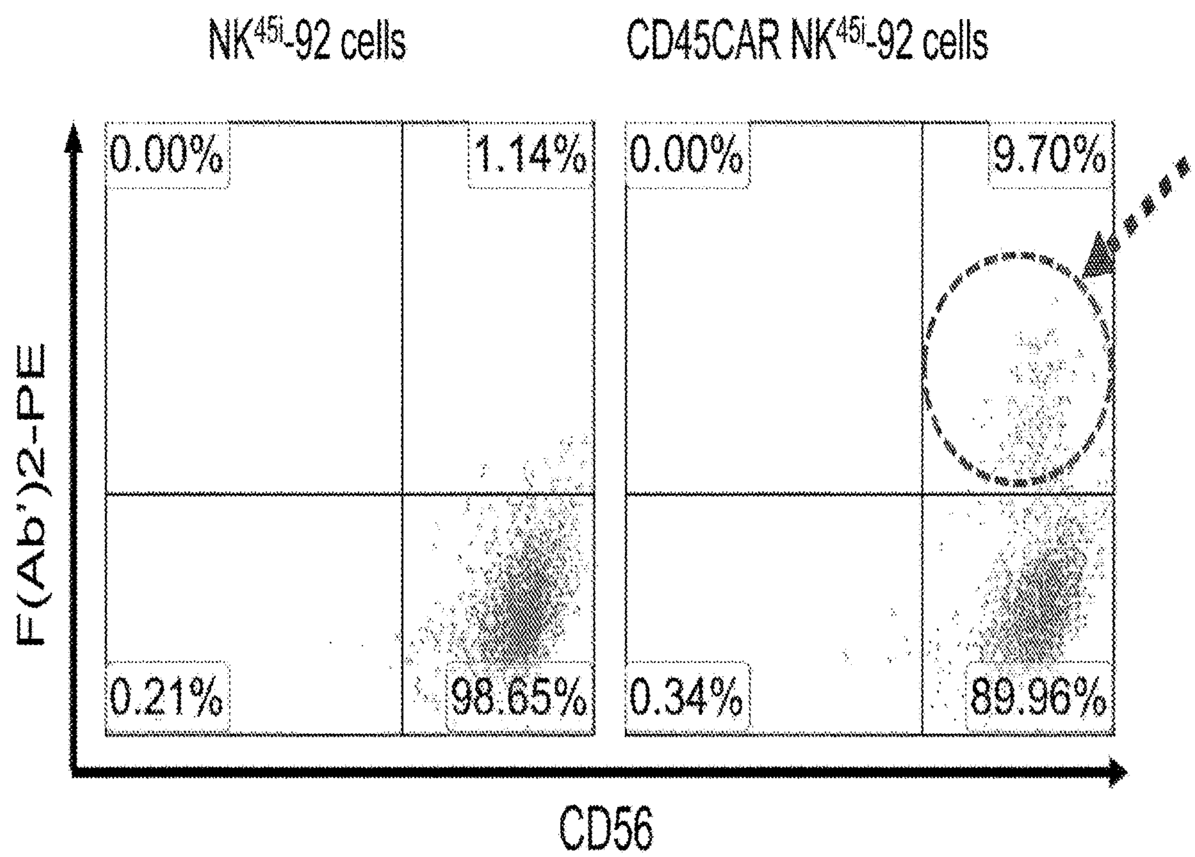
FIGS. 30A-B. Transduction of CD45CAR into $NK^{45i}$-92 cells and cell sorting of CD45CAR transduced cells. (A) The expression levels of CD45CAR on $NK^{45i}$-92 were determined by flow cytometry analysis (circled in blue at middle panel) compared to $NK^{45i}$-92 cells (left panel) after CD45CAR lentviruses were transduced into $NK^{45i}$-92 cells. CD45CAR expressed $NK^{45i}$-92 cells were sorted and CD45 expression levels on cell surface were determined by Flow cytometry analysis (right panel). (B) About 87% of CD45CAR expression on cell surface was detected by flow cytometry analysis.
Figure 30B:
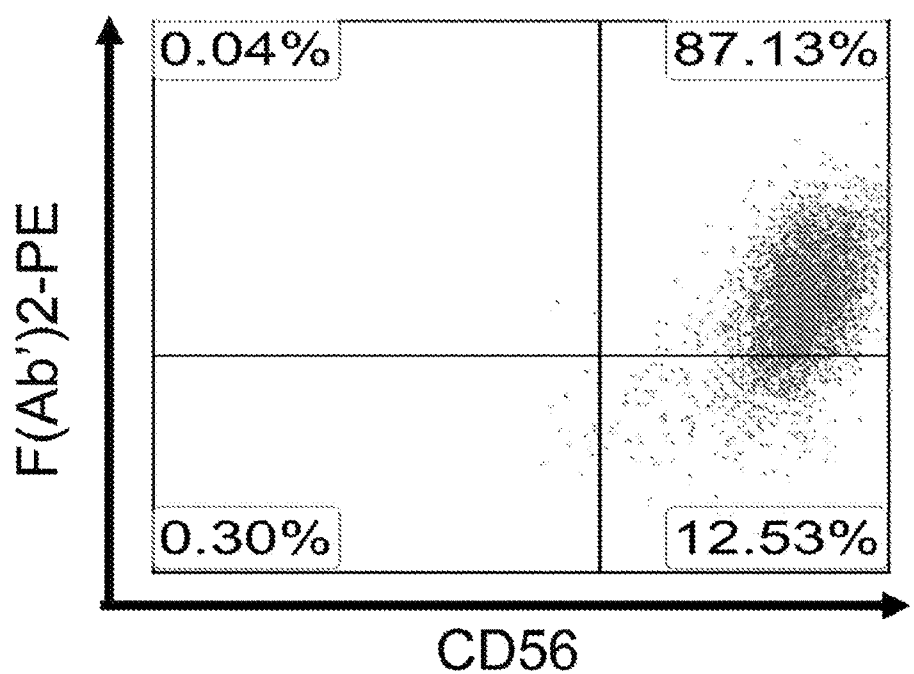

Following fluorescence-activated cell sorting (FACS) to enrich for $NK^{45i}$-92 cells, CD45CAR NK-92 transduction efficiency was determined to be 87%, as determined by flow cytometry (FIG. 30) after sorting. After FACS collection of $NK^{45i}$-92 cells, CD45CAR expression levels remained consistently stable for at least 10 passages.

CD45CAR $NK^{45i}$-92 Cells Specifically Lyse CD45+ Leukemic Cells.

Figure 31A:
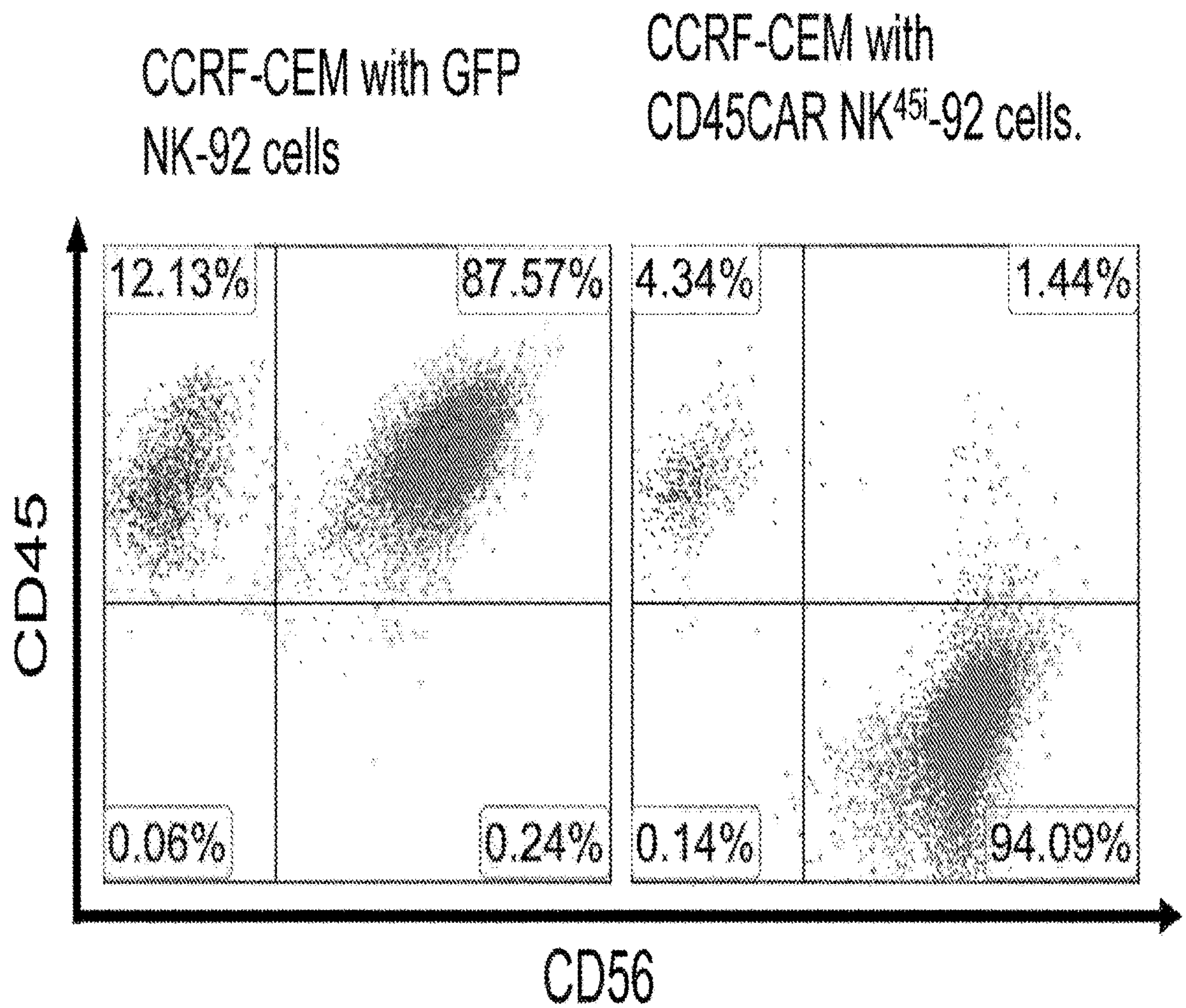
FIGS. 31A-B. Co-culture assay with CCRF-CEM (target: T) and GFP NK-92 or CD45CAR $NK^{45i}$-92 cells (effector: E). 5:1 (E:T) ratio. 16 hours incubation. (A) Flow cytometry analysis of in co-culture with CCRF-CEM and control GFP transduced NK-92 cells (left panel) or CD45CAR $NK^{45i}$-92 cells (right panel). Blue dots in all of panels indicates the leftover target CCRF-CEM cells and red dots shows effector NK-92 cells by co-culture assay. All of incubation times were 16 h and the ratio of effector T-cells: target cell is 5:1. All experiments were performed in duplicate. (B) Bar graph indicates the percent of cell lysis by CD45CAR $NK^{45i}$-92 cells compared to the control GFP NK92 cells in co-culture assay with CCRF-CEM. Data are mean±S.D. CD45CAR $NK^{45i}$-92 cells shows about 70% cell lysis against CCRF-CEM cells compared to control GFP NK-92 cells. These data suggest that CD45CAR $NK^{45i}$-92 cells effectively lyse CCRF-CEM cells that express CD45 compared to GFP-control NK-92 cells in vitro co-culture assay.
Figure 31B:
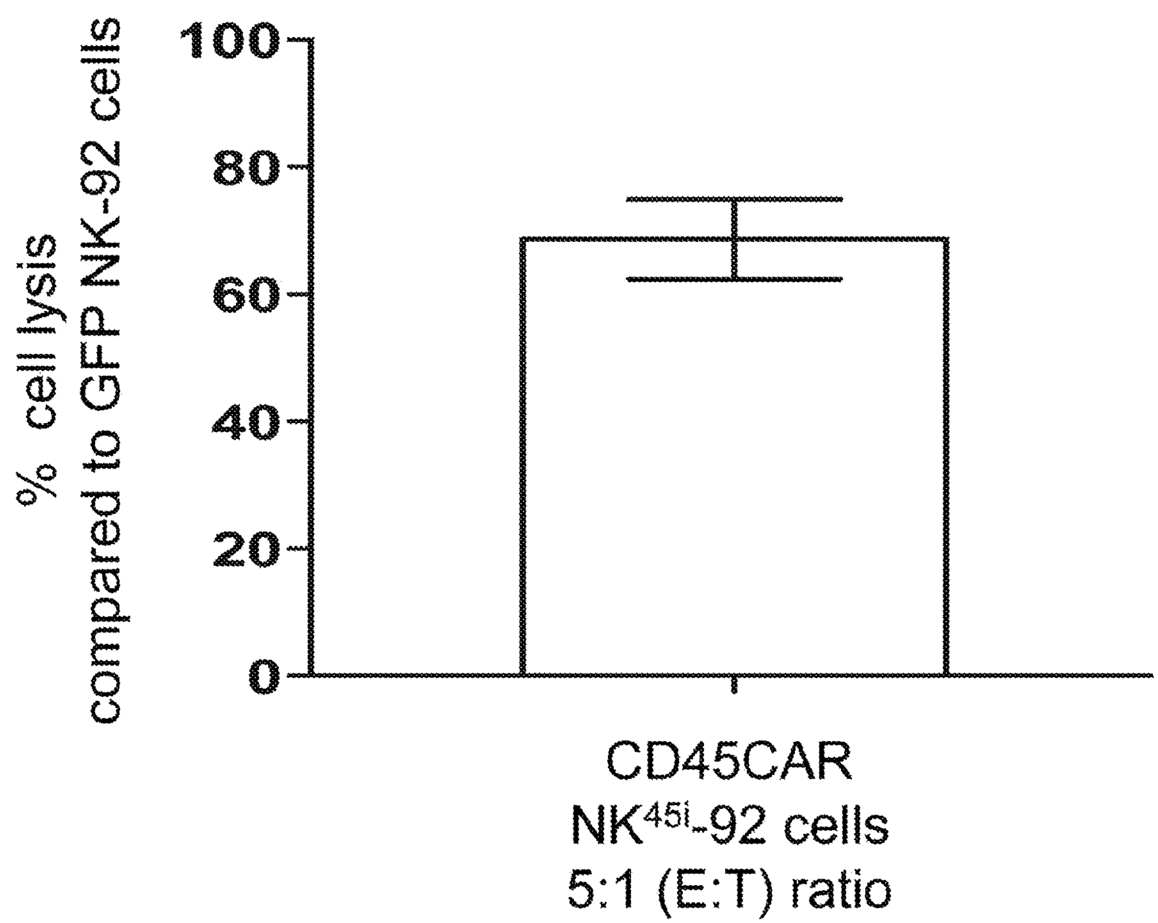
Figure 32A:
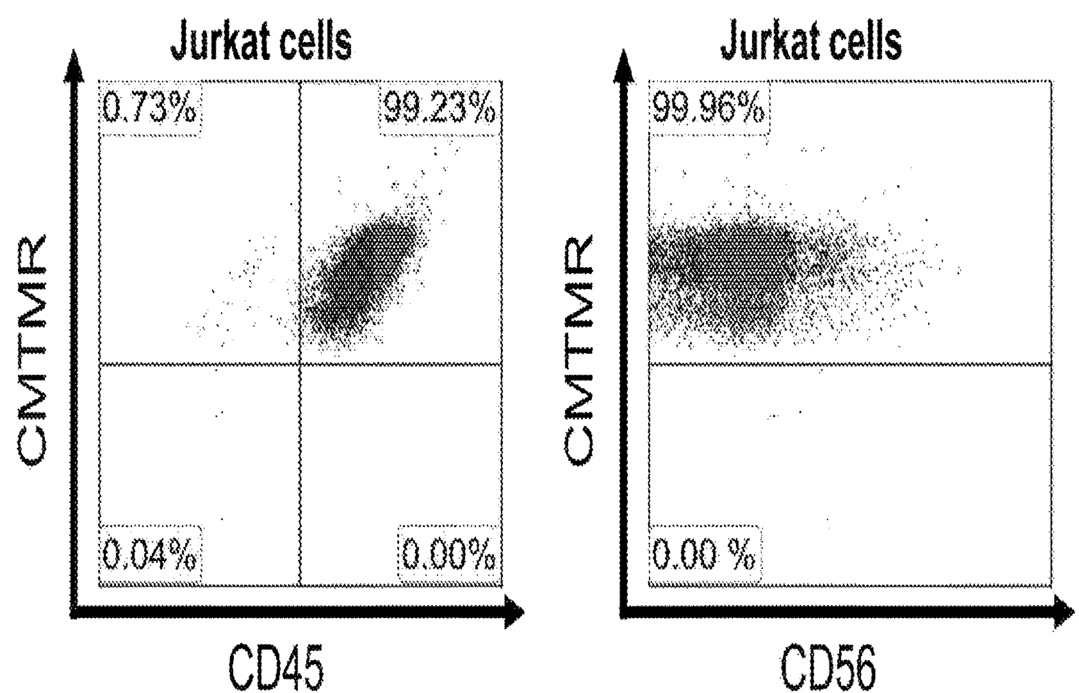
FIGS. 32A-C. Co-culture assay with Jurkat cells (target: T) and GFP-control or CD45CAR $NK^{45i}$-92 cells (effector: E). 5:1 or 2:1 (E:T) ratio. 6 hours incubation. (A) Flow cytometry analysis was carried out after Jurkat cells were stained by CMTMR cell tracker dye. These data shows that Jurkat cells are CD45 positive (left panels) and mostly CD56 negative cells (right panel). (B) Flow cytometry analysis of co-culture assay with Jurkat cells (target: T) and control or CD45CAR $NK^{45i}$-92 cells (effector: E). The ratio of co-culture assay was performed in 5:1 or 2:1 (E:T). Left panels showed that in co-culture with control GFP or CD45CAR/CD45KD NK-92 cells in 5:1 (E:T) ratio and right panels indicated that in co-culture with control GFP or CD45CAR $NK^{45i}$-92 cells in 2:1 (E:T) ratio. Blue dots in panels indicate the leftover target Jurkat cells and red dots represent effector cells by co-culture assay. All of incubation time were 6 h. All experiments were performed in duplicate. (C) Bar graph shows percent cell lysis by CD45CAR $NK^{45i}$-92 cells compared to control GFP NK92 cells at in 5:1 or 2:1 (E:T) ratio. Data are mean±S.D. CD45CAR $NK^{45i}$-92 cells shows about 60% cell lysis against Jurkat cells compared to control GFP NK-92 cells in both conditions. This data suggests that CD45CAR $NK^{45i}$-92 cells effectively lyse Jurkat cells that express CD45 on cell surface compared to GFP-control NK-92 cells in vitro co-culture assay.
Figure 32B:
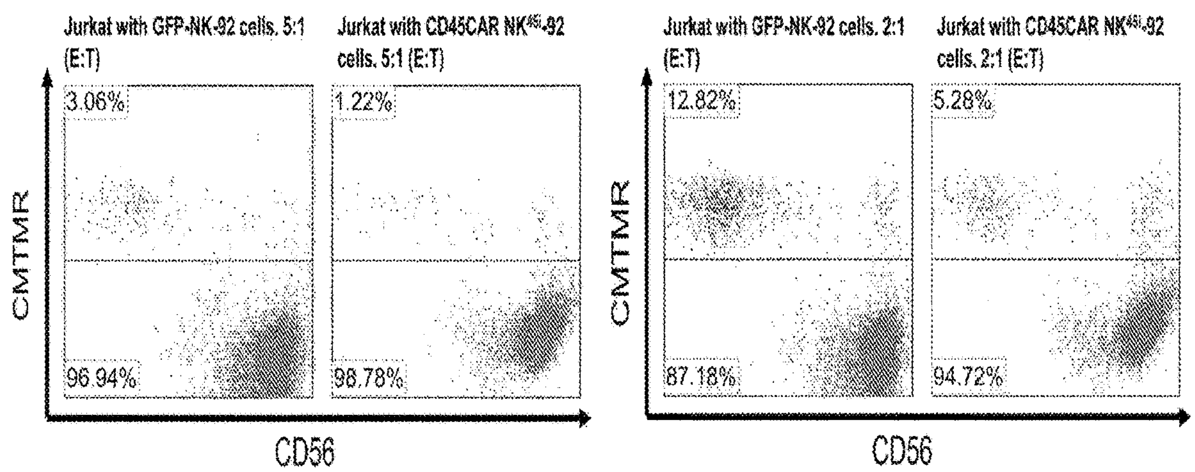
Figure 32C:
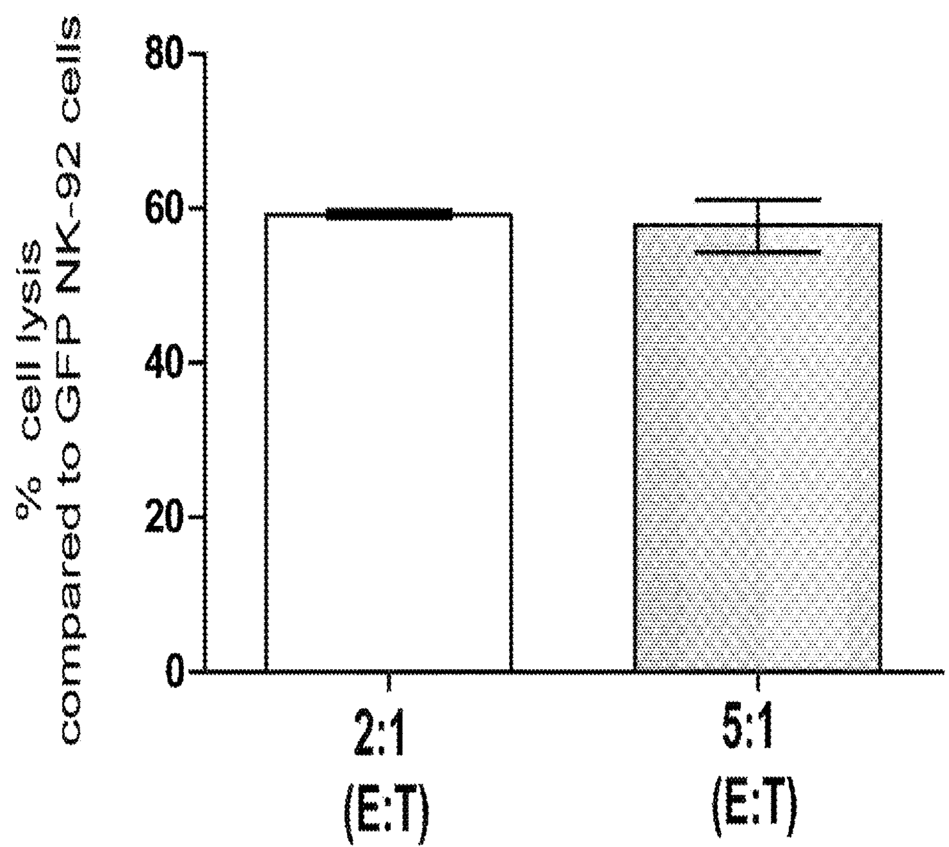
Figure 33A:
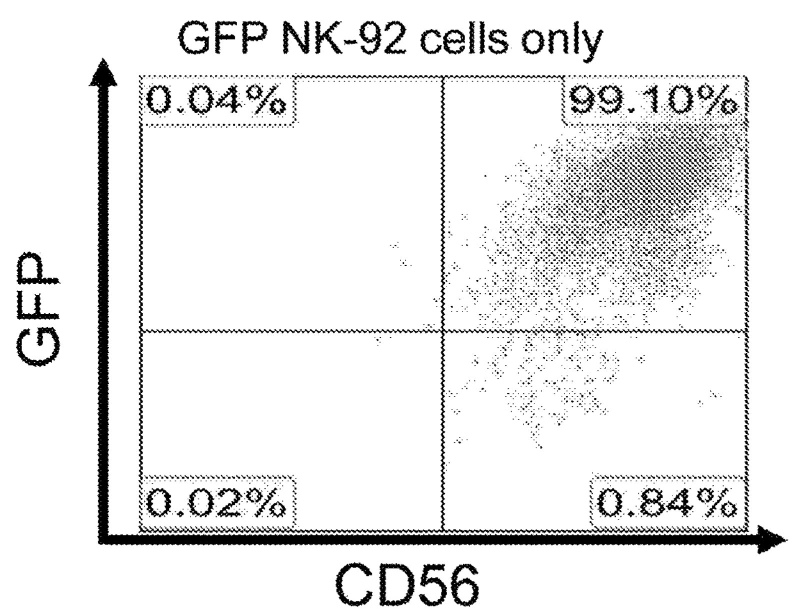
FIGS. 33A-C. Co-culture assay with GFP-NK-92 cells (target: T) and non-transduced NK-92 cells or CD45CAR $NK^{45i}$-92 cells (effector: E). 5:1 or 2:1 (E:T) ratio. 6 hours incubation (A) Flow cytometry analysis was carried out using GFP control NK-92 cells. These data proof that GFP control NK-92 cells are about 99% GFP positive cells (green dots). (B) Flow cytometry analysis of co-culture assay with GFP control NK-92 cells (target: T) and non-transduced or CD45CAR $NK^{45i}$-92 cells (effector: E). The ratio of co-culture assay was performed in 5:1 or 2:1 (E:T). Left panels showed that in co-culture with non-transduced or CD45CAR $NK^{45i}$-92 cells in 5:1 (E:T) ratio and right panels indicated that in co-culture with non-transduced or CD45CAR $NK^{45i}$-92 cells in 2:1 (E:T) ratio. Green dots in panels indicate the leftover target GFP NK-92 cells and red dots represent effector cells by co-culture assay. The incubation time was 6 h. All experiments were performed in duplicate. (C) Bar graph shows percent cell lysis of GFP NK-92 cells by CD45CAR $NK^{45i}$-92 cells compared to non-transduced NK-92 cells at in 5:1 or 2:1 (E:T) ratio. Data are mean±S.D. CD45CAR $NK^{45i}$-92 cells shows about 20% cell lysis in 2:1 (E:T) ratio and about 55% cell lysis in 5:1 (E:T) ratio against GFP NK-92 cells compared to non-transduced NK-92 cells. This data suggests that CD45CAR $NK^{45i}$-92 cells effectively lyse GFP NK-92 cells that express CD45 on cell surface compared to non-transduced NK-92 cells in vitro co-culture assay. Green dots are in the upper right quadrant of each panel.
Figure 33B:
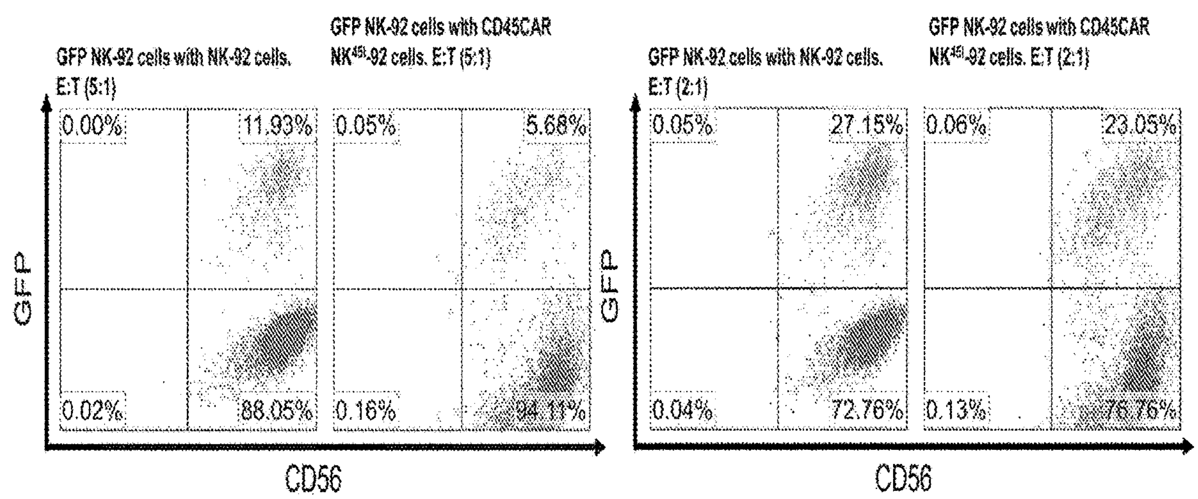
Figure 33C:
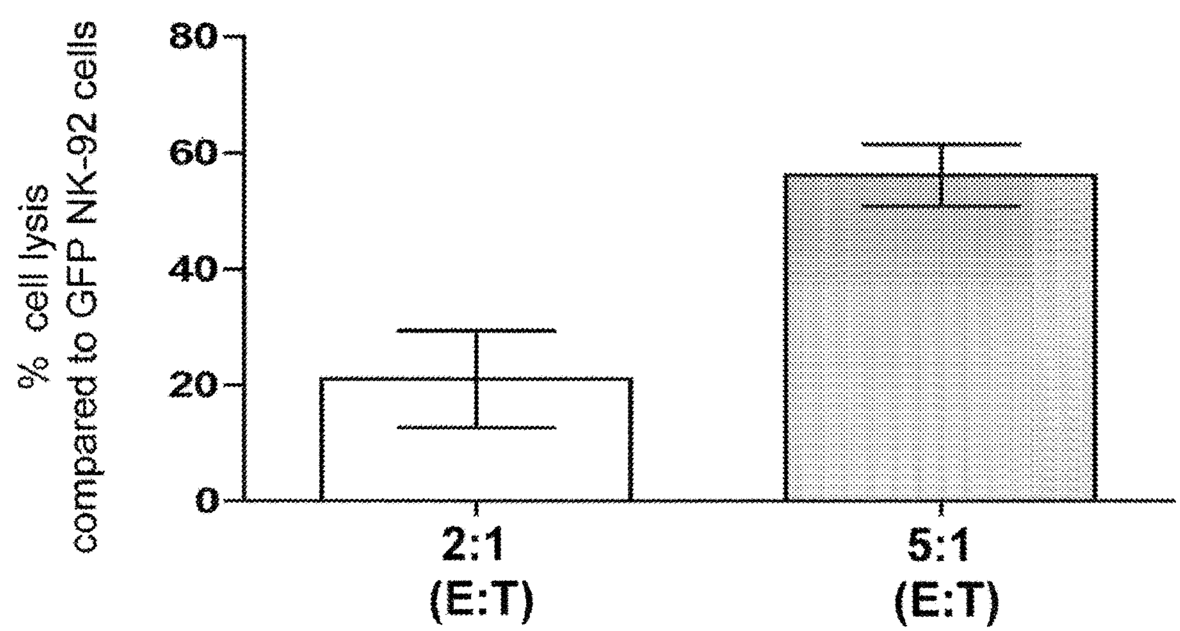
Figure 33D:
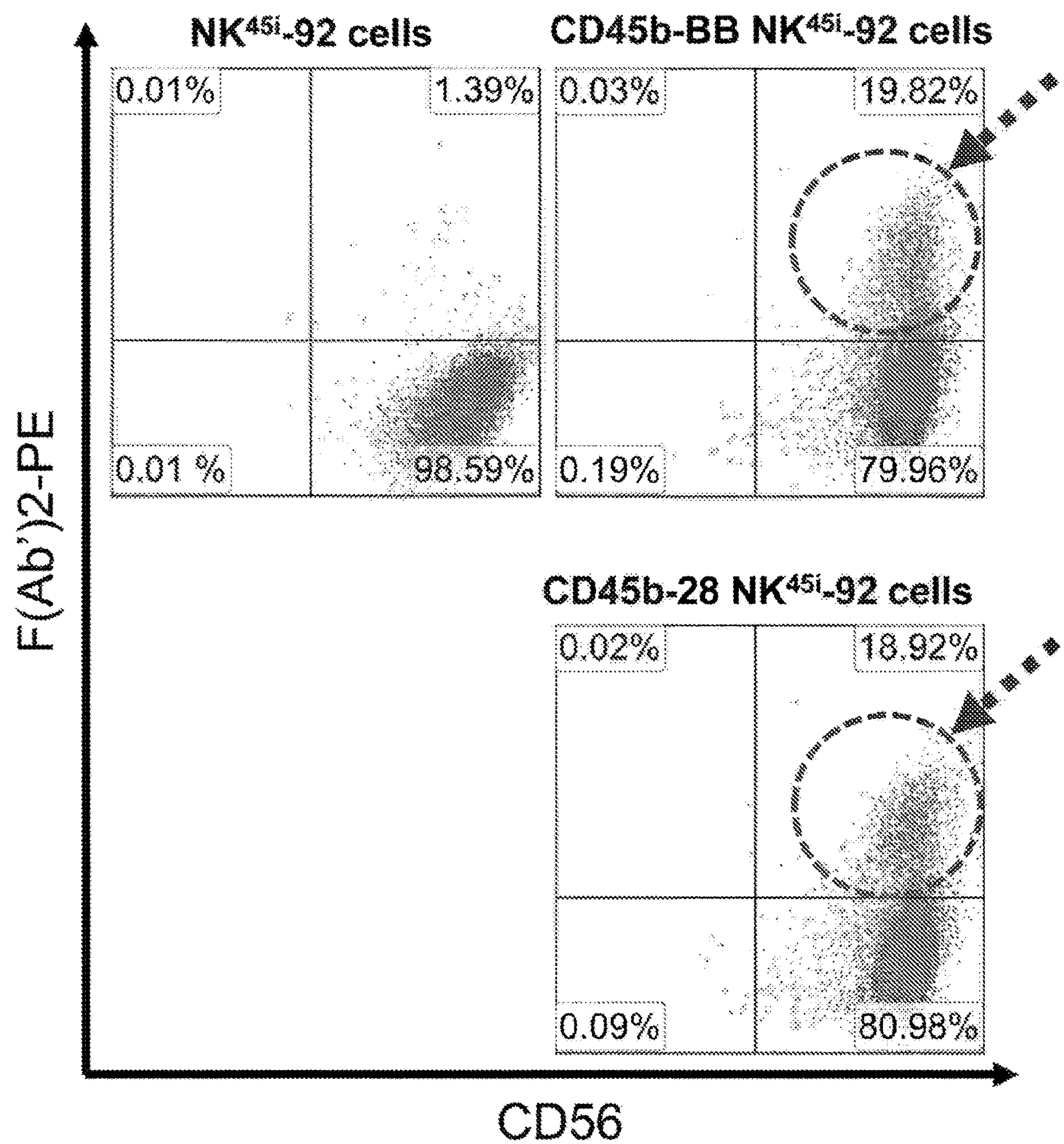
FIGS. 33D-E. Transduction of CD45b-BB or CD45b-28 into $NK^{45i}$-92 cells and cell sorting of CD45b-BB or CD45b-28 transduced $NK^{45i}$-92 cells. (D) The surface expression levels of CD45b-BB CAR or CD45b-28 CAR on $NK^{45i}$-92 were determined by flow cytometry analysis (circled in blue at middle panel) compared to $NK^{45i}$-92 cells (left panel) after CD45b-BB or CD45b-28 lentviruses transduced into NK45i-92 cells. (E) NK45i-92 cells expressing the CD45b-BB or CD45b-28 CAR were sorted by Flow cytometry analysis. About 74% of CD45b-BB CAR or 82% of CD45b-28 CAR expression on cell surface was detected by flow cytometry analysis.
Figure 33E:
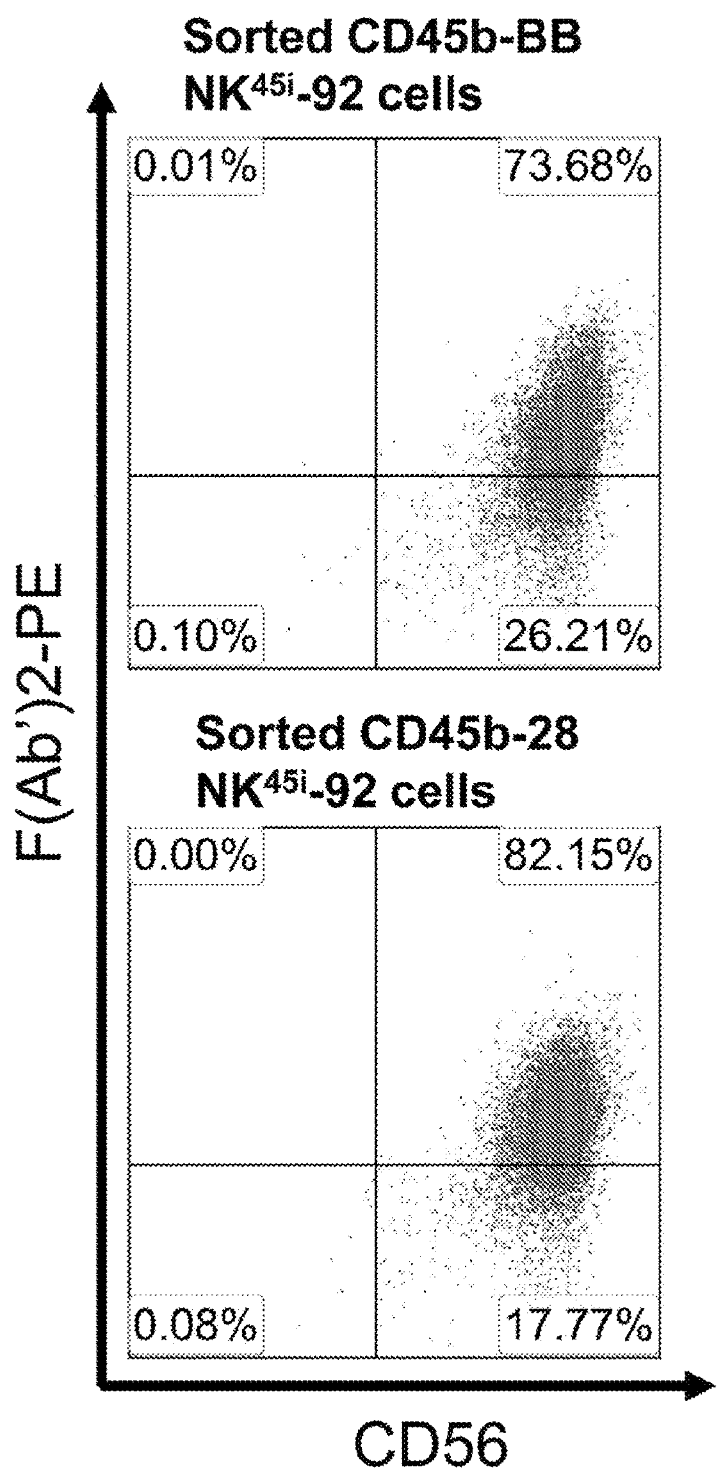
Figure 33F:
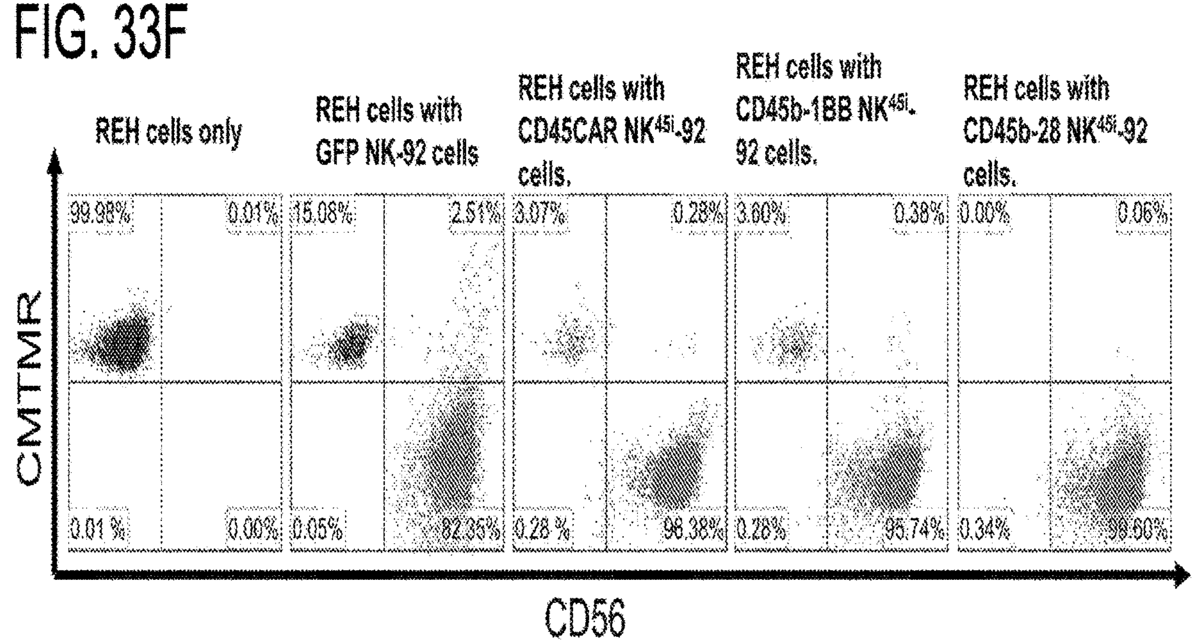
FIGS. 33F-G. Co-culture assay with REH cells (target: T) and GFP NK-92 cells or CD45CAR $NK^{45i}$-92 cells or CD45b-BB $NK^{45i}$-92 cells or CD45b-28 $NK^{45i}$-92 cells (effector: E). 5:1 (E:T) ratio. 20 hours incubation. (F) Flow cytometry analysis of REH cells only (left panel), in co-culture with REH cells and control GFP transduced NK-92 cells (2nd left panel), CD45CAR $NK^{45i}$-92 cells (middle panel), CD45b-BB $NK^{45i}$-92 cells (4th from left panel) or CD45b-28 $NK^{45i}$-92 cells (right panel). Blue dots in all of panels indicate the leftover target REH cells and red dots shows effector GFP or CARs-NK-92 cells by co-culture assay. REH is a B acute lymphoblastic cell line. All of incubation times were 20 h and the ratio of effector NK-cells: target cell is 5:1. All experiments were performed in duplicate. (G) Bar graph indicates the percent of cell lysis by CD45CAR $NK^{45i}$-92 cells, CD45b-BB $NK^{45i}$-92 cells or CD45b-28 NK45i-92 cells compared to the control GFP NK92 cells in co-culture assay with REH cells. Data are mean±S.D. CD45CAR $NK^{45i}$-92 cells shows about 76% cell lysis, CD45b-BB $NK^{45i}$-92 cells shows about 79% cell lysis and CD45b-28 $NK^{45i}$-92 shows 100% cell lysis against REH cells compared to control GFP NK-92 cells. These data suggest that all three CD45CARs effectively lyse REH cells.
Figure 33G:
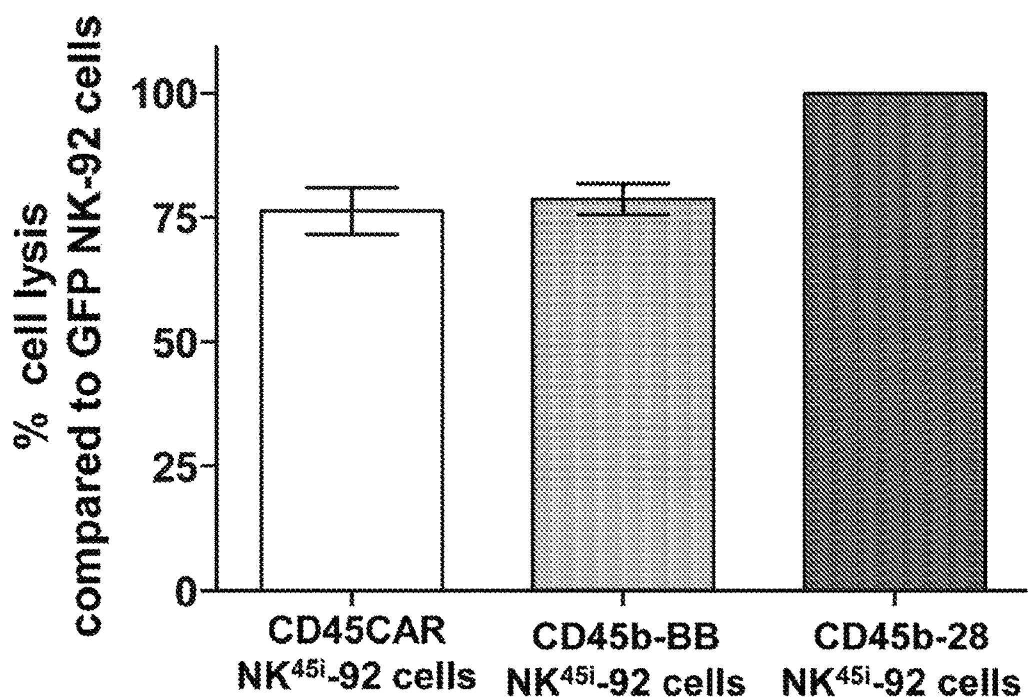

To assess CD45CAR $NK^{45i}$-92 anti-leukemic activity, we conducted co-culture assays using T-ALL cell lines, CCRF-CEM and Jurkat, and NK cell line and NK-92 cells since they all express CD45 (FIGS. 31, 32 and 33). We demonstrated that CD45CAR $NK^{45i}$-92 cells consistently displayed robust lysis of leukemic cells. Following 6-hour incubation at a low effective to target cell (E:T ratio 5:1), CD45CAR $NK^{45i}$-92 cells effectively lysed more than 60% of CCRF-CEMcells (FIG. 31). After 6-hour co-culture, CD45CAR $NK^{45i}$-92 cells were also able to eliminate about 60% of Jurkat cells at a ratio of E:T, 2:1 or 5:1(FIG. 32). After 6 hours of co-culture, CD45CAR $NK^{45i}$-92 cells efficiently lysed 20% CD45 positive NK-92 cells at an E:T ratio of 2:1, with close to 60% lysis at an E:T of 5:1 (FIGS. 33A-33C).

To further analyze the CD45 target for hematologic malignancies, we also generated additional two CARs: CD45-28 and CD45-BB, and the lentiviruses expressing CD45-28 or CD45-BB CAR were used to transduce NK45i-92 cells. CD45-28 and CD45-BB CARs contain a new anti-CD45 scFv, which is different from that of CD45CAR described above. CD45-28 CAR uses a CD28 co-stimulatory domain while the CD45-BB bears a 4-BB co-stimulatory domain. Both CARs use the CD8-derived hinge (H), transmembrane (TM) regions and CD3ζ signaling domain. CD45CARs displayed robust lysis of B acute lymphoblastic cell line, REH. CD45CAR NK45i-92 cells lysed about 76% REH cells. CD45b-BB CAR NK45i-92 cells and CD45b-28 CAR NK45i-92 cells showed about 79% and 100% lysis of REH cells, respectively compared to control GFP NK-92 cells (FIGS. 33D-G). CD45b-28 CAR NK45i-92 cells exhibited the highest ability of lysis of REH cells.

IL15 and Its Receptor in Enhancing CAR T and NK Cell Functions

Recent studies have demonstrated that T cell persistence correlates well with CAR T cell therapeutic efficacy. Recent trials demonstrate that potent and persistent antitumor activity can be generated by an infused small number of CAR T cells indicative that quality rather than quantity of infused products is more important in contributing to the anti-tumor activity. Interleukin (IL)-15 is a cytokine that promotes the development and hemostasis of lymphocytes. Increased levels of IL-15 promote T-cell proliferation and enhance T cell effector response. Data from recent studies have shown that IL-15 is crucial for the generation and maintenance of memory CD8 T-cells, one of the key factors associated with anti-tumor activity. IL-15 binds the IL-15 receptor alpha chain (also called IL15RA or RA) contributing to IL-15-mediated effects such as T-cell survival, proliferation and memory T cell generation.

IL-15RA binds the βγ complex in the surface of T cells and IL15 signals by binding with this IL-15RA/βγ complex on the cell surface of T cells and other types of cells.

Recent data have shown that while transfection of IL-15 alone does not significantly influence T-cell function, transfection of IL-15/1IL-15RA allows T cells to survive and proliferate autonomously.

The efficacy of administered IL-15 alone may be limited by the availability of free IL-15RA and its short half-life. Administration of soluble IL-15/RA complexes greatly enhanced II-15 half-life and bioavailability in vivo. Therefore, treatment of mice with this complex, but not with IL-15 alone results in robust proliferation and maintenance of memory CD8 T cells and NK cells. Recent studies have shown that a portion of the extracellular region of IL-15RA called sushi domain is required for its binding of IL15 (WEI et al., J. Immunol., vol.167(1), p:277-282, 2001). The IL-15/RA fusion protein or IL-15/sushi fusion protein containing the linker is more potent than IL-15 and soluble IL-15RA alone. The combination of IL-15/RA or IL-15/sushi can maximize IL-15 activity. However, it is unclear if a design incorporating both CAR and Il-15/RA or IL15/sushi in the same construct maintains its desired biological properties in T or NK cells as insert sequence length is able to affect transfection efficiency and gene expression levels.

The present disclosure provides an engineered cell having both CAR and IL15/RA or IL15/sushi in a single construct.

In some embodiments, the disclosure includes methods to generate higher virus titer and use a stronger promoter to drive both CAR and IL15/RA or IL-15/sushi.

In some embodiments, the present disclosure provides an engineered cell having: (1) a CAR targeting an antigen including, but not limited to, CD4, CD2, CD3, CD7, CD5, CD45, CD20, CD19, CD33, CD123, CS1, and B-cell mature antigen (BCMA); and (2) IL-15; (3) IL15RA (RA) or sushi. In further embodiments, CAR comprises chimeric antigen receptor, one or more of co-stimulatory endodomains, such as CD28, CD2, 4-1BB and OX40 and intracellular domain of CD3 zeta chain. In further embodiments, a strong promoter can be, but is not limited to, SFFV. CARs, IL-15/RA or sushi and inducible suicide gene ("safety switch"), or a combination can be assembled on a vector, such as a lentiviral vector, adenoviral vector and retroviral vector or a plasmid. The introduction of "safety switch" could significantly increase safety profile, and limit on-target or off-tumor toxicities of CARs.

Characterization of CD4IL15RA-CAR

Figure 34A:
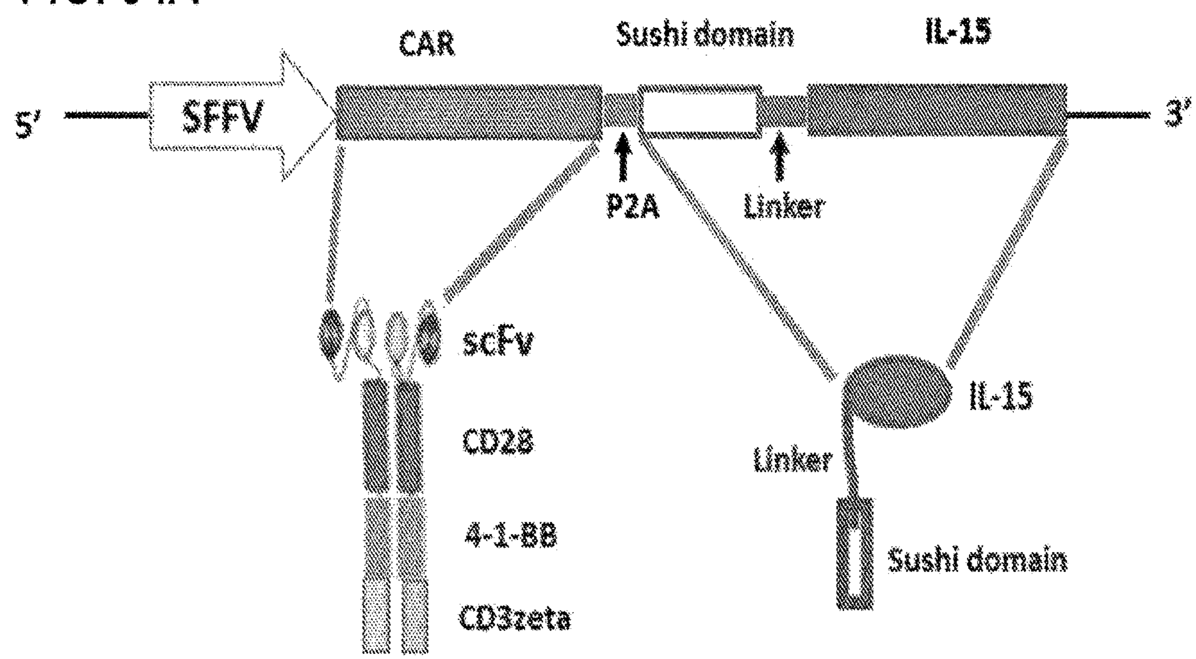
FIGS. 34A-B. Schematic diagram to elucidate the construct and its expression in T or NK cells. (A) a combination of CAR, (third generation), sushi/IL-15 is assembled on an expression vector and their expression is driven by the SFFV promoter. CAR with sushi/IL-15 is linked with the P2A cleaving sequence. The sushi/IL-15 portion is composed of IL-2 signal peptide fused to sushi domain and linked to IL-5 via a 26-amino acid poly-proline linker. (B) CAR and sushi/IL15 are present on the T or NK cells.

The CD4IL15RA-CAR has been generated and it contains the third generation of CD4CAR linked to IL15RA (FIG. 34). A combination of CAR, (third generation), sushi/IL-15 is assembled on an expression vector and their expression is driven by the SFFV promoter (FIG. 34). CAR with sushi/IL-15 is linked with the P2A cleaving sequence. The sushi/IL-15 portion is composed of IL-2 signal peptide fused to sushi domain and linked to IL-5 via a 26-amino acid poly-proline linker (FIG. 34).

Figure 34B:
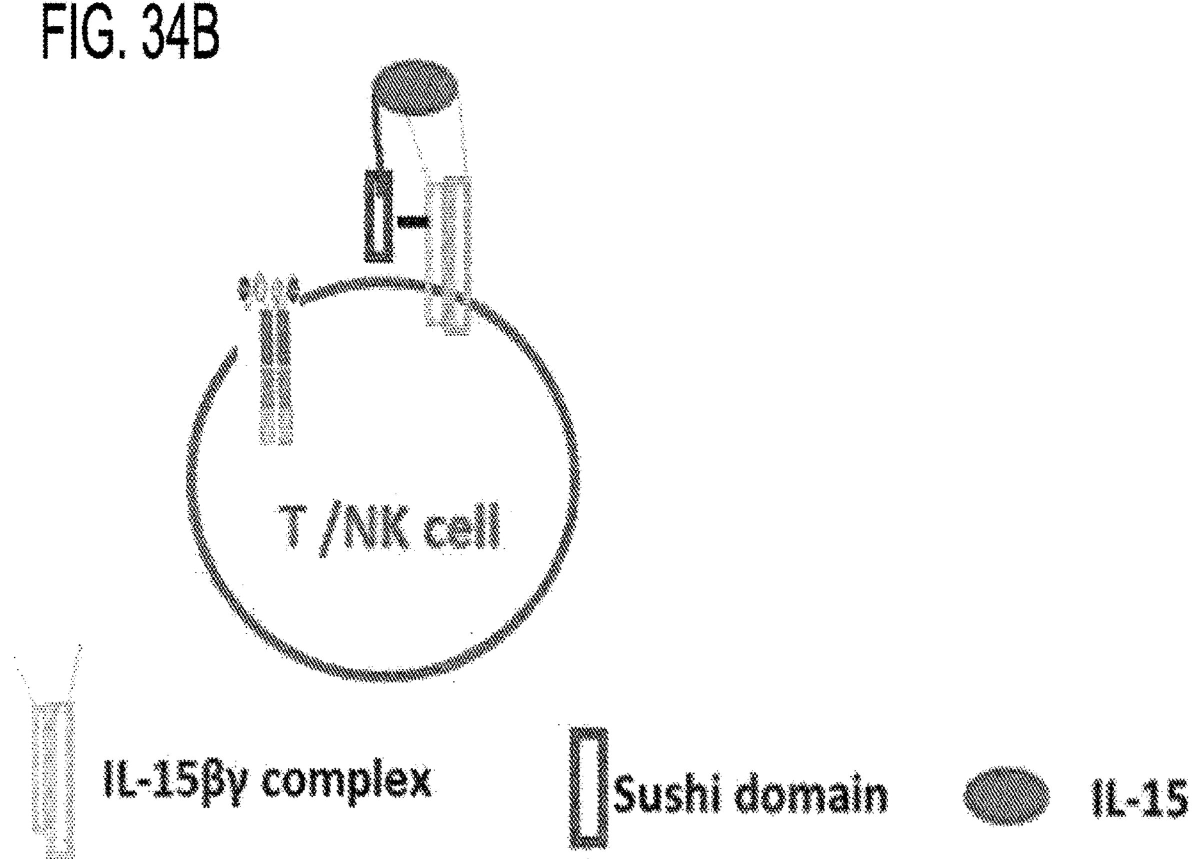
Figures 35A, 35B:
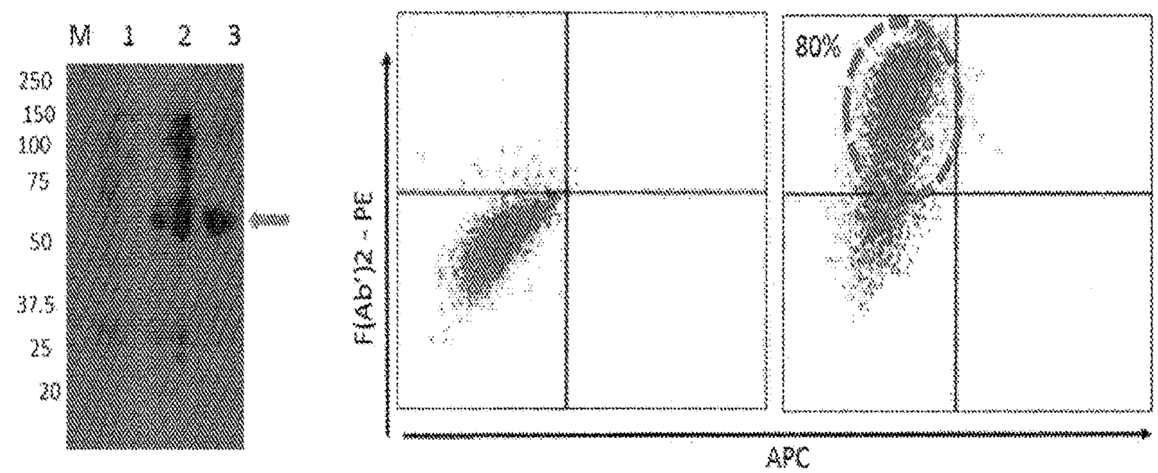
FIGS. 35A-B. CD4IL15RA-CAR expression. (A) HEK-293FT cells were transfected with lentiviral plasmids for GFP (lane 1) and CD4IL15RA CAR (lane 2), and positive control, CD4CAR (lane 3). 48 hours after transfection, supernatant was removed, and cells were also removed for a Western blot with mouse anti-human CD3z antibody. (B) HEK-293 cells were transduced with either GFP (left) or CD4IL15RA-CAR(right) viral supernatant from transfected HEK-293FT cells. After 3 days incubation, cells were harvested, stained with goat-anti-mouse F(Ab+)2 and analyzed by flow cytometry.

To verify the CD4IL15RA construct, HEK293FT cells were transfected with lentiviral plasmids for either GFP (control) or CD4IL15RA. Approximately 60 hours after transfection, both HEK-293FT cells and supernatant were collected. Cells were lysed in RIM buffer containing protease inhibitor cocktail and electrophoresed. The gel was transferred to Immobilon FL blotting membrane, blocked, and probed with mouse anti-human CD3z antibody at 1:500. After washes, membrane was probed with goat anti-mouse HRP conjugate, washed, and exposed to film following treatment with HyGlo HRP substrate. The CD4IL15RA-CAR was successfully expressed in HEK 293 cells (Lane 2, FIG. 35*a*, as shown next to recombinant IL-15 protein in Lane 3 (arrow). The CD4IL15RA-CAR lentiviral supernatant was further examined by the transduction of fresh HEK-293 cells (FIG. 35*a*). HEK-293 cells were transduced with either GFP or CD4IL15RA-CAR viral supernatant from transfected HEK-293FT cells. Polybrene was added to 4 uL/mL. Media was changed after 16 hours and replaced with media containing no viral supernatant or polybrene. Three days after transduction, cells were harvested and stained with goat-anti-mouse F(Ab+)2 antibody at 1:250 for 30 minutes. Cells were washed and stained with streptavidin-PE conjugate at 1:500, washed, suspended in 2% formalin, and analyzed by flow cytometry. FIG. 34*b* shows that HEK-293 cells that were transduced with the CD4IL15RA-CAR lentivirus were 80% positive for F(Ab)2-PE (circled, FIG. 35*b*), while transduction with GFP control lentivirus was minimal for F(Ab)2-PE (FIG. 35*b*, left).

Production of CD4IL15RA-CAR NK Cells

Figure 36:
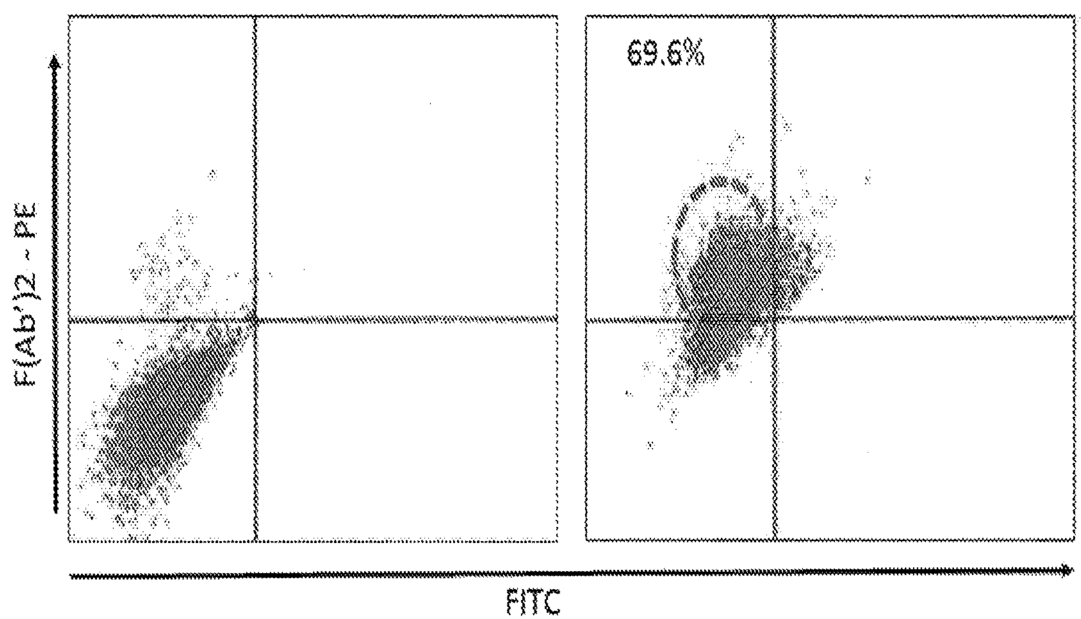
FIG. 36. Transduction of NK cells with CD4IL15RACAR. NK-92 cells were transduced with either GFP (left) or CD4IL15RACAR (right) viral supernatant from transfected HEK-293FT cells. A second transduction was performed 24 hours after the first. 24 hours after the second transduction, cells were harvested, washed and moved to tissue culture plates with fresh media and IL-2. After 3 days incubation, cells were harvested and stained with goat-anti-mouse F(Ab+)2 antibody or goat IgG (control) at 1:250 for 30 minutes. Cells were washed and stained with streptavidin-PE conjugate at 1:500, washed, suspended in 2% formalin, and analyzed by flow cytometry.

NK-92 cells were transduced with CD4IL15RA-CAR lentiviral supernatant. After 5 days incubation, cells were harvested and incubated with goat anti-mouse F(Ab+)2 at 1:250 for 30 minutes. Cells were washed, suspended and stained with streptavidin-PE for 30 minutes. Cells were washed and suspended in 2% formalin, and analyzed by flow cytometry, resulting in nearly 70% of the transduced cells expressing CD4IL15RA-CAR (circled, FIG. 36). Further experimental tests for CD4IL15RA-CAR will include leukemia/lymphoma killing assays in vitro and vivo, and comparison of target killing and proliferation rates with cells transduced with CD4CAR. The inventor also used the same strategy described above to generate CD19IL15RA-CAR.

Production of CD4IL15RA-CAR T Cells

Figure 37:
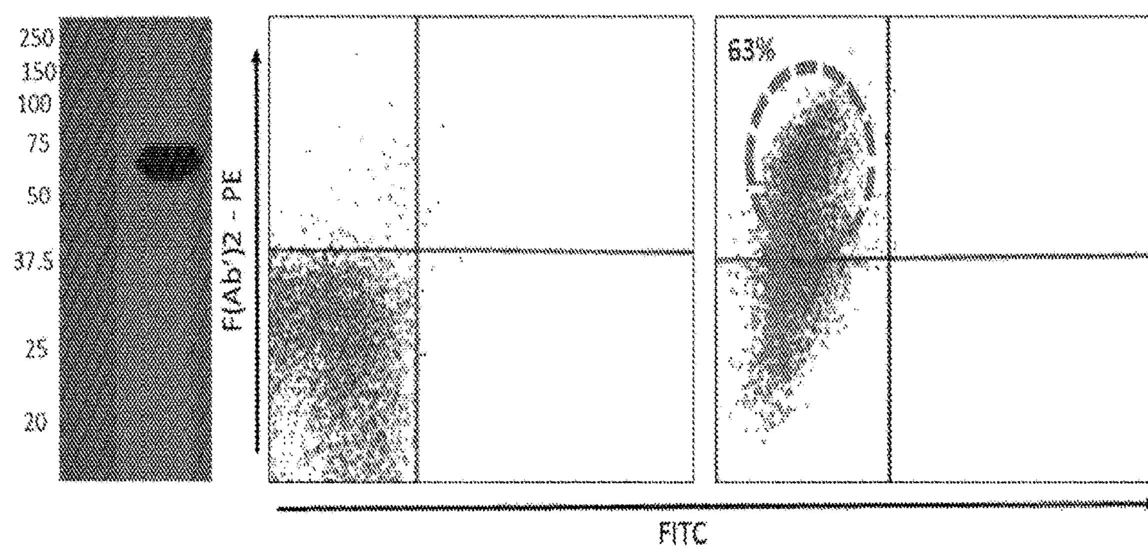
FIG. 37. Transduction of T cells with CD4IL15RACAR. Left is the Western blot. HEK-293FT cells were transfected with lentiviral plasmids for GFP (lane 1) and CD4IL15RA-CAR (lane 2). 48 hours after transfection, supernatant was removed, and cells were also collected for a Western blot with mouse anti-human CD3zeta antibody. Right is CD4IL15RACAR expression. Activated T cells from cord blood buffy coat were transduced with either GFP (left) or CD4IL15RACAR (right) viral supernatant from transfected HEK-293FT cells. A second transduction was performed 24 hours after the first. 24 hours after the second transduction, cells were harvested, washed and moved to tissue culture plates with fresh media and IL-2. After 3 days incubation, cells were harvested and stained with goat-anti-mouse F(Ab+)2 or isotype control for 30 minutes. Transduced with either GFP (left) or CD4IL15RA (right). Cells were washed and stained with streptavidin-PE conjugate at 1:250, washed, suspended in 2% formalin, and analyzed by flow cytometry FIGS. 38A-B. CD4CAR NK-92 cells and CD4IL15RA CAR NK-92 cells eliminate KARPAS 299 T leukemic cells in co-culture. (A) NK-92 cells transduced with either GFP control (upper right), CD4CAR (lower left), or CD4IL15RA (lower right) lentiviral supernatant were incubated with KARPAS 299 cells at a ratio of 5:1. After 4 hours co-culture, cells were stained with mouse-anti-human CD4 (APC) and CD3 (PerCp) antibodies and analyzed by flow cytometry (N=2). The upper left panel shows labeled Karpas 299 cells alone. (B) The percentage of target cells lysed is shown in the graph.

Human umbilical cord buffy coat cells were transduced with CD4IL15RA-CAR lentiviral supernatant. After 5 days incubation, cells were harvested and incubated with goat anti-mouse F(Ab+)2 at 1:250 for 30 minutes. Cells were washed, suspended and stained with streptavidin-PE for 30 minutes. Cells were washed and suspended in 2% formalin, and analyzed by flow cytometry, resulting in 63% of the transduced cells expressing CD4IL15RA-CAR (circled, FIG. 37). Further experimental tests for CD4IL15RA-CAR will include leukemia/lymphoma killing assays in vitro and vivo, and comparison of target killing and proliferation rates with cells transduced with CD4CAR.

CD4IL15RACAR NK Cells Were Tested for Anti-Leukemic Activity Relative to CD4CAR NK Cells In Vitro by Co-Culturing Them With the Following CD4 Positive Cell Lines: Karpas 299 and MOLT4.

Figure 38A:
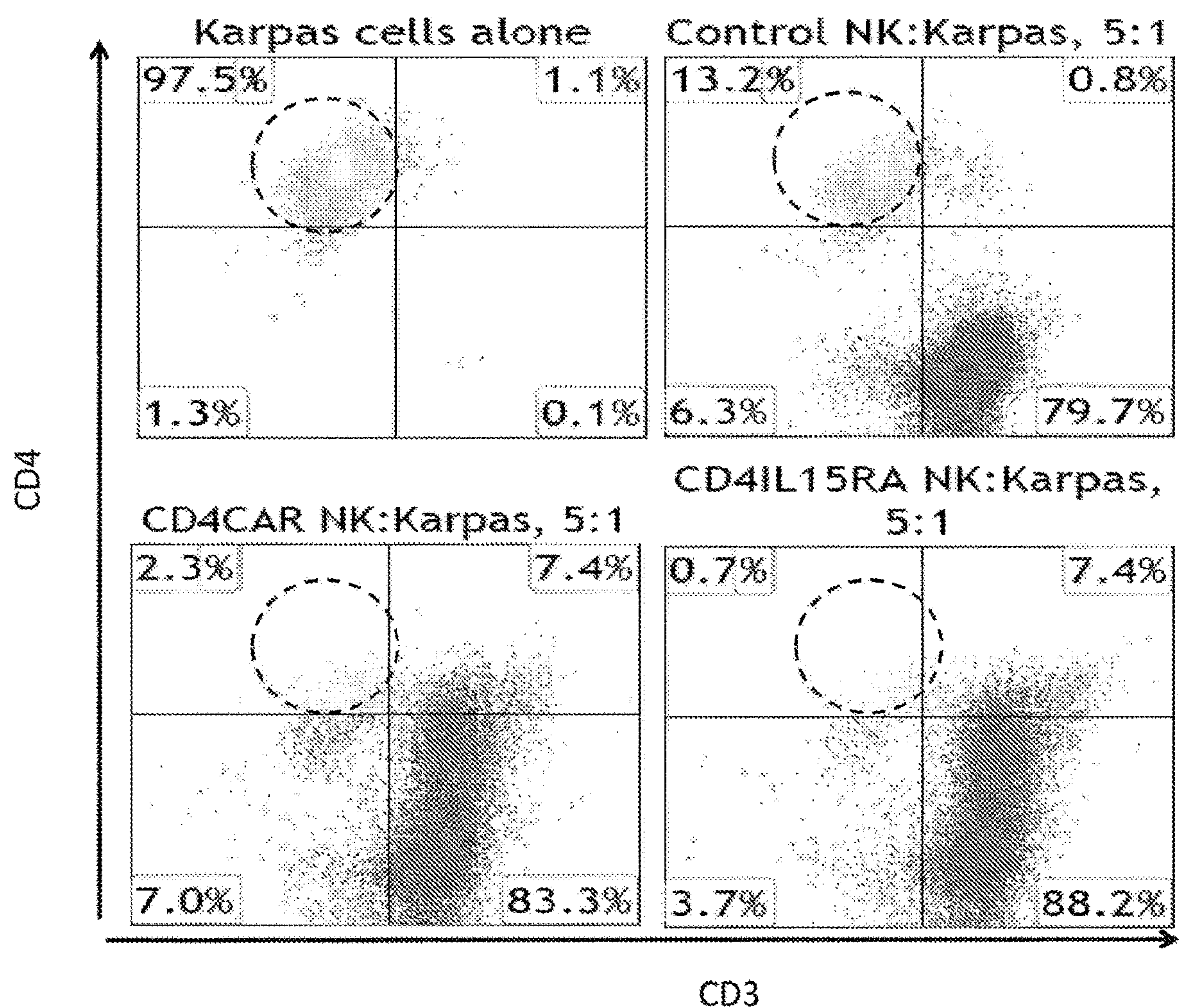
Figure 38B:
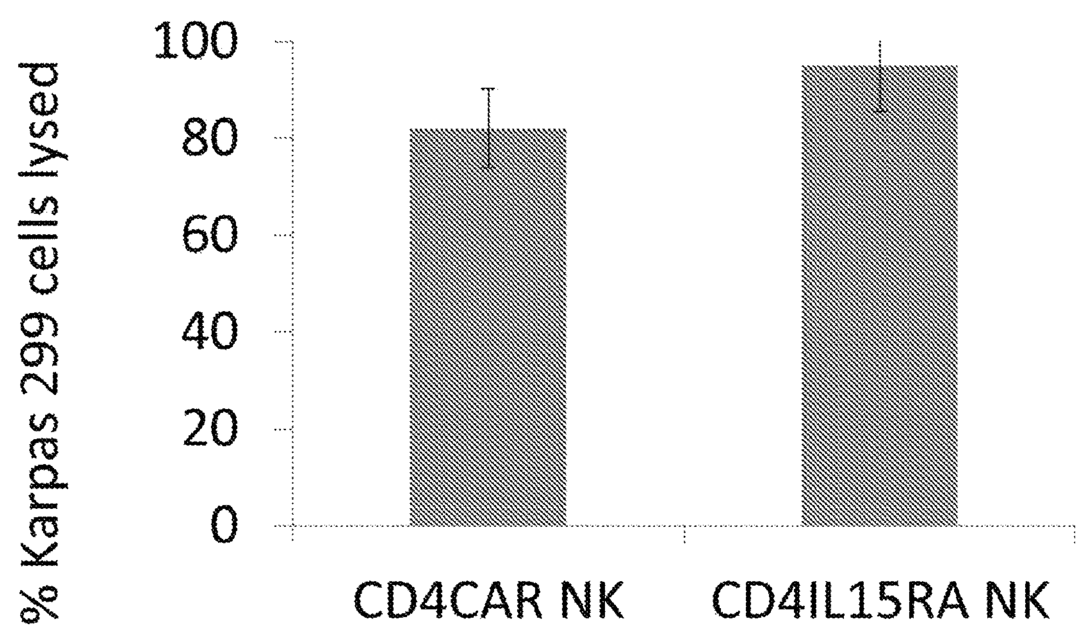
Figure 39:
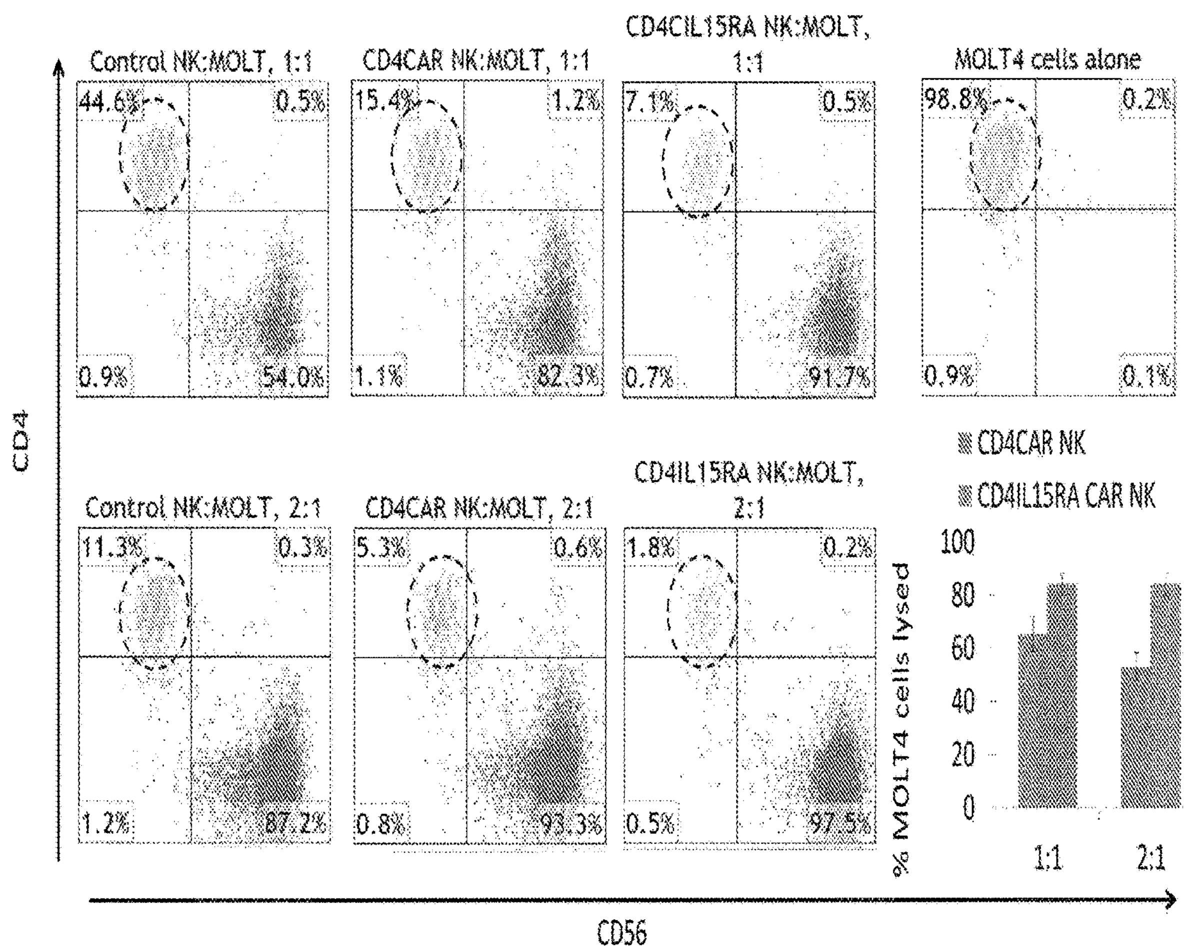
FIG. 39. CD4CAR NK-92 cells and CD4IL15RA CAR NK-92 cells eliminate MOLT4 T leukemic cells expressing CD4 in co-culture. NK-92 cells transduced with either GFP control (left), CD4CAR (center), or CD4IL15RA (second from right) lentiviral supernatant were incubated with MOLT4 cells at effector:target ratios of 1:1 or 2:1. After overnight co-culture, cells were stained with mouse-anti-human CD4 (APC) and CD56 (PerCp) antibodies and analyzed by flow cytometry (N=2). The upper right panel shows labeled MOLT4 cells alone. The percentage of target cells lysed is shown in the graph.

The Karpas 299 cell line was derived from a patient with anaplastic large T cell lymphoma. The MOLT4 cell line expressing CD4 was established from the peripheral blood of a 19-year-old patient with acute lymphoblastic leukemia (T-ALL). During 4-hour co-culture experiments, CD4IL15RA CAR NK cells showed profound killing (95%) of Karpas 299 cells at a 5:1 ratio of effector:target, at an even higher rate than that of CD4CAR NK cells (82%; FIG. 38). Similarly, when co-cultured 1:1 with MOLT4 cells, CD4IL15RA CAR NK cells lysed target cells at a higher rate (84% to 65%) than CD4CAR NK cells in an overnight assay (FIG. 39). These results show that CD4IL15 CAR NK cells can ablate tumor cells at least as well as CD4CAR NK cells.

Figure 40:
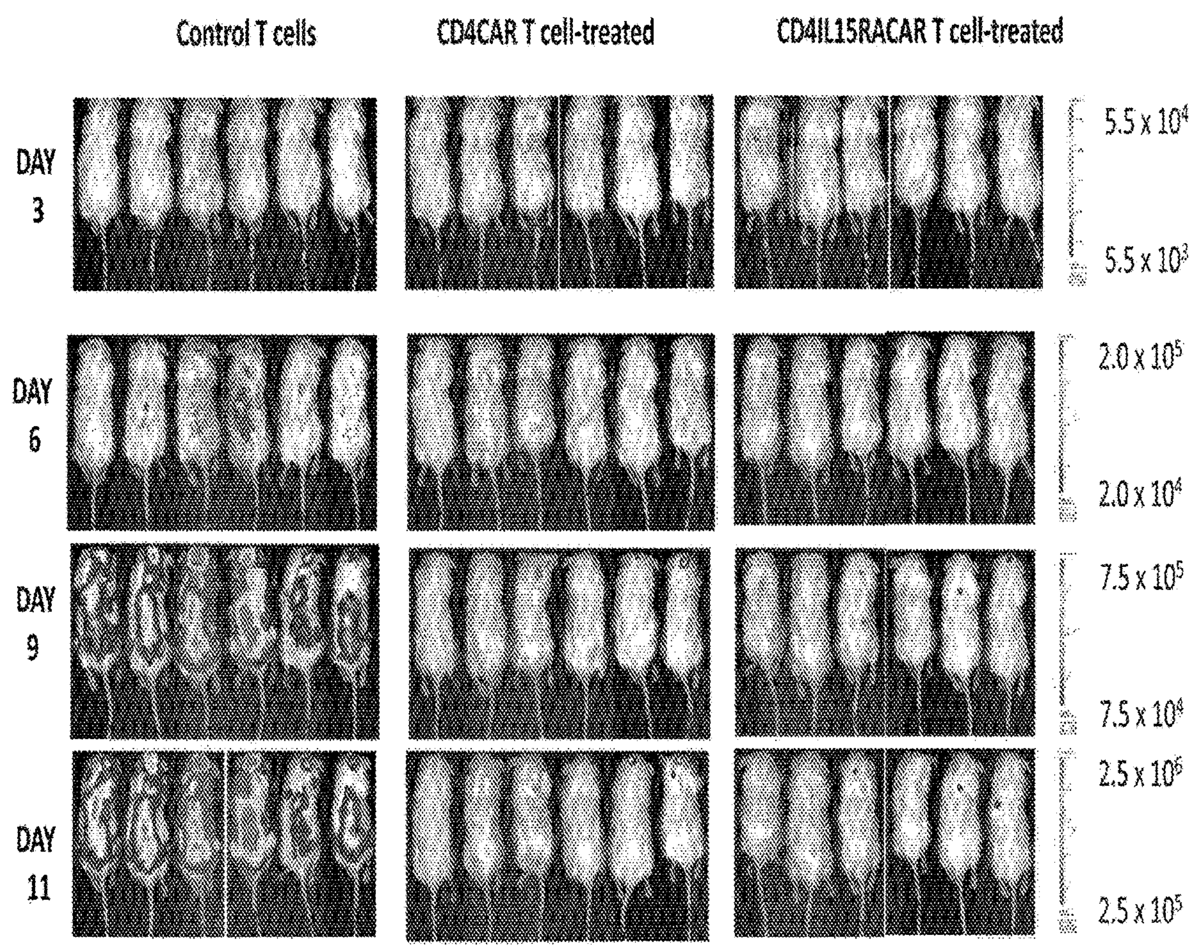
FIG. 40. CD4IL15RACAR T cells demonstrate more potent anti-leukemic effects in vivo than CD4CAR. NSG mice were sublethally irradiated and intravenously (tail vein) injected the following day with luciferase-expressing MOLM13 cells to induce measurable tumor formation. After 3 days, the mice were intravenously injected with one course of $8\times10^6$ CD4CAR, or CD4IL15RACAR T cells, or vector control T control cells. On days 3, 6, 9 and 11, mice were injected subcutaneously with RediJect D-Luciferin and subjected to IVIS imaging.
Figure 41:
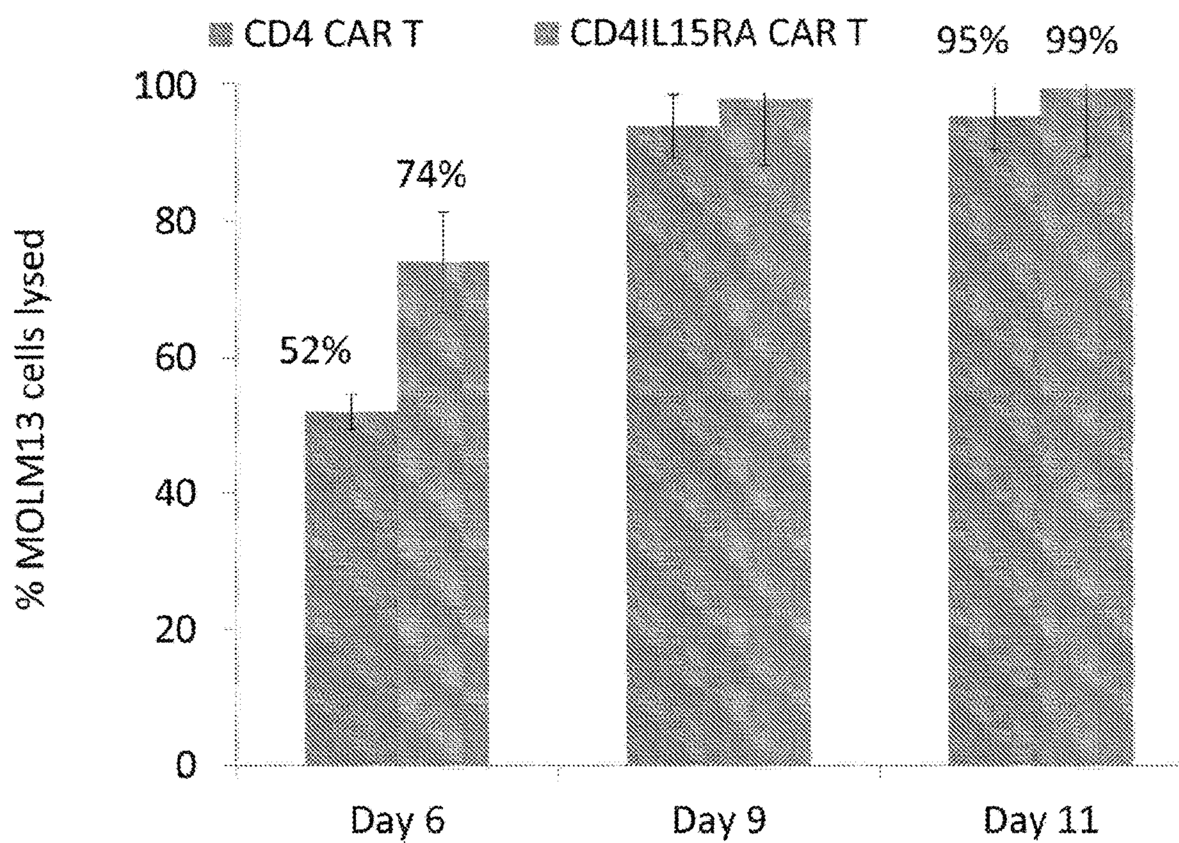
FIG. 41. Percent tumor reduction in mice was measured and compared between the three groups based on the studies from FIG. 40. Average light intensity measured for the CD4CAR and CD4IL15RACAR T injected mice was compared to that of vector control T injected mice, and correlated with remaining tumor burden. In each set of two, CD4CAR T is on the left and CD4IL15RA CAR T is on the right.

CD4CAR and CD4IL15RA CAR T Cells Exhibit More Potent Anti-Tumor Activity In Vivo Than CD4CAR In order to evaluate the in vivo anti-tumor activity of CD4CAR and CD4IL15RACAR T cells, and to determine the possible increase in persistence of the CD4IL15RA CAR T cells relative to the CD4CAR T cells, we developed a xenogeneic mouse model using NSG mice sublethally irradiated and intravenously injected with luciferase-expressing MOLM13 cells, an acute myeloid leukemia cell line (M5) that is 100% CD4, to induce measurable tumor formation. Three days following tumor cell injection, 6 mice each were intravenously injected with a course of $8\times10^6$ CD4CAR, CD4IL15RACAR T cells or vector control T cells. On days 3, 6, 9 and 11, mice were injected subcutaneously with RediJect D-Luciferin (Perkin Elmer) and subjected to IVIS imaging to measure tumor burden (FIG. 40). CD4CAR T cell-treated mice had a 52% lower tumor burden relative to control on Day 6, whereas CD4IL15RA CAR T cell-treated mice had a 74% lower tumor burden (FIG. 41). On Day 11, nearly all tumor cells had been lysed in both of these groups. Unpaired T test analysis revealed an very significant difference (P=0.0045) between control and the two groups by day 9 with less light intensity and thus less tumor burden in the CD4CAR and CD4IL15RACAR T cells treated group compared to control. Promoter testing using the GFP reporter HEK293FT cells were transfected with lentiviral plasmids expressing GFP under the SFFV, EF1 or CAG promoters. Approximately 60 hours after transfection, supernatant was collected from each. Relative viral titer was determined by first transducing HEK293 cells with supernatant from each of the 3 promoters. HEK-293 cells were transduced with GFP viral supernatant from each of the 3 transfected HEK-293FT cells. Polybrene was added to 4 uL/mL. Media was changed after 16 hours and replaced with media containing no viral supernatant or polybrene. Three days after transduction, cells were harvested and washed, suspended in 2% formalin, and analyzed by flow cytometry for GFP expression (FITC). GFP expression was seen in each sample, but was highest for the cells transduced with virus made using the SFFV promoter.

Activated human umbilical cord buffy coat cells were transduced with GFP lentiviral supernatant (amount based on the results of the HEK293 transduction efficiency) from each of the promoters. After 5 days incubation, cells were harvested, washed and suspended in 2% formalin, and analyzed by flow cytometry for GFP expression. 43% of cells expressed GFP at high levels (>$10^3$) while GFP-expression for cells transduced with virus using promoters EF1 (15%) and CAG (3%) were considerably lower. Five days later, cells analyzed the same way showed nearly the same percentages for each (46%, 15% and 3%, respectively; FIG. 23). These results indicate that SFFV promoter leads to stronger expression than EF1 or CAG promoters, and that the expression remains high for at least 10 days post-transduction. Further experimental tests will include longer incubation times for transduced cells beyond the 10-day window.

Methods of generating the CAR gene including at least one of a T antigen recognition moiety (at least one of CD4, CD8, CD3, CD5, CD7, and CD2, or a part or a combination thereof), a hinge region and T-cell activation domains is provided.

Methods of generating multiple units of CARs (cCAR) targeting antigen (s) including at least one of CD33, CD123, CD19, CD20, CD22, CD269, CS1, CD38, CD52, ROR1, PSMA, CD138, and GPC3, or a part or a combination of a hinge region and T-cell activation domains is provided. All references cited and/or disclosed herein are hereby incorporated by reference in their entirety.

The provided methods also include: 1) generating of the CAR T or NK cells targeting leukemias and lymphomas expressing CD45 and avoiding self-killing; 2) generation of “armored” CAR T or NK cells designed to both overcome the inhibitory tumor microenvironment and exhibit enhanced anti-tumor activity and long-term persistence. The present invention is not limited to the embodiments described and exemplified above, but is capable of variation and modification within the scope of the appended claims. Various publications, including patents, published applications, technical articles and scholarly articles are cited throughout the specification. Each cited publication is incorporated by reference herein, in its entirety and for all purposes. Various terms relating to aspects of the invention are used throughout the specification and claims. Such terms are to be given their ordinary meaning in the art, unless otherwise indicated. Other specifically defined terms are to be construed in a manner consistent with the definition provided herein.

Functional Titer of Viral Vector Particles in Supernatants (The % GFP Cells as Determined by Flow Cytometry Allows for Proxy Viral Titer Adjustments as Higher Titer Virus Infiltrates More Cells, Leading to Higher % GFP Cell Populations).

To determine functional titer of viral vector particles in each of our supernatants, HEK 293 cells were transduced with either EF1-GFP or SFFV-GFP viral supernatant, with either 30 μL (low), 125 μL (medium), or 500 μL (high) per well of a 12 well tissue-culture treated plate. Culture media was changed the following morning to DMEM plus 10% FBS.

Figure 42:
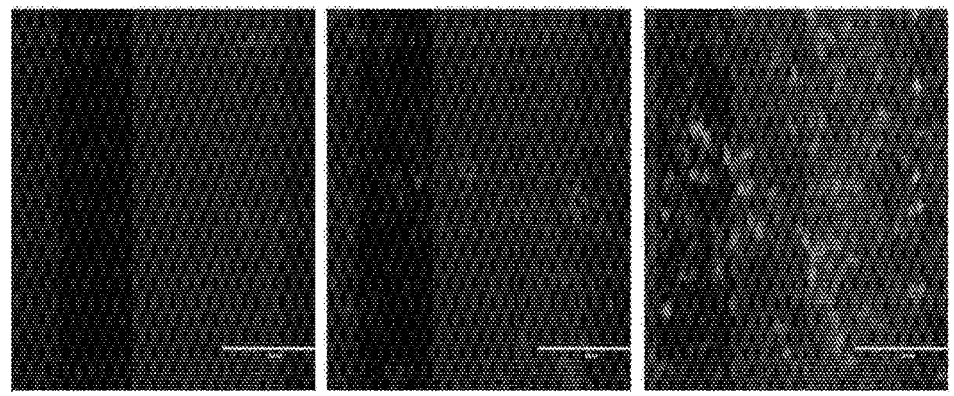
FIG. 42. HEK 293 cells were transduced with either EF1-GFP or SFFV-GFP viral supernatant, using the volumes indicated, in DMEM with 10% FBS in a 6 well tissue culture plate. Culture media was changed the following morning. Forty-eight hours later, transduced cells were visualized on an EVOS fluorescent microscope using GFP at 10×.
Figure 42:
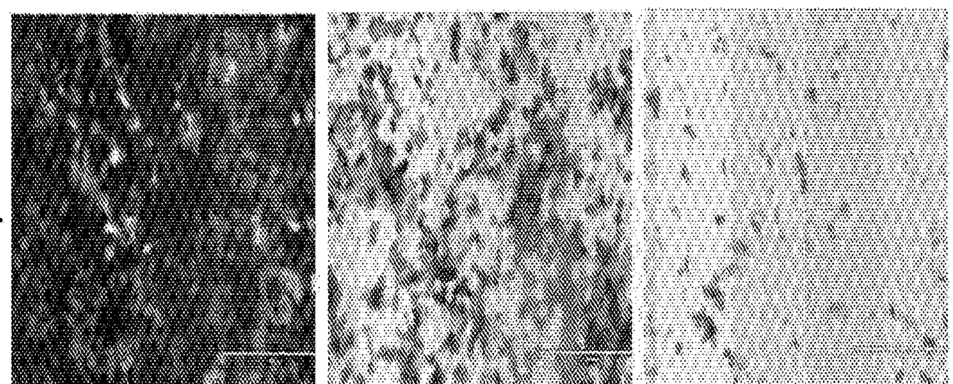
Figure 43:
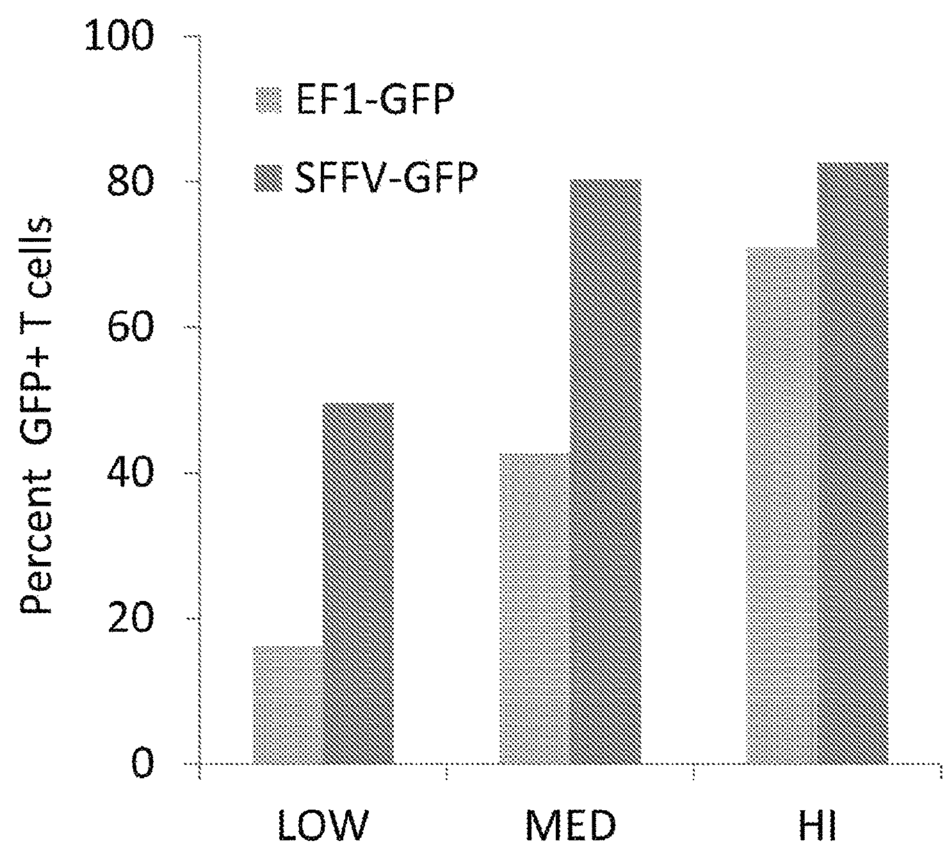
FIG. 43. HEK 293 cells transduced with either EF1-GFP or SFFV-GFP viral supernatant, using the volumes from the previous figure, were trypsinized, suspended in formalin, and subjected to flow cytometry analysis, using the FITC channel to determine the percentage of GFP+ cells.

Transduced cells were then trypsinized, washed, and suspended in formalin and subjected to flow analysis. The percentage of GFP+ cells in each of the conditions was determined by flow cytometry using the FITC channel (FIG. 43). In each case, the percentage of GFP+ was higher in cells transduced with SFFV-GFP than the cells transduced with the corresponding volume of EF1-GFP viral supernatant (50% to 18% for low, 80% to 40% for medium, and 82% to 70% for high). From this, we determined that using the highest volume of EF1-promoter virus was comparable to using the lowest volume of SFFV-promoter virus in terms of titer, and would allow for comparison of relative promoter strengths for the following transduction experiments Transduced cells were also visualized on an EVOS fluorescent microscope using GFP at 20× at the same exposure conditions for each well (FIG. 42). Cells transduced with SFFV-GFP viral supernatant were dramatically brighter than cells transduced with EF1-GFP. Furthermore, comparing the image of the EF1-promoter under high viral volume loads with the image of the SFFV-promoter using low viral volume loads show similar fluorescent intensity. This suggests that the SFFV promoter is a stronger driver of gene expression.

Comparison of Surface Expression and Persistence of Different Promoters in Primary T-Cells (The % GFP Cells as Determined by Flow Cytometry for T-Cell Transductions Show Expected Differences in GFP Cell Populations as Expected From the Prior Experiments on HEK293 Cells)

Figure 44A:
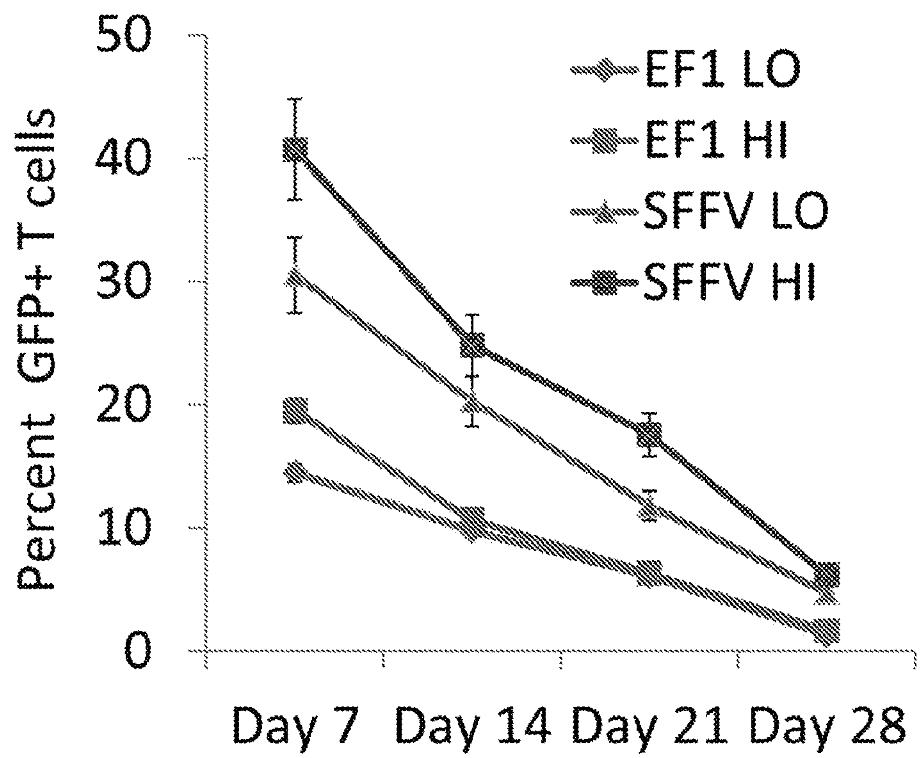
FIGS. 44A-B. Activated cord blood buffy coat T cells transduced with either EF1-GFP or SFFV-GFP viral supernatant, with either low or high amounts of viral supernatant, were trypsinized, suspended in formalin, and subjected to flow cytometry analysis, using the FITC channel to determine the percentage of GFP+ cells, 7, 14, 21 and 28 days after transduction. (A) Percent GFP+ T cells for cells transduced with either low or high amounts of supernatant. (B) Percent of GFP+ T cells transduced with the high amount of EF1-GFP supernatant, relative to the percent GFP+ cells in the T cells transduced with the lower amount of SFFV-GFP supernatant. (50 μL of SFFV-GFP and 1 mL of EF1-GFP supernatant was used). (N=2).
Figure 44B:
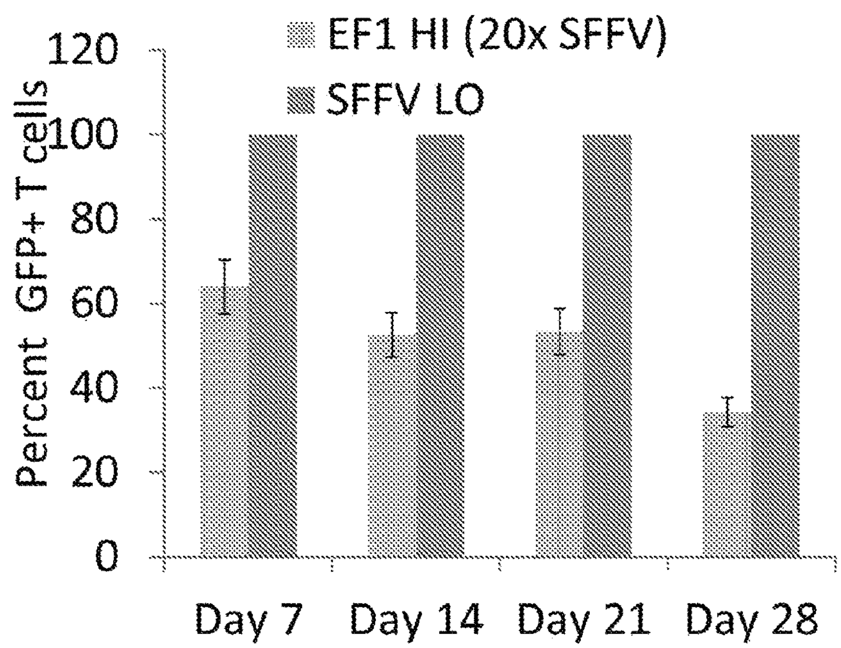

To determine promoter transduction efficiency and persistence of surface expression in primary T cells, activated cord blood buffy coat T cells were transduced with either 50 μL of SFFV-GFP or 1 mL of EF1-GFP EF1-GFP viral supernatant, in 12-well tissue culture-treated plates pre-coated with retronectin (Clontech). Following two overnight transductions, cells were cultured on T cell media with 300 IU/mL IL-2 (Peprotech) and maintained at 1.0-4.0×$10^6$/mL. Cells were washed, suspended in formalin, and subjected to flow cytometry analysis, using the FITC channel to determine the percentage of GFP+ cells, on 7, 14, 21 and 28 days after transduction. The percentage of GFP+ cells was consistently higher for T cells transduced with SFFV-GFP compared to EF1-GFP-transduced T cells (FIG. 44A), even as the percentage of total GFP+ cells decreased over this period. A further comparison showed that T cells transduced with the higher (1 mL) amount of EF1-GFP supernatant actually decreased in percentage relative to the percent of GFP+ cells transduced with the lower amount (50 μL, or 20-fold less) of SFFV-GFP, between Day 7 and Day 28, from over 60% to under 40% (FIG. 44B). This suggests that transduction using the SFFV promoter led to greater persistence of transduced cells.

BCMA or TACI or BAFF-R CAR NK Cells or T-Cells Targeting Cells Expressing at Least One of BCMA or TACI or BAFF-R CAR Antigen To assess the cytotoxicity ability of CAR targeting at least one of BCMA or TACI or BAFF-R NK cells or T cells, co-culture assays are conducted with cell lines or primary human cells expressing at least one of BCMA or TACI or BAFF-R. The ability of the aforementioned CAR NK cells or T cells to lyse the target cells was quantified by flow cytometry analysis, and target cells were stained with Cytotracker dye (CMTMR). Lysis is observed at 24 hour long cultures.

BAFF or APRIL CAR NK or T Cells Targeting Cells Expressing at Least One of BCMA or TACI or BAFF-R Antigen.

The chimeric antigen receptor in the CAR is the ligand for BCMA or TACI or BAFF-R.

To assess the cytotoxicity ability of CAR targeting at least one of BCMA or TACI or BAFF-R NK or T cells, co-culture assays are conducted with cell lines or human primary cells expressing at least one of of BCMA or TACI or BAFF-R. The ability of the aforementioned CAR NK or T cells to lyse the target cells was quantified by flow cytometry analysis, and target cells were stained with Cytotracker dye (CMTMR). Lysis is observed at 24 hour-long cultures.

REFERENCES

Arai, S., R. Meagher, M. Swearingen, H. Myint, E. Rich, J. Martinson and H. Klingemann (2008). "Infusion of the allogeneic cell line NK-92 in patients with advanced renal cell cancer or melanoma: a phase I trial." *Cytotherapy* 10(6): 625-632.

Boissel, L., M. Betancur-Boissel, W. Lu, D. S. Krause, R. A. Van Etten, W. S. Wels and H. Klingemann (2013). "Retargeting NK-92 cells by means of CD19- and CD20-specific chimeric antigen receptors compares favorably with antibody-dependent cellular cytotoxicity." *Oncoimmunology* 2(10): e26527.

Burnett, A. K. (2012). "Treatment of acute myeloid leukemia: are we making progress?" *Hematology-American Society Hematology Education Program:* 1-6.

Chu, J., Y. Deng, D. M. Benson, S. He, T. Hughes, J. Zhang, Y. Peng, H. Mao, L. Yi, K. Ghoshal, X. He, S. M. Devine, X. Zhang, M. A. Caligiuri, C. C. Hofmeister and J. Yu (2014). "CS1-specific chimeric antigen receptor (CAR)-engineered natural killer cells enhance in vitro and in vivo antitumor activity against human multiple myeloma." *Leukemia* 28(4): 917-927.

Corbin, A. S., A. Agarwal, M. Loriaux, J. Cortes, M. W. Deininger and B. J. Druker (2011). "Human chronic myeloid leukemia stem cells are insensitive to imatinib despite inhibition of BCR-ABL activity." *J Clin Invest* 121(1): 396-409.

Dinndorf, P. A., R. G. Andrews, D. Benjamin, D. Ridgway, L. Wolff and I. D. Bernstein (1986). "Expression of normal myeloid-associated antigens by acute leukemia cells." *Blood* 67(4): 1048-1053.

Djokic, M., E. Bjorklund, E. Blennow, J. Mazur, S. Soderhall and A. Porwit (2009). "Overexpression of CD123 correlates with the hyperdiploid genotype in acute lymphoblastic leukemia." *Haematologica* 94(7): 1016-1019.

Ehninger, A., M. Kramer, C. Rollig, C. Thiede, M. Bornhauser, M. von Bonin, M. Wermke, A. Feldmann, M. Bachmann, G. Ehninger and U. Oelschlagel (2014). "Distribution and levels of cell surface expression of CD33 and CD123 in acute myeloid leukemia." *Blood Cancer J* 4: e218.

Firor, A. E., A. Jares and Y. Ma (2015). "From humble beginnings to success in the clinic: Chimeric antigen receptor-modified T-cells and implications for immunotherapy." *Exp Biol Med* (*Maywood*).

Garfall, A. L., M. V. Maus, W. T. Hwang, S. F. Lacey, Y. D. Mahnke, J. J. Melenhorst, Z. Zheng, D. T. Vogl, A. D. Cohen, B. M. Weiss, K. Dengel, N. D. Kerr, A. Bagg, B. L. Levine, C. H. June and E. A. Stadtmauer (2015). "Chimeric Antigen Receptor T Cells against CD19 for Multiple Myeloma." *N Engl J Med* 373(11): 1040-1047.

Ghosh, N. and W. Matsui (2009). "Cancer stem cells in multiple myeloma." *Cancer Lett* 277(1): 1-7.

Griffin, J. D., D. Linch, K. Sabbath, P. Larcom and S. F. Schlossman (1984). "A monoclonal antibody reactive with normal and leukemic human myeloid progenitor cells." *Leuk Res* 8(4): 521-534.

Jilani, I., E. Estey, Y. Huh, Y. Joe, T. Manshouri, M. Yared, F. Giles, H. Kantarjian, J. Cortes, D. Thomas, M. Keating, E. Freireich and M. Albitar (2002). "Differences in CD33 intensity between various myeloid neoplasms." *Am J Clin Pathol* 118(4): 560-566.

Jordan, C. T., D. Upchurch, S. J. Szilvassy, M. L. Guzman, D. S. Howard, A. L. Pettigrew, T. Meyerrose, R. Rossi, B. Grimes, D. A. Rizzieri, S. M. Luger and G. L. Phillips (2000). "The interleukin-3 receptor alpha chain is a unique marker for human acute myelogenous leukemia stem cells." *Leukemia* 14(10): 1777-1784.

Klingemann, H. (2014). "Are natural killer cells superior CAR drivers?" *Oncoimmunology* 3: e28147.

Kumar, S. K., S. V. Rajkumar, A. Dispenzieri, M. Q. Lacy, S. R. Hayman, F. K. Buadi, S. R. Zeldenrust, D. Dingli, S. J. Russell, J. A. Lust, P. R. Greipp, R. A. Kyle and M. A. Gertz (2008). "Improved survival in multiple myeloma and the impact of novel therapies." *Blood* 111(5): 2516-2520.

Lang, S., N. L. Vujanovic, B. Wollenberg and T. L. Whiteside (1998). "Absence of B7.1-CD28/CTLA-4-mediated co-stimulation in human NK cells." *Eur J Immunol* 28(3): 780-786.

Lanitis, E., M. Poussin, A. W. Klattenhoff, D. Song, R. Sandaltzopoulos, C. H. June and D. J. Powell, Jr. (2013). "Chimeric antigen receptor T Cells with dissociated signaling domains exhibit focused antitumor activity with reduced potential for toxicity in vivo." *Cancer Immunol Res* 1(1): 43-53.

Loke, J., J. N. Khan, J. S. Wilson, C. Craddock and K. Wheatley (2015). "Mylotarg has potent anti-leukaemic effect: a systematic review and meta-analysis of anti-CD33 antibody treatment in acute myeloid leukaemia." *Annals of Hematology* 94(3): 361-373.

Maus, M. V., J. A. Fraietta, B. L. Levine, M. Kalos, Y. Zhao and C. H. June (2014). "Adoptive immunotherapy for cancer or viruses." *Annu Rev Immunol* 32: 189-225.

Olson, J. A., D. B. Leveson-Gower, S. Gill, J. Baker, A. Beilhack and R. S. Negrin (2010). "NK cells mediate reduction of GVHD by inhibiting activated, alloreactive T cells while retaining GVT effects." *Blood* 115(21): 4293-4301.

Ruiz-Arguelles, G. J. and J. F. San Miguel (1994). "Cell surface markers in multiple myeloma." *Mayo Clin Proc* 69(7): 684-690.

Testa, U., E. Pelosi and A. Frankel (2014). "CD 123 is a membrane biomarker and a therapeutic target in hematologic malignancies." *Biomark Res* 2(1): 4.

Vergez, F., A. S. Green, J. Tamburini, J. E. Sarry, B. Gaillard, P. Cornillet-Lefebvre, M. Pannetier, A. Neyret, N. Chapuis, N. Ifrah, F. Dreyfus, S. Manenti, C. Demur, E. Delabesse, C. Lacombe, P. Mayeux, D. Bouscary, C. Recher and V. Bardet (2011). "High levels of CD34+ CD38low/-CD123+ blasts are predictive of an adverse outcome in acute myeloid leukemia: a Groupe Ouest-Est des Leucemies Aigues et Maladies du Sang (GOELAMS) study." *Haematologica* 96(12): 1792-1798.

Wilkie, S., M. C. van Schalkwyk, S. Hobbs, D. M. Davies, S. J. van der Stegen, A. C. Pereira, S. E. Burbridge, C. Box, S. A. Eccles and J. Maher (2012). "Dual targeting of ErbB2 and MUC1 in breast cancer using chimeric antigen receptors engineered to provide complementary signal-ing." *J Clin Immunol* 32(5): 1059-1070.

INCORPORATION OF UPDATED SEQUENCE LISTING

Incorporated herein by reference in its entirety is the Sequence Listing for the application. The Sequence Listing is disclosed on a computer-readable ASCII text file titled, "Substitute_SequenceListing_2541_3PCTUS.txt", created on Jun. 30, 2021. The.txt file is 141.7 kb in size.

The invention claimed is:

1. An ex vivo engineered T cell or NK cell co-expressing two distinct chimeric antigen receptor (CAR) units at the cell surface, wherein the engineered T cell or NK cell comprises a nucleotide sequence comprising from 5' to 3' a single promoter selected from human elongation factor-1 alpha (EF-1α) or spleen focus forming virus (SFFV), a first polynucleotide encoding a first chimeric antigen receptor polypeptide (CAR), a nucleotide encoding a viral self-cleavage peptide, a second polynucleotide encoding a second chimeric antigen receptor polypeptide (CAR), and an enhancer selected from the group consisting of secreted IL-15/IL-15sushi, Il-15/Il-15 sushi anchor, PD-1, PD-L1, CSF1R, CTLA-4, TIM-3, TGFR-beta, IL-2, Il-7, IL-12, IL-15, IL-15RA, IL-21 or a functional fragment thereof, or a combination thereof, wherein said enhancer is separated from the first CAR and second CAR by a second cleavage site that flanks either end of the two distinct CAR units, wherein:

the first CAR comprises a first signal peptide, a first antibody binding domain, a first hinge region, a first transmembrane domain, a first co-stimulatory domain, and a first signaling domain; and the second CAR comprises a second signal peptide, a second antibody binding domain, a second hinge region, a second transmembrane domain, a second co-stimulatory domain, and a second signaling domain; and wherein the first antibody binding domain and the second antibody binding domain are different and each bind to a different target, wherein the targets of the first and second antibody binding domains irrespective of order are CD19 and CD20, or CD123 and CD33, or B cell maturation antigen (BCMA) (CD269) and CD19, or BCMA (CD269) and CD38, or and BCMA (CD269) and CS1, wherein the first and second co-stimulatory domains are intracellular, and wherein the cleavage site is selected from the group consisting of porcine teschovirus-1 2A (P2A), thoseaasigna virus 2A (T2A), equine rhinitis A virus (ERAV) 2A (E2A), and FMDV 2A (F2A).

2. The engineered T cell or NK cell according to claim 1, wherein the target of the first antibody binding domain comprises CD123, the target of the second antibody binding domain comprises CD33, the first co-stimulatory domain comprises CD28, the second co-stimulatory domain comprises 4-1BB, the cleavage site comprises P2A, and the engineered cell is a T cell.

3. The engineered T cell or NK cell according to claim 1, wherein the first co-stimulatory domain and the second co-stimulatory domain are different.

4. The engineered T cell or NK cell according to claim 1, wherein the first co-stimulatory domain comprises CD28, and the second co-stimulatory domain comprises 4-1BB.

* * * * *

UNITED STATES PATENT AND TRADEMARK OFFICE

CERTIFICATE OF CORRECTION

PATENT NO. : 11,655,452 B2
APPLICATION NO. : 15/739596
DATED : May 23, 2023
INVENTOR(S) : Yupo Ma et al.

It is certified that error appears in the above-identified patent and that said Letters Patent is hereby corrected as shown below:

In the Specification

Column 9, Line 50:
Now reads: "with goat-anti-mouse F(Ab+)2 antibody"
Should read: --with goat-anti-mouse F(Ab')2 antibody--.

Column 12, Line 10:
Now reads: "that binds specifically to a target antigen. The antibody nay"
Should read: --that binds specifically to a target antigen. The antibody may--

Column 19, Lines 1 and 2:
Now reads: "receptor in T cells. All possible safety switches are have been"
Should read: --receptor in T cells. All possible safety switches have been--

Column 21, Line 2:
Now reads: "for polypeptide having a CD123antigen recognition domain."
Should read: --for polypeptide having a CD 123 antigen recognition domain.--

Column 21, Line 22:
Now reads: "receptor polypeptide have a CS lantigen recognition"
Should read: -- receptor polypeptide have a CS antigen recognition --

Column 22, Line 3:
Now reads: "Engineered Cell Having CAR Polypeptide and Enhancer"
Should read: --Engineered cell having CAR Polypeptide and Enhancer--

Column 22, Line 39:
Now reads: "includes the Human Interleukin 15 with human interleukin"
Should read: --includes the human interleukin 15 with human interleukin--

Signed and Sealed this
Fifteenth Day of July, 2025

Coke Morgan Stewart
*Acting Director of the United States Patent and Trademark Office*

Column 23, Line 27:
Now reads: "expression vectors. There are several strategies can be"
Should read: --expression vectors. There are several strategies that can be--

Column 24, Lines 7 and 8:
Now reads: "There are several strategies can be"
Should read: --There are several strategies that can be--

Column 24, Line 49:
Now reads: "in regulation of 7-cell activation in response to antigen. The"
Should read: --in regulation of T-cell activation in response to antigen. The--

Column 24, Line 64:
Now reads: "referred to as 'antigen escape'."
Should read: --referred to as "antigen escape".--

Column 29, Line 48:
Now reads: "In one aspect of the present invention, CD 33 antigen is"
Should read: --In one aspect of the present invention, CD33 antigen is--

Column 31, Line 20:
Now reads: "Its expression is absent other tissues, indicating the potential"
Should read: --Its expression is absent in other tissues, indicating the potential--

Column 32, Line 43:
Now reads: "In a further embodiment, BCMA or TAC1 or BAFF-R"
Should read: --In a further embodiment, BCMA or TACI or BAFF-R--

Column 33, Lines 50 and 51:
Now reads: "from allogeneic donors and used as an 'off-the-shelf product"."
Should read: --from allogeneic donors and used as an "off-the-shelf product".--

Column 37, Line 61:
Now reads: "compoundCAR CD3ζ fusion protein (FIG. 1B)."
Should read: --compound CAR CD3ζ fusion protein (FIG. 1B).--

Column 38, Line 33:
Now reads: "enriched for CD33. About100% of its cell population is"
Should read: --enriched for CD33. About 100% of its cell population is--

Column 39, Line 53:
Now reads: "anti-mouse F(Ab+)2 at about 1:250 for about 30 minutes."
Should read: --anti-mouse F(Ab')2 at about 1:250 for about 30 minutes.--

Column 39, Line 59:
Now reads: "F(Ab+2 expressing cells collected and cultured."
Should read: --F(Ab')2 expressing cells collected and cultured.--

Column 40, Line 65:
Now reads: "of the BC1cCAR) CAR molecule on the T-cell surface."
Should read: --of the BC1cCAR CAR molecule on the T-cell surface.--

Column 43, Lines 65 and 66:
Now reads: "60% of CCRF-CEMcells (FIG. 31)."
Should read: --60% of CCRF-CEM cells (FIG. 31).--

Column 44, Line 62:
Now reads: "incorporating both CAR and I1-15/RA or IL 15/sushi in the"
Should read: --incorporating both CAR and IL-15/RA or IL 15/sushi in the--

Column 45, Line 34:
Now reads: "Cells were lysed in RIM buffer containing"
Should read: --Cells were lysed in RIPA buffer containing--

Column 49, Line 9:
Now reads: "expressing at least one of of BCMA or TACI or BAFF-R."
Should read: --expressing at least one of BCMA or TACI or BAFF-R.--